US010865248B2

(12) United States Patent
Lazar et al.

(10) Patent No.: US 10,865,248 B2
(45) Date of Patent: Dec. 15, 2020

(54) ANTIGEN BINDING COMPLEX HAVING AGONISTIC ACTIVITY AND METHODS OF USE

(71) Applicant: Genentech, Inc., South San Francisco, CA (US)

(72) Inventors: Greg Lazar, South San Francisco, CA (US); Jeong Kim, San Francisco, CA (US); Jing Zhu, Moraga, CA (US); Yanli Yang, South San Francisco, CA (US); Randall Brezski, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/725,208

(22) Filed: Oct. 4, 2017

(65) Prior Publication Data

US 2018/0022813 A1    Jan. 25, 2018

Related U.S. Application Data

(63) Continuation of application No. PCT/US2016/026245, filed on Apr. 6, 2016.

(60) Provisional application No. 62/387,485, filed on Dec. 23, 2015, provisional application No. 62/207,315, filed on Aug. 19, 2015, provisional application No. 62/144,237, filed on Apr. 7, 2015.

(51) Int. Cl.
| | |
|---|---|
| *A61K 39/395* | (2006.01) |
| *C07K 16/28* | (2006.01) |
| *C07K 16/32* | (2006.01) |
| *A61K 47/68* | (2017.01) |
| *A61K 38/02* | (2006.01) |
| *A61K 39/00* | (2006.01) |

(52) U.S. Cl.
CPC .......... *C07K 16/2875* (2013.01); *A61K 38/02* (2013.01); *A61K 39/395* (2013.01); *A61K 47/6881* (2017.08); *C07K 16/2863* (2013.01); *C07K 16/2878* (2013.01); *C07K 16/32* (2013.01); *A61K 2039/505* (2013.01); *A61K 2039/54* (2013.01); *A61K 2039/545* (2013.01); *C07K 2317/21* (2013.01); *C07K 2317/24* (2013.01); *C07K 2317/31* (2013.01); *C07K 2317/524* (2013.01); *C07K 2317/526* (2013.01); *C07K 2317/622* (2013.01); *C07K 2317/71* (2013.01); *C07K 2317/73* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| RE30,985 E | 6/1982 | Cartaya |
| 4,419,446 A | 12/1983 | Howley et al. |
| 4,560,655 A | 12/1985 | Baker et al. |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Dafler |
| 4,943,533 A | 7/1990 | Mendelsohn et al. |
| 4,965,199 A | 10/1990 | Capon et al. |
| 5,122,469 A | 6/1992 | Mather et al. |
| 5,212,290 A | 5/1993 | Vogelstein et al. |
| 5,264,365 A | 11/1993 | Georgiou et al. |
| 5,457,105 A | 10/1995 | Barker |
| 5,475,001 A | 12/1995 | Barker |
| 5,500,362 A | 3/1996 | Robinson et al. |
| 5,508,192 A | 4/1996 | Georgiou et al. |
| 5,571,894 A | 11/1996 | Wels et al. |
| 5,587,458 A | 12/1996 | King et al. |
| 5,591,828 A | 1/1997 | Bosslet et al. |
| 5,616,582 A | 4/1997 | Barker |
| 5,639,635 A | 6/1997 | Joly et al. |
| 5,641,870 A | 6/1997 | Rinderknecht et al. |
| 5,648,237 A | 7/1997 | Carter |
| 5,654,307 A | 7/1997 | Carter |
| 5,679,683 A | 10/1997 | Bridges et al. |
| 5,693,780 A | 12/1997 | Newman et al. |
| 5,731,168 A | 3/1998 | Carter et al. |
| 5,747,498 A | 5/1998 | Schnur et al. |
| 5,750,373 A | 5/1998 | Garrard et al. |
| 5,760,041 A | 6/1998 | Wissner et al. |

(Continued)

FOREIGN PATENT DOCUMENTS

| | | |
|---|---|---|
| EP | 0 404 097 B1 | 12/1990 |
| EP | 0 659 439 B1 | 6/1995 |

(Continued)

OTHER PUBLICATIONS

De Pascalis et al. (2002). Journal of Immunology. 169:3076-3084.*

(Continued)

*Primary Examiner* — Joanne Hama
*Assistant Examiner* — Jon M Lockard
(74) *Attorney, Agent, or Firm* — Morrison & Foerster LLP

(57) ABSTRACT

Provided herein are antigen binding polypeptides and complexes thereof having agonist activity. Also provided are methods for screening for complexes or polypeptides having agonist activity, enhancing the agonist activity of a polypeptide, and for agonizing a cell surface receptor using the complexes and polypeptide described herein.

17 Claims, 33 Drawing Sheets

Specification includes a Sequence Listing.

(56) References Cited

U.S. PATENT DOCUMENTS

| | | |
|---|---|---|
| 5,770,429 A | 6/1998 | Lonberg et al. |
| 5,770,599 A | 6/1998 | Gibson et al. |
| 5,804,396 A | 9/1998 | Plowman |
| 5,821,337 A | 10/1998 | Carter et al. |
| 5,866,527 A | 2/1999 | Mertens et al. |
| 5,866,572 A | 2/1999 | Barker et al. |
| 5,869,046 A | 2/1999 | Presta et al. |
| 5,891,996 A | 4/1999 | Mateo de Acosta del Rio et al. |
| 6,002,008 A | 12/1999 | Wissner et al. |
| 6,075,181 A | 6/2000 | Kucherlapati et al. |
| 6,084,095 A | 7/2000 | Bridges et al. |
| 6,140,332 A | 10/2000 | Traxler et al. |
| 6,150,584 A | 11/2000 | Kucherlapati et al. |
| 6,194,551 B1 | 2/2001 | Idusogie et al. |
| 6,235,883 B1 | 5/2001 | Jakobovits et al. |
| 6,248,516 B1 | 6/2001 | Winter et al. |
| 6,265,410 B1 | 7/2001 | Bridges et al. |
| 6,344,455 B1 | 2/2002 | Bridges et al. |
| 6,344,459 B1 | 2/2002 | Bridges et al. |
| 6,391,874 B1 | 5/2002 | Cockerill et al. |
| 6,399,602 B1 | 6/2002 | Barker et al. |
| 6,455,534 B2 | 9/2002 | Bridges et al. |
| 6,521,620 B1 | 2/2003 | Bridges et al. |
| 6,596,726 B1 | 7/2003 | Bridges et al. |
| 6,602,863 B1 | 8/2003 | Bridges et al. |
| 6,713,484 B2 | 3/2004 | Bridges et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,189,826 B2 | 3/2007 | Rodman |
| 7,332,581 B2 | 2/2008 | Presta |
| 7,527,791 B2 | 5/2009 | Adams et al. |
| 7,550,140 B2 | 6/2009 | Bakker et al. |
| 7,696,175 B2 | 4/2010 | Epstein et al. |
| 7,960,515 B2 | 6/2011 | Min et al. |
| 2005/0079574 A1 | 4/2005 | Bond |
| 2005/0119455 A1 | 6/2005 | Fuh et al. |
| 2005/0266000 A1 | 12/2005 | Bond et al. |
| 2006/0025576 A1 | 2/2006 | Miller et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2012/0251531 A1 | 10/2012 | Baehner et al. |
| 2014/0037621 A1 | 2/2014 | Tsurushita et al. |

FOREIGN PATENT DOCUMENTS

| | | |
|---|---|---|
| EP | 0 672 141 B1 | 9/1995 |
| JP | 2000515731 A | 11/2000 |
| JP | 2003512019 A | 4/2003 |
| JP | 2014514287 A | 6/2014 |
| JP | 2015501291 A | 1/2015 |
| WO | WO-1987/00195 A1 | 1/1987 |
| WO | WO-1990/03430 A1 | 4/1990 |
| WO | WO-1993/08829 A1 | 5/1993 |
| WO | WO-1993/11161 A1 | 6/1993 |
| WO | WO-1993/16185 A2 | 8/1993 |
| WO | WO-1993/16185 A3 | 8/1993 |
| WO | WO-1994/11026 A2 | 5/1994 |
| WO | WO-1994/11026 A3 | 5/1994 |
| WO | WO-1996/30347 A1 | 10/1996 |
| WO | WO-1996/33978 A1 | 10/1996 |
| WO | WO-1996/33979 A1 | 10/1996 |
| WO | WO-1996/33980 A1 | 10/1996 |
| WO | WO-1996/40210 A1 | 12/1996 |
| WO | WO-1997/38983 A1 | 10/1997 |
| WO | WO199747732 A2 | 12/1997 |
| WO | WO-1998/14451 A1 | 4/1998 |
| WO | WO-1998/43960 A1 | 10/1998 |
| WO | WO-1998/50038 A1 | 11/1998 |
| WO | WO-1998/50433 A2 | 11/1998 |
| WO | WO-1998/50433 A3 | 11/1998 |
| WO | WO-1999/06378 A1 | 2/1999 |
| WO | WO-1999/06396 A1 | 2/1999 |
| WO | WO-1999/09016 A1 | 2/1999 |
| WO | WO-1999/24037 A1 | 5/1999 |
| WO | WO-1999/51642 A1 | 10/1999 |
| WO | WO-2000/29004 A1 | 5/2000 |
| WO | WO200042072 A2 | 7/2000 |
| WO | WO-2002/051870 A2 | 7/2002 |
| WO | WO-2002/051870 A3 | 7/2002 |
| WO | WO-2003/035694 A2 | 5/2003 |
| WO | WO-2003/035694 A3 | 5/2003 |
| WO | WO-2004/056312 A2 | 7/2004 |
| WO | WO-2004/056312 A3 | 7/2004 |
| WO | WO-2005/035572 A2 | 4/2005 |
| WO | WO-2005/035572 A3 | 4/2005 |
| WO | WO-2005/100402 A1 | 10/2005 |
| WO | WO-2006/029879 A2 | 3/2006 |
| WO | WO-2006/029879 A3 | 3/2006 |
| WO | WO-2006/121168 A1 | 11/2006 |
| WO | WO-2006/121810 A2 | 11/2006 |
| WO | WO-2006/121810 A3 | 11/2006 |
| WO | WO-2007/005874 A2 | 1/2007 |
| WO | WO-2007/005874 A3 | 1/2007 |
| WO | WO-2008/049227 A1 | 5/2008 |
| WO | WO-2009/089004 A1 | 7/2009 |
| WO | WO-2009/101611 A1 | 8/2009 |
| WO | WO-2009/114335 A2 | 9/2009 |
| WO | WO-2009/114335 A3 | 9/2009 |
| WO | WO-2010/005958 A2 | 1/2010 |
| WO | WO-2010/005958 A3 | 1/2010 |
| WO | WO-2010/005959 A1 | 1/2010 |
| WO | WO-2010/027827 A2 | 3/2010 |
| WO | WO-2010/027827 A3 | 3/2010 |
| WO | WO-2010/077634 A1 | 7/2010 |
| WO | WO-2011/066342 A2 | 6/2011 |
| WO | WO-2011/066342 A3 | 6/2011 |
| WO | WO-2012/027328 A2 | 3/2012 |
| WO | WO-2012/027328 A3 | 3/2012 |
| WO | WO2012130831 A1 | 10/2012 |
| WO | WO-2013/004842 A2 | 1/2013 |
| WO | WO-2013/004842 A3 | 1/2013 |
| WO | WO-2013/004843 A1 | 1/2013 |
| WO | WO-2013/028231 A1 | 2/2013 |
| WO | WO-2013/038191 A2 | 3/2013 |
| WO | WO-2013/038191 A3 | 3/2013 |
| WO | WO2013049254 A1 | 4/2013 |
| WO | WO-2014/006217 A1 | 1/2014 |
| WO | WO2014022592 A1 | 2/2014 |
| WO | WO-2014/108198 A1 | 7/2014 |
| WO | WO-2014/148895 A1 | 9/2014 |

OTHER PUBLICATIONS

Casset et al. (2003). Biochemical and Biophysical Reseaerch Commnications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Alexander, S.P.H. et al. (2013) "The Concise Guide to Pharmacology 2013/14: Enzymes," *Br. J. Pharmacol.* 170:1797-1867.
Almagro, J.C. et al. (Jan. 1, 2008). "Humanization of Antibodies," *Front. Biosci.* 13:1619-1633.
Baca, M. et al. (Apr. 18, 1997). "Antibody Humanization Using Monvalent Phage Display," *J. Biol. Chem.* 272(16):10678-10684.
Bachmann, B.J. (1987). "Derivations and Genotypes of Some Mutant Derivatives of *Escherichia coli* K-12," Chapter 133, Section F in *Cellular and Molecular Biology*, vol. 2, American Society for Microbiology, Washington, D.C., pp. 1190-1219.
Barnes, D. et al. (1980). "Methods for Growth of Cultured Cells in Serum-Free Medium," *Anal. Biochem.*102:255-270.
Barton, W.A. et al. (Jun. 2006, e-pub. May 28, 2006). "Crystal Structures of the Tie2 Receptor Ectodomain and the Angiopoietin-2-Tie2 Complex," *Nat. Struct. & Mol. Biol.* 13(6):524-532.
Bass, S. et al. (1990). "Hormone Phage: An Enrichment Method for Variant Proteins With Altered Binding Properties" *Proteins* 8:309-314.

(56) References Cited

OTHER PUBLICATIONS

Birnbaumer, J.C. et al. (1988). "Hormones and their Actions Part II," Chapter 1 in *Biochemistry, New Comprehensive Biochemistry*, Cooke, B.A. ed., Elsevier Science Publishers BV, vol. 18B, New York, pp. 1-46.

Boerner, P. et al. (Jul. 1, 1991). "Production of a Antigen-Specific Human Monoclonal Antibodies from In Vitro-Primed Human Splenocytes," *J. Immunol.* 147(1):86-95.

Brazil, M. (Jan. 2006). "TNFR Superfamily Trimers," *Nature* 5:20-21.

Brennan, M. et al. (Jul. 5, 1985). "Preparation of Bispecific Antibodies by Chemical Recombination of Monoclonal Immunoglobulin $G_1$ Fragments," *Science* 229:81-83.

Brodeur, B.R. et al. (1987). "Mouse-Human Myeloma Partners ro the Production Monoclonal Antibody Production of Heterohybridomas," Chapter 4 in *Techniques and Applications*, Marcel Dekker, Inc., New York, pp. 51-63.

Brüggemann, M. et al. (Nov. 1, 1987). "Comparison of the Effector Functions of Human Immunoglobulins Using a Matched Set of Chimeric Antibodies," *J. Exp. Med.* 166:1351-1361.

Camidge, D.R. (Aug. 2008). "Apomab: An Agonist Monoclonal Antibody Directed Against Death Receptor 5/TRAIL-Receptor 2 for Use in the Treatment of Solid Tumors," *Expert Opinion Biol. Ther.* 8(8):1167-1176.

Capel, P.J.A. et al. (1994). "Heterogeneity of Human IgG Fc Receptors," *Immunomethods* 4:25-34.

Carter, P. et al. (May 1992). "Humanization of a Anti-p185$^{HER2}$ Antibody for Human Cancer Therapy," *Proc. Natl. Acad. Sci. USA* 89:4285-4289.

Chemidplus. (Apr. 1, 2019). "ChemIDSplus, RN: CAS Registry No. 946414-94-4m UNII: 31YO63LBSN, Substance Name: Nivolumab," located at <http://chem.nlm.nih.gov/chemidplus/rn/946414-94-4>, last visited on Apr. 1, 2019, 2 pages.

Chothia, C. et al. (1987). "Canonical Structures of the Hypervariable Regions of Immunoglobulins," *J. Mol. Biol.* 196:901-917.

Clackson, T. et al. (Aug. 15, 1991). "Making Antibody Fragments Using Phage Display Libraries," *Nature* 352:624-628.

ClinicalTrials.gov. (Apr. 29, 2009). "Her2 and Tgfbeta Cytotoxic T Cells in Treatment of Her2 Positive Malignancy (HERCREEM)," *Clinicaltrailsgov.*, Located at <HTTP://HTTPS/CLINICALTRAILS. GOV/CT2/SHOW/nct00889954>, Last Visited on April 1, 2019, 8 Pages.

Clynes, R. et al. (Jan. 1998). "Fc Receptors are Required in Passive and Active Immunity to Meanoma," *Proc. Natl. Acad. Sci. USA* 95:652-656.

Cragg, M.S., et al. (2003). "Complement-mediated lysis by anti-CD20 mAb correlates with segregation into lipid rafts," *Blood* 101:1045-1052.

Cragg et al. (2004). "Antibody specificity controls in vivo effector mechanisms of anti-CD20 reagents," *Blood* 103:2738-2743.

Daëron, M. (1997). "Fc Receptor Biology," *Annu. Rev. Immunol.* 15:203-234.

Dall'Acqua, W. et al. (2005). "Antibody Humanization by Framework Shuffling," *Methods* 36:43-60.

D'Andrea, A.D. et al. (Apr. 21, 1989) "Expression Cloning of the Murine Erythropoietin Receptor," *Cell* 57:277-285.

Davies, J. et al. (1994). 'Camelising' Human Antibody Fragments: NMR Studies on VH Domains, *Febs. Lett.* 339(3):285-290.

Davies, A.M. et al. (2014). "Crystal Structure of Deglycosylated Human IgG4-Fc," *Molecular Immunology* 62:46-53.

De Hass, M. et al. (1995). "Fcγ Receptors of Phagocytes," *J. Lab. Clin. Med.* 126(4):330-341.

Diebolder, C.A. et al. (2014). "Complement is activated by IgG hexamers assembled at the cell surface," *Science* 343:1260-1263.

Dooley, H. et al. (2006, e-pub. Jul. 22, 2005). "Antibody repertoire development in cartilaginous fish," *Dev. Comp. Immunol.* 30(1-2):43-56.

Eaton, D.L. et al. (Dec. 30, 1986). "Construction and Characterization of an Active Factor VIII Variant Lacking the Central One-Third of the Molecule," *Biochemistry* 25(26):8343-8347.

Fantl, W.I. et al. (1993). "Signalling by Receptor Tyrosine Kinases," *Annu. Rev. Biochem.* 62:453-481.

Fellouse, F.A. et al. (Aug. 24, 2004). "Synthetic Antibodies from a Four-Amino-Acid Code: A Dominant Role for Tyrosine in Antigen Recognition," *Proc. Natl. Acad. Sci. USA* 101(34):12467-12472.

Flatman, S. et al. (2007, e-pub. Dec. 11, 2006). "Process Analytics for Purification of Monoclonal Antibodies," *J. Chromatogr. B.* 848:79-87.

Flower, D R. (1999) "Modelling G-Protein-Coupled Receptors for Drug Design," *Biochim. Biophys. Acta* 1422:207-234.

Fukunaga, R. et al. (Apr. 20, 1990). "Expression Cloning of a Receptor for Murine Granulocyte Colony-Stimulating Factor," *Cell* 61:341-350.

Fukunaga, R. et al. (Nov. 1990). "Three Different mRNAs Encoding Human Granulocyte Colony-Stimulating Factor Receptor," *Proc. Natl. Acad. Sci. USA* 87:8702-8706.

Gazzano-Santoro, H. et al. (1996). "A Non-Radioactive Complement-Dependent Cytotoxicity Assay for Anti-CD20 Monoclonal Antibody," *J. Immunol. Methods* 202:163-171.

Graham, F.L., et al. (1977). "Characteristics of a Human Cell Line Transformed by DNA From Human Adenovirus Type 5," *J. Gen Virol.* 36:59-74.

Griffiths et al. (1993). "Human Anti-Self Antibodies with High Specificity from Phage Display Libraries," *EMBO J*, 12(2):725-734 (1993).

Gronwald, R.G.K.et al. (May 1988). "Cloning and Expression of a cDNA Coding for the Human Platelet-Derived Growth Factor Receptor: Evidence for More Than One Receptor," *Proc. Natl. Acad. Sci. USA* 85:3435-3439.

Gruber, M. et al. (1994). "Efficient Tumor Cell Lysis Mediated by a Bispecific Single Chain Antibody Expressed in *Escherichia coli,*" *J. Immunol.* 152:5368-5374.

Guss, B. et al. (1986). "Structure of the IgG-binding regions of streptococcal protein G," *EMBO J.* 5(7):1567-1575.

Guyer, R.L. et al. (Aug. 1976). "Immunoglobulin Binding by Mouse Intestinal Epithelial Cell Receptors," *J. Immunol.* 117(2):587-593.

Ham, R.G. et al. (1979). "Media and Growth Requirements," *Meth. Enz.* 58:44-93.

Hara, H. et al. (1996). "Overproduction of Penicillin-Binding Protein 7 Suppresses. Thermosensitive Growth Defect at Low Osmolarity due to an spr Mutation of *Escherichia coli,*" *Microbial Drug Resistance* 2(1):63-72.

Heidin, C.-H. (Jan. 27, 1995). "Dimerization of Cell Surface Receptors in Signal Transduction," *Cell* 80:213-223.

Hellstrom, I. et al. (Mar. 1985). "Strong Antitumor Activities of IgG3 Antibodies to a Human Melanoma-associated Ganglioside," *Proc. Natl. Acad. Sci. USA* 82:1499-1502.

Hellstrom, I. et al. (Sep. 1986). "Antitumor Effects of L6, an IgG2a Antibody That Reacts With Most Human Carcinomas," *Proc. Natl. Acad. Sci. USA* 83:7059-7063.

Holliger, P. et al. (Jul. 1993). ""Diabodies": Small Bivalent and Bispecific Antibody Fragments," *Proc. Natl. Acad. Sci. USA* 90:6444-6448.

Holliger, P. et al. (1996). "Specific Killing of Lymphoma Cells by Cytotoxic T-Cells Mediated by a Bispecific Diabody," *Protein Engineering* 9(3):299-305.

Holt, L.J. et al. (Nov. 2003). "Domain Antibodies: Proteins for Therapy," *Trends Biotechnol.* 21(11):484-490.

Hoogenboom, H.R. et al. (2001). "Overview of Antibody Phage-Display Technology and Its Applications," Chapter 1 in *Methods in Molecular Biology*, O'Brien et al. ed., Humana Press, Totowa, NJ, 178:1-37.

Hoogenboom , H.R. et al. (Sep. 20, 1992). "By-Passing Immunisation: Human Antibodies from Synthetic Repertoires of Germline VH Gene Segments Rearranged in Vitro," *J. Mol. Biol.* 227:381-388.

Hudson, P.J. et al. (Jan. 2003). "Engineered Antibodies," *Nat. Med.* 9(1):129-134.

Idusogie, E.E. et al. (2000). "Mapping of the C1q Binding Site on Rituxan, a Chimeric Antibody with a Human IgG1 Fc," *J. Immunol.* 164:4178-4184.

(56) References Cited

OTHER PUBLICATIONS

International Preliminary Report on Patentability dated Oct. 19, 2017, for PCT Application No. PCT/US2016/026245, filed on Apr. 6, 2016, 8 pages.

International Search Report dated Jun. 21, 2016, for PCT Application No. PCT/US2016/026245, filed on Apr. 6, 2016, 5 pages.

Johns, F.G. et al. (Jul. 16, 2004, e-pub. Apr. 9, 2004). "Identification of the Epitope for the Epidermal Growth Factor Receptor-Specific Monoclonal Antibody 806 Reveals that it Preferentially Recognizes an Untethered Form of the Receptor," *J. Biol. Chem.* 279(29):30375-303784.

Joly, J.C. et al. (Mar. 1998). "Overexpression of *Escherichia coli* Oxidoreductases Increases Recombinant Insulin-Like Growth Factor-I Accumulation," *Proc. Natl. Acad. Sci. USA* 95:2773-2777.

Jones, P.T. et al. (May 29, 1996). "Replacing the Complementarity-Determining Regions in a Human Antibody With Those From a Mouse," *Nature* 321:522-525.

Jones, S.S. et al. (Jul. 1, 1990). "Human Erythropoietin Receptor: Cloning, Expression, and Biologic Characterization," *Blood* 76(1):31-35.

Kabat, E.A. et al. (Sequences of Proteins of Immunological Interest, $5^{th}$ Ed. Public Health Service, National Institutes of Health, Bethesda, MD (1991), vol. 1-3. (Table of Contents), 21 pages.

Kashmiri, S.V. et al. (2005). "SDR grafting—A New Approach to Antibody Humanization," *Methods* 36:25-34.

Kim, J.K. et al. (1994). "Localization of the Site of the Murine IgG1 Molecule That is Involved in Binding to the Murine Intestinal Fc Receptor," *Eur. J. Immunol.* 249:2429-2432.

Kim, J.M. et al. (2013). "Fcγ Receptors Enable Anticancer Action of Proapoptotic and Immune-Modulatory Antibodies," *J. Exp. Med* 210(9):1647-1651.

Klimka, A. et al. (2000). "Human Anti-CD30 Recombinant Antibodies by Guided Phage Antibody Selection Using Cell Panning," *Br. J. Cancer* 83(2):252-260.

Köhler, C. et al. (Aug. 7, 1975). "Continuous Cultures of Fused Cells Secreting Antibody of Predefined Specificity," *Nature* 256:495-497.

Kostelny, S.A. et al. (Mar. 1, 1992). "Formation of a Bispecific Antibody by the Use of Leucine Zippers," *J. Immunol.* 148(5):1547-1553.

Kozbor, D. (Dec. 1984). "A Human Hybrid Myeloma for Production of Human Monoclonal Antibodies," *J. Immunol.* 133(6):3001-3004.

Lee, C.V. et al. (2004). "Bivalent Antibody Phage Display Mimics Natural Immunoglobulin," *J. Immunol. Methods* 284(1-2):119-132.

Lee, C.V. et al. (2004). "High-affinity Human Antibodies From Phage-Displayed Synthetic Fab Libraries With a Single Framework Scaffold," *J. Mol. Biol.* 340:1073-1093.

Lemmon, M.A. et al. (Jun. 25, 2010). Cell Signalling by Receptor-Tyrosine Kinases, *Cell* 141(7):1117-1134.

Li, J. et al. (Mar. 7, 2006). "Human Antibodies for Immunotherapy Development Generated via a Human B Cell Hybridoma Technology," *Proc. Natl. Acad. Sci. USA* 103:3557-3562.

Li, E. et al. (Jun. 2010). "Receptor Tyrosine Kinase Transmembrane Domains. Function, Dimer Structure and Dimerization Energetics," *Cell Adhesion and Migration* 4(2):249-254.

Lindmark, R. et al. (1983). "Binding of Immunoglobulins to Protein A and Immunoglobulin Levels in Mammalian Sera," *J. Immunol. Meth.* 62:1-13.

Lonberg, N. (Sep. 2005). "Human Antibodies From Transgenic Animals," *Nat. Biotech.* 23(9):1117-1125.

Lonberg, N. et al. (2008, e-pub. Jul. 21, 2008). "Fully Human Antibodies From Transgenic Mouse and Phage Display Platforms," *Curr. Opin. Immunol.* 20:450-459.

Lotz, M et al. (Jul. 1996). "The Nerve Growth Factor/Tumor Necrosis Factor Receptor Family," *J. of Leukocyte Biology* 60(1):1-7.

MacCallum, R.M. et al. (Oct. 11, 1996). "Antibody-Antigen Interactions: Contact Analysis and Binding Site Topography," *J. Mol. Biol.* 262:732-745.

Marks, J.D. et al. (Dec. 5, 1991). "By-Passing Immunization. Human Antibodies From V-gene Libraries Displayed on Phage," *J. Mol. Biol.* 222(3):581-597.

Marks, J.D. et al. (2003). "Antibody Engineering," Chapter 8 in *Methods in Molecular Biology* 248:161-175.

Massagué, J. (Jun. 26, 1992) "Receptors for the TGF-β Family," *Cell* 69:1067-1070.

Mather, J.P. (1980). "Establishment and Characterization of Two Distinct Mouse Testicular Epithelial Cell Lines," *Biol. Reprod.* 23:243-252.

Mather, J.P. et al. (1982). "Culture of Testicular Cells in Hormone-Supplemented Serum-Free Medium," *Annals N.Y. Acad. Sci.* 383:44-68.

McCafferty, J. et al. (Dec. 6, 1990). "Phage Antibodies: Filamentous Phage Displaying Antibody Variable Domains," *Nature* 348(6301):552-554.

Milstein, C. (Oct. 6, 1983). "Hybrid Hybridomas and Their Use in Immunohistochemistry," *Nature* 305:537-540.

Miyajima A. et al. (1992). "Cytokine Receptors and Signal Transduction," *Annu. Rev. Immunol.* 10:295-331.

Morris, N.P. et al. (May 7, 2007). "Development and Characterization of Recombinant Human Fc:OX40L Fusion Protein Linked via a Coiled-Coil Trimerization Domain," *Molecular immunology* 44(12):3112-3121, 18 pages.

Morrison, S.L. et al. (Nov. 1984). "Chimeric Human Antibodies Molecules: Mouse Antigen-Binding Domains With Human Constant Region Domains," *Proc. Natl. Acad. Sci. USA* 81:6851-6855.

Muyldermans, S. et al. (Apr. 2001). "Recognition of Antigens by Single-Domain Antibody Fragments: The Superfluous Luxury of Paired Domains," *Trends Biochem. Sci.* 26(4):230-235.

Naismith, J.H. et al. (Feb. 1998). "Modularity in the TNF-Receptor Family," *Trends in Biochemical Sciences* 23(2):74-79.

Ni, J. (Oct. 23, 2006). "Research Progress and Future Perspectives in Antibodmics and Antibodomic Drugs," *J. General Review* 26(4):265-268, 3 pages.

Nicolaou, K.C. et al. (Feb. 1, 1994). "Calicheamicin θ1: A Rationally Designed Molecule with Extremely Potent and Selective DNA Cleaving Properties and Apoptosis Inducing Activity," *Angewandte International Edition Chemie* 33(2):183-186.

Novick, D. et al. (May 6, 1994). "The Human Interferon α/β Receptor: Characterization and Molecular Cloning," *Cell* 77:391-400.

Osbourn, J. et al. (2005). "From Rodent Reagents to Human Therapeutics Using Antibody Guided Selection," *Methods* 36:61-68.

Padlan, E.A. (1991). "A Possible Procedure for Reducing the Immunogenicity of Antibody Variable Domains While Preserving Their Ligand-Binding Properties," *Mol. Immunol.* 28(4/5):489-498.

Patthy, L. (Apr. 6, 1990). "Homology of a Domain of the Growth Hormone/Prolactin Receptor Family with Type III Modules of Fibronectin," *Cell* 61:13-14.

Plückthun, A. (1994). "Antibodies from *Escherichia coli*," Chapter 11 in *The Pharmacology of Monoclonal Antibodies* vol. 113, Rosenburg and Moore eds., Springer-Verlag, New York, pp. 269-315.

Presta, L. (1992). "Antibody Engineering," *Curr. Op. Struct. Biol.* 2:593-596.

Presta, L.G. et al. (Sep. 1, 1993). "Humanization of an Antibody Directed Against IgE," *J. Immunol.* 151(5):2623-2632.

Proba, K. et al. (1995). "Functional Antibody Single-Chain Fragments From the Cytoplasm of *Escherichia coli*: Influence of Thioredoxin Reductase (TrxB)," *Gene* 159:203-207.

Queen, C. et al. (Dec. 1989). "A Humanized Antibody That Binds to the Interleukin 2 Receptor," *Proc. Natl. Acad. Sci. USA* 86:10029-10033.

Ravetch, J.V. et al. (1991). "Fc Receptors," *Annu. Rev. Immunol.* 9:457-492.

Remington's Pharmaceutical Sciences ($20^{th}$ edition), A. Gennaro ed., 2000, Lippincott, Williams & Wilkins, Philadelphia, PA, 2 pages.

Reyes, G.R. et al. (Jun. 17, 1982). "Expression of Human β-interferon cDNA Under the Control of a Thymidine Kinase Promoter From Herpes Simplex Virus," *Nature* 297:598-601.

(56) References Cited

OTHER PUBLICATIONS

Riechmann, L. et al. (Mar. 24, 1988). "Reshaping Human Antibodies for Therapy," *Nature* 332:323-327.
Rosok, M.J. et al. (Sep. 13, 1996). "A Combinatorial Library Strategy for the Rapid Humanization of Anticarcinoma BR96 Fab," *J. Biol. Chem.* 271(37):22611-22618.
Rupert, S. et al. (Mar. 11, 1993). "Cloning and Expression of Human $TAF_{II}250$: a TBP-Associated Factor Implicated in Cell-Cycle Regulation," *Nature* 362:175-179.
Shields, R.L. et al. (Mar. 2, 2001). "High Resolution Mapping of the Binding Site on Human IgG1 for FcγRI, FcγRII, FcγIII, and FcRn and Design of IgF1 Variants with Improved Binding to the FcγR," *J. Biol. Chem.* 276(9): 6591-6604.
Sidhu, S.S. et al. (2004). "Phage-Displayed Antibody Libraries of Synthetic Heavy Chain Complementarity Determining Regions," *J. Mol. Biol.* 338(2):299-310.
Siebenlist, U. et al. (1980). "*E. coli* RNA Polymerase Interacts Homologuously With Two Different Promoters," *Cell* 20:269-291.
Simmons, L.C. et al. (2002). "Expression of Full-Length Immunglobulins in *Escherichia coli*: Rapid and Efficient Production of Aglycosylated Antibodies," *J. Immunol. Methods* 263:133-147.
Sims, LC. et al. (Aug. 15, 1993). "A Humanized CD18 Antibody Can Block Function Without Cell Destruction," *J. Immunol.* 151(4):2296-2308.
Skoda, R.C. et al. (1993). "Murine *c-mpl*: A Member of the Hematopoietic Growth Factor Receptor Superfamily That Transduces a Proliferative Signal," *The EMBO Journal* 12(7):2645-2653.
Small, D. et al. (Jan. 1994). "STK-1, the Human Homolog of Flk-2/Flt-3, is Selectively Expressed in CD34 + Human Bone Marrow Cells and is Involved in the Proliferation of Early Progenitor/ Stem Cells," *Proc. Natl. Acad. Sci. USA* 91:459-569.
Smith, C A. et al. (Mar. 25, 1994). "The TNF Receptor Superfamily of Cellular and Viral Proteins: Activation, Costimulation, and Death" *Cell* 76:959-962.
Spiess, C. et al. (Aug. 2013, e-pub. Jul. 7, 2013). "Bispecific Antibodies With Natural Architecture Produced by Co-Culture of Bacteria Expressing Two Distinct Half-Antibodies," *Nature Biotech.* 31(8):753-758.
Stewart, R. et al. (2014). "The Role of Fc Gamma Receptors in the Activity of Immunomodulatory Antibodies for Cancer," *Journal for Immmunotherapy of Cancer* 2(29):1-10.
Stragliotto, G. et al. (Apr. 1996). "Multiple Infusion of Anti-Epidermal Growth Factor Receptor (EGFR) Monoclonal Antibody (EMD 55,900) in Patient with Recurrent Malignant Gliomas," *Eur. J. Cancer* 32A(4):636-640.
Strohl, W.R. (2009, e-pub. Nov. 4, 2009). "Optimization of Fc-Mediated Effector Functions of Monoclonal Antibodies," *Curr. Opin. In Biotech.* 20:685-691.
Taga, T. et al. (1992). "Cytokine Receptor and Signal Transduction," *FASEB J.* 7:3387-3396.

Traunecker, A. et al. (1991). "Bispecific Single Chain Molecules (Janusins) Target Cytotoxic Lymphocytes on HIV Infected Cells," *EMBO J.* 10(12):3655-3659.
Tutt, A. et al. (Jul. 1, 1991). "Trispecific F(ab')₃ Derivatives That Use Cooperative Signaling Via the TCR/CD3 Complex and CD2 to Activate and Redirect Resting Cytotoxic T Cells," *J. Immunol.* 147(1):60-69.
Ullrich, A. et al. (Feb. 28, 1985). "Human Insulin Receptor and Its Relationship to the Tyrosine Kinase Family of Oncogenes," *Nature* 313:756-761.
Ullrich, A. et al. (Apr. 20, 1990). "Signal Transduction by Receptors With Tyrosine Kinase Activity," *Cell* 61:203-212.
Urlaub, G., et al. (Jul. 1980). "Isolation of Chinese Hamster Cell Mutants Deficient in Dihydrofolate Reductase Activity," *Proc. Natl. Acad. Sci. USA* 77(7):4216-4220.
Uzé, G. et al. (Jan. 26, 1990). "Genetic Transfer of a Functional Human Interferon α Receptor into Mouse Cells: Cloning and Expression of Its cDNA" *Cell* 60:225-234.
Van Dijk, M.A. et al. (2001). "Human Antibodies as Next Generation Therapeutics," *Curr. Opin. Pharmacol* 5:368-374.
Vigon, I. et al. (Jun. 1992). "Molecular Cloning and Characterization of *MPL*, the human Homolog of the v-*mpl* Oncogene: Identification of a Member of the Hematopoietic Growth Factor Receptor Superfamily," *Proc. Natl. Acad. Sci. USA* 89:5640-5644.
Vollmers, H.P. et al. (2005). "Death by Stress: Natural IgM-Induced Apoptosis," *Methods and Findings in Experimental and Clinical Pharmacology* 27(3):185-191.
Vollmers, H.P. et al. (2005). "The 'Early Birds': Natural IgM Antibodies and Immune Surveillance," *Histology and Histopathology*, 20(3):927-937.
Voo, K.S. et al. (2013, e-pub. Sep. 6, 2013). "Antibodies Targeting Human OX40 Expand Effector T Cells and Block Inducible and Natural Regulatory T Cell Function," *J. Immunol.* 191:3641-3650.
Wang, X. et al. (Apr. 9, 2009). "Structural Biology of Shared Cytokine Receptors," *Ann. Rev. Immunol.* 27:29-60.
Ward, E.S. et al. (Oct. 12, 1989). "Binding Activities of a Repertoire of Single Immunoglobulin Variable Domains Secreted From *Escherichia coli,*" *Nature* 341(6242):544-546.
Wilson, N.S. et al. (Jan. 18, 2011). "An Fcγ Receptor-Dependent Mechanism Drives Antibody-Mediated Target-Receptor Signaling in Cancer Cells," *Cancer Cell* 19:101-113.
Winter, G. el al. (1994). "Making Antibodies by Phage Display Technology," *Ann. Rev. Inununol.* 12:433-455.
Written Opinion dated Jun. 21, 2016, for PCT Application No. PCT/US2016/026245, filed on Apr. 6, 2016, 8 pages.
Yamada, A. et al. (Jan. 2013). "Next-generation Peptide Vaccines for Advanced Cancer," *Cancer Sci.* 104(1):14-21.
Yaniv, M. (May 6, 1982). "Enhancing Elements for Activation of Eukaryotic Promoters," *Nature* 297:17-18.
Zapata, G. et al. (1995). "Engineering Linear F(ab')₂ Fragments for Efficient Production in *Escherichia coli* and Enhanced Antiproliferative Activity," *Protein Eng.* 8(10):1057-1062.

\* cited by examiner

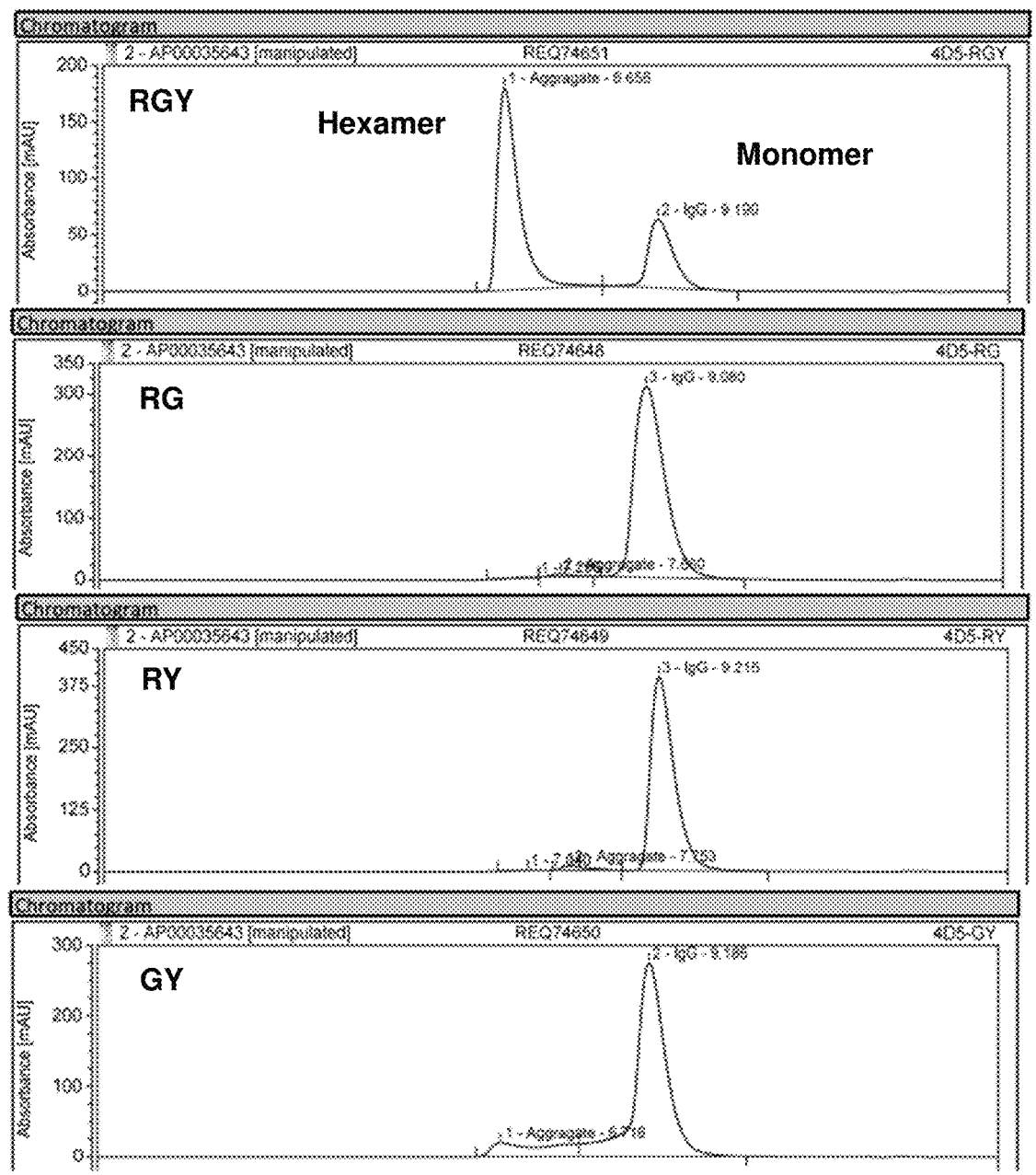
FIG. 3 (cont.'d)

SEQUENCE LISTING

<160> NUMBER OF SEQ ID NOS: 229

<210> SEQ ID NO 1
<211> LENGTH: 249
<212> TYPE: PRT
<213> ORGANISM: Homo sapien

<400> SEQUENCE: 1

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Asp Ser Tyr Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

```
<400> SEQUENCE: 3

Asp Met Tyr Pro Asp Asn Gly Asp Ser Ser Tyr Asn Gln Lys Phe Arg
1               5                   10                  15

Glu

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Ala Pro Arg Trp Tyr Phe Ser Val
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Arg Ala Ser Gln Asp Ile Ser Asn Tyr Leu Asn
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Tyr Thr Ser Arg Leu Arg Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gln Gln Gly His Thr Leu Pro Pro Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asp Ala Tyr Met Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 9

Glu Ser Tyr Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Asp Met Tyr Pro Asp Asn Ala Asp Ser Ser Tyr Asn Gln Lys Phe Arg
1               5                   10                  15
Glu

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Asp Met Tyr Pro Asp Asn Ala Asp Ala Ser Tyr Asn Gln Lys Phe Arg
1               5                   10                  15
Glu

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Asp Met Tyr Pro Asp Asn Gly Asp Ala Ser Tyr Asn Gln Lys Phe Arg
1               5                   10                  15
Glu

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Asp Met Tyr Pro Asp Ser Gly Asp Ser Ser Tyr Asn Gln Lys Phe Arg
1               5                   10                  15
Glu

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Asp Met Tyr Pro Asp Asn Gly Ser Ser Ser Tyr Asn Gln Lys Phe Arg
1               5                   10                  15
```

Glu

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Ala Pro Arg Trp Tyr Phe Ser Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Ala Pro Arg Trp Tyr Ala Ser Val
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ala Pro Arg Trp Ala Phe Ser Val
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Ala Pro Ala Trp Tyr Phe Ser Val
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Ala Pro Arg Trp Tyr Phe Ala Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Ala Pro Arg Ala Tyr Phe Ser Val
1               5

```
<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Ala Ala Arg Trp Tyr Phe Ser Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Gly His Thr Leu Pro Ala Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Gly His Thr Ala Pro Pro Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gln Gln Gly Ala Thr Leu Pro Pro Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Gln Gln Gly His Ala Leu Pro Pro Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Gln Ala His Thr Leu Pro Pro Thr
1               5
```

```
<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Gln Gln Gly His Thr Leu Ala Pro Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Gln Ala Gly His Thr Leu Pro Pro Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Asn Tyr Leu Ile Glu
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Val Ile Asn Pro Gly Ser Gly Asp Thr Tyr Tyr Ser Glu Lys Phe Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Val Ile Asn Pro Gly Ser Gly Asp Ala Tyr Tyr Ser Glu Lys Phe Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32
```

```
Val Ile Asn Pro Gly Ser Gly Asp Gln Tyr Tyr Ser Glu Lys Phe Lys
1               5                   10                  15
Gly

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Asp Arg Leu Asp Tyr
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Construct

<400> SEQUENCE: 34

Ala Arg Leu Asp Tyr
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Asp Ala Leu Asp Tyr
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Asp Arg Ala Asp Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct

<400> SEQUENCE: 37

His Ala Ser Gln Asp Ile Ser Ser Tyr Ile Val
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38
```

```
His Gly Thr Asn Leu Glu Asp
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

His Gly Thr Asn Leu Glu Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

His Gly Thr Asn Leu Glu Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

His Gly Thr Asn Leu Glu Gln
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Val His Tyr Ala Gln Phe Pro Tyr Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Ala His Tyr Ala Gln Phe Pro Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44
```

Val Ala Tyr Ala Gln Phe Pro Tyr Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Val His Ala Ala Gln Phe Pro Tyr Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Val His Tyr Ala Ala Phe Pro Tyr Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Val His Tyr Ala Gln Ala Pro Tyr Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Val His Tyr Ala Gln Phe Ala Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Val His Tyr Ala Gln Phe Pro Ala Thr
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Construct

<400> SEQUENCE: 50

Asp Tyr Gly Val Leu

```
1               5

<210> SEQ ID NO 51
<211> LENGTH: 16
<212> TYPE: PRT
<213> ORGANISM: Artificial Sequence
<220> FEATURE:
<223> OTHER INFORMATION: Synthetic Construct

<400> SEQUENCE: 51

Met Ile Trp Ser Gly Gly Thr Thr Asp Tyr Asn Ala Ala Phe Ile Ser
1               5                   10                  15

<210> SEQ ID NO 52
<211> LENGTH: 5
<212> TYPE: PRT
<213> ORGANISM: Artificial Sequence
<220> FEATURE:
<223> OTHER INFORMATION: Synthetic Construct

<400> SEQUENCE: 52

Glu Glu Met Asp Tyr
1               5

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Arg Ala Ser Gln Asp Ile Ser Asn Phe Leu Asn
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Tyr Thr Ser Arg Leu His Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Gln Gln Gly Asn Thr Leu Pro Trp Thr
1               5

<210> SEQ ID NO 56
<211> LENGTH: 117
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
 50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 58
<211> LENGTH: 117
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
 50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys 85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 60
<211> LENGTH: 117
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 61
<211> LENGTH: 107
<212> TYPE: PRT
<213> ORGANISM: Artificial Sequence
<220> FEATURE:

<223> OTHER INFORMATION: Synthetic Construct

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 62
<211> LENGTH: 117
<212> TYPE: PRT
<213> ORGANISM: Artificial Sequence
<220> FEATURE:
<223> OTHER INFORMATION: Synthetic Construct

<400> SEQUENCE: 62

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 63
<211> LENGTH: 107
<212> TYPE: PRT
<213> ORGANISM: Artificial Sequence
<220> FEATURE:
<223> OTHER INFORMATION: Synthetic Construct

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                    85                  90                  95

Thr Phe Gly Gln Gly Thr Lys Val Glu Ile Lys
                100                 105

<210> SEQ ID NO 64
<211> LENGTH: 117
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 65
<211> LENGTH: 107
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Thr Val Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 66
<211> LENGTH: 117
```

<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Val Asp Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 67
<211> LENGTH: 107
<212> TYPE: PRT
<213> ORGANISM: Artificial Sequence
<220> FEATURE:
<223> OTHER INFORMATION: Synthetic Construct

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Val Glu Ile Lys
            100                 105

<210> SEQ ID NO 68
<211> LENGTH: 117
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile

```
                    35                  40                  45

Gly Asp Met Tyr Pro Asp Asn Gly Asp Ser Ser Tyr Asn Gln Lys Phe
         50                  55                  60

Arg Glu Arg Val Thr Ile Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 69
<211> LENGTH: 107
<212> TYPE: PRT
<213> ORGANISM: Artificial Sequence
<220> FEATURE:
<223> OTHER INFORMATION: Synthetic Construct

<400> SEQUENCE: 69

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Thr Val Lys Leu Leu Ile
         35                  40                  45

Tyr Tyr Thr Ser Arg Leu Arg Ser Gly Val Pro Ser Arg Phe Ser Gly
     50                  55                  60

Ser Gly Ser Gly Lys Asp Tyr Thr Leu Thr Ile Ser Ser Leu Gln Pro
 65                  70                  75                  80

Glu Asp Phe Ala Thr Tyr Phe Cys Gln Gln Gly His Thr Leu Pro Pro
                 85                  90                  95

Thr Phe Gly Gln Gly Thr Lys Val Glu Ile Lys
            100                 105

<210> SEQ ID NO 70
<211> LENGTH: 117
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ala
             20                  25                  30

Tyr Met Ser Trp Val Arg Gln Ala Pro Gly Gln Gly Leu Glu Trp Ile
         35                  40                  45

Gly Asp Met Tyr Pro Asp Asn Gly Asp Ser Ser Tyr Asn Gln Lys Phe
         50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110
```

Val Thr Val Ser Ser
            115

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 72
<211> LENGTH: 117
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 73
<211> LENGTH: 107
<212> TYPE: PRT
<213> ORGANISM: Artificial Sequence
<220> FEATURE:
<223> OTHER INFORMATION: Synthetic Construct

<400> SEQUENCE: 73

Asp Ile Gln Met Thr Gln Ser Pro Ser Ser Leu Ser Ala Ser Val Gly

```
                1               5                  10                 15
Asp Arg Val Thr Ile Thr Cys Arg Ala Ser Gln Asp Ile Ser Asn Tyr
                20                 25                 30

Leu Asn Trp Tyr Gln Gln Lys Pro Gly Lys Ala Pro Lys Leu Leu Ile
            35                 40                 45

Tyr Tyr Thr Ser Arg Leu Arg Ser Gly Val Pro Ser Arg Phe Ser Gly
        50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Gly His Thr Leu Pro Pro
                85                 90                 95

Thr Phe Gly Gln Gly Thr Lys Val Glu Ile Lys
                100                105

<210> SEQ ID NO 74
<211> LENGTH: 117
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Asp Ser
                20                 25                 30

Tyr Met Ser Trp Val Arg Gln Ala Pro Gly Gln Gly Leu Glu Trp Ile
            35                 40                 45

Gly Asp Met Tyr Pro Asp Asn Ala Asp Ser Ser Tyr Asn Gln Lys Phe
        50                 55                 60

Arg Glu Arg Val Thr Ile Thr Arg Asp Thr Ser Thr Ser Thr Ala Tyr
65                 70                 75                 80

Leu Glu Leu Ser Ser Leu Arg Ser Glu Asp Thr Ala Val Tyr Tyr Cys
                85                 90                 95

Val Leu Ala Pro Arg Trp Tyr Phe Ser Val Trp Gly Gln Gly Thr Leu
                100                105                110

Val Thr Val Ser Ser
        115

<210> SEQ ID NO 75
<211> LENGTH: 107
<212> TYPE: PRT
<213> ORGANISM: Artificial Sequence
<220> FEATURE:
<223> OTHER INFORMATION: Synthetic Construct

<400> SEQUENCE: 75

Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Asp Ile Ser Asn Tyr
                20                 25                 30

Leu Asn Trp Tyr Gln Gln Lys Pro Gly Lys Ala Pro Lys Leu Leu Ile
            35                 40                 45

Tyr Tyr Thr Ser Arg Leu Arg Ser Gly Val Pro Ser Arg Phe Ser Gly
        50                 55                 60

Ser Gly Ser Gly Thr Asp Phe Thr Leu Thr Ile Ser Ser Leu Gln Pro
65                 70                 75                 80
```

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 76
<211> LENGTH: 117
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Ala Asp Ala Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 77
<211> LENGTH: 107
<212> TYPE: PRT
<213> ORGANISM: Artificial Sequence
<220> FEATURE:
<223> OTHER INFORMATION: Synthetic Construct

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 78
<211> LENGTH: 117
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ala Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 79
<211> LENGTH: 107
<212> TYPE: PRT
<213> ORGANISM: Artificial Sequence
<220> FEATURE:
<223> OTHER INFORMATION: Synthetic Construct

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 80
<211> LENGTH: 117
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Ser Gly Asp Ser Ser Tyr Asn Gln Lys Phe
    50                  55                  60

```
Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 81
<211> LENGTH: 107
<212> TYPE: PRT
<213> ORGANISM: Artificial Sequence
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105

<210> SEQ ID NO 82
<211> LENGTH: 117
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Ser Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 83
```

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 84
<211> LENGTH: 117
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ala
            20                  25                  30

Tyr Met Ser Trp Val Arg Gln Ala Pro Gly Gln Gly Leu Glu Trp Ile
        35                  40                  45

Gly Asp Met Tyr Pro Asp Asn Ala Asp Ala Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 85
<211> LENGTH: 107
<212> TYPE: PRT
<213> ORGANISM: Artificial Sequence
<220> FEATURE:
<223> OTHER INFORMATION: Synthetic Construct

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30
```

```
Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 86
<211> LENGTH: 117
<212> TYPE: PRT
<213> ORGANISM: Artificial Sequence
<220> FEATURE:
<223> OTHER INFORMATION: Synthetic Construct

<400> SEQUENCE: 86

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Ala
                85                  90                  95

Thr Phe Gly Gln Gly Thr Lys Val Glu Ile Lys
            100                 105
```

<210> SEQ ID NO 88
<211> LENGTH: 117
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 89
<211> LENGTH: 107
<212> TYPE: PRT
<213> ORGANISM: Artificial Sequence
<220> FEATURE:
<223> OTHER INFORMATION: Synthetic Construct

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Ala Pro Pro
                85                  90                  95

Thr Phe Gly Gln Gly Thr Lys Val Glu Ile Lys
            100                 105

<210> SEQ ID NO 90
<211> LENGTH: 117
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 91
<211> LENGTH: 107
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Pro
                85                  90                  95

Thr Phe Gly Gln Gly Thr Lys Val Glu Ile Lys
            100                 105

<210> SEQ ID NO 92
<211> LENGTH: 117
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 93
<211> LENGTH: 107
<212> TYPE: PRT
<213> ORGANISM: Artificial Sequence
<220> FEATURE:
<223> OTHER INFORMATION: Synthetic Construct

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Ala Leu Pro Pro
                85                  90                  95

Thr Phe Gly Gln Gly Thr Lys Val Glu Ile Lys
            100                 105

<210> SEQ ID NO 94
<211> LENGTH: 117
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 95
<211> LENGTH: 107
<212> TYPE: PRT
<213> ORGANISM: Artificial Sequence
<220> FEATURE:
<223> OTHER INFORMATION: Synthetic Construct

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Thr Leu Pro Pro
                85                  90                  95

Thr Phe Gly Gln Gly Thr Lys Val Glu Ile Lys
            100                 105

<210> SEQ ID NO 96
<211> LENGTH: 117
<212> TYPE: PRT
<213> ORGANISM: Artificial Sequence
<220> FEATURE:
<223> OTHER INFORMATION: Synthetic Construct

<400> SEQUENCE: 96

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 97
<211> LENGTH: 107
<212> TYPE: PRT
<213> ORGANISM: Artificial Sequence
<220> FEATURE:
<223> OTHER INFORMATION: Synthetic Construct

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Ala Pro
                85                  90                  95

Thr Phe Gly Gln Gly Thr Lys Val Glu Ile Lys
            100                 105

<210> SEQ ID NO 98
<211> LENGTH: 117
<212> TYPE: PRT
<213> ORGANISM: Artificial Sequence
<220> FEATURE:
<223> OTHER INFORMATION: Synthetic Construct

<400> SEQUENCE: 98

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 99
<211> LENGTH: 107
<212> TYPE: PRT
<213> ORGANISM: Artificial Sequence
<220> FEATURE:
<223> OTHER INFORMATION: Synthetic Construct

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly His Thr Leu Pro Pro
                85                  90                  95

Thr Phe Gly Gln Gly Thr Lys Val Glu Ile Lys
            100                 105

<210> SEQ ID NO 100
<211> LENGTH: 117
<212> TYPE: PRT

<213> ORGANISM: Artificial Sequence
<220> FEATURE:
<223> OTHER INFORMATION: Synthetic Construct

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ala Tyr
65                  70                  75                  80

Leu Glu Leu Ser Ser Leu Arg Ser Glu Asp Thr Ala Val Tyr Tyr Cys
            85                  90                  95

Val Leu Ala Pro Arg Trp Tyr Phe Ser Ala Trp Gly Gln Gly Thr Leu
            100                 105                 110

Val Thr Val Ser Ser
        115

<210> SEQ ID NO 101
<211> LENGTH: 107
<212> TYPE: PRT
<213> ORGANISM: Artificial Sequence
<220> FEATURE:
<223> OTHER INFORMATION: Synthetic Construct

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
            85                  90                  95

Thr Phe Gly Gln Gly Thr Lys Val Glu Ile Lys
            100                 105

<210> SEQ ID NO 102
<211> LENGTH: 117
<212> TYPE: PRT
<213> ORGANISM: Artificial Sequence
<220> FEATURE:
<223> OTHER INFORMATION: Synthetic Construct

<400> SEQUENCE: 102

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
            50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Ala Ser Val Trp Gly Gln Gly Thr Leu
                100                 105                 110

Val Thr Val Ser Ser
            115

<210> SEQ ID NO 103
<211> LENGTH: 107
<212> TYPE: PRT
<213> ORGANISM: Artificial Sequence
<220> FEATURE:
<223> OTHER INFORMATION: Synthetic Construct

<400> SEQUENCE: 103

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Arg Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105

<210> SEQ ID NO 104
<211> LENGTH: 117
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Ser
                 20                  25                  30

Tyr Met Ser Trp Val Arg Gln Ala Pro Gly Gln Gly Leu Glu Trp Ile
             35                  40                  45

Gly Asp Met Tyr Pro Asp Asn Gly Asp Ser Ser Tyr Asn Gln Lys Phe
         50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Ala Phe Ser Val Trp Gly Gln Gly Thr Leu
                100                 105                 110

Val Thr Val Ser Ser

```
<210> SEQ ID NO 105
<211> LENGTH: 107
<212> TYPE: PRT
<213> ORGANISM: Artificial Sequence
<220> FEATURE:
<223> OTHER INFORMATION: Synthetic Construct

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 106
<211> LENGTH: 117
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Ala Trp Tyr Phe Ser Val Trp Gly Gln Gly Thr Leu
            100                 105                 110

Val Thr Val Ser Ser
        115

<210> SEQ ID NO 107
<211> LENGTH: 107
<212> TYPE: PRT
<213> ORGANISM: Artificial Sequence
<220> FEATURE:
<223> OTHER INFORMATION: Synthetic Construct

<400> SEQUENCE: 107

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 108
<211> LENGTH: 117
<212> TYPE: PRT
<213> ORGANISM: Artificial Sequence
<220> FEATURE:
<223> OTHER INFORMATION: Synthetic Construct

<400> SEQUENCE: 108

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ala Val Trp Gly Gln Gly Thr Leu
            100                 105                 110

Val Thr Val Ser Ser
        115

<210> SEQ ID NO 109
<211> LENGTH: 107
<212> TYPE: PRT
<213> ORGANISM: Artificial Sequence
<220> FEATURE:
<223> OTHER INFORMATION: Synthetic Construct

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro

```
                    85                  90                  95

Thr Phe Gly Gln Gly Thr Lys Val Glu Ile Lys
                100                 105

<210> SEQ ID NO 110
<211> LENGTH: 117
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Ala Tyr Phe Ser Val Trp Gly Gln Gly Thr Leu
                100                 105                 110

Val Thr Val Ser Ser
            115

<210> SEQ ID NO 111
<211> LENGTH: 107
<212> TYPE: PRT
<213> ORGANISM: Artificial Sequence
<220> FEATURE:
<223> OTHER INFORMATION: Synthetic Construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 112
<211> LENGTH: 117
<212> TYPE: PRT
<213> ORGANISM: Artificial Sequence
<220> FEATURE:
<223> OTHER INFORMATION: Synthetic Construct

<400> SEQUENCE: 112
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Ala Arg Trp Tyr Phe Ser Val Trp Gly Gln Gly Thr Leu
            100                 105                 110

Val Thr Val Ser Ser
            115

<210> SEQ ID NO 113
<211> LENGTH: 107
<212> TYPE: PRT
<213> ORGANISM: Artificial Sequence
<220> FEATURE:
<223> OTHER INFORMATION: Synthetic Construct

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 114
<211> LENGTH: 117
<212> TYPE: PRT
<213> ORGANISM: Artificial Sequence
<220> FEATURE:
<223> OTHER INFORMATION: Synthetic Construct

<400> SEQUENCE: 114

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr

```
                        65                  70                  75                  80
Leu Glu Leu Ser Ser Leu Arg Ser Glu Asp Thr Ala Val Tyr Tyr Cys
                    85                  90                  95

Ala Leu Ala Pro Arg Trp Tyr Phe Ser Val Trp Gly Gln Gly Thr Leu
                100                 105                 110

Val Thr Val Ser Ser
            115

<210> SEQ ID NO 115
<211> LENGTH: 107
<212> TYPE: PRT
<213> ORGANISM: Artificial Sequence
<220> FEATURE:
<223> OTHER INFORMATION: Synthetic Construct

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 116
<211> LENGTH: 117
<212> TYPE: PRT
<213> ORGANISM: Artificial Sequence
<220> FEATURE:
<223> OTHER INFORMATION: Synthetic Construct

<400> SEQUENCE: 116

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Ala Ala Pro Arg Trp Tyr Phe Ser Val Trp Gly Gln Gly Thr Leu
                100                 105                 110

Val Thr Val Ser Ser
            115

<210> SEQ ID NO 117
<211> LENGTH: 107
```

```
<212> TYPE: PRT
<213> ORGANISM: Artificial Sequence
<220> FEATURE:
<223> OTHER INFORMATION: Synthetic Construct

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 118
<211> LENGTH: 114
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 119
<211> LENGTH: 107
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45
```

```
Tyr His Gly Thr Asn Leu Glu Asp Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
                100                 105

<210> SEQ ID NO 120
<211> LENGTH: 114
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                 20                  25                  30

Leu Ile Glu Trp Val Arg Gln Ala Pro Gly Gln Gly Leu Glu Trp Ile
             35                  40                  45

Gly Val Ile Asn Pro Gly Ser Gly Asp Thr Tyr Tyr Ser Glu Lys Phe
         50                  55                  60

Lys Gly Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
                100                 105                 110

Ser Ser

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                 20                  25                  30

Ile Val Trp Tyr Gln Gln Lys Pro Gly Lys Ala Pro Lys Leu Leu Ile
             35                  40                  45

Tyr His Gly Thr Asn Leu Glu Asp Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
                100                 105

<210> SEQ ID NO 122
```

```
<211> LENGTH: 114
<212> TYPE: PRT
<213> ORGANISM: Artificial Sequence
<220> FEATURE:
<223> OTHER INFORMATION: Synthetic Construct

<400> SEQUENCE: 122
```

| Glu | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Ala | Phe | Thr | Asn | Tyr |
|---|---|---|---|---|---|---|---|---|---|---|---|---|---|---|---|
| | | | 20 | | | | | 25 | | | | | 30 | | |

| Leu | Ile | Glu | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | | 35 | | | | | 40 | | | | | 45 | | |

| Gly | Val | Ile | Asn | Pro | Gly | Ser | Gly | Asp | Thr | Tyr | Tyr | Ser | Glu | Lys | Phe |
|---|---|---|---|---|---|---|---|---|---|---|---|---|---|---|---|
| | 50 | | | | | 55 | | | | | 60 | | | | |

| Lys | Gly | Arg | Val | Thr | Leu | Thr | Ala | Asp | Thr | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Leu | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Arg | Leu | Asp | Tyr | Trp | Gly | Gln | Gly | Thr | Leu | Val | Thr | Val |
|---|---|---|---|---|---|---|---|---|---|---|---|---|---|---|---|
| | | | 100 | | | | | 105 | | | | | 110 | | |

Ser Ser

```
<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123
```

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | His | Ala | Ser | Gln | Asp | Ile | Ser | Ser | Tyr |
|---|---|---|---|---|---|---|---|---|---|---|---|---|---|---|---|
| | | | 20 | | | | | 25 | | | | | 30 | | |

| Ile | Val | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | | 35 | | | | | 40 | | | | | 45 | | |

| Tyr | His | Gly | Thr | Asn | Leu | Glu | Asp | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Val | His | Tyr | Ala | Gln | Phe | Pro | Tyr |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Val | Glu | Ile | Lys |
|---|---|---|---|---|---|---|---|---|---|---|
| | | | 100 | | | | | 105 | | |

```
<210> SEQ ID NO 124
<211> LENGTH: 114
<212> TYPE: PRT
<213> ORGANISM: Artificial Sequence
<220> FEATURE:
<223> OTHER INFORMATION: Synthetic Construct

<400> SEQUENCE: 124
```

| Glu | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Ala | Phe | Thr | Asn | Tyr |
|---|---|---|---|---|---|---|---|---|---|---|---|---|---|---|---|
| | | | 20 | | | | | 25 | | | | | 30 | | |

| Leu | Ile | Glu | Trp | Val | Arg | Gln | Ala | Pro | Gly | Gln | Gly | Leu | Glu | Trp | Ile |
|---|---|---|---|---|---|---|---|---|---|---|---|---|---|---|---|

```
                35                  40                  45
Gly Val Ile Asn Pro Gly Ser Gly Asp Thr Tyr Tyr Ser Glu Lys Phe
 50                  55                  60
Lys Gly Arg Val Thr Ile Thr Ala Asp Thr Ser Thr Ser Thr Ala Tyr
 65                  70                  75                  80
Leu Glu Leu Ser Ser Leu Arg Ser Glu Asp Thr Ala Val Tyr Tyr Cys
                 85                  90                  95
Ala Arg Asp Arg Leu Asp Tyr Trp Gly Gln Gly Thr Leu Val Thr Val
                100                 105                 110
Ser Ser

<210> SEQ ID NO 125
<211> LENGTH: 107
<212> TYPE: PRT
<213> ORGANISM: Artificial Sequence
<220> FEATURE:
<223> OTHER INFORMATION: Synthetic Construct

<400> SEQUENCE: 125

Asp Ile Gln Met Thr Gln Ser Pro Ser Ser Leu Ser Ala Ser Val Gly
  1               5                  10                  15
Asp Arg Val Thr Ile Thr Cys His Ala Ser Gln Asp Ile Ser Ser Tyr
                 20                  25                  30
Ile Val Trp Tyr Gln Lys Pro Gly Lys Ser Phe Lys Gly Leu Ile
             35                  40                  45
Tyr His Gly Thr Asn Leu Glu Asp Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Val His Tyr Ala Gln Phe Pro Tyr
                 85                  90                  95
Thr Phe Gly Gln Gly Thr Lys Val Glu Ile Lys
                100                 105

<210> SEQ ID NO 126
<211> LENGTH: 114
<212> TYPE: PRT
<213> ORGANISM: Artificial Sequence
<220> FEATURE:
<223> OTHER INFORMATION: Synthetic Construct

<400> SEQUENCE: 126

Glu Val Gln Leu Val Gln Ser Gly Ala Glu Val Lys Lys Pro Gly Ala
  1               5                  10                  15
Ser Val Lys Val Ser Cys Lys Ala Ser Gly Tyr Ala Phe Thr Asn Tyr
                 20                  25                  30
Leu Ile Glu Trp Val Arg Gln Ala Pro Gly Gln Gly Leu Glu Trp Ile
             35                  40                  45
Gly Val Ile Asn Pro Gly Ser Gly Asp Thr Tyr Tyr Ser Glu Lys Phe
         50                  55                  60
Lys Gly Arg Val Thr Leu Thr Ala Asp Thr Ser Thr Ser Thr Ala Tyr
 65                  70                  75                  80
Leu Glu Leu Ser Ser Leu Arg Ser Glu Asp Thr Ala Val Tyr Tyr Cys
                 85                  90                  95
Ala Arg Asp Arg Leu Asp Tyr Trp Gly Gln Gly Thr Leu Val Thr Val
                100                 105                 110
Ser Ser
```

```
<210> SEQ ID NO 127
<211> LENGTH: 107
<212> TYPE: PRT
<213> ORGANISM: Artificial Sequence
<220> FEATURE:
<223> OTHER INFORMATION: Synthetic Construct

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 128
<211> LENGTH: 114
<212> TYPE: PRT
<213> ORGANISM: Artificial Sequence
<220> FEATURE:
<223> OTHER INFORMATION: Synthetic Construct

<400> SEQUENCE: 128

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 129
<211> LENGTH: 107
<212> TYPE: PRT
<213> ORGANISM: Artificial Sequence
<220> FEATURE:
<223> OTHER INFORMATION: Synthetic Construct

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
```

```
                20                  25                  30
Ile Val Trp Tyr Gln Gln Lys Pro Gly Lys Ser Phe Lys Gly Leu Ile
            35                  40                  45

Tyr His Gly Thr Asn Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 130
<211> LENGTH: 114
<212> TYPE: PRT
<213> ORGANISM: Artificial Sequence
<220> FEATURE:
<223> OTHER INFORMATION: Synthetic Construct

<400> SEQUENCE: 130

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 131
<211> LENGTH: 107
<212> TYPE: PRT
<213> ORGANISM: Artificial Sequence
<220> FEATURE:
<223> OTHER INFORMATION: Synthetic Construct

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
```

<210> SEQ ID NO 132
<211> LENGTH: 114
<212> TYPE: PRT
<213> ORGANISM: Artificial Sequence
<220> FEATURE:
<223> OTHER INFORMATION: Synthetic Construct

<400> SEQUENCE: 132

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 133
<211> LENGTH: 107
<212> TYPE: PRT
<213> ORGANISM: Artificial Sequence
<220> FEATURE:
<223> OTHER INFORMATION: Synthetic Construct

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 134
<211> LENGTH: 114
<212> TYPE: PRT
<213> ORGANISM: Artificial Sequence
<220> FEATURE:
<223> OTHER INFORMATION: Synthetic Construct

<400> SEQUENCE: 134

Glu Val Gln Leu Val Gln Ser Gly Ala Glu Val Lys Lys Pro Gly Ala
1               5                   10                  15

```
Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 135
<211> LENGTH: 107
<212> TYPE: PRT
<213> ORGANISM: Artificial Sequence
<220> FEATURE:
<223> OTHER INFORMATION: Synthetic Construct

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 136
<211> LENGTH: 114
<212> TYPE: PRT
<213> ORGANISM: Artificial Sequence
<220> FEATURE:
<223> OTHER INFORMATION: Synthetic Construct

<400> SEQUENCE: 136

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

Ala Arg Asp Arg Leu Asp Tyr Trp Gly Gln Gly Thr Leu Val Thr Val
            100                 105                 110

Ser Ser

<210> SEQ ID NO 137
<211> LENGTH: 107
<212> TYPE: PRT
<213> ORGANISM: Artificial Sequence
<220> FEATURE:
<223> OTHER INFORMATION: Synthetic Construct

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 138
<211> LENGTH: 114
<212> TYPE: PRT
<213> ORGANISM: Artificial Sequence
<220> FEATURE:
<223> OTHER INFORMATION: Synthetic Construct

<400> SEQUENCE: 138

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 139
<211> LENGTH: 107
<212> TYPE: PRT
<213> ORGANISM: Artificial Sequence
<220> FEATURE:
<223> OTHER INFORMATION: Synthetic Construct

<400> SEQUENCE: 139

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105
```

<210> SEQ ID NO 140
<211> LENGTH: 114
<212> TYPE: PRT
<213> ORGANISM: Artificial Sequence
<220> FEATURE:
<223> OTHER INFORMATION: Synthetic Construct

<400> SEQUENCE: 140

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser
```

<210> SEQ ID NO 141
<211> LENGTH: 107
<212> TYPE: PRT
<213> ORGANISM: Artificial Sequence
<220> FEATURE:
<223> OTHER INFORMATION: Synthetic Construct

<400> SEQUENCE: 141

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Pro Lys Leu Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 142
<211> LENGTH: 114
<212> TYPE: PRT
<213> ORGANISM: Artificial Sequence
<220> FEATURE:
<223> OTHER INFORMATION: Synthetic Construct

<400> SEQUENCE: 142

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 143
<211> LENGTH: 107
<212> TYPE: PRT
<213> ORGANISM: Artificial Sequence
<220> FEATURE:
<223> OTHER INFORMATION: Synthetic Construct

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 144
<211> LENGTH: 114
<212> TYPE: PRT
<213> ORGANISM: Artificial Sequence
<220> FEATURE:
<223> OTHER INFORMATION: Synthetic Construct

<400> SEQUENCE: 144
```

Glu Val Gln Leu Val Gln Ser Gly Ala Glu Val Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 145
<211> LENGTH: 107
<212> TYPE: PRT
<213> ORGANISM: Artificial Sequence
<220> FEATURE:
<223> OTHER INFORMATION: Synthetic Construct

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 146
<211> LENGTH: 114
<212> TYPE: PRT
<213> ORGANISM: Artificial Sequence
<220> FEATURE:
<223> OTHER INFORMATION: Synthetic Construct

<400> SEQUENCE: 146

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

```
Leu Glu Leu Ser Ser Leu Arg Ser Glu Asp Thr Ala Val Tyr Tyr Cys
            85                  90                  95

Ala Arg Asp Arg Leu Asp Tyr Trp Gly Gln Gly Thr Leu Val Thr Val
        100                 105                 110

Ser Ser

<210> SEQ ID NO 147
<211> LENGTH: 107
<212> TYPE: PRT
<213> ORGANISM: Artificial Sequence
<220> FEATURE:
<223> OTHER INFORMATION: Synthetic Construct

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala His Tyr Ala Gln Phe Pro Tyr
                85                  90                  95

Thr Phe Gly Gln Gly Thr Lys Val Glu Ile Lys
            100                 105

<210> SEQ ID NO 148
<211> LENGTH: 114
<212> TYPE: PRT
<213> ORGANISM: Artificial Sequence
<220> FEATURE:
<223> OTHER INFORMATION: Synthetic Construct

<400> SEQUENCE: 148

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 149
<211> LENGTH: 107
<212> TYPE: PRT
<213> ORGANISM: Artificial Sequence
<220> FEATURE:
```

<223> OTHER INFORMATION: Synthetic Construct

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Ala Tyr Ala Gln Phe Pro Tyr
                85                  90                  95

Thr Phe Gly Gln Gly Thr Lys Val Glu Ile Lys
            100                 105

<210> SEQ ID NO 150
<211> LENGTH: 114
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Ala Ala Gln Phe Pro Tyr
                 85                  90                  95

Thr Phe Gly Gln Gly Thr Lys Val Glu Ile Lys
            100                 105

<210> SEQ ID NO 152
<211> LENGTH: 114
<212> TYPE: PRT
<213> ORGANISM: Artificial Sequence
<220> FEATURE:
<223> OTHER INFORMATION: Synthetic Construct

<400> SEQUENCE: 152

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
     50                  55                  60

Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
            100                 105                 110

Ser Ser

<210> SEQ ID NO 153
<211> LENGTH: 107
<212> TYPE: PRT
<213> ORGANISM: Artificial Sequence
<220> FEATURE:
<223> OTHER INFORMATION: Synthetic Construct

<400> SEQUENCE: 153

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Ala Phe Pro Tyr
                 85                  90                  95

Thr Phe Gly Gln Gly Thr Lys Val Glu Ile Lys
            100                 105

<210> SEQ ID NO 154
<211> LENGTH: 114
<212> TYPE: PRT
<213> ORGANISM: Artificial Sequence
```

```
<220> FEATURE:
<223> OTHER INFORMATION: Synthetic Construct

<400> SEQUENCE: 154

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 155
<211> LENGTH: 107
<212> TYPE: PRT
<213> ORGANISM: Artificial Sequence
<220> FEATURE:
<223> OTHER INFORMATION: Synthetic Construct

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Ala Pro Tyr
                85                  90                  95

Thr Phe Gly Gln Gly Thr Lys Val Glu Ile Lys
            100                 105

<210> SEQ ID NO 156
<211> LENGTH: 114
<212> TYPE: PRT
<213> ORGANISM: Artificial Sequence
<220> FEATURE:
<223> OTHER INFORMATION: Synthetic Construct

<400> SEQUENCE: 156

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
```

```
                        50                  55                  60
Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
            100                 105                 110

Ser Ser

<210> SEQ ID NO 157
<211> LENGTH: 107
<212> TYPE: PRT
<213> ORGANISM: Artificial Sequence
<220> FEATURE:
<223> OTHER INFORMATION: Synthetic Construct

<400> SEQUENCE: 157

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
             20                  25                  30

Ile Val Trp Tyr Gln Gln Lys Pro Gly Lys Ser Phe Lys Gly Leu Ile
         35                  40                  45

Tyr His Gly Thr Asn Leu Glu Asp Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Ala Tyr
                 85                  90                  95

Thr Phe Gly Gln Gly Thr Lys Val Glu Ile Lys
            100                 105

<210> SEQ ID NO 158
<211> LENGTH: 114
<212> TYPE: PRT
<213> ORGANISM: Artificial Sequence
<220> FEATURE:
<223> OTHER INFORMATION: Synthetic Construct

<400> SEQUENCE: 158

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
             20                  25                  30

Leu Ile Glu Trp Val Arg Gln Ala Pro Gly Gln Gly Leu Glu Trp Ile
         35                  40                  45

Gly Val Ile Asn Pro Gly Ser Gly Asp Thr Tyr Tyr Ser Glu Lys Phe
     50                  55                  60

Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
            100                 105                 110

Ser Ser

<210> SEQ ID NO 159
```

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Ala
                85                  90                  95

Thr Phe Gly Gln Gly Thr Lys Val Glu Ile Lys
            100                 105

<210> SEQ ID NO 160
<211> LENGTH: 114
<212> TYPE: PRT
<213> ORGANISM: Artificial Sequence
<220> FEATURE:
<223> OTHER INFORMATION: Synthetic Construct

<400> SEQUENCE: 160

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ala Arg Leu Asp Tyr Trp Gly Gln Gly Thr Leu Val Thr Val
            100                 105                 110

Ser Ser

<210> SEQ ID NO 161
<211> LENGTH: 107
<212> TYPE: PRT
<213> ORGANISM: Artificial Sequence
<220> FEATURE:
<223> OTHER INFORMATION: Synthetic Construct

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
```

```
                35                  40                  45
Tyr His Gly Thr Asn Leu Glu Asp Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
            100                 105

<210> SEQ ID NO 162
<211> LENGTH: 114
<212> TYPE: PRT
<213> ORGANISM: Artificial Sequence
<220> FEATURE:
<223> OTHER INFORMATION: Synthetic Construct

<400> SEQUENCE: 162

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                 20                  25                  30

Leu Ile Glu Trp Val Arg Gln Ala Pro Gly Gln Gly Leu Glu Trp Ile
             35                  40                  45

Gly Val Ile Asn Pro Gly Ser Gly Asp Thr Tyr Tyr Ser Glu Lys Phe
         50                  55                  60

Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Ala Leu Asp Tyr Trp Gly Gln Gly Thr Leu Val Thr Val
                100                 105                 110

Ser Ser

<210> SEQ ID NO 163
<211> LENGTH: 107
<212> TYPE: PRT
<213> ORGANISM: Artificial Sequence
<220> FEATURE:
<223> OTHER INFORMATION: Synthetic Construct

<400> SEQUENCE: 163

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                 20                  25                  30

Ile Val Trp Tyr Gln Gln Lys Pro Gly Lys Ser Phe Lys Gly Leu Ile
             35                  40                  45

Tyr His Gly Thr Asn Leu Glu Asp Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
            100                 105
```

```
<210> SEQ ID NO 164
<211> LENGTH: 114
<212> TYPE: PRT
<213> ORGANISM: Artificial Sequence
<220> FEATURE:
<223> OTHER INFORMATION: Synthetic Construct

<400> SEQUENCE: 164
```

Glu Val Gln Leu Val Gln Ser Gly Ala Glu Val Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Ala Asp Tyr Trp Gly Gln Gly Thr Leu Val Thr Val
            100                 105                 110

Ser Ser

```
<210> SEQ ID NO 165
<211> LENGTH: 107
<212> TYPE: PRT
<213> ORGANISM: Artificial Sequence
<220> FEATURE:
<223> OTHER INFORMATION: Synthetic Construct

<400> SEQUENCE: 165
```

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

```
<210> SEQ ID NO 166
<211> LENGTH: 113
<212> TYPE: PRT
<213> ORGANISM: Artificial Sequence
<220> FEATURE:
<223> OTHER INFORMATION: Synthetic Construct

<400> SEQUENCE: 166
```

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

```
Gly Val Leu Trp Ile Arg Gln Pro Gly Lys Gly Leu Glu Trp Ile
            35                  40                  45

Gly Met Ile Trp Ser Gly Gly Thr Thr Asp Tyr Asn Ala Ala Phe Ile
 50                      55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Val
                 85                  90                  95

Arg Glu Glu Met Asp Tyr Trp Gly Gln Gly Thr Leu Val Thr Val Ser
            100                 105                 110

Ser
```

<210> SEQ ID NO 167
<211> LENGTH: 107
<212> TYPE: PRT
<213> ORGANISM: Artificial Sequence
<220> FEATURE:
<223> OTHER INFORMATION: Synthetic Construct

<400> SEQUENCE: 167

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Val Glu Ile Lys
            100                 105
```

<210> SEQ ID NO 168
<211> LENGTH: 113
<212> TYPE: PRT
<213> ORGANISM: Artificial Sequence
<220> FEATURE:
<223> OTHER INFORMATION: Synthetic Construct

<400> SEQUENCE: 168

```
Glu Val Gln Leu Val Glu Ser Gly Pro Gly Leu Val Lys Pro Ser Glu
 1               5                  10                  15

Thr Leu Ser Leu Thr Cys Thr Val Ser Gly Phe Ser Leu Thr Asp Tyr
            20                  25                  30

Gly Val Leu Trp Ile Arg Gln Pro Pro Gly Lys Gly Leu Glu Trp Ile
        35                  40                  45

Gly Met Ile Trp Ser Gly Gly Thr Thr Asp Tyr Asn Ala Ala Phe Ile
 50                  55                  60

Ser Arg Val Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Tyr Cys Val
                 85                  90                  95

Arg Glu Glu Met Asp Tyr Trp Gly Gln Gly Thr Leu Val Thr Val Ser
            100                 105                 110
```

Ser

<210> SEQ ID NO 169
<211> LENGTH: 107
<212> TYPE: PRT
<213> ORGANISM: Artificial Sequence
<220> FEATURE:
<223> OTHER INFORMATION: Synthetic Construct

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 170
<211> LENGTH: 113
<212> TYPE: PRT
<213> ORGANISM: Artificial Sequence
<220> FEATURE:
<223> OTHER INFORMATION: Synthetic Construct

<400> SEQUENCE: 170

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Leu Trp Val Arg Gln Pro Pro Gly Lys Gly Leu Glu Trp Leu
        35                  40                  45

Gly Met Ile Trp Ser Gly Gly Thr Thr Asp Tyr Asn Ala Ala Phe Ile
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Val
                85                  90                  95

Arg Glu Glu Met Asp Tyr Trp Gly Gln Gly Thr Leu Val Thr Val Ser
            100                 105                 110

Ser

<210> SEQ ID NO 171
<211> LENGTH: 107
<212> TYPE: PRT
<213> ORGANISM: Artificial Sequence
<220> FEATURE:
<223> OTHER INFORMATION: Synthetic Construct

<400> SEQUENCE: 171

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Ser Asn Phe
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Val Glu Ile Lys
             100                 105
```

<210> SEQ ID NO 172
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2
<223> OTHER INFORMATION: Xaa = Ser or Ala

<400> SEQUENCE: 172

```
Xaa Xaa Tyr Met Ser
1               5
```

<210> SEQ ID NO 173
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asn or Ser
<220> FEATURE:
<221> NAME/KEY: VARIANT
<222> LOCATION: 7
<223> OTHER INFORMATION: Xaa = Ala or Gly
<220> FEATURE:
<221> NAME/KEY: VARIANT
<222> LOCATION: 8
<223> OTHER INFORMATION: Xaa = Asp or Ser
<220> FEATURE:
<221> NAME/KEY: VARIANT
<222> LOCATION: 9
<223> OTHER INFORMATION: Xaa = Ala or Ser

<400> SEQUENCE: 173

```
Asp Met Tyr Pro Asp Xaa Xaa Xaa Xaa Ser Tyr Asn Gln Lys Phe Arg
1               5                   10                  15

Glu
```

<210> SEQ ID NO 174
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT

```
<222> LOCATION: 5
<223> OTHER INFORMATION: Xaa = Tyr or Ala
<220> FEATURE:
<221> NAME/KEY: VARIANT
<222> LOCATION: 6
<223> OTHER INFORMATION: Xaa = Ala or Phe
<220> FEATURE:
<221> NAME/KEY: VARIANT
<222> LOCATION: 7
<223> OTHER INFORMATION: Xaa = Ser or Ala
<220> FEATURE:
<221> NAME/KEY: VARIANT
<222> LOCATION: 8
<223> OTHER INFORMATION: Xaa = Ala or Val

<400> SEQUENCE: 174

Ala Pro Arg Trp Xaa Xaa Xaa Xaa
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala or Gln
<220> FEATURE:
<221> NAME/KEY: VARIANT
<222> LOCATION: 3
<223> OTHER INFORMATION: Xaa = Ala or Gly
<220> FEATURE:
<221> NAME/KEY: VARIANT
<222> LOCATION: 4
<223> OTHER INFORMATION: Xaa = Ala or His
<220> FEATURE:
<221> NAME/KEY: VARIANT
<222> LOCATION: 5
<223> OTHER INFORMATION: Xaa = Ala or Thr
<220> FEATURE:
<221> NAME/KEY: VARIANT
<222> LOCATION: 6
<223> OTHER INFORMATION: Xaa = Ala or Leu
<220> FEATURE:
<221> NAME/KEY: VARIANT
<222> LOCATION: 7
<223> OTHER INFORMATION: Xaa = Ala or Pro
<220> FEATURE:
<221> NAME/KEY: VARIANT
<222> LOCATION: 8
<223> OTHER INFORMATION: Xaa = Ala or Pro

<400> SEQUENCE: 175

Gln Xaa Xaa Xaa Xaa Xaa Xaa Xaa Thr
1               5

<210> SEQ ID NO 176
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = Thr, Ala or Gln

<400> SEQUENCE: 176

Val Ile Asn Pro Gly Ser Gly Asp Xaa Tyr Tyr Ser Glu Lys Phe Lys
1               5                   10                  15

Gly
```

```
<210> SEQ ID NO 177
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Ser, Glu, or Gln

<400> SEQUENCE: 177

His Gly Thr Asn Leu Glu Xaa
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Val or Ala
<220> FEATURE:
<221> NAME/KEY: VARIANT
<222> LOCATION: 2
<223> OTHER INFORMATION: Xaa = His or Ala
<220> FEATURE:
<221> NAME/KEY: VARIANT
<222> LOCATION: 9
<223> OTHER INFORMATION: Xaa = Tyr or Ala

<400> SEQUENCE: 178

Xaa Xaa Tyr Ala Gln Phe Pro Tyr Xaa
1               5

<210> SEQ ID NO 179
<211> LENGTH: 107
<212> TYPE: PRT
<213> ORGANISM: Artificial Sequence
<220> FEATURE:
<223> OTHER INFORMATION: Synthetic Construct

<400> SEQUENCE: 179

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Lys Asp Tyr Phe Leu Thr Ile Ser Asn Leu Glu Gln
65                  70                  75                  80

Glu Asp Val Ala Ala Tyr Phe Cys Gln Gln Gly His Thr Leu Pro Pro
                85                  90                  95

Thr Phe Gly Gly Gly Thr Lys Leu Glu Ile Lys
            100                 105

<210> SEQ ID NO 180
<211> LENGTH: 117
<212> TYPE: PRT
<213> ORGANISM: Artificial Sequence
```

```
<220> FEATURE:
<223> OTHER INFORMATION: Synthetic Construct

<400> SEQUENCE: 180

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
            20                  25                  30

Tyr Met Ser Trp Val Lys Gln Ser His Gly Lys Thr Leu Glu Trp Ile
        35                  40                  45

Gly Asp Met Tyr Pro Asp Asn Gly Asp Ser Ser Tyr Asn Gln Lys Phe
    50                  55                  60

Arg Glu Lys Val Thr Leu Thr Val Asp Lys Ser Ser Thr Thr Ala Tyr
65                  70                  75                  80

Met Glu Phe Arg Ser Leu Thr Ser Glu Asp Ser Ala Val Tyr Tyr Cys
                85                  90                  95

Val Leu Ala Pro Arg Trp Tyr Phe Ser Val Trp Gly Thr Gly Thr Thr
            100                 105                 110

Val Thr Val Ser Ser
            115

<210> SEQ ID NO 181
<211> LENGTH: 107
<212> TYPE: PRT
<213> ORGANISM: Artificial Sequence
<220> FEATURE:
<223> OTHER INFORMATION: Synthetic Construct

<400> SEQUENCE: 181

Asp Ile Leu Met Thr Gln Ser Pro Ser Ser Met Ser Val Ser Leu Gly
1               5                   10                  15

Asp Thr Val Ser Ile Thr Cys His Ala Ser Gln Asp Ile Ser Ser Tyr
            20                  25                  30

Ile Val Trp Leu Gln Gln Lys Pro Gly Lys Ser Phe Arg Gly Leu Ile
        35                  40                  45

Tyr His Gly Thr Asn Leu Glu Asp Gly Ile Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val His Tyr Ala Gln Phe Pro Tyr
                85                  90                  95

Thr Phe Gly Gly Gly Thr Lys Leu Glu Ile Lys
            100                 105

<210> SEQ ID NO 182
<211> LENGTH: 114
<212> TYPE: PRT
<213> ORGANISM: Artificial Sequence
<220> FEATURE:
<223> OTHER INFORMATION: Synthetic Construct

<400> SEQUENCE: 182

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45
```

Gly Val Ile Asn Pro Gly Ser Gly Asp Thr Tyr Tyr Ser Glu Lys Phe
            50                  55                  60

Lys Gly Lys Val Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                    85                  90                  95

Ala Arg Asp Arg Leu Asp Tyr Trp Gly Gln Gly Thr Thr Leu Thr Val
                100                 105                 110

Ser Ser

<210> SEQ ID NO 183
<211> LENGTH: 117
<212> TYPE: PRT
<213> ORGANISM: Artificial Sequence
<220> FEATURE:
<223> OTHER INFORMATION: Synthetic Construct

<400> SEQUENCE: 183

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 184
<211> LENGTH: 117
<212> TYPE: PRT
<213> ORGANISM: Artificial Sequence
<220> FEATURE:
<223> OTHER INFORMATION: Synthetic Construct

<400> SEQUENCE: 184

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Leu Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
          115

<210> SEQ ID NO 185
<211> LENGTH: 451
<212> TYPE: PRT
<213> ORGANISM: Artificial Sequence
<220> FEATURE:
<223> OTHER INFORMATION: Synthetic Construct

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 186
<211> LENGTH: 393
<212> TYPE: PRT
<213> ORGANISM: Artificial Sequence
<220> FEATURE:
<223> OTHER INFORMATION: Synthetic Construct

<400> SEQUENCE: 186

Asp Ile Gln Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ile
                165                 170                 175

Val Met Thr Gln Ser Pro Asp Ser Leu Pro Val Thr Pro Gly Glu Pro
            180                 185                 190

Ala Ser Ile Ser Cys Arg Ser Ser Gln Ser Leu Leu His Ser Asn Gly
        195                 200                 205

Tyr Asn Tyr Leu Asp Trp Tyr Leu Gln Lys Ala Gly Gln Ser Pro Gln
    210                 215                 220

Leu Leu Ile Tyr Leu Gly Ser Asn Arg Ala Ser Gly Val Pro Asp Arg
225                 230                 235                 240

Phe Ser Gly Ser Gly Ser Gly Thr Asp Phe Thr Leu Lys Ile Ser Arg
                245                 250                 255
```

Val Glu Ala Glu Asp Val Gly Val Tyr Tyr Cys Gln Gln Tyr Tyr Asn
            260                 265                 270

His Pro Thr Thr Phe Gly Gln Gly Thr Lys Leu Glu Ile Lys Arg Thr
        275                 280                 285

Val Ala Ala Pro Ser Val Phe Ile Phe Pro Pro Ser Asp Glu Gln Leu
    290                 295                 300

Lys Ser Gly Thr Ala Ser Val Val Cys Leu Leu Asn Asn Phe Tyr Pro
305                 310                 315                 320

Arg Glu Ala Lys Val Gln Trp Lys Val Asp Asn Ala Leu Gln Ser Gly
                325                 330                 335

Asn Ser Gln Glu Ser Val Thr Glu Gln Asp Ser Lys Asp Ser Thr Tyr
            340                 345                 350

Ser Leu Ser Ser Thr Leu Thr Leu Ser Lys Ala Asp Tyr Glu Lys His
        355                 360                 365

Lys Val Tyr Ala Cys Glu Val Thr His Gln Gly Leu Ser Ser Pro Val
370                 375                 380

Thr Lys Ser Phe Asn Arg Gly Glu Cys
385                 390

<210> SEQ ID NO 187
<211> LENGTH: 219
<212> TYPE: PRT
<213> ORGANISM: Artificial Sequence
<220> FEATURE:
<223> OTHER INFORMATION: Synthetic Construct

<400> SEQUENCE: 187

Asp Ile Gln Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 188
<211> LENGTH: 450
<212> TYPE: PRT
<213> ORGANISM: Artificial Sequence
<220> FEATURE:
<223> OTHER INFORMATION: Synthetic Construct

<400> SEQUENCE: 188

```
Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Asn Val Met Gly Leu Tyr Trp Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

-continued

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 189
<211> LENGTH: 214
<212> TYPE: PRT
<213> ORGANISM: Artificial Sequence
<220> FEATURE:
<223> OTHER INFORMATION: Synthetic Construct

<400> SEQUENCE: 189

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 190
<211> LENGTH: 118
<212> TYPE: PRT
<213> ORGANISM: Artificial Sequence
<220> FEATURE:
<223> OTHER INFORMATION: Synthetic Construct

<400> SEQUENCE: 190
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
            85                  90                  95

Ala Arg Glu Ser Gly Trp Tyr Leu Phe Asp Tyr Trp Gly Gln Gly Thr
            100                 105                 110

Leu Val Thr Val Ser Ser
            115

<210> SEQ ID NO 191
<211> LENGTH: 107
<212> TYPE: PRT
<213> ORGANISM: Artificial Sequence
<220> FEATURE:
<223> OTHER INFORMATION: Synthetic Construct

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
            85                  90                  95

Thr Phe Gly Gly Gly Thr Lys Val Glu Ile Lys
            100                 105

<210> SEQ ID NO 192
<211> LENGTH: 124
<212> TYPE: PRT
<213> ORGANISM: Artificial Sequence
<220> FEATURE:
<223> OTHER INFORMATION: Synthetic Construct

<400> SEQUENCE: 192

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr

Leu Gln Met Asn Ser Leu Arg Ala Glu Asp Thr Ala Leu Tyr Tyr Cys
                    85                  90                  95

Ala Lys Asp Gln Ser Thr Ala Asp Tyr Tyr Phe Tyr Tyr Gly Met Asp
                100                 105                 110

Val Trp Gly Gln Gly Thr Thr Val Thr Val Ser Ser
            115                 120

<210> SEQ ID NO 193
<211> LENGTH: 106
<212> TYPE: PRT
<213> ORGANISM: Artificial Sequence
<220> FEATURE:
<223> OTHER INFORMATION: Synthetic Construct

<400> SEQUENCE: 193

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
                100                 105

<210> SEQ ID NO 194
<211> LENGTH: 122
<212> TYPE: PRT
<213> ORGANISM: Artificial Sequence
<220> FEATURE:
<223> OTHER INFORMATION: Synthetic Construct

<400> SEQUENCE: 194

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
                100                 105                 110

Gly Gln Gly Thr Thr Val Thr Val Ser Ser
            115                 120

<210> SEQ ID NO 195
<211> LENGTH: 107

```
<212> TYPE: PRT
<213> ORGANISM: Artificial Sequence
<220> FEATURE:
<223> OTHER INFORMATION: Synthetic Construct

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105

<210> SEQ ID NO 196
<211> LENGTH: 120
<212> TYPE: PRT
<213> ORGANISM: Artificial Sequence
<220> FEATURE:
<223> OTHER INFORMATION: Synthetic Construct

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 197
<211> LENGTH: 111
<212> TYPE: PRT
<213> ORGANISM: Artificial Sequence
<220> FEATURE:
<223> OTHER INFORMATION: Synthetic Construct

<400> SEQUENCE: 197

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
```

```
            35                  40                  45
Arg Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Glu Leu Pro Leu Thr Phe Gly Gly Gly Thr Lys Val Glu Ile Lys
            100                 105                 110

<210> SEQ ID NO 198
<211> LENGTH: 469
<212> TYPE: PRT
<213> ORGANISM: Artificial Sequence
<220> FEATURE:
<223> OTHER INFORMATION: Synthetic Construct

<400> SEQUENCE: 198

Met Tyr Leu Gly Leu Asn Tyr Val Phe Ile Val Phe Leu Leu Asn Gly
  1               5                  10                  15

Val Gln Ser Glu Val Lys Leu Glu Glu Ser Gly Gly Gly Leu Val Gln
                 20                  25                  30

Pro Gly Gly Ser Met Lys Leu Ser Cys Ala Ala Ser Gly Phe Thr Phe
             35                  40                  45

Ser Asp Ala Trp Met Asp Trp Val Arg Gln Ser Pro Glu Lys Gly Leu
 50                  55                  60

Glu Trp Val Ala Glu Ile Arg Ser Lys Ala Asn Asn His Ala Thr Tyr
 65                  70                  75                  80

Tyr Ala Glu Ser Val Asn Gly Arg Phe Thr Ile Ser Arg Asp Asp Ser
                 85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Phe Tyr Phe Asp Tyr Trp
            115                 120                 125

Gly Gln Gly Thr Thr Leu Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Thr Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
```

```
                290                 295                 300
Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 199
<211> LENGTH: 233
<212> TYPE: PRT
<213> ORGANISM: Artificial Sequence
<220> FEATURE:
<223> OTHER INFORMATION: Synthetic Construct

<400> SEQUENCE: 199

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ser Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
```

180                 185                 190
Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115

<210> SEQ ID NO 201
<211> LENGTH: 108
<212> TYPE: PRT
<213> ORGANISM: Artificial Sequence
<220> FEATURE:
<223> OTHER INFORMATION: Synthetic Construct

<400> SEQUENCE: 201

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 202
<211> LENGTH: 121

```
<212> TYPE: PRT
<213> ORGANISM: Artificial Sequence
<220> FEATURE:
<223> OTHER INFORMATION: Synthetic Construct

<400> SEQUENCE: 202

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
    50                  55                  60

Lys Asp Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 203
<211> LENGTH: 108
<212> TYPE: PRT
<213> ORGANISM: Artificial Sequence
<220> FEATURE:
<223> OTHER INFORMATION: Synthetic Construct

<400> SEQUENCE: 203

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105

<210> SEQ ID NO 204
<211> LENGTH: 119
<212> TYPE: PRT
<213> ORGANISM: Artificial Sequence
<220> FEATURE:
<223> OTHER INFORMATION: Synthetic Construct

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
```

```
            35                  40                  45
Gly Tyr Ile Asn Pro Tyr Asn Asp Gly Thr Lys Tyr Asn Glu Lys Phe
        50                  55                  60
Lys Gly Arg Val Thr Ile Thr Ser Asp Thr Ser Ala Ser Thr Ala Tyr
 65                  70                  75                  80
Met Glu Leu Ser Ser Leu Arg Ser Glu Asp Thr Ala Val Tyr Tyr Cys
                85                  90                  95
Ala Asn Tyr Tyr Gly Ser Ser Leu Ser Met Asp Tyr Trp Gly Gln Gly
            100                 105                 110
Thr Leu Val Thr Val Ser Ser
            115

<210> SEQ ID NO 205
<211> LENGTH: 108
<212> TYPE: PRT
<213> ORGANISM: Artificial Sequence
<220> FEATURE:
<223> OTHER INFORMATION: Synthetic Construct

<400> SEQUENCE: 205

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Ile Ser Asn Tyr
            20                  25                  30
Leu Asn Trp Tyr Gln Gln Lys Pro Gly Lys Ala Pro Lys Leu Leu Ile
            35                  40                  45
Tyr Tyr Thr Ser Arg Leu His Ser Gly Val Pro Ser Arg Phe Ser Gly
        50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Tyr Cys Gln Gln Gly Asn Thr Leu Pro Trp
                85                  90                  95
Thr Phe Gly Gln Gly Thr Lys Val Glu Ile Lys Arg
            100                 105

<210> SEQ ID NO 206
<211> LENGTH: 108
<212> TYPE: PRT
<213> ORGANISM: Artificial Sequence
<220> FEATURE:
<223> OTHER INFORMATION: Synthetic Construct

<400> SEQUENCE: 206

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Ile Ser Asn Tyr
            20                  25                  30
Leu Asn Trp Tyr Gln Gln Lys Pro Gly Lys Ala Val Lys Leu Leu Ile
            35                  40                  45
Tyr Tyr Thr Ser Arg Leu His Ser Gly Val Pro Ser Arg Phe Ser Gly
        50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Phe Cys Gln Gln Gly Asn Thr Leu Pro Trp
                85                  90                  95
Thr Phe Gly Gln Gly Thr Lys Val Glu Ile Lys Arg
            100                 105
```

<210> SEQ ID NO 207
<211> LENGTH: 119
<212> TYPE: PRT
<213> ORGANISM: Artificial Sequence
<220> FEATURE:
<223> OTHER INFORMATION: Synthetic Construct

<400> SEQUENCE: 207

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115
```

<210> SEQ ID NO 208
<211> LENGTH: 119
<212> TYPE: PRT
<213> ORGANISM: Artificial Sequence
<220> FEATURE:
<223> OTHER INFORMATION: Synthetic Construct

<400> SEQUENCE: 208

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115
```

<210> SEQ ID NO 209
<211> LENGTH: 121
<212> TYPE: PRT
<213> ORGANISM: Artificial Sequence
<220> FEATURE:
<223> OTHER INFORMATION: Synthetic Construct

<400> SEQUENCE: 209

```
Gln Val Gln Leu Val Gln Ser Gly Ala Glu Val Lys Lys Pro Gly Ser
```

-continued

```
                1               5                  10                 15
            Ser Val Lys Val Ser Cys Lys Ala Ser Gly Tyr Thr Phe Lys Asp Tyr
                        20                  25                  30

Thr Met His Trp Val Arg Gln Ala Pro Gly Gln Gly Leu Glu Trp Met
                        35                  40                  45

Gly Gly Ile Tyr Pro Asn Asn Gly Gly Ser Thr Tyr Asn Gln Asn Phe
                        50                  55                  60

Lys Asp Arg Val Thr Ile Thr Ala Asp Lys Ser Thr Ser Thr Ala Tyr
             65                  70                  75                  80

Met Glu Leu Ser Ser Leu Arg Ser Glu Asp Thr Ala Val Tyr Tyr Cys
                        85                  90                  95

Ala Arg Met Gly Tyr His Gly Pro His Leu Asp Phe Asp Val Trp Gly
                        100                 105                 110

Gln Gly Thr Thr Val Thr Val Ser Ser
                        115                 120

<210> SEQ ID NO 210
<211> LENGTH: 108
<212> TYPE: PRT
<213> ORGANISM: Artificial Sequence
<220> FEATURE:
<223> OTHER INFORMATION: Synthetic Construct

<400> SEQUENCE: 210

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
            100                 105

<210> SEQ ID NO 211
<211> LENGTH: 108
<212> TYPE: PRT
<213> ORGANISM: Artificial Sequence
<220> FEATURE:
<223> OTHER INFORMATION: Synthetic Construct

<400> SEQUENCE: 211

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Gly Gly Ser Gly Thr Asp Phe Thr Leu Thr Ile Ser Ser Leu Gln Pro
 65                  70                  75                  80
```

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
            100                 105

<210> SEQ ID NO 212
<211> LENGTH: 121
<212> TYPE: PRT
<213> ORGANISM: Artificial Sequence
<220> FEATURE:
<223> OTHER INFORMATION: Synthetic Construct

<400> SEQUENCE: 212

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 213
<211> LENGTH: 121
<212> TYPE: PRT
<213> ORGANISM: Artificial Sequence
<220> FEATURE:
<223> OTHER INFORMATION: Synthetic Construct

<400> SEQUENCE: 213

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 214
<211> LENGTH: 138
<212> TYPE: PRT
<213> ORGANISM: Artificial Sequence

```
<220> FEATURE:
<223> OTHER INFORMATION: Synthetic Construct

<400> SEQUENCE: 214

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
                20                  25                  30

Pro Gly Gly Ser Met Lys Leu Ser Cys Ala Ala Ser Gly Phe Thr Phe
            35                  40                  45

Ser Asp Ala Trp Met Asp Trp Val Arg Gln Ser Pro Glu Lys Gly Leu
        50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Phe Tyr Phe Asp Tyr Trp
        115                 120                 125

Gly Gln Gly Thr Thr Leu Thr Val Ser Ser
    130                 135

<210> SEQ ID NO 215
<211> LENGTH: 126
<212> TYPE: PRT
<213> ORGANISM: Artificial Sequence
<220> FEATURE:
<223> OTHER INFORMATION: Synthetic Construct

<400> SEQUENCE: 215

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
                20                  25                  30

Ala Ser Leu Gly Gly Lys Val Thr Ile Thr Cys Lys Ser Ser Gln Asp
            35                  40                  45

Ile Asn Lys Tyr Ile Ala Trp Tyr Gln His Lys Pro Gly Lys Gly Pro
        50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys
        115                 120                 125

<210> SEQ ID NO 216
<211> LENGTH: 17
<212> TYPE: PRT
<213> ORGANISM: Artificial Sequence
<220> FEATURE:
<223> OTHER INFORMATION: Synthetic Construct

<400> SEQUENCE: 216

Asp Met Tyr Pro Asp Ala Ala Ala Ser Tyr Asn Gln Lys Phe Arg
1               5                   10                  15
```

Glu

<210> SEQ ID NO 217
<211> LENGTH: 8
<212> TYPE: PRT
<213> ORGANISM: Artificial Sequence
<220> FEATURE:
<223> OTHER INFORMATION: Synthetic Construct

<400> SEQUENCE: 217

Ala Pro Arg Trp Ala Ala Ala Ala
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic Construct

<400> SEQUENCE: 218

Gln Ala Ala Ala Ala Ala Ala Ala Thr
1               5

<210> SEQ ID NO 219
<211> LENGTH: 19
<212> TYPE: PRT
<213> ORGANISM: Artificial Sequence
<220> FEATURE:
<223> OTHER INFORMATION: Synthetic Construct

<400> SEQUENCE: 219

Cys Asp Lys Thr His Thr Cys Pro Pro Cys Pro Ala Pro Glu Leu Leu
1               5                   10                  15

Gly Gly Pro

<210> SEQ ID NO 220
<211> LENGTH: 4
<212> TYPE: PRT
<213> ORGANISM: Artificial Sequence
<220> FEATURE:
<223> OTHER INFORMATION: Synthetic Construct

<400> SEQUENCE: 220

Gly Gly Gly Ser
1

<210> SEQ ID NO 221
<211> LENGTH: 4
<212> TYPE: PRT
<213> ORGANISM: Artificial Sequence
<220> FEATURE:
<223> OTHER INFORMATION: Synthetic Construct

<400> SEQUENCE: 221

Ser Gly Gly Gly
1

<210> SEQ ID NO 222
<211> LENGTH: 5
<212> TYPE: PRT
<213> ORGANISM: Artificial Sequence
<220> FEATURE:
<223> OTHER INFORMATION: Synthetic Construct

<400> SEQUENCE: 222

Gly Gly Gly Gly Ser
1               5

<210> SEQ ID NO 223
<211> LENGTH: 5
<212> TYPE: PRT
<213> ORGANISM: Artificial Sequence
<220> FEATURE:
<223> OTHER INFORMATION: Synthetic Construct

<400> SEQUENCE: 223

Ser Gly Gly Gly Gly
1               5

<210> SEQ ID NO 224
<211> LENGTH: 6
<212> TYPE: PRT
<213> ORGANISM: Artificial Sequence
<220> FEATURE:
<223> OTHER INFORMATION: Synthetic Construct

<400> SEQUENCE: 224

Gly Gly Gly Gly Gly Ser
1               5

<210> SEQ ID NO 225
<211> LENGTH: 6
<212> TYPE: PRT
<213> ORGANISM: Artificial Sequence
<220> FEATURE:
<223> OTHER INFORMATION: Synthetic Construct

<400> SEQUENCE: 225

Ser Gly Gly Gly Gly Gly
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic Construct

<400> SEQUENCE: 226

Gly Gly Gly Gly Gly Gly Ser
1               5

<210> SEQ ID NO 227
<211> LENGTH: 7
<212> TYPE: PRT
<213> ORGANISM: Artificial Sequence
<220> FEATURE:
<223> OTHER INFORMATION: Synthetic Construct

<400> SEQUENCE: 227

Ser Gly Gly Gly Gly Gly Gly
1               5

<210> SEQ ID NO 228
<211> LENGTH: 100
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)...(100)
<223> OTHER INFORMATION: May be present or absent

```
<400> SEQUENCE: 228

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 229
<211> LENGTH: 100
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)...(100)
<223> OTHER INFORMATION: May be present or absent

<400> SEQUENCE: 229

Ser Gly Gly Gly Gly Ser Gly Gly Gly Ser Gly Gly Gly Gly Ser
1               5                   10                  15

Gly Gly Gly Gly Ser Gly Gly Gly Gly Ser Gly Gly Gly Gly Ser Gly
                20                  25                  30

Gly Gly Gly Ser Gly Gly Gly Gly Ser Gly Gly Gly Gly Ser Gly Gly
            35                  40                  45

Gly Gly Ser Gly Gly Gly Gly Ser Gly Gly Gly Gly Ser Gly Gly Gly
        50                  55                  60

Gly Ser Gly Gly Gly Gly Ser Gly Gly Gly Gly Ser Gly Gly Gly Gly
65                  70                  75                  80

Ser Gly Gly Gly Gly Ser Gly Gly Gly Gly Ser Gly Gly Gly Gly Ser
                85                  90                  95

Gly Gly Gly Gly
            100
```

ANTIGEN BINDING COMPLEX HAVING AGONISTIC ACTIVITY AND METHODS OF USE

CROSS REFERENCE TO RELATED APPLICATIONS

This application is a continuation of International Patent Application No. PCT/US2016/026245, filed Apr. 6, 2016, which claims the priority benefit of U.S. Provisional Application Ser. No. 62/144,237, filed Apr. 7, 2015; 62/207,315, filed Aug. 19, 2015; and 62/387,485, filed Dec. 23, 2015; each of which is incorporated herein by reference in its entirety.

SEQUENCE LISTING

The content of the following submission on ASCII text file is incorporated herein by reference in its entirety: a computer readable form (CRF) of the Sequence Listing (file name: 146392033501SEQLIST.txt, date recorded: Oct. 4, 2017, size: 188 KB).

FIELD OF THE INVENTION

The present invention relates to antigen binding complexes having agonistic activity and methods of using the same.

BACKGROUND

Functional antibodies are an important therapeutic option for treatment of a wide variety of diseases. There is a need in the art for better means for identifying functional antibodies, particularly antibodies having agonistic activity, from pools of candidate molecules. The present invention is directed to this and other needs.

SUMMARY

The invention provides antigen binding polypeptides and complexes having agonistic activity and methods of using the same.

In one aspect, the application provides a hexameric antigen binding complex having agonist activity comprising six subunits, wherein each subunit comprises at least one antigen binding polypeptide comprising at least one antigen binding region for a cell surface receptor and a modified Fc region that enhances hexamer formation, and wherein the complex has agonist activity for a cell surface receptor bound by the complex.

In certain embodiments, each antigen binding polypeptide in an antigen binding complex binds to the same cell surface receptor.

In certain embodiments, the antigen binding region binds to a cell surface receptor that is a member of receptor family selected from the group consisting of tumor necrosis factor receptor (TNFR) superfamily and G-Protein Coupled Receptor (GPCR) superfamily.

In certain embodiments, the antigen binding region binds to a cell surface receptor selected from the group consisting of OX40, Death Receptor 5 (DR5), CD27, GITR, CD137, and Tie2.

In certain embodiments, the antigen binding polypeptide comprises an antigen binding region of an antibody. In certain embodiments, the antigen binding region of an antibody is selected from the group consisting of Fv, Fab, Fab', F(ab')$_2$, single-chain antibody molecules (e.g. scFv), and antibody variable region.

In certain embodiments, the modified Fc region is a modified human IgG1 Fc region.

In certain embodiments, the Fc region further comprises a modification for diminished C1q binding and/or Complement Dependent Cytotoxicity (CDC). In exemplary embodiments, the modification for diminished C1q binding and/or CDC comprises a K322A amino acid substitution in the Fc region of a human IgG1 (EU numbering).

In certain embodiments, the modified Fc region comprises one or more amino acid modifications selected from the group consisting of:

(i) P247A, P247C, P247D, P247F, P247G, P247H, P247I, P247K, P247L, P247M, P247N, P247R, P247S, P247T, P247V, or P247W;

(ii) I253A, I253D, I253K, I253L, I253M, I253N, I253R, I253S, I253V, I253E, I253Q, or I253T;

(iii) S254E, S254F, S254G, S254H, S254I, S254K, S254L, S254P, S254T, S254V, or S254W;

(iv) H310A, H310G, H310F, H310K, H310L, H310P, H310R, H310T, H310V, H310W, H310N, H310Q, or H310Y;

(v) Q311A, Q311C, Q311E, Q311G, Q311H, Q311F, Q311I, Q311K, Q311L, Q311N, Q311P, Q311R, Q311S, Q311T, Q311W, or Q311Y;

(vi) E345A, E345C, E345D, E345G, E345H, E345F, E345I, E345K, E345L, E345M, E345N, E345P, E345Q, E345R, E345S, E345T, E345V, E345W, or E345Y;

(vii) D/E356G, D/E356I, D/E356L, D/E356R, D/E356T, or D/E356V;

(viii) T359G, T359N, T359P, or T359R;

(ix) E382F, E382K, E382L, E382M, E382P, E382V, E382W, E382D, E382H, E382N, E382Q, E382S, E382T, or E382Y;

(x) G385A, G385D, G385H, G385I, G385L, G385N, G385P, G385Q, G385R, G385S, G385T, G385V, G385E, G385K, G385W, or G385Y;

(xi) Q386A, Q386C, Q386D, Q386E, Q386G, Q386H, Q386F, Q386I, Q386K, Q386L, Q386N, Q386P, Q386R, Q386S, Q386T, Q386V, Q386W, or Q386Y;

(xii) E430A, E430C, E430D, E430F, E430G, E430H, E430I, E430K, E430L, E430M, E430N, E430P, E430Q, E430R, E430S, E430T, E430V, E430W, or E430Y;

(xiii) H433R;

(xiv) N434D, N434E, N434G, N434K, N434R, N434S, N434V, N434W, N434H, N434Q, N434T, or N434Y;

(xv) Y436I, Y436K, Y436L, Y436R, Y436S, Y436T, Y436V, Y436W, Y436A, Y436E, Y436F, Y436H, Y436M, Y436N, or Y436Q;

(xvi) Q438C, Q438E, Q438I, Q438K, Q438L, Q438S, Q438T, Q438V, Q438W, Q438Y, Q438A, Q438G, Q438H, Q438N, Q438Q, or Q438R;

(xvii) K439A, K439D, K439E, K439H, K439L, K439P, K439R, K439T, K439Y, K439Q, or K439W;

(xviii) S440A, S440C, S440D, S440E, S440G, S440H, S440F, S440I, S440K, S440L, S440M, S440N, S440P, S440Q, S440R, S440T, S440V, S440W, or S440Y; and (xix) K447D, K447E, K447N, K447Q, or a deletion of K447.

In certain embodiments, the modified Fc region comprises one or more amino acid modifications selected from the group consisting of:

(i) P247G;

(ii) I253L, I253N, I253V, or I253Q;

(iii) S254L;

(iv) H310P, H310W, or H310Q;
(v) Q311E, Q311L, Q311R, or Q311W;
(vi) E345A, E345D, E345G, E345H, E345F, E345I, E345K, E345L, E345M, E345N, E345P, E345Q, E345R, E345S, E345T, E345V, E345W, or E345Y;
(vii) D/E356R;
(viii) T359R;
(ix) E382K, E382L, E382V, E382D, E382Q, or E382S;
(x) G385D, G385N, G385R, G385E, or G385K;
(xi) Q386K;
(xii) E430A, E430D, E430F, E430G, E430H, E430I, E430K, E430L, E430M, E430N, E430P, E430Q, E430R, E430S, E430T, E430V, E430W, or E430Y;
(xiii) H433R;
(xiv) N434K, N434R, N434W, N434H, or N434Q;
(xv) Y436I, Y436S, Y436T, Y436V, Y436N, or Y436Q;
(xvi) Q438C, Q438L, Q438S, Q438T, or Q438N;
(xvii) K439D, K439E, K439H, K439R, or K439Q;
(xviii) S440D, S440E, S440Q, S440W, or S440Y; and
(xix) K447D, K447E, K447N, K447Q, or a deletion of K447.

In certain embodiments, the modified Fc region comprises one or more amino acid modifications selected from the group consisting of:
(i) P247D, P247F, P247G, P247K, P247R, or P247S;
(ii) I253V;
(iii) S254G, S254I, or S254L;
(iv) Q311I, Q311K, Q311L, Q311P, or Q311W;
(v) E345A, E345C, E345F, E345I, E345K, E345L, E345M, E345N, E345P, E345S, E345T, E345V, E345W, or E345Y;
(vi) D/E356I, D/E356L, D/E356R, D/E356T, or D/E356V;
(vii) T359N;
(viii) E382L or E382V;
(ix) G385A, G385D, G385H, G385I, G385L, G385N, G385P, G385Q, G385R, G385S, G385T, G385V, G385E, G385K, G385W, or G385Y;
(x) Q386K;
(xi) E430A, E430F, E430H, E430L, E430P, E430R, E430S, E430V, E430W, or E430Y;
(xii) N434W;
(xiii) Y436I; and
(xiv) S440D.

In certain embodiments, the modified Fc region comprises one or more amino acid substitutions selected from the group consisting of: E345R, E430G and S440Y in the Fc region of a human IgG1 (EU numbering). In certain embodiments, the modified Fc region comprises a single amino acid substitution selected from the group consisting of: E345R, E430G and S440Y in the Fc region of a human IgG1 (EU numbering). In certain embodiments, the modified Fc region comprises a set of amino acid substitutions selected from the group consisting of: (a) E345R and E430G, (b) E345R and S440Y, (c) E430G and S440Y, wherein the substitutions are in the Fc region of a human IgG1 (EU numbering). In certain embodiments, the modified Fc region comprises amino acid substitutions E345R, E430G and S440Y in the Fc region of a human IgG1 (EU numbering).

In certain embodiments, the antigen binding region comprises an antigen binding region from a monospecific antibody, bispecific antibody or multispecific antibody.

In certain embodiments, each antigen binding region is from a monospecific antibody that binds to the same cell surface receptor.

In certain embodiments, each antigen binding region is from a monospecific antibody that binds to OX40. In exemplary embodiments, the complex comprises at least one subunit that comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In certain embodiments, each of the six subunits comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In other exemplary embodiments, the complex comprises at least one subunit that comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42. In certain embodiments, each of the six subunits comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In certain embodiments, the complex comprises a mixture of at least two monospecific antibodies that bind to different epitopes on the same cell surface receptor.

In certain embodiments, the complex comprises (a) at least a first subunit that binds a first epitope of OX40; and (b) at least a second subunit that binds a second epitope of OX40, wherein the first epitope of OX40 is different from the second epitope of OX40. In exemplary embodiments, the first subunit comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; and wherein the second subunit comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In certain embodiments, the antigen binding region comprises two arms of a bispecific antibody, and wherein each arm of the bispecific antibody binds to a different epitope on the same cell surface receptor.

In certain embodiments, the bispecific antibody comprises (a) at least a first arm that binds a first epitope of OX40 and (b) at least a second arm that binds a second epitope of OX40, wherein the first epitope of OX40 is different from the second epitope of OX40. In exemplary embodiments, the first arm comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; and wherein the second arm comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In certain embodiments, the Fc region further comprises a modification for attenuating effector function. In exemplary embodiments, the modification for attenuating effector function comprises amino acid substitutions at one or more amino acid residues (EU numbering) selected from the group consisting of:
  (a) 297 in the Fc region of human IgG1,
  (b) 234 and 235 in the Fc region of human IgG1,
  (c) 234, 235 and 329 in the Fc region of human IgG1,
  (d) 234 and 237 in the Fc region of human IgG2,
  (e) 235, 237 and 318 in the Fc region of human IgG4,
  (f) 228 and 236 in the Fc region of human IgG4,
  (g) 268, 309, 330 and 331 in the Fc region of human IgG2,
  (h) 220, 226, 229 and 238 in the Fc region of human IgG1,
  (i) 226, 229, 233, 234 and 235 in the Fc region of human IgG1,
  (j) 234, 235 and 331 in the Fc region of human IgG1,
  (k) 226 and 230 in the Fc region of human IgG1, and
  (l) 267 and 328 in the Fc region of human IgG1.
In certain embodiments, the modification for attenuating effector function comprises one or more amino acid substitutions (EU numbering) selected from the group consisting of:
  (a) N297A in the Fc region of human IgG1,
  (b) L234A and L235A in the Fc region of human IgG1,
  (c) L234A, L235A and P329G in the Fc region of human IgG1,
  (d) V234A and G237A in the Fc region of human IgG2,
  (e) L235A, G237A and E318A in the Fc region of human IgG4,
  (f) S228P and L236E in the Fc region of human IgG4,
  (g) 118 to 260 in the Fc region of human IgG2 or 261 to 447 in the Fc region of human IgG4,
  (h) H268Q, V309L, A330S and A331S in the Fc region of human IgG2,
  (i) C220S, C226S, C229S and P238S in the Fc region of human IgG1,
  (j) C226S, C229S, E233P, L234V and L235A in the Fc region of human IgG1,
  (k) L234F, L235E and P331S in the Fc region of human IgG1,
  (l) C226S and P230S in the Fc region of human IgG1, and
  (m) S267E and L328F in the Fc region of human IgG1.

In certain embodiments, the modification for attenuating effector function does not result in a modification of the glycosylation pattern of the Fc region.

In certain embodiments, the antigen binding complex enhances signal transduction mediated by a cell surface receptor bound by the complex.

In another aspect, the application provides a hexameric antigen binding complex having agonist activity comprising six subunits, wherein each subunit comprises at least one antigen binding polypeptide comprising at least one antigen binding region for a cell surface receptor and a modified Fc region that enhances hexamer formation, wherein the modified Fc region further comprises a modification for diminished C1q binding and/or Complement Dependent Cytotoxicity (CDC), and wherein the complex has agonist activity for a cell surface receptor bound by the complex.

In certain embodiments, each antigen binding polypeptide in an antigen binding complex binds to the same cell surface receptor.

In certain embodiments, the antigen binding region binds to a cell surface receptor that is a member of receptor family selected from the group consisting of tumor necrosis factor receptor (TNFR) superfamily and G-Protein Coupled Receptor (GPCR) superfamily.

In certain embodiments, the antigen binding region binds to a cell surface receptor selected from the group consisting of OX40, Death Receptor 5 (DR5), CD27, GITR, CD137, and Tie2.

In certain embodiments, the antigen binding polypeptide comprises an antigen binding region of an antibody. In certain embodiments, the antigen binding region of an antibody is selected from the group consisting of Fv, Fab, Fab', F(ab')$_2$, single-chain antibody molecules (e.g. scFv), and antibody variable region.

In certain embodiments, the modified Fc region is a modified human IgG1 Fc region.

In certain embodiments, the modification for diminished C1q binding and/or CDC comprises a K322A amino acid substitution in the Fc region of a human IgG1 (EU numbering).

In certain embodiments, the modified Fc region comprises one or more amino acid modifications selected from the group consisting of:
  (i) P247A, P247C, P247D, P247F, P247G, P247H, P247I, P247K, P247L, P247M, P247N, P247R, P247S, P247T, P247V, or P247W;
  (ii) I253A, I253D, I253K, I253L, I253M, I253N, I253R, I253S, I253V, I253E, I253Q, or I253T;
  (iii) S254E, S254F, S254G, S254H, S254I, S254K, S254L, S254P, S254T, S254V, or S254W;
  (iv) H310A, H310G, H310F, H310K, H310L, H310P, H310R, H310T, H310V, H310W, H310N, H310Q, or H310Y;
  (v) Q311A, Q311C, Q311E, Q311G, Q311H, Q311F, Q311I, Q311K, Q311L, Q311N, Q311P, Q311R, Q311S, Q311T, Q311W, or Q311Y;
  (vi) E345A, E345C, E345D, E345G, E345H, E345F, E345I, E345K, E345L, E345M, E345N, E345P, E345Q, E345R, E345S, E345T, E345V, E345W, or E345Y;
  (vii) D/E356G, D/E356I, D/E356L, D/E356R, D/E356T, or D/E356V;
  (viii) T359G, T359N, T359P, or T359R;
  (ix) E382F, E382K, E382L, E382M, E382P, E382V, E382W, E382D, E382H, E382N, E382Q, E382S, E382T, or E382Y;

(x) G385A, G385D, G385H, G385I, G385L, G385N, G385P, G385Q, G385R, G385S, G385T, G385V, G385E, G385K, G385W, or G385Y;

(xi) Q386A, Q386C, Q386D, Q386E, Q386G, Q386H, Q386F, Q386I, Q386K, Q386L, Q386N, Q386P, Q386R, Q386S, Q386T, Q386V, Q386W, or Q386Y;

(xii) E430A, E430C, E430D, E430F, E430G, E430H, E430I, E430K, E430L, E430M, E430N, E430P, E430Q, E430R, E430S, E430T, E430V, E430W, or E430Y;

(xiii) H433R;

(xiv) N434D, N434E, N434G, N434K, N434R, N434S, N434V, N434W, N434H, N434Q, N434T, or N434Y;

(xv) Y436I, Y436K, Y436L, Y436R, Y436S, Y436T, Y436V, Y436W, Y436A, Y436E, Y436F, Y436H, Y436M, Y436N, or Y436Q;

(xvi) Q438C, Q438E, Q438I, Q438K, Q438L, Q438S, Q438T, Q438V, Q438W, Q438Y, Q438A, Q438G, Q438H, Q438N, Q438Q, or Q438R;

(xvii) K439A, K439D, K439E, K439H, K439L, K439P, K439R, K439T, K439Y, K439Q, or K439W;

(xviii) S440A, S440C, S440D, S440E, S440G, S440H, S440F, S440I, S440K, S440L, S440M, S440N, S440P, S440Q, S440R, S440T, S440V, S440W, or S440Y; and (xix) K447D, K447E, K447N, K447Q, or a deletion of K447.

In certain embodiments, the modified Fc region comprises one or more amino acid modifications selected from the group consisting of:

(i) P247G;

(ii) I253L, I253N, I253V, or I253Q;

(iii) S254L;

(iv) H310P, H310W, or H310Q;

(v) Q311E, Q311L, Q311R, or Q311W;

(vi) E345A, E345D, E345G, E345H, E345F, E345I, E345K, E345L, E345M, E345N, E345P, E345Q, E345R, E345S, E345T, E345V, E345W, or E345Y;

(vii) D/E356R;

(viii) T359R;

(ix) E382K, E382L, E382V, E382D, E382Q, or E382S;

(x) G385D, G385N, G385R, G385E, or G385K;

(xi) Q386K;

(xii) E430A, E430D, E430F, E430G, E430H, E430I, E430K, E430L, E430M, E430N, E430P, E430Q, E430R, E430S, E430T, E430V, E430W, or E430Y;

(xiii) H433R;

(xiv) N434K, N434R, N434W, N434H, or N434Q;

(xv) Y436I, Y436S, Y436T, Y436V, Y436N, or Y436Q;

(xvi) Q438C, Q438L, Q438S, Q438T, or Q438N;

(xvii) K439D, K439E, K439H, K439R, or K439Q;

(xviii) S440D, S440E, S440Q, S440W, or S440Y; and (xix) K447D, K447E, K447N, K447Q, or a deletion of K447.

In certain embodiments, the modified Fc region comprises one or more amino acid modifications selected from the group consisting of:

(i) P247D, P247F, P247G, P247K, P247R, or P247S;

(ii) I253V;

(iii) S254G, S254I, or S254L;

(iv) Q311I, Q311K, Q311L, Q311P, or Q311W;

(v) E345A, E345C, E345F, E345I, E345K, E345L, E345M, E345N, E345P, E345S, E345T, E345V, E345W, or E345Y;

(vi) D/E356I, D/E356L, D/E356R, D/E356T, or D/E356V;

(vii) T359N;

(viii) E382L or E382V;

(ix) G385A, G385D, G385H, G385I, G385L, G385N, G385P, G385Q, G385R, G385S, G385T, G385V, G385E, G385K, G385W, or G385Y;

(x) Q386K;

(xi) E430A, E430F, E430H, E430L, E430P, E430R, E430S, E430V, E430W, or E430Y;

(xii) N434W;

(xiii) Y436I; and (xiv) S440D.

In certain embodiments, the modified Fc region comprises one or more amino acid substitutions selected from the group consisting of: E345R, E430G and S440Y in the Fc region of a human IgG1 (EU numbering). In certain embodiments, the modified Fc region comprises a single amino acid substitution selected from the group consisting of: E345R, E430G and S440Y in the Fc region of a human IgG1 (EU numbering). In certain embodiments, the modified Fc region comprises a set of amino acid substitutions selected from the group consisting of: (a) E345R and E430G, (b) E345R and S440Y, (c) E430G and S440Y, wherein the substitutions are in the Fc region of a human IgG1 (EU numbering). In certain embodiments, the modified Fc region comprises amino acid substitutions E345R, E430G and S440Y in the Fc region of a human IgG1 (EU numbering).

In certain embodiments, the antigen binding region comprises an antigen binding region from a monospecific antibody, bispecific antibody or multispecific antibody.

In certain embodiments, each antigen binding region is from a monospecific antibody that binds to the same cell surface receptor.

In certain embodiments, each antigen binding region is from a monospecific antibody that binds to OX40. In exemplary embodiments, the complex comprises at least one subunit that comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In certain embodiments, each of the six subunits comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In other exemplary embodiments, the complex comprises at least one subunit that comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42. In certain embodiments, each of the six subunits comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In certain embodiments, the complex comprises a mixture of at least two monospecific antibodies that bind to different epitopes on the same cell surface receptor.

In certain embodiments, the complex comprises (a) at least a first subunit that binds a first epitope of OX40; and (b) at least a second subunit that binds a second epitope of OX40, wherein the first epitope of OX40 is different from the second epitope of OX40. In exemplary embodiments, the first subunit comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; and wherein the second subunit comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In certain embodiments, the antigen binding region comprises two arms of a bispecific antibody, and wherein each arm of the bispecific antibody binds to a different epitope on the same cell surface receptor.

In certain embodiments, the bispecific antibody comprises (a) at least a first arm that binds a first epitope of OX40 and (b) at least a second arm that binds a second epitope of OX40, wherein the first epitope of OX40 is different from the second epitope of OX40. In exemplary embodiments, the first arm comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; and wherein the second arm comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In certain embodiments, the Fc region further comprises a modification for attenuating effector function. In exemplary embodiments, the modification for attenuating effector function comprises amino acid substitutions at one or more amino acid residues (EU numbering) selected from the group consisting of:
 (a) 297 in the Fc region of human IgG1,
 (b) 234 and 235 in the Fc region of human IgG1,
 (c) 234, 235 and 329 in the Fc region of human IgG1,
 (d) 234 and 237 in the Fc region of human IgG2,
 (e) 235, 237 and 318 in the Fc region of human IgG4,
 (f) 228 and 236 in the Fc region of human IgG4,
 (g) 268, 309, 330 and 331 in the Fc region of human IgG2,
 (h) 220, 226, 229 and 238 in the Fc region of human IgG1,
 (i) 226, 229, 233, 234 and 235 in the Fc region of human IgG1,
 (j) 234, 235 and 331 in the Fc region of human IgG1,
 (k) 226 and 230 in the Fc region of human IgG1, and
 (l) 267 and 328 in the Fc region of human IgG1.

In certain embodiments, the modification for attenuating effector function comprises one or more amino acid substitutions (EU numbering) selected from the group consisting of:
 (a) N297A in the Fc region of human IgG1,
 (b) L234A and L235A in the Fc region of human IgG1,
 (c) L234A, L235A and P329G in the Fc region of human IgG1,
 (d) V234A and G237A in the Fc region of human IgG2,
 (e) L235A, G237A and E318A in the Fc region of human IgG4,
 (f) S228P and L236E in the Fc region of human IgG4,
 (g) 118 to 260 in the Fc region of human IgG2 or 261 to 447 in the Fc region of human IgG4,
 (h) H268Q, V309L, A330S and A331S in the Fc region of human IgG2,
 (i) C220S, C226S, C229S and P238S in the Fc region of human IgG1,
 (j) C226S, C229S, E233P, L234V and L235A in the Fc region of human IgG1,
 (k) L234F, L235E and P331S in the Fc region of human IgG1,
 (l) C226S and P230S in the Fc region of human IgG1, and
 (m) S267E and L328F in the Fc region of human IgG1.

In certain embodiments, the modification for attenuating effector function does not result in a modification of the glycosylation pattern of the Fc region.

In certain embodiments, the antigen binding complex enhances signal transduction mediated by a cell surface receptor bound by the complex.

In another aspect, the application provides an antigen binding polypeptide comprising an antigen binding region for a cell surface receptor and a modified Fc region, wherein the modified Fc region comprises (i) a modification that enhances hexamer formation of the antigen binding polypeptides, and (ii) a modification that attenuates effector function.

In certain embodiments, the antigen binding polypeptide binds to a cell surface receptor that is a member of receptor family selected from the group consisting of tumor necrosis factor receptor (TNFR) superfamily and G-Protein Coupled Receptor (GPCR) superfamily.

In certain embodiments, the antigen binding polypeptide binds to a cell surface receptor selected from the group consisting of OX40, DR5, GITR, CD27, CD137, and Tie2.

In certain embodiments, the antigen binding polypeptide comprises antigen binding region of antibody. In certain embodiments, the antigen binding region of an antibody is selected from the group consisting of Fv, Fab, Fab', F(ab')$_2$, single-chain antibody molecules (e.g. scFv), and antibody variable region.

In certain embodiments, the modified Fc region is a modified human IgG1 Fc region.

In certain embodiments, the modified Fc region comprises one or more amino acid modifications selected from the group consisting of:

(i) P247A, P247C, P247D, P247F, P247G, P247H, P247I, P247K, P247L, P247M, P247N, P247R, P247S, P247T, P247V, or P247W;

(ii) I253A, I253D, I253K, I253L, I253M, I253N, I253R, I253S, I253V, I253E, I253Q, or I253T;

(iii) S254E, S254F, S254G, S254H, S254I, S254K, S254L, S254P, S254T, S254V, or S254W;

(iv) H310A, H310G, H310F, H310K, H310L, H310P, H310R, H310T, H310V, H310W, H310N, H310Q, or H310Y;

(v) Q311A, Q311C, Q311E, Q311G, Q311H, Q311F, Q311I, Q311K, Q311L, Q311N, Q311P, Q311R, Q311S, Q311T, Q311W, or Q311Y;

(vi) E345A, E345C, E345D, E345G, E345H, E345F, E345I, E345K, E345L, E345M, E345N, E345P, E345Q, E345R, E345S, E345T, E345V, E345W, or E345Y;

(vii) D/E356G, D/E356I, D/E356L, D/E356R, D/E356T, or D/E356V;

(viii) T359G, T359N, T359P, or T359R;

(ix) E382F, E382K, E382L, E382M, E382P, E382V, E382W, E382D, E382H, E382N, E382Q, E382S, E382T, or E382Y;

(x) G385A, G385D, G385H, G385I, G385L, G385N, G385P, G385Q, G385R, G385S, G385T, G385V, G385E, G385K, G385W, or G385Y;

(xi) Q386A, Q386C, Q386D, Q386E, Q386G, Q386H, Q386F, Q386I, Q386K, Q386L, Q386N, Q386P, Q386R, Q386S, Q386T, Q386V, Q386W, or Q386Y;

(xii) E430A, E430C, E430D, E430F, E430G, E430H, E430I, E430K, E430L, E430M, E430N, E430P, E430Q, E430R, E430S, E430T, E430V, E430W, or E430Y;

(xiii) H433R;

(xiv) N434D, N434E, N434G, N434K, N434R, N434S, N434V, N434W, N434H, N434Q, N434T, or N434Y;

(xv) Y436I, Y436K, Y436L, Y436R, Y436S, Y436T, Y436V, Y436W, Y436A, Y436E, Y436F, Y436H, Y436M, Y436N, or Y436Q;

(xvi) Q438C, Q438E, Q438I, Q438K, Q438L, Q438S, Q438T, Q438V, Q438W, Q438Y, Q438A, Q438G, Q438H, Q438N, Q438Q, or Q438R;

(xvii) K439A, K439D, K439E, K439H, K439L, K439P, K439R, K439T, K439Y, K439Q, or K439W;

(xviii) S440A, S440C, S440D, S440E, S440G, S440H, S440F, S440I, S440K, S440L, S440M, S440N, S440P, S440Q, S440R, S440T, S440V, S440W, or S440Y; and (xix) K447D, K447E, K447N, K447Q, or a deletion of K447.

In certain embodiments, the modified Fc region comprises one or more amino acid modifications selected from the group consisting of:

(i) P247G;

(ii) I253L, I253N, I253V, or I253Q;

(iii) S254L;

(iv) H310P, H310W, or H310Q;

(v) Q311E, Q311L, Q311R, or Q311W;

(vi) E345A, E345D, E345G, E345H, E345F, E345I, E345K, E345L, E345M, E345N, E345P, E345Q, E345R, E345S, E345T, E345V, E345W, or E345Y;

(vii) D/E356R;

(viii) T359R;

(ix) E382K, E382L, E382V, E382D, E382Q, or E382S;

(x) G385D, G385N, G385R, G385E, or G385K;

(xi) Q386K;

(xii) E430A, E430D, E430F, E430G, E430H, E430I, E430K, E430L, E430M, E430N, E430P, E430Q, E430R, E430S, E430T, E430V, E430W, or E430Y;

(xiii) H433R;

(xiv) N434K, N434R, N434W, N434H, or N434Q;

(xv) Y436I, Y436S, Y436T, Y436V, Y436N, or Y436Q;

(xvi) Q438C, Q438L, Q438S, Q438T, or Q438N;

(xvii) K439D, K439E, K439H, K439R, or K439Q;

(xviii) S440D, S440E, S440Q, S440W, or S440Y; and (xix) K447D, K447E, K447N, K447Q, or a deletion of K447.

In certain embodiments, the modified Fc region comprises one or more amino acid modifications selected from the group consisting of:

(i) P247D, P247F, P247G, P247K, P247R, or P247S;

(ii) I253V;

(iii) S254G, S254I, or S254L;

(iv) Q311I, Q311K, Q311L, Q311P, or Q311W;

(v) E345A, E345C, E345F, E345I, E345K, E345L, E345M, E345N, E345P, E345S, E345T, E345V, E345W, or E345Y;

(vi) D/E356I, D/E356L, D/E356R, D/E356T, or D/E356V;

(vii) T359N;

(viii) E382L or E382V;

(ix) G385A, G385D, G385H, G385I, G385L, G385N, G385P, G385Q, G385R, G385S, G385T, G385V, G385E, G385K, G385W, or G385Y;

(x) Q386K;

(xi) E430A, E430F, E430H, E430L, E430P, E430R, E430S, E430V, E430W, or E430Y;

(xii) N434W;

(xiii) Y436I; and (xiv) S440D.

In an exemplary embodiment, the modified Fc region comprises one or more amino acid substitutions selected from the group consisting of: E345R, E430G and S440Y in the Fc region of a human IgG1 (EU numbering). In an exemplary embodiment, the modified Fc region comprises a single amino acid substitution selected from the group consisting of: E345R, E430G and S440Y in the Fc region of a human IgG1 (EU numbering). In an exemplary embodiment, the modified Fc region comprises a set of amino acid substitutions selected from the group consisting of: (a) E345R and E430G, (b) E345R and S440Y, (c) E430G and S440Y, wherein the substitutions are in the Fc region of a human IgG1 (EU numbering). In an exemplary embodiment, the modified Fc region comprises amino acid substitutions E345R, E430G and S440Y in the Fc region of a human IgG1 (EU numbering).

In certain embodiments, the antigen binding polypeptide comprises an antigen binding region from a monospecific antibody, bispecific antibody or multispecific antibody.

In certain embodiments, the antigen binding region binds to OX40. In an exemplary embodiment, the antigen binding region comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In an exemplary embodiment, the antigen binding region comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In certain embodiments, the antigen binding region comprises two arms of a bispecific antibody, and wherein each arm of the bispecific antibody binds to a different epitope on the same cell surface receptor.

In certain embodiments, the bispecific antibody comprises (a) at least a first arm that binds a first epitope of OX40 and (b) at least a second arm that binds a second epitope of OX40, wherein the first epitope of OX40 is different from the second epitope of OX40. In an exemplary embodiment, the first arm comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; and the second arm comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In exemplary embodiments, the modification for attenuating effector function comprises amino acid substitutions at one or more amino acid residues (EU numbering) selected from the group consisting of:

(a) 297 in the Fc region of human IgG1,
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1 (EU numbering),
(k) 226 and 230 in the Fc region of human IgG1, and
(l) 267 and 328 in the Fc region of human IgG1.

In certain embodiments, the modification for attenuating effector function comprises one or more amino acid substitutions (EU numbering) selected from the group consisting of:

(a) N297A in the Fc region of human IgG1,
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) 118 to 260 in the Fc region of human IgG2 or 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human,
(k) L234F, L235E and P331S in the Fc region of human IgG1,
(l) C226S and P230S in the Fc region of human IgG1, and
(m) S267E and L328F in the Fc region of human IgG1.

In certain embodiments, the modification for attenuating effector function does not result in a modification of the glycosylation pattern of the Fc region.

In another aspect, the application provides a hexamer comprising six antigen binding polypeptides according to any one of the embodiments described herein.

In another aspect, the application provides a method for agonizing a cell surface receptor in a subject comprising administering to the subject a complex or antigen binding polypeptide according to any of the embodiments described herein.

In certain embodiments, the hexamer enhances signal transduction mediated by a cell surface receptor bound by the complex, hexamer or antigen binding polypeptide.

In another aspect, the application provides a method of increasing agonist activity of an antigen binding polypeptide, comprising: (a) providing an antigen binding polypeptide which comprises an antigen binding region for a cell surface receptor and a Fc region, and (b) introducing a modification into the Fc region, wherein the modification enhances hexamer formation of the antigen binding polypeptide, and wherein the hexamer has increased agonist activity for a cell surface receptor bound by the antigen binding polypeptide as compared to an individual subunit of the hexamer.

In certain embodiments, the cell surface receptor is a member of receptor family selected from the group consisting of tumor necrosis factor receptor (TNFR) superfamily and G-Protein Coupled Receptor (GPCR) superfamily. In an exemplary embodiment, the cell surface receptor is selected from the group consisting of OX40, DR5, GITR, CD27, CD137, and Tie2.

In certain embodiments, the antigen binding polypeptide comprises an antigen binding region of an antibody. In exemplary embodiments, the antigen binding region of an antibody is selected from the group consisting of Fv, Fab, Fab', F(ab')$_2$, single-chain antibody molecules (e.g. scFv), and antibody variable region.

In certain embodiments, the modified Fc region is a modified human IgG1 Fc region.

In certain embodiments, the Fc region further comprises a modification for diminished C1q binding and/or Complement Dependent Cytotoxicity (CDC). In exemplary embodiments, the modification for diminished C1q binding and/or CDC comprises a K322A amino acid substitution in the Fc region of a human IgG1 (EU numbering).

In certain embodiments, the modified Fc region comprises one or more amino acid modifications selected from the group consisting of:

(i) P247A, P247C, P247D, P247F, P247G, P247H, P247I, P247K, P247L, P247M, P247N, P247R, P247S, P247T, P247V, or P247W;
(ii) I253A, I253D, I253K, I253L, I253M, I253N, I253R, I253S, I253V, I253E, I253Q, or I253T;
(iii) S254E, S254F, S254G, S254H, S254I, S254K, S254L, S254P, S254T, S254V, or S254W;
(iv) H310A, H310G, H310F, H310K, H310L, H310P, H310R, H310T, H310V, H310W, H310N, H310Q, or H310Y;

(v) Q311A, Q311C, Q311E, Q311G, Q311H, Q311F, Q311I, Q311K, Q311L, Q311N, Q311P, Q311R, Q311S, Q311T, Q311W, or Q311Y;

(vi) E345A, E345C, E345D, E345G, E345H, E345F, E345I, E345K, E345L, E345M, E345N, E345P, E345Q, E345R, E345S, E345T, E345V, E345W, or E345Y;

(vii) D/E356G, D/E356I, D/E356L, D/E356R, D/E356T, or D/E356V;

(viii) T359G, T359N, T359P, or T359R;

(ix) E382F, E382K, E382L, E382M, E382P, E382V, E382W, E382D, E382H, E382N, E382Q, E382S, E382T, or E382Y;

(x) G385A, G385D, G385H, G385I, G385L, G385N, G385P, G385Q, G385R, G385S, G385T, G385V, G385E, G385K, G385W, or G385Y;

(xi) Q386A, Q386C, Q386D, Q386E, Q386G, Q386H, Q386F, Q386I, Q386K, Q386L, Q386N, Q386P, Q386R, Q386S, Q386T, Q386V, Q386W, or Q386Y;

(xii) E430A, E430C, E430D, E430F, E430G, E430H, E430I, E430K, E430L, E430M, E430N, E430P, E430Q, E430R, E430S, E430T, E430V, E430W, or E430Y;

(xiii) H433R;

(xiv) N434D, N434E, N434G, N434K, N434R, N434S, N434V, N434W, N434H, N434Q, N434T, or N434Y;

(xv) Y436I, Y436K, Y436L, Y436R, Y436S, Y436T, Y436V, Y436W, Y436A, Y436E, Y436F, Y436H, Y436M, Y436N, or Y436Q;

(xvi) Q438C, Q438E, Q438I, Q438K, Q438L, Q438S, Q438T, Q438V, Q438W, Q438Y, Q438A, Q438G, Q438H, Q438N, Q438Q, or Q438R;

(xvii) K439A, K439D, K439E, K439H, K439L, K439P, K439R, K439T, K439Y, K439Q, or K439W;

(xviii) S440A, S440C, S440D, S440E, S440G, S440H, S440F, S440I, S440K, S440L, S440M, S440N, S440P, S440Q, S440R, S440T, S440V, S440W, or S440Y; and (xix) K447D, K447E, K447N, K447Q, or a deletion of K447.

In certain embodiments, the modified Fc region comprises one or more amino acid modifications selected from the group consisting of:

(i) P247G;

(ii) I253L, I253N, I253V, or I253Q;

(iii) S254L;

(iv) H310P, H310W, or H310Q;

(v) Q311E, Q311L, Q311R, or Q311W;

(vi) E345A, E345D, E345G, E345H, E345F, E345I, E345K, E345L, E345M, E345N, E345P, E345Q, E345R, E345S, E345T, E345V, E345W, or E345Y;

(vii) D/E356R;

(viii) T359R;

(ix) E382K, E382L, E382V, E382D, E382Q, or E382S;

(x) G385D, G385N, G385R, G385E, or G385K;

(xi) Q386K;

(xii) E430A, E430D, E430F, E430G, E430H, E430I, E430K, E430L, E430M, E430N, E430P, E430Q, E430R, E430S, E430T, E430V, E430W, or E430Y;

(xiii) H433R;

(xiv) N434K, N434R, N434W, N434H, or N434Q;

(xv) Y436I, Y436S, Y436T, Y436V, Y436N, or Y436Q;

(xvi) Q438C, Q438L, Q438S, Q438T, or Q438N;

(xvii) K439D, K439E, K439H, K439R, or K439Q;

(xviii) S440D, S440E, S440Q, S440W, or S440Y; and (xix) K447D, K447E, K447N, K447Q, or a deletion of K447.

In certain embodiments, the modified Fc region comprises one or more amino acid modifications selected from the group consisting of:

(i) P247D, P247F, P247G, P247K, P247R, or P247S;

(ii) I253V;

(iii) S254G, S254I, or S254L;

(iv) Q311I, Q311K, Q311L, Q311P, or Q311W;

(v) E345A, E345C, E345F, E345I, E345K, E345L, E345M, E345N, E345P, E345S, E345T, E345V, E345W, or E345Y;

(vi) D/E356I, D/E356L, D/E356R, D/E356T, or D/E356V;

(vii) T359N;

(viii) E382L or E382V;

(ix) G385A, G385D, G385H, G385I, G385L, G385N, G385P, G385Q, G385R, G385S, G385T, G385V, G385E, G385K, G385W, or G385Y;

(x) Q386K;

(xi) E430A, E430F, E430H, E430L, E430P, E430R, E430S, E430V, E430W, or E430Y;

(xii) N434W;

(xiii) Y436I; and (xiv) S440D.

In certain embodiments, the modified Fc region comprises one or more amino acid substitutions selected from the group consisting of: E345R, E430G and S440Y in the Fc region of a human IgG1 (EU numbering). In exemplary embodiments, the modified Fc region comprises a single amino acid substitution selected from the group consisting of: E345R, E430G and S440Y in the Fc region of a human IgG1 (EU numbering). In exemplary embodiments, the modified Fc region comprises a set of amino acid substitutions selected from the group consisting of: (a) E345R and E430G, (b) E345R and S440Y, (c) E430G and S440Y, wherein the substitutions are in the Fc region of a human IgG1 (EU numbering). In exemplary embodiments, the modified Fc region comprises amino acid substitutions E345R, E430G and S440Y in the Fc region of a human IgG1 (EU numbering).

In certain embodiments, the antigen binding region comprises an antigen binding region from a monospecific antibody, bispecific antibody or multispecific antibody.

In certain embodiments, the antigen binding region binds to OX40. In exemplary embodiments, the antigen binding region comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7. In exemplary embodiments, the antigen binding region comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and (b) a VL domain comprising (i) HVR-L1 comprising the amino acid sequence of SEQ ID NO:37, (ii) HVR-L2 comprising the amino acid sequence of SEQ ID NO:38, and (iii) HVR-L3 comprising an amino acid sequence selected from SEQ ID NO:42.

In certain embodiments, the Fc region further comprises a modification for attenuating effector function. In exemplary embodiments, the modification for attenuating effector function comprises amino acid substitutions at one or more amino acid residues (EU numbering) selected from the group consisting of:

(a) 297 in the Fc region of human IgG1,
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1.

In certain embodiments, the modification for attenuating effector function comprises one or more amino acid substitutions (EU numbering) selected from the group consisting of:
(a) N297A in the Fc region of human IgG1,
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) 118 to 260 in the Fc region of human IgG2 or 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

In certain embodiments, the modification for attenuating effector function does not result in a modification of the glycosylation pattern of the Fc region.

In certain embodiments, the hexamer enhances signal transduction mediated by a cell surface receptor bound by the hexamer.

In another aspect, the application provides a method of identifying an antigen binding polypeptide having agonist activity for a cell surface receptor, comprising: (a) providing a plurality of hexameric antigen binding complexes, wherein each complex comprises six subunits each comprising an antigen binding polypeptide comprising at least one antigen binding region and a modified Fc region that enhances hexamer formation, (b) screening the antigen binding complexes against a cell surface receptor, and (c) selecting antigen binding complexes having agonist activity for the cell surface receptor.

In certain embodiments, the Fc region further comprises a modification that attenuates effector function.

In another aspect, the application provides a nucleic acid encoding any of the complexes or antigen binding polypeptides described herein.

In another aspect, the application provides a vector comprising a nucleic acid encoding any of the complexes or antigen binding polypeptides described herein. In certain embodiments, the vector is an expression vector.

In another aspect, the application provides a host cell comprising a vector comprising a nucleic acid encoding any of the complexes or antigen binding polypeptides described herein. In certain embodiments, the host cell is prokaryotic or eukaryotic.

In another aspect, the application provides a method for making an antigen binding polypeptide having agonist activity comprising culturing a host cell comprising a vector comprising a nucleic acid encoding any of the complexes or antigen binding polypeptides described herein under conditions suitable for expression of the nucleic acid encoding the complex or antigen binding polypeptide. In certain embodiments, the methods may further comprises recovering the complex, hexamer or polypeptide from the host cell.

In another aspect, the application provides a pharmaceutical composition comprising any of the complexes or antigen binding polypeptides described herein and a pharmaceutically acceptable carrier.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION OF EMBODIMENTS OF THE INVENTION

I. Definitions

Figure 1:
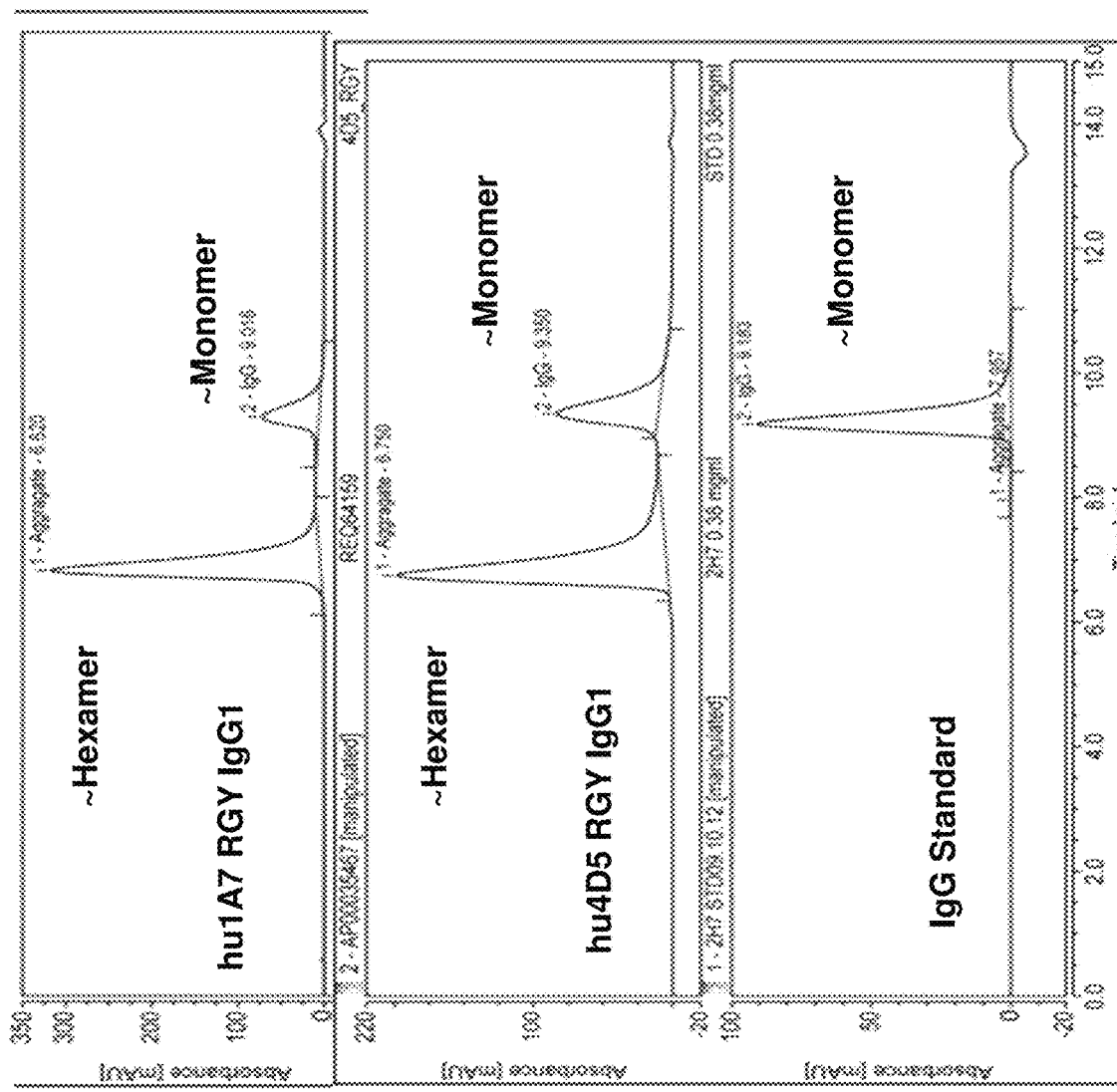
FIG. 1 shows analytical Size Exclusion Chromatography (SEC) chromatograms demonstrating that RGY variant versions of hu1A7 and hu4D5 populate hexameric and monomeric species, relative to native IgG1 standard control.

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al, Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

"Antibody fragments" comprise a portion of an intact antibody, preferably comprising the "antigen binding region" thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Plückthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et ah, Proc. Natl. Acad. Set USA, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 µM, 3 µM to 0.001 µM, 1 µM to 0.001 µM, 0.5 µM to 0.001 µM, or 0.1 µM to 0.001 µM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al, Proc. Natl. Acad. Sci. USA 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., Nature 321:522-525 (1986); Riechmann et al, Nature 332: 323-329 (1988); and Presta, Curr. Op. Struct. Biol. 2:593-596 (1992).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding and antibody-dependent cell-mediated cytotoxicity (ADCC); phagocytosis; down regulation of cell surface receptors.

"Antibody-dependent cell-mediated cytotoxicity" or "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et ah, Proc. Natl. Acad. Set (USA) 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

"Complement dependent cytotoxicity" or "CDC" refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., J. Immunol. Methods 202: 163 (1996), may be performed.

The terms "Fc receptor" or "FcR" are used to describe a receptor that binds to the Fc region of an antibody. In some embodiments, the FcR is a native sequence human FcR.

Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an activating receptor) and FcγRIIB (an inhibiting receptor), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, {see Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al, J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al, J. Immunol. 117:587 (1976) and Kim et al, J. Immunol. 24:249 (1994)).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. The Fc sequence of an immunoglobulin generally comprises two constant domains, a CH2 domain and a CH3 domain, and optionally comprises a CH4 domain. By "Fc polypeptide" herein is meant one of the polypeptides that make up an Fc region, e.g., a monomeric Fc. An Fc region may be obtained from any suitable immunoglobulin, such as IgG1 IgG2, IgG3, or IgG4 subtypes, IgA, IgE, IgD or IgM. The Fc region comprises the carboxy-terminal portions of both H chains held together by disulfides. The effector functions of antibodies are determined by sequences in the Fc region; this region is also the part recognized by Fc receptors (FcR) found on certain types of cells. In some embodiments, an Fc polypeptide comprises part or all of a wild type hinge sequence (generally at its N terminus). In some embodiments, an Fc polypeptide does not comprise a functional or wild type hinge sequence.

A "modified Fc region" or "Fc variant" comprises an amino acid sequence which differs from that of a native sequence Fc region by virtue of at least one amino acid modification, preferably one or more amino acid substitution(s). Preferably, the modified Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The modified Fc region herein will preferably possess at least about 80% homology with a native sequence Fc region and/or with an Fc region of a parent polypeptide, and most preferably at least about 90% homology therewith, more preferably at least about 95%, at least about 96%, at least about 97%, at least about 98% or at least about 99% homology therewith.

The term "agonist", "agonistic", "agonism" or "agonize" as used herein in general refers to a binding molecule (e.g., an antigen binding polypeptide or antigen binding complex) which binds to a receptor on the surface of a cell and is capable of initiating/mimicking/stimulating a reaction or activity that is similar to or the same as that initiated/mimicked/stimulated by the receptor's natural ligand. In exemplary embodiments, an agonist as described herein is capable of inducing/augmenting/enhancing/stimulating the activation of a signal transduction pathway associated with the receptor.

The term "cell surface receptor," as used herein, refers to any native cell surface receptor from any vertebrate source, including mammals such as primates (e.g. humans) and rodents (e.g., mice and rats), unless otherwise indicated. The term encompasses "full-length," unprocessed cell surface receptor as well as any form of cell surface receptor that results from processing in the cell. The term also encompasses naturally occurring variants of cell surface receptor, e.g., splice variants or allelic variants.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include epithelial ovarian cancer, fallopian tube cancer, primary peritoneal cancer, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer (including platinum sensitive and platinum resistant ovarian cancer), liver cancer, bladder cancer, hepatoma, breast cancer, colon cancer, colorectal cancer, fallopian tube, peritoneal, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "effective amount" of an agent, e.g., a pharmaceutical formulation, refers to an amount effective, at dosages and for periods of time necessary, to achieve the desired therapeutic or prophylactic result.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Antigen Binding Complexes with Agonist Activity

Provided herein are antigen binding complexes that bind to at least one cell surface receptor and have agonistic activity (e.g., an agonist antigen binding complex). The complexes may comprise two, three, four, five, six or more antigen binding polypeptides. In exemplary embodiments, the antigen binding complex comprises six antigen binding polypeptides thereby forming a hexamer.

In certain embodiments, the antigen binding polypeptides that form the complex have agonist activity when not in the complex (e.g., an antibody in its native bivalent form may have agonist activity). In such embodiments, the agonist activity of the antigen binding polypeptide may be increased in the context of the complex, e.g., a complex comprising six antibody subunits may have greater agonist activity than the native bivalent antibody. In other embodiments, the antigen binding polypeptides that form the complex do not have agonist activity in non-complexed form (e.g., an antibody in its native bivalent form does not have agonist activity) but do have agonist activity when formed into the complex.

In certain embodiments, all of the antigen binding polypeptides that form a complex may be the same, e.g., a hexamer formed of six subunits of the same monospecific antibody, the same bispecific antibody, the same multispecific antibody, the same DAF, etc. In certain embodiments, a complex may be formed of two or more different antigen binding polypeptides. For example, a complex may be formed of at least two different antibodies that bind to different epitopes on the same target, two different antibodies that bind to different targets, at least two different bispecifics (each arm of a bispecific may bind to different epitopes on the same target or to two different targets), at least two different DAFs, etc. In one embodiment, a complex comprises at least two different antibodies that bind to different epitopes on the same cell surface receptor. In another embodiment, a complex comprises a bispecific antibody, wherein each arm of the bispecific antibody binds to a different epitope on the same cell surface receptor.

In one embodiment, an antigen binding complex comprises six antibodies that all bind to the same target.

In another embodiment, an antigen binding complex comprises six antibodies, wherein at least one of the antibodies binds to a first target and at least one of the antibodies binds to a second target. In such embodiments, the ratio of antibody 1 to antibody 2 in the complex may be any possible combination, e.g., 1 antibody subunit binds to target 1 and 5 antibody subunits bind to target 2, 2 antibody subunits bind to target 1 and 4 antibody subunits bind to target 2, 3 antibody subunits bind to target 1 and 3 antibody subunits bind to target 2, 4 antibody subunits bind to target 1 and 2 antibody subunits bind to target 2, or 5 antibody subunits bind to target 1 and 1 antibody subunit binds to target 2. The ratio of antibodies that make up the complex may be controlled by mixing the desired ratio of antibody 1 to antibody 2 (e.g., 1:1 to form complexes having equal parts antibody 1 and antibody 2) and allowing the complex to self assemble. Alternatively, the ratio of antibodies that make up the complex may be controlled by using Fc mutations in the different antibodies that do not promote self assembly, but only promote assembly with an antibody having a different Fc mutation (such mutations are described further below). In an exemplary embodiment, antibody 1 and antibody 2 bind to cell surface receptors that heterodimerize.

In another embodiment, an antigen binding complex comprises six antibodies, wherein at least three, four, five or all six of the antibodies bind to different targets. In one embodiment, an antigen binding complex comprises six antibodies or subunits that each bind to a different target.

In another embodiment, an antigen binding complex comprises six bispecific antibodies (or DAFs) that bind to the same set of targets.

In another embodiment, an antigen binding complex comprises six bispecific antibodies (or DAFs), wherein at least one of the bispecifics binds to antigens 1 and 2 and at least one of the bispecifics binds to antigens 3 and 4. As described above for the monospecific antibody complex, any ratio of the bispecific 1 to bispecific 2 within the complex is contemplated herein.

In another embodiment, an antigen binding complex comprises six bispecific antibodies, wherein at least three, four, five or all six of the bispecific antibodies bind to different sets of targets. In one embodiment, an antigen binding complex comprises six bispecific antibodies that each bind to a different set of targets (e.g., the complex binds to 12 different targets).

In some embodiments, an antigen binding complex comprises six subunits, with each subunit comprising an antibody having two heavy chains and two light chains. In some embodiments, each heavy chain comprises a heavy chain variable domain (VH) and a set of heavy chain constant domains, e.g., a CH1 domain, a CH2 domain, a CH3 domain, and, optionally (e.g., for IgM or IgE antibodies), a CH4 domain. In some embodiments, each light chain comprises a light chain variable domain (VL) and a constant light (CL) domain (e.g., kappa or lambda). In some embodiments, the heavy chains of each subunit comprise one or more modifications that promote hexamer formation, e.g., as described below. In some embodiments, the heavy chains of each subunit comprise one or more modifications that reduce effector function, e.g., as described below.

In an exemplary embodiment, the application provides an agonist antigen binding complex comprising six antibodies, wherein the antibodies comprise a human IgG1 Fc region that comprises a E345R, E430G and S440Y modification that promotes hexamer formation.

In another exemplary embodiment, the application provides an agonist antigen binding complex comprising six antibodies, wherein the antibodies comprise a human IgG1 Fc region that comprises a E345R, E430G and S440Y modification that promotes hexamer formation and one or more modifications that reduce effector function.

In another exemplary embodiment, the application provides an agonist antigen binding complex comprising six antibodies, wherein the antibodies comprise a human IgG1 Fc region that comprises a E345R, E430G and S440Y modification that promotes hexamer formation and a L234A, L235A and P329G modification that reduces effector function.

Antigen Binding Polypeptides

Antigen binding polypeptides suitable for forming the complexes described herein comprise at least one antigen binding region for a cell surface receptor and a modified Fc region that enhances intermolecular interactions between Fc regions, e.g., complex formation such as hexamer formation. The antigen binding polypeptides described herein may comprise an antibody, an antigen binding region of an antibody (e.g., an antibody fragment) fused to an Fc region, or a non-antibody antigen binding region protein fused to an Fc region. In exemplary embodiments, the antigen binding polypeptide is an antibody which binds to a cell surface receptor and has a modified Fc region.

The antigen binding polypeptides described herein each typically contain at least two polypeptides. In particular, the Fc region for each antigen binding polypeptide is a dimer formed between two polypeptides (either a homodimer or a heterodimer as described further below). Similarly, the antigen binding region attached to one of the polypeptides of the Fc region may contain two polypeptides, e.g., when the antigen binding region is an antibody fragment it may contain heavy and light chain variable regions. Accordingly, in one embodiment, an antigen binding polypeptide that is an antibody comprises 4 polypeptide chains, e.g., two heavy chains (comprising a heavy chain variable region and an Fc domain) and two light chains (comprising a light chain variable region). A complex comprising six such antigen binding polypeptides therefore contains 24 polypeptides (e.g., 6 subunits each comprising 2 heavy chains and 2 light chains).

Antibodies

In certain embodiments, an antigen binding polypeptide provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, an antigen binding polypeptide provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In certain embodiments, an antigen binding polypeptide provided herein is a multispecific antibody, e.g. a bispecific antibody. Multispecific antibodies are monoclonal antibodies that have binding specificities for at least two different sites. In certain embodiments, one of the binding specificities is for cell surface receptor and the other is for any other antigen. In certain embodiments, bispecific antibodies may bind to two different epitopes of the same or different cell surface receptor. Bispecific antibodies may also be used to localize cytotoxic agents to cells which express the cell surface receptor.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to cell surface receptor as well as another, different antigen (see, US 2008/0069820, for example).

Antibodies suitable as antigen binding polypeptides as described herein may be isolated by screening combinatorial libraries for polypeptides with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360. Antibodies or antibody fragments isolated from human antibody libraries are considered human antibodies or human antibody fragments herein.

Antigen Binding Region of an Antibody

In certain embodiments, the antigen binding polypeptides described herein comprise an antigen binding region that binds to a cell surface receptor and an Fc region. In an exemplary embodiment, the antigen binding polypeptides described herein comprise an antigen binding region of an antibody that binds to a cell surface receptor fused to an Fc region. In exemplary embodiments, an antigen binding region of an antibody refers to an antibody fragment, such as, for example, a Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein. Antibody fragments can be made from any of the antibodies described herein, including for example, monoclonal, chimeric, humanized, human, bispecific, multispecific, DAF, etc. antibody formats.

The antigen binding regions described herein may comprise one or more polypeptides. In certain embodiments, the antigen binding regions comprises one polypeptide, such as, for example a single chain Fv (scFv) wherein the heavy and light chain variable regions of an antibody are attached via a linker. In other embodiments, the antigen binding region comprises two polypeptide, such as, for example a Fab antibody fragment wherein the heavy and light chain variable regions are separate polypeptide chains that naturally associate to form an antigen binding region having 6 CDRs.

Non-Antibody Antigen Binding Regions

In certain embodiments, the antigen binding polypeptides described herein comprise an antigen binding region that binds to a cell surface receptor and an Fc region. In an exemplary embodiment, the antigen binding polypeptides described herein comprise a non-antibody antigen binding region that binds to a cell surface receptor fused to an Fc region. Examples of non-antibody antigen binding regions include, for example, ligands, ligand fragments, or multimers thereof, that bind to a cell surface receptor. Examples of non-antibody antigen binding regions that bind to OX40 are described below. Examples of non-antibody binding regions that bind to Tie2 are described in WO 2008/049227.

Attachment of an Antigen Binding Region to an Fc Region

The antigen binding regions described herein (both antibody derived antigen binding regions and non-antibody antigen binding regions) may be fused to a variant Fc region as described herein. Any method for covalently attaching two polypeptides may be used to fuse together the antigen binding region with the Fc domain, including for example, expression as a single polypeptide (with or without an intervening polypeptide linker), chemical linkage or linkage via a polymeric group (such as, for example, a single or branched polyethylene glycol (PEG) linker). In certain embodiments, the linker may be a cleavable linker.

In certain embodiments, a linker may be a polypeptide linker. In one embodiment, the polypeptide linker is a hinge sequence from an antibody, or a variant thereof. For example, the hinge sequence may comprise amino acid residues 216-238 (EU numbering) of an antibody, such as, for example, an IgG1, IgG2, IgG3 or IgG4 antibody, or fragments or derivatives thereof. In an exemplary embodiment, a hinge based linker comprises the sequence CDKTH-TCPPCPAPELLGGP (SEQ ID NO:219), or fragments or derivatives thereof. In certain embodiments, the polypeptide linker may be a flexible linker of varying length (e.g., 5, 10, 15, 20, 25, 30, 35, 40, 45, 50 or more amino acids). Suitable linkers are known in the art, see for example, Protein Engineering, 9(3), 299-305, 1996. Exemplary peptide linkers include, for example:

```
Ser

Gly-Ser

Gly-Gly-Ser

Ser-Gly-Gly (SEQ ID NO: 220)
Gly-Gly-Gly-Ser (SEQ ID NO: 221)
Ser-Gly-Gly-Gly (SEQ ID NO: 222)
Gly-Gly-Gly-Gly-Ser (SEQ ID NO: 223)
Ser-Gly-Gly-Gly-Gly (SEQ ID NO: 224)
Gly-Gly-Gly-Gly-Gly-Ser (SEQ ID NO: 225)
Ser-Gly-Gly-Gly-Gly-Gly (SEQ ID NO: 226)
Gly-Gly-Gly-Gly-Gly-Gly-Ser (SEQ ID NO: 227)
Ser-Gly-Gly-Gly-Gly-Gly-Gly (SEQ ID NO: 228)
(Gly-Gly-Gly-Gly-Ser)$_n$
and (SEQ ID NO: 229)
(Ser-Gly-Gly-Gly-Gly)$_n$
``` wherein n is an integer not less than one. In certain embodiments n may be 1, 2, 3, 4, 5, 6, 7, 8, 9, 10, 15, or 20.

In certain embodiments, a linker may be a chemical linker. Suitable chemical linkers are known in the art and commercially available. Exemplary chemical linkers include, for example, N-hydroxy succinimide (NHS), disuccinimidyl suberate (DSS), bis(sulfosuccinimidyl)suberate (BS$^3$), dithiobis(succinimidyl propionate) (DSP), dithiobis (sulfosuccinimidyl propionate) (DTSSP), ethylene glycolbis (succinimidyl succinate) (EGS), ethylene glycolbis(sulfosuccinimidyl succinate) (sulfo-EGS), disuccinimidyl tartrate (DST), disulfosuccinimidyl tartrate (sulfo-DST), bis[2-(succinimido oxycarbonyloxy)ethyl]sulfone (BSOCOES), and bis[2-(sulfosuccinimido oxycarbonyloxy) ethyl]sulfone (sulfo-BSOCOES).

In certain embodiments, an antigen binding region of an antibody is expressed as a single polypeptide with the Fc domain. As the Fc domain is a dimer, each polypeptide contained in the Fc dimer may be fused to an antigen binding region of an antibody (e.g., such that a hexameric complex contains 12 antigen binding regions) or only of the polypeptides contained in the Fc dimer may be fused to an antigen binding region of an antibody (e.g., such that a hexameric complex contains 6 antigen binding regions). In one exemplary embodiment, each polypeptide in the Fc dimer is fused to a Fab fragment, such that a hexameric complex contains 12 Fab fragments. In one exemplary embodiment, only of the polypeptides in the Fc dimer is fused to a Fab fragment, such that a hexameric complex contains 6 Fab fragments. In one exemplary embodiment, each polypeptide in the Fc dimer is fused to a F(ab')$_2$ fragment, such that a hexameric complex contains 12 F(ab')$_2$ fragments. In one exemplary embodiment, only one of the polypeptides in the Fc dimer is fused to a F(ab')$_2$ fragment, such that a hexameric complex contains 6 F(ab')$_2$ fragments.

In certain embodiments, a non-antibody antigen binding region is expressed as a single polypeptide with the Fc domain. As the Fc domain is a dimer, each polypeptide contained in the Fc dimer may be fused to a non-antibody antigen binding region (e.g., such that a hexameric complex contains 12 non-antibody antigen binding regions) or only of the polypeptides contained in the Fc dimer may be fused to a non-antibody antigen binding region (e.g., such that a hexameric complex contains 6 non-antibody antigen binding regions).

Antigen Binding Regions Comprising OX40 Agonists

In one embodiment, the antigen binding polypeptide described herein comprises an antigen binding region that binds to and agonizes human OX40. In certain embodiments, the antigen binding polypeptide comprises an antigen binding region of an anti-human OX40 agonist antibody. In certain embodiments, the antigen binding polypeptide comprises an antigen binding region that is a non-antibody OX40 agonist.

OX40 Agonist Antibodies

Provided herein is an agonist antigen binding complex that binds OX40. In some embodiments, the agonist antigen binding complex comprises six OX40 agonist antibodies (e.g., a hexameric antigen binding complex comprising six OX40 agonist antibody subunits). Exemplary antibody subunits and exemplary features thereof are described infra. In some embodiments, the hexameric antigen binding complex is an agonist antigen binding complex that activates a biological activity of the antigen it binds (e.g., OX40). Without wishing to be bound to theory, it is thought that agonist antigen binding complexes (e.g., hexameric agonist antigen binding complexes) may be particularly advantageous for scenarios in which antibody cross-linking by effector cells may be important for agonist activity (e.g., by inducing clustering of, and subsequent signaling by, the target), but effector cells may not be plentiful at the site of action (e.g., in a tumor with low levels of effector cells). In these scenarios, an agonist antigen binding complex such as a hexameric agonist antigen binding complex may allow for and/or enhance agonist activity in the absence of plentiful effector cells.

In some embodiments, the antigen binding complex comprises an anti-human OX40 agonist antibody that comprises at least one, two, three, four, five, or all six HVRs for the same antibody as listed in Table A below. For example, in certain embodiments, the OX40 antibody included in the complex contains all six of the HVRs from the same antibody as listed in Table A. In other embodiments, the complex comprises an anti-human OX40 agonist antibody that comprises a heavy chain variable region ($V_H$) and/or a light chain variable region ($V_L$) as for the same antibody as listed in Table A below. It will be appreciated, however, that the the HVR, $V_H$, and/or $V_L$ sequences as listed in Table A with reference to particular antibodies are not limited to these particular antibodies; instead, these sequences can be suitably combined in a variety of configurations not explicitly listed in Table A by one of skill in the art.

In some embodiments, the anti-human OX40 agonist antibody comprises at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7.

In some embodiments, the anti-human OX40 agonist antibody comprises at least one, at least two, or all three VH HVR sequences selected from (a) HVR-H1 comprising the amino acid sequence of SEQ ID NO:2; (b) HVR-H2 comprising the amino acid sequence of SEQ ID NO:3; and (c) HVR-H3 comprising the amino acid sequence of SEQ ID NO:4. In one embodiment, the antibody comprises HVR-H3 comprising the amino acid sequence of SEQ ID NO:4. In another embodiment, the antibody comprises HVR-H3 comprising the amino acid sequence of SEQ ID NO:4 and HVR-L3 comprising the amino acid sequence of SEQ ID NO:7. In a further embodiment, the antibody comprises HVR-H3 comprising the amino acid sequence of SEQ ID NO:4, HVR-L3 comprising the amino acid sequence of SEQ ID NO:7, and HVR-H2 comprising the amino acid sequence of SEQ ID NO:3. In a further embodiment, the antibody comprises (a) HVR-H1 comprising the amino acid sequence of SEQ ID NO:2; (b) HVR-H2 comprising the amino acid sequence of SEQ ID NO:3; and (c) HVR-H3 comprising the amino acid sequence of SEQ ID NO:4.

In some embodiments, the anti-human OX40 agonist antibody comprises at least one, at least two, or all three VL HVR sequences selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7. In one embodiment, the antibody comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:7.

In one embodiment, the anti-human OX40 agonist antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7.

In some embodiments, the anti-human OX40 agonist antibody comprises at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:26.

In some embodiments, the anti-human OX40 agonist antibody comprises HVR-H3 comprising the amino acid sequence of SEQ ID NO:4 and HVR-L3 comprising the amino acid sequence of SEQ ID NO:26. In a further embodiment, the antibody comprises HVR-H3 comprising the amino acid sequence of SEQ ID NO:4, HVR-L3 comprising the amino acid sequence of SEQ ID NO:26, and HVR-H2 comprising the amino acid sequence of SEQ ID NO:3.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:26.

In one embodiment, the anti-human OX40 agonist antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:26.

In some embodiments, the anti-human OX40 agonist antibody comprises at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:27.

In one embodiment, the anti-human OX40 agonist antibody comprises HVR-H3 comprising the amino acid sequence of SEQ ID NO:4 and HVR-L3 comprising the amino acid sequence of SEQ ID NO:27. In a further embodiment, the antibody comprises HVR-H3 comprising the amino acid sequence of SEQ ID NO:4, HVR-L3 comprising the amino acid sequence of SEQ ID NO:27, and HVR-H2 comprising the amino acid sequence of SEQ ID NO:3.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:27.

In one embodiment, the anti-human OX40 agonist antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:27.

In some embodiments, the anti-human OX40 agonist antibody comprises at least one, two, three, four, five, or six HVRs selected from (a) HVR-H1 comprising the amino acid sequence of SEQ ID NO:2, 8 or 9; (b) HVR-H2 comprising the amino acid sequence of SEQ ID NO:3, 10, 11, 12, 13 or 14; (c) HVR-H3 comprising the amino acid sequence of SEQ ID NO:4, 15, or 19; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7, 22, 23, 24, 25, 26, 27, or 28.

In some embodiments, the anti-human OX40 agonist antibody comprises at least one, at least two, or all three VH HVR sequences selected from (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; and (c) HVR-H3 comprising the amino acid sequence of SEQ ID NO: 4, 15, or 19. In one embodiment, the antibody comprises HVR-H3 comprising the amino acid sequence of SEQ ID NO: 4, 15, or 19. In another embodiment, the antibody comprises HVR-H3 comprising the amino acid sequence of SEQ ID NO:4, 15, or 19 and HVR-L3 comprising the amino acid sequence of SEQ ID NO: 7, 22, 23, 24, 25, 26, 27, or 28. In a further embodiment, the antibody comprises HVR-H3 comprising the amino acid sequence of SEQ ID NO: 4, 15, or 19, HVR-L3 comprising the amino acid sequence of SEQ ID NO: 7, 22, 23, 24, 25, 26, 27, or 28, and HVR-H2 comprising the amino acid sequence of SEQ ID NO: 3, 10, 11, 12, 13 or 14. In a further embodiment, the antibody comprises (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; and (c) HVR-H3 comprising the amino acid sequence of SEQ ID NO: 4, 15, or 19.

In some embodiments, the anti-human OX40 agonist antibody comprises at least one, at least two, or all three VL HVR sequences selected from (a) HVR-L1 comprising the amino acid sequence of SEQ ID NO: 5; (b) HVR-L2 comprising the amino acid sequence of SEQ ID NO:6; and (c) HVR-L3 comprising the amino acid sequence of SEQ ID NO: 7, 22, 23, 24, 25, 26, 27, or 28. In one embodiment, the antibody comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO: 7, 22, 23, 24, 25, 26, 27, or 28.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO: 2, 8 or 9, (ii) HVR-H2 comprising the amino acid sequence of SEQ ID NO: 3, 10, 11, 12, 13 or 14, and (iii) HVR-H3 comprising an amino acid sequence selected from SEQ ID NO: 4, 15, or 19; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO: 7, 22, 23, 24, 25, 26, 27, or 28.

In some embodiments, the anti-human OX40 agonist antibody comprises (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; (c) HVR-H3 comprising the amino acid sequence of SEQ ID NO: 4, 15, or 19; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO: 7, 22, 23, 24, 25, 26, 27, or 28.

In some embodiments, the anti-human OX40 agonist antibody comprises at least one, two, three, four, five, or six HVRs selected from (a) HVR-H1 comprising the amino acid sequence of SEQ ID NO:172; (b) HVR-H2 comprising the amino acid sequence of SEQ ID NO:173; (c) HVR-H3 comprising the amino acid sequence of SEQ ID NO:174; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:175. In some embodiment, HVR-H2 is not DMYPDAAAASYNQKFRE (SEQ ID NO: 216). In some embodiments, HVR-H3 is not APRWAAAA (SEQ ID NO: 217). In some embodiments, HVR-L3 is not QAAAAAAAT (SEQ ID NO: 218).

In some embodiments, the anti-human OX40 agonist antibody comprises at least one, at least two, or all three VH HVR sequences selected from (a) HVR-H1 comprising the amino acid sequence of SEQ ID NO:172; (b) HVR-H2 comprising the amino acid sequence of SEQ ID NO:173; and (c) HVR-H3 comprising the amino acid sequence of SEQ ID NO:174. In one embodiment, the antibody comprises HVR-H3 comprising the amino acid sequence of SEQ ID NO:174. In another embodiment, the antibody comprises HVR-H3 comprising the amino acid sequence of SEQ ID NO:174 and HVR-L3 comprising the amino acid sequence of SEQ ID NO:175. In a further embodiment, the antibody comprises HVR-H3 comprising the amino acid sequence of SEQ ID NO:174, HVR-L3 comprising the amino acid sequence of SEQ ID NO:175, and HVR-H2 comprising the amino acid sequence of SEQ ID NO:173. In a further embodiment, the antibody comprises (a) HVR-H1 comprising the amino acid sequence of SEQ ID NO:172; (b) HVR-H2 comprising the amino acid sequence of SEQ ID NO:173; and (c) HVR-H3 comprising the amino acid sequence of SEQ ID NO:174. In some embodiment, HVR-H2 is not DMYPDAAAASYNQKFRE (SEQ ID NO: 216). In some embodiments, HVR-H3 is not APRWAAAA (SEQ ID NO: 217). In some embodiments, HVR-L3 is not QAAAAAAAT (SEQ ID NO: 218).

In one embodiment, the anti-human OX40 agonist antibody comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:175. In some embodiments, HVR-L3 is not QAAAAAAAT (SEQ ID NO: 218).

In some embodiments, the anti-human OX40 agonist antibody comprises at least one, at least two, or all three VH HVR sequences selected from (i) HVR-H1 comprising the amino acid sequence of SEQ ID NO:172, (ii) HVR-H2 comprising the amino acid sequence of SEQ ID NO:173, and (iii) HVR-H3 comprising an amino acid sequence selected from SEQ ID NO:174; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:175.

In some embodiments, the anti-human OX40 agonist antibody comprises (a) HVR-H1 comprising the amino acid sequence of SEQ ID NO:172; (b) HVR-H2 comprising the amino acid sequence of SEQ ID NO:173; (c) HVR-H3 comprising the amino acid sequence of SEQ ID NO:174; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:175. In some embodiment, HVR-H2 is not DMYPDAAAASYNQKFRE (SEQ ID NO: 216). In some embodiments, HVR-H3 is not APRWAAAA (SEQ ID NO: 217). In some embodiments, HVR-L3 is not QAAAAAAAT (SEQ ID NO: 218).

All possible combinations of the above substitutions are encompassed by the consensus sequences of SEQ ID NO:172, 173, 174 and 175.

In some embodiments, the anti-human OX40 agonist antibody comprises at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39; and (f) HVR-L3 comprising the amino acid sequence of SEQ ID NO:42.

In some embodiments, the anti-human OX40 agonist antibody comprises at least one, at least two, or all three VH HVR sequences selected from (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33. In one embodiment, the antibody comprises HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO:42. In a further embodiment, the antibody comprises HVR-H3 comprising the amino acid sequence of SEQ ID NO:33, HVR-L3 comprising the amino acid sequence of SEQ ID NO:42, and HVR-H2 comprising the amino acid sequence of SEQ ID NO:30. In a further embodiment, the antibody comprises (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33.

In some embodiments, the anti-human OX40 agonist antibody comprises at least one, at least two, or all three VL HVR sequences selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42. In one embodiment, the antibody comprises (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42. In some embodiments, the anti-human OX40 agonist antibody comprises at least one, at least two, or all three VH HVR sequences selected from (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33. In one embodiment, the antibody comprises (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:39, and (c) HVR-L3 comprising the amino acid sequence of SEQ ID NO:42.

In one embodiment, the anti-human OX40 agonist antibody comprises (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39; and (f) HVR-L3 comprising an amino acid sequence selected from SEQ ID NO:42.

In some embodiments, the anti-human OX40 agonist antibody comprises at least one, at least two, or all three VL HVR sequences selected from (a) HVR-L1 comprising the amino acid sequence of SEQ ID NO:37; (b) HVR-L2 comprising the amino acid sequence of SEQ ID NO:38; and (c) HVR-L3 comprising the amino acid sequence of SEQ ID NO:42. In one embodiment, the antibody comprises (a) HVR-L1 comprising the amino acid sequence of SEQ ID NO:37; (b) HVR-L2 comprising the amino acid sequence of SEQ ID NO:38; and (c) HVR-L3 comprising the amino acid sequence of SEQ ID NO:42. In some embodiments, the anti-human OX40 agonist antibody comprises at least one, at least two, or all three VH HVR sequences selected from (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33. In one embodiment, the antibody comprises (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (c) HVR-L3 comprising the amino acid sequence of SEQ ID NO:42.

In some embodiments, the anti-human OX40 agonist antibody comprises at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:40; and (f) HVR-L3 comprising the amino acid sequence of SEQ ID NO:42.

In some embodiments, the anti-human OX40 agonist antibody comprises at least one, at least two, or all three VL HVR sequences selected from (a) HVR-L1 comprising the amino acid sequence of SEQ ID NO:37; (b) HVR-L2 comprising the amino acid sequence of SEQ ID NO:40; and (c) HVR-L3 comprising the amino acid sequence of SEQ ID NO:42. In one embodiment, the antibody comprises (a) HVR-L1 comprising the amino acid sequence of SEQ ID NO:37; (b) HVR-L2 comprising the amino acid sequence of SEQ ID NO:40; and (c) HVR-L3 comprising the amino acid sequence of SEQ ID NO:42.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:40, and (c) HVR-L3 comprising the amino acid sequence of SEQ ID NO:42.

In one embodiment, the anti-human OX40 agonist antibody comprises (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:40; and (f) HVR-L3 comprising an amino acid sequence selected from SEQ ID NO:42.

In some embodiments, the anti-human OX40 agonist antibody comprises at least one, two, three, four, five, or six HVRs selected from (a) HVR-H1 comprising the amino acid sequence of SEQ ID NO:29; (b) HVR-H2 comprising the amino acid sequence of SEQ ID NO:30, 31, or 32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39, 40 or 41; and (f) HVR-L3 comprising the amino acid sequence of SEQ ID NO:42, 43, or 44.

In some embodiments, the anti-human OX40 agonist antibody comprises at least one, at least two, or all three VH HVR sequences selected from (a) HVR-H1 comprising the amino acid sequence of SEQ ID NO:29; (b) HVR-H2 comprising the amino acid sequence of SEQ ID NO: 30, 31, or 32; and (c) HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO: 42, 43, or 44. In a further embodiment, the antibody comprises HVR-H3 comprising the amino acid sequence of SEQ ID NO:33, HVR-L3 comprising the amino acid sequence of SEQ ID NO: 42, 43, or 44, and HVR-H2 comprising the amino acid sequence of SEQ ID NO: 39, 40 or 41. In a further embodiment, the antibody comprises (a) HVR-H1 comprising the amino acid sequence of SEQ ID NO:29; (b) HVR-H2 comprising the amino acid sequence of SEQ ID NO:30, 31, or 32; and (c) HVR-H3 comprising the amino acid sequence of SEQ ID NO:33.

In some embodiments, the anti-human OX40 agonist antibody comprises at least one, at least two, or all three VL HVR sequences selected from (a) HVR-L1 comprising the amino acid sequence of SEQ ID NO:37; (b) HVR-L2 comprising the amino acid sequence of SEQ ID NO: 39, 40 or 41; and (c) HVR-L3 comprising the amino acid sequence of SEQ ID NO: 42, 43, or 44. In one embodiment, the antibody comprises (a) HVR-L1 comprising the amino acid sequence of SEQ ID NO:37; (b) HVR-L2 comprising the amino acid sequence of SEQ ID NO: 39, 40 or 41; and (c) HVR-L3 comprising the amino acid sequence of SEQ ID NO: 42, 43, or 44.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO: 30, 31, or 32, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO: 39, 40 or 41, and (c) HVR-L3 comprising the amino acid sequence of SEQ ID NO: 42, 43, or 44.

In some embodiments, the anti-human OX40 agonist antibody comprises (a) HVR-H1 comprising the amino acid sequence of SEQ ID NO:29; (b) HVR-H2 comprising the amino acid sequence of SEQ ID NO: 30, 31, or 32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO: 39, 40 or 41; and (f) HVR-L3 comprising an amino acid sequence selected from SEQ ID NO: 42, 43, or 44.

In some embodiments, the anti-human OX40 agonist antibody comprises at least one, at least two, or all three VH HVR sequences selected from (a) HVR-H1 comprising the amino acid sequence of SEQ ID NO:29; (b) HVR-H2 comprising the amino acid sequence of SEQ ID NO:175; and (c) HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO:177. In a further embodiment, the antibody comprises HVR-H3 comprising the amino acid sequence of SEQ ID NO:33, HVR-L3 comprising the amino acid sequence of SEQ ID NO:178, and HVR-H2 comprising the amino acid sequence of SEQ ID NO:176. In a further embodiment, the antibody comprises (a) HVR-H1 comprising the amino acid sequence of SEQ ID NO:29; (b) HVR-H2 comprising the amino acid sequence of SEQ ID NO:176; and (c) HVR-H3 comprising the amino acid sequence of SEQ ID NO:33.

In some embodiments, the anti-human OX40 agonist antibody comprises at least one, at least two, or all three VL HVR sequences selected from (a) HVR-L1 comprising the amino acid sequence of SEQ ID NO:37; (b) HVR-L2 comprising the amino acid sequence of SEQ ID NO:177; and (c) HVR-L3 comprising the amino acid sequence of SEQ ID NO:177. In one embodiment, the antibody comprises (a) HVR-L1 comprising the amino acid sequence of SEQ ID NO:37; (b) HVR-L2 comprising the amino acid sequence of SEQ ID NO:177; and (c) HVR-L3 comprising the amino acid sequence of SEQ ID NO:178.

In some embodiments, the anti-human OX40 agonist antibody comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:176, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:177, and (c) HVR-L3 comprising the amino acid sequence of SEQ ID NO:178.

In one embodiment, the anti-human OX40 agonist antibody comprises (a) HVR-H1 comprising the amino acid sequence of SEQ ID NO:29; (b) HVR-H2 comprising the amino acid sequence of SEQ ID NO:176; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:177; and (f) HVR-L3 comprising an amino acid sequence selected from SEQ ID NO:178.

In any of the above embodiments, an anti-OX40 agonist antibody is humanized. In one embodiment, an anti-OX40 antibody comprises HVRs as in any of the above embodiments and further comprises an acceptor human framework, e.g. a human immunoglobulin framework or a human consensus framework.

In another embodiment, the anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56, 58, 60, 62, 64, 66, 68, 70, 72, 74, 76, 78, 80, 82, 84, 86, 88, 90, 92, 94, 96, 98, 100, 108, 114, 116, 183 or 184. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:56, 58, 60, 62, 64, 66, 68, 70, 72, 74, 76, 78, 80, 82, 84, 86, 88, 90, 92, 94, 96, 98, 100, 108, 114, 116, 183 or 184. In certain embodiments, substitutions, insertions, or deletions occur in regions outside the HVRs (i.e., in the FRs). Optionally, the anti-human OX40 agonist antibody comprises the VH sequence in SEQ ID NO: SEQ ID NO:56, 58, 60, 62, 64, 66, 68, 70, 72, 74, 76, 78, 80, 82, 84, 86, 88, 90, 92, 94, 96, 98, 100, 108, 114, 116, 183 or 184, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57, 59, 61, 63, 65, 67, 69, 71, 73, 75, 77, 79, 81, 83, 85, 87, 89, 91, 93, 95, 97, 99, 101, 109, 115 or 117. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 57, 59, 61, 63, 65, 67, 69, 71, 73, 75, 77, 79, 81, 83, 85, 87, 89, 91, 93, 95, 97, 99, 101, 109, 115 or 117. In certain embodiments, the substitutions, insertions, or deletions occur in regions outside the HVRs (i.e., in the FRs). Optionally, the anti-human OX40 agonist antibody comprises the VL sequence in SEQ ID NO: 57, 59, 61, 63, 65, 67, 69, 71, 73, 75, 77, 79, 81, 83, 85, 87, 89, 91, 93, 95, 97, 99, 101, 109, 115 or 117, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another embodiment, the anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:56. In certain embodiments, substitutions, insertions, or deletions occur in regions outside the HVRs (i.e., in the FRs). Optionally, the anti-human OX40 agonist antibody comprises the VH sequence in SEQ ID NO:56, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 57. In certain embodiments, the substitutions, insertions, or deletions occur in regions outside the HVRs (i.e., in the FRs). Optionally, the anti-human OX40 agonist antibody comprises the VL sequence in SEQ ID NO: 57, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another embodiment, the anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:180. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:180. In certain embodiments, substitutions, insertions, or deletions occur in regions outside the HVRs (i.e., in the FRs). Optionally, the anti-human OX40 agonist antibody comprises the VH sequence in SEQ ID NO:180, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody comprises a light chain variable domain (VL) having at least 90%, 91%, 92%, 93%, 94%, 95%, 96%, 97%, 98%, 99%, or 100% sequence identity to the amino acid sequence of SEQ ID NO:179. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 179. In certain embodiments, the substitutions, insertions, or deletions occur in regions outside the HVRs (i.e., in the FRs). Optionally, the anti-human OX40 agonist antibody comprises the VL sequence in SEQ ID NO: 179, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another embodiment, the anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:94. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:94. In certain embodiments, substitutions, insertions, or deletions occur in regions outside the HVRs (i.e., in the FRs). Optionally, the anti-human OX40 agonist antibody comprises the VH sequence in SEQ ID NO:94, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody comprises a light chain variable domain (VL) having at least 90%, 91%, 92%, 93%, 94%, 95%, 96%, 97%, 98%, 99%, or 100% sequence identity to the amino acid sequence of SEQ ID NO:95. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:95. In certain embodiments, the substitutions, insertions, or deletions occur in regions outside the HVRs (i.e., in the FRs). Optionally, the anti-human OX40 agonist antibody comprises the VL sequence in SEQ ID NO:95, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:26.

In another embodiment, the anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:96. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:96. In certain embodiments, substitutions, insertions, or deletions occur in regions outside the HVRs (i.e., in the FRs). Optionally, the anti-human OX40 agonist antibody comprises the VH sequence in SEQ ID NO:96, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another embodiment, the anti-human OX40 agonist antibody comprises a light chain variable domain (VL) having at least 90%, 91%, 92%, 93%, 94%, 95%, 96%, 97%, 98%, 99%, or 100% sequence identity to the amino acid sequence of SEQ ID NO:97. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:97. In certain embodiments, the substitutions, insertions, or deletions occur in regions outside the HVRs (i.e., in the FRs). Optionally, the anti-human OX40 agonist antibody comprises the VL sequence in SEQ ID NO:97, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:27.

In another embodiment, the anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 118, 120, 122, 124, 126, 128, 130, 132, 134, 136, 138, 140, 142, 144, 146, or 148. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 118, 120, 122, 124, 126, 128, 130, 132, 134, 136, 138, 140, 142, 144, 146, or 148. In certain embodiments, substitutions, insertions, or deletions occur in regions outside the HVRs (i.e., in the FRs). Optionally, the anti-human OX40 agonist antibody comprises the VH sequence in SEQ ID NO: SEQ ID NO: 118, 120, 122, 124, 126, 128, 130, 132, 134, 136, 138, 140, 142, 144, 146, or 148, including post-translational modifications of that sequence. In a particular embodiment, the VH comprises one, two or three HVRs selected from: (a) HVR-H1 comprising the amino acid sequence of SEQ ID NO: 29, (b) HVR-H2 comprising the amino acid sequence of SEQ ID NO:30, and (c) HVR-H3 comprising the amino acid sequence of SEQ ID NO:33.

In another embodiment, the anti-human OX40 agonist antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 119, 121, 123, 125, 127, 129, 131, 133, 135, 137, 139, 141, 143, 145, 147, or 149. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 119, 121, 123, 125, 127, 129, 131, 133, 135, 137, 139, 141, 143, 145, 147, or 149. In certain embodiments, the substitutions, insertions, or deletions occur in regions outside the HVRs (i.e., in the FRs). Optionally, the anti-human OX40 agonist antibody comprises the VL sequence in SEQ ID NO: 119, 121, 123, 125, 127, 129, 131, 133, 135, 137, 139, 141, 143, 145, 147, or 149, including post-translational modifications of that sequence. In a particular embodiment, the VL comprises one, two or three HVRs selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42.

In certain embodiments, the anti-human OX40 agonist antibody comprises the VH and VL sequences in SEQ ID NO:56 and SEQ ID NO:57, respectively, including post-translational modifications of those sequences. In one embodiment, the anti-human OX40 agonist antibody comprises the VH and VL sequences in SEQ ID NO:58 and SEQ ID NO:59, respectively, including post-translational modifications of those sequences. In one embodiment, the anti-human OX40 agonist antibody comprises the VH and VL sequences in SEQ ID NO:60 and SEQ ID NO:61, respectively, including post-translational modifications of those sequences. In one embodiment, the anti-human OX40 agonist antibody comprises the VH and VL sequences in SEQ ID NO:62 and SEQ ID NO:63, respectively, including post-translational modifications of those sequences. In one embodiment, the anti-human OX40 agonist antibody comprises the VH and VL sequences in SEQ ID NO:64 and SEQ ID NO:65, respectively, including post-translational modifications of those sequences. In one embodiment, the anti-human OX40 agonist antibody comprises the VH and VL sequences in SEQ ID NO:66 and SEQ ID NO:67, respectively, including post-translational modifications of those sequences. In one embodiment, the anti-human OX40 agonist antibody comprises the VH and VL sequences in SEQ ID NO:68 and SEQ ID NO:69, respectively, including post-translational modifications of those sequences. In one embodiment, the anti-human OX40 agonist antibody comprises the VH and VL sequences in SEQ ID NO:70 and SEQ ID NO:71, respectively, including post-translational modifications of those sequences. In one embodiment, the anti-human OX40 agonist antibody comprises the VH and VL sequences in SEQ ID NO:72 and SEQ ID NO:73, respectively, including post-translational modifications of those sequences. In one embodiment, the anti-human OX40 agonist antibody comprises the VH and VL sequences in SEQ ID NO:74 and SEQ ID NO:75, respectively, including post-translational modifications of those sequences. In one embodiment, the anti-human OX40 agonist antibody comprises the VH and VL sequences in SEQ ID NO:76 and SEQ ID NO:77, respectively, including post-translational modifications of those sequences. In one embodiment, the anti-human OX40 agonist antibody comprises the VH and VL sequences in SEQ ID NO:78 and SEQ ID NO:79, respectively, including post-translational modifications of those sequences. In one embodiment, the anti-human OX40 agonist antibody comprises the VH and VL sequences in SEQ ID NO:80 and SEQ ID NO:81, respectively, including post-translational modifications of those sequences. In one embodiment, the anti-human OX40 agonist antibody comprises the VH and VL sequences in SEQ ID NO:82 and SEQ ID NO:83, respectively, including post-translational modifications of those sequences. In one embodiment, the anti-human OX40 agonist antibody comprises the VH and VL sequences in SEQ ID NO:84 and SEQ ID NO:85, respectively, including post-translational modifications of those sequences. In one embodiment, the anti-human OX40 agonist antibody comprises the VH and VL sequences in SEQ ID NO:86 and SEQ ID NO:87, respectively, including post-translational modifications of those sequences. In one embodiment, the anti-human OX40 agonist antibody comprises the VH and VL sequences in SEQ ID NO:88 and SEQ ID NO:89, respectively, including post-translational modifications of those sequences. In one embodiment, the anti-human OX40 agonist antibody comprises the VH and VL sequences in SEQ ID NO:90 and SEQ ID NO:91, respectively, including post-translational modifications of those sequences. In one embodiment, the anti-human OX40 agonist antibody comprises the VH and VL sequences in SEQ ID NO:92 and SEQ ID NO:93, respectively, including post-translational modifications of those sequences. In one embodiment, the anti-human OX40 agonist antibody comprises the VH and VL sequences in SEQ ID NO:94 and SEQ ID NO:95, respectively, including post-translational modifications of those sequences. In one embodiment, the anti-human OX40 agonist antibody comprises the VH and VL sequences in SEQ ID NO:96 and SEQ ID NO:97, respectively, including post-translational modifications of those sequences. In one embodiment, the anti-human OX40 agonist antibody comprises the VH and VL sequences in SEQ ID NO:98 and SEQ ID NO:99, respectively, including post-translational modifications of those sequences. In one embodiment, the anti-human OX40 agonist antibody comprises the VH and VL sequences in SEQ ID NO:100 and SEQ ID NO:101, respectively, including post-translational modifications of those sequences. In one embodiment, the anti-human OX40 agonist antibody comprises the VH and VL sequences in SEQ ID NO:108 and SEQ ID NO:109, respectively, including post-translational modifications of those sequences. In one embodiment, the anti-human OX40 agonist antibody comprises the VH and VL sequences in SEQ ID NO:114 and SEQ ID NO:115, respectively, including post-translational modifications of those sequences. In one embodiment, the anti-human OX40 agonist antibody comprises the VH and VL sequences in SEQ ID NO:116 and SEQ ID NO:117, respectively, including post-translational modifications of those sequences. In one embodiment, the antibody comprises the VH and VL sequences in SEQ ID NO:183 and SEQ ID NO:65, respectively, including post-translational modifications of those sequences. In one embodiment, the antibody comprises the VH and VL sequences in SEQ ID NO:184 and SEQ ID NO:69, respectively, including post-translational modifications of those sequences.

In one embodiment, the anti-human OX40 agonist antibody comprises the VH and VL sequences in SEQ ID NO:118 and SEQ ID NO:119, respectively, including post-translational modifications of those sequences. In one embodiment, the anti-human OX40 agonist antibody comprises the VH and VL sequences in SEQ ID NO:120 and SEQ ID NO:121, respectively, including post-translational modifications of those sequences. In one embodiment, the anti-human OX40 agonist antibody comprises the VH and VL sequences in SEQ ID NO:122 and SEQ ID NO:123, respectively, including post-translational modifications of those sequences. In one embodiment, the anti-human OX40 agonist antibody comprises the VH and VL sequences in SEQ ID NO:124 and SEQ ID NO:125, respectively, including post-translational modifications of those sequences. In one embodiment, the anti-human OX40 agonist antibody comprises the VH and VL sequences in SEQ ID NO:126 and SEQ ID NO:127, respectively, including post-translational modifications of those sequences. In one embodiment, the anti-human OX40 agonist antibody comprises the VH and VL sequences in SEQ ID NO:128 and SEQ ID NO:129, respectively, including post-translational modifications of those sequences. In one embodiment, the anti-human OX40 agonist antibody comprises the VH and VL sequences in SEQ ID NO:130 and SEQ ID NO:131, respectively, including post-translational modifications of those sequences. In one embodiment, the anti-human OX40 agonist antibody comprises the VH and VL sequences in SEQ ID NO:132 and SEQ ID NO:133, respectively, including post-translational modifications of those sequences. In one embodiment, the anti-human OX40 agonist antibody comprises the VH and VL sequences in SEQ ID NO:134 and SEQ ID NO:135, respectively, including post-translational modifications of those sequences. In one embodiment, the anti-human OX40 agonist antibody comprises the VH and VL sequences in SEQ ID NO:136 and SEQ ID NO:137, respectively, including post-translational modifications of those sequences. In one embodiment, the anti-human OX40 agonist antibody comprises the VH and VL sequences in SEQ ID NO:138 and SEQ ID NO:139, respectively, including post-translational modifications of those sequences. In one embodiment, the anti-human OX40 agonist antibody comprises the VH and VL sequences in SEQ ID NO:140 and SEQ ID NO:141, respectively, including post-translational modifications of those sequences. In one embodiment, the anti-human OX40 agonist antibody comprises the VH and VL sequences in SEQ ID NO:142 and SEQ ID NO:143, respectively, including post-translational modifications of those sequences. In one embodiment, the anti-human OX40 agonist antibody comprises the VH and VL sequences in SEQ ID NO:144 and SEQ ID NO:145, respectively, including post-translational modifications of those sequences. In one embodiment, the anti-human OX40 agonist antibody comprises the VH and VL sequences in SEQ ID NO:146 and SEQ ID NO:147, respectively, including post-translational modifications of those sequences.

It will be appreciated that the HVR, VH, and VL sequences disclosed herein may be combined with any of the Fc variants disclosed herein in any number or combination. In some embodiments, an OX40 agonist antibody described herein comprises any of the HVR sequences or a combination thereof, $V_H$ sequences, and/or $V_L$ sequences described in Table A and an Fc region. In some embodiments, an OX40 agonist antibody comprises any of the HVR, $V_H$, and/or $V_L$ sequences described in Table A and a variant Fc region of the present disclosure. For example, in some embodiments, an OX40 agonist antibody comprises any of the HVR, $V_H$, and/or $V_L$ sequences described in Table A and a K322A modification in the Fc region of human IgG1 (EU numbering of residues). In some embodiments, an OX40 agonist antibody comprises any of the HVR, $V_H$, and/or $V_L$ sequences described in Table A and one or more amino acid substitutions selected from E345R, E430G and S440Y in the Fc region of a human IgG1 (EU numbering). In some embodiments, an OX40 agonist antibody comprises any of the HVR, $V_H$, and/or $V_L$ sequences described in Table A and a single amino acid substitution selected from E345R, E430G and S440Y in the Fc region of a human IgG1 (EU numbering). In some embodiments, an OX40 agonist antibody comprises any of the HVR, $V_H$, and/or $V_L$ sequences described in Table A and a set of amino acid substitutions selected from (a) E345R and E430G, (b) E345R and S440Y, (c) E430G and S440Y, wherein the substitutions are in the Fc region of a human IgG1 (EU numbering). In some embodiments, an OX40 agonist antibody comprises any of the HVR, $V_H$, and/or $V_L$ sequences described in Table A and amino acid substitutions E345R, E430G and S440Y in the Fc region of a human IgG1 (EU numbering). In some embodiments, an OX40 agonist antibody comprises any of the HVR, $V_H$, and/or $V_L$ sequences described in Table A and one or more amino acid substitutions selected from Table 4 in the Fc region of human IgG1 (EU numbering of residues). In some embodiments, an OX40 agonist antibody comprises any of the HVR, $V_H$, and/or $V_L$ sequences described in Table A, one or more amino acid substitutions selected from Table 4 in the Fc region of human IgG1 (EU numbering of residues), and one or more modifications in the Fc region that result in diminished C1q binding and/or Complement Dependent Cytotoxicity (CDC), e.g., K322A in the Fc region of human IgG1 (EU numbering of residues).

TABLE 4

Additional Hexamer Promoting Variants.

| | |
|---|---|
| P247K | E345Q |
| P247G | E345P |
| P247D | E345M |
| P247S | E345F |
| P247R | E356R |
| P247F | E356I |
| I253V | E356V |
| S254L | E356T |
| S254G | E356L |
| S254I | T359N |
| Q311W | E382L |
| Q311P | E382V |
| Q311L | Q386K |
| Q311I | E430S |
| Q311K | E430V |
| E345T | E430W |
| E345A | E430Y |
| E345Y | E430H |
| E345N | E430F |
| E345S | E430P |
| E345V | E430R |
| E345W | E430L |
| E345K | E430A |
| E345I | N434W |
| E345C | Y436I |
| E345L | S440D |

In some embodiments, the anti-human OX40 agonist antibody comprises (a) a K322A modification in the Fc region of human IgG1 (EU numbering of residues); (b) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (c) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (iii) HVR-L3 comprising the amino acid sequence of SEQ ID NO:7.

In some embodiments, the anti-human OX40 agonist antibody comprises (a) one or more amino acid substitutions selected from Table 4 in the Fc region of human IgG1 (EU numbering of residues); (b) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (c) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (iii) HVR-L3 comprising the amino acid sequence of SEQ ID NO:7.

In some embodiments, the anti-human OX40 agonist antibody comprises (a) one or more amino acid substitutions selected from E345R, E430G and S440Y in the Fc region of a human IgG1 (EU numbering); (b) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (c) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (iii) HVR-L3 comprising the amino acid sequence of SEQ ID NO:7.

In some embodiments, the anti-human OX40 agonist antibody comprises (a) a K322A modification in the Fc region of human IgG1 (EU numbering of residues); (b) one or more amino acid substitutions selected from E345R, E430G and S440Y in the Fc region of a human IgG1 (EU numbering); (c) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (d) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (iii) HVR-L3 comprising the amino acid sequence of SEQ ID NO:7.

In some embodiments, the anti-human OX40 agonist antibody comprises (a) a single amino acid substitution selected from E345R, E430G and S440Y in the Fc region of a human IgG1 (EU numbering); (b) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (c) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (iii) HVR-L3 comprising the amino acid sequence of SEQ ID NO:7.

In some embodiments, the anti-human OX40 agonist antibody comprises (a) a set of amino acid substitutions selected from (i) E345R and E430G, (ii) E345R and S440Y, and (iii) E430G and S440Y in the Fc region of a human IgG1 (EU numbering); (b) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (c) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (iii) HVR-L3 comprising the amino acid sequence of SEQ ID NO:7.

In some embodiments, the anti-human OX40 agonist antibody comprises (a) E345R, E430G, and S440Y substitutions in the Fc region of human IgG1 (EU numbering of residues); (b) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (c) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (iii) HVR-L3 comprising the amino acid sequence of SEQ ID NO:7.

In some embodiments, the anti-human OX40 agonist antibody comprises (a) a K322A modification in the Fc region of human IgG1 (EU numbering of residues); (b) a VH domain comprising the VH sequence of SEQ ID NO:56; and (c) a VL domain comprising the VL sequence of SEQ ID NO:57.

In some embodiments, the anti-human OX40 agonist antibody comprises (a) one or more amino acid substitutions selected from Table 4 in the Fc region of human IgG1 (EU numbering of residues); (b) a VH domain comprising the VH sequence of SEQ ID NO:56; and (c) a VL domain comprising the VL sequence of SEQ ID NO:57.

In some embodiments, the anti-human OX40 agonist antibody comprises (a) one or more amino acid substitutions selected from E345R, E430G and S440Y in the Fc region of a human IgG1 (EU numbering); (b) a VH domain comprising the VH sequence of SEQ ID NO:56; and (c) a VL domain comprising the VL sequence of SEQ ID NO:57.

In some embodiments, the anti-human OX40 agonist antibody comprises (a) a K322A modification in the Fc region of human IgG1 (EU numbering of residues); (b) one or more amino acid substitutions selected from E345R, E430G and S440Y in the Fc region of a human IgG1 (EU numbering); (c) a VH domain comprising the VH sequence of SEQ ID NO:56; and (d) a VL domain comprising the VL sequence of SEQ ID NO:57.

In some embodiments, the anti-human OX40 agonist antibody comprises (a) a single amino acid substitution selected from E345R, E430G and S440Y in the Fc region of a human IgG1 (EU numbering); (b) a VH domain comprising the VH sequence of SEQ ID NO:56; and (c) a VL domain comprising the VL sequence of SEQ ID NO:57.

In some embodiments, the anti-human OX40 agonist antibody comprises (a) a set of amino acid substitutions selected from (i) E345R and E430G, (ii) E345R and S440Y, and (iii) E430G and S440Y in the Fc region of a human IgG1 (EU numbering); (b) a VH domain comprising the VH sequence of SEQ ID NO:56; and (c) a VL domain comprising the VL sequence of SEQ ID NO:57.

In some embodiments, the anti-human OX40 agonist antibody comprises (a) E345R, E430G, and S440Y substitutions in the Fc region of human IgG1 (EU numbering of residues); (b) a VH domain comprising the VH sequence of SEQ ID NO:56; and (c) a VL domain comprising the VL sequence of SEQ ID NO:57.

In some embodiments, the anti-human OX40 agonist antibody comprises (a) a K322A modification in the Fc region of human IgG1 (EU numbering of residues); (b) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (c) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (iii) HVR-L3 comprising the amino acid sequence of SEQ ID NO:42.

In some embodiments, the anti-human OX40 agonist antibody comprises (a) one or more amino acid substitutions selected from Table 4 in the Fc region of human IgG1 (EU numbering of residues); (b) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (c) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (iii) HVR-L3 comprising the amino acid sequence of SEQ ID NO:42.

In some embodiments, the anti-human OX40 agonist antibody comprises (a) one or more amino acid substitutions selected from E345R, E430G and S440Y in the Fc region of a human IgG1 (EU numbering); (b) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (c) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (iii) HVR-L3 comprising the amino acid sequence of SEQ ID NO:42.

In some embodiments, the anti-human OX40 agonist antibody comprises (a) a K322A modification in the Fc region of human IgG1 (EU numbering of residues); (b) one or more amino acid substitutions selected from E345R, E430G and S440Y in the Fc region of a human IgG1 (EU numbering); (c) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (d) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (iii) HVR-L3 comprising the amino acid sequence of SEQ ID NO:42.

In some embodiments, the anti-human OX40 agonist antibody comprises (a) a single amino acid substitution selected from E345R, E430G and S440Y in the Fc region of a human IgG1 (EU numbering); (b) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (c) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (iii) HVR-L3 comprising the amino acid sequence of SEQ ID NO:42.

In some embodiments, the anti-human OX40 agonist antibody comprises (a) a set of amino acid substitutions selected from (i) E345R and E430G, (ii) E345R and S440Y, and (iii) E430G and S440Y in the Fc region of a human IgG1 (EU numbering); (b) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (c) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (iii) HVR-L3 comprising the amino acid sequence of SEQ ID NO:42.

In some embodiments, the anti-human OX40 agonist antibody comprises (a) E345R, E430G, and S440Y substitutions in the Fc region of human IgG1 (EU numbering of residues); (b) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (c) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:38, and (iii) HVR-L3 comprising the amino acid sequence of SEQ ID NO:42.

In some embodiments, the anti-human OX40 agonist antibody comprises (a) a K322A modification in the Fc region of human IgG1 (EU numbering of residues); (b) a VH domain comprising the VH sequence of SEQ ID NO:118; and (c) a VL domain comprising the VL sequence of SEQ ID NO:119.

In some embodiments, the anti-human OX40 agonist antibody comprises (a) one or more amino acid substitutions selected from Table 4 in the Fc region of human IgG1 (EU numbering of residues); (b) a VH domain comprising the VH sequence of SEQ ID NO:118; and (c) a VL domain comprising the VL sequence of SEQ ID NO:119.

In some embodiments, the anti-human OX40 agonist antibody comprises (a) one or more amino acid substitutions selected from E345R, E430G and S440Y in the Fc region of a human IgG1 (EU numbering); (b) a VH domain comprising the VH sequence of SEQ ID NO:118; and (c) a VL domain comprising the VL sequence of SEQ ID NO:119.

In some embodiments, the anti-human OX40 agonist antibody comprises (a) a K322A modification in the Fc region of human IgG1 (EU numbering of residues); (b) one or more amino acid substitutions selected from E345R, E430G and S440Y in the Fc region of a human IgG1 (EU numbering); (c) a VH domain comprising the VH sequence of SEQ ID NO:118; and (d) a VL domain comprising the VL sequence of SEQ ID NO:119.

In some embodiments, the anti-human OX40 agonist antibody comprises (a) a single amino acid substitution selected from E345R, E430G and S440Y in the Fc region of a human IgG1 (EU numbering); (b) a VH domain comprising the VH sequence of SEQ ID NO:118; and (c) a VL domain comprising the VL sequence of SEQ ID NO:119.

In some embodiments, the anti-human OX40 agonist antibody comprises (a) a set of amino acid substitutions selected from (i) E345R and E430G, (ii) E345R and S440Y, and (iii) E430G and S440Y in the Fc region of a human IgG1 (EU numbering); (b) a VH domain comprising the VH sequence of SEQ ID NO:118; and (c) a VL domain comprising the VL sequence of SEQ ID NO:119.

In some embodiments, the anti-human OX40 agonist antibody comprises (a) E345R, E430G, and S440Y substitutions in the Fc region of human IgG1 (EU numbering of residues); (b) a VH domain comprising the VH sequence of SEQ ID NO:118; and (c) a VL domain comprising the VL sequence of SEQ ID NO:119.

As described above, certain aspects of the present disclosure relate to complexes such as hexamers. It is to be understood that any of the exemplary antibodies, antigen binding domains, and/or antibody fragments that bind OX40

(e.g., HVRs, VH, and/or VL domains of any of the OX40 agonist antibodies described herein) may be combined in a complex or hexamer of the present disclosure in any combination or configuration. For example, in some embodiments, a hexamer may be formed by six subunits of the same OX40 agonist antibody. In some embodiments, a hexamer may comprise two or more different OX40 agonist antibodies that bind to the same epitope of OX40. In some embodiments, a hexamer may comprise two or more different OX40 agonist antibodies that bind to different epitopes of OX40 (e.g., partially non-overlapping or completely non-overlapping epitopes of an OX40 polypeptide, such as human OX40). In some embodiments, a hexamer may comprise two or more different antibodies, one of which binds OX40, and another of which binds a different polypeptide described herein or otherwise known in the art.

Further contemplated herein are bispecific or multispecific antibodies, wherein at least one arm of the antibody binds OX40 (e.g., any of the OX40 agonist antibodies described herein, or any antibody comprising any of the HVRs, VH, and/or VL domains of any of the OX40 agonist antibodies described herein). In some embodiments, each arm of a bispecific or multispecific antibody binds to the same cell surface receptor, e.g., OX40. In some embodiments, each arm of a bispecific or multispecific antibody binds to a different epitope of the same cell surface receptor, e.g., OX40. For example, in certain embodiments, a bispecific antibody may comprise two arms, wherein each arm binds a different epitope of OX40. It is to be understood that any of the exemplary antibodies, antigen binding domains, and/or antibody fragments that bind OX40 (e.g., HVRs, VH, and/or VL domains of any of the OX40 agonist antibodies described herein) may be combined in a bispecific or multispecific antibody in any combination.

In some embodiments, the OX40 agonist antibody binds human OX40 with an affinity of less than or equal to about 0.45 nM. In some embodiments, the OX40 agonist antibody binds human OX40 with an affinity of less than or equal to about 1 nM. In some embodiments, the OX40 antibody binds human OX40 with an affinity of less than or equal to about 0.4 nM. In some embodiments, the OX40 antibody binds human OX40 with an affinity of less than or equal to about 0.5 nM. In some embodiments, the binding affinity is determined using radioimmunoassay.

In some embodiments, the OX40 agonist antibody binds human OX40 and cynomolgus OX40. In some embodiments, binding is determined using a FACS assay. In some embodiments, binding to human OX40 has an EC50 of about 0.2 ug/ml. In some embodiments, binding to human OX40 has an EC50 of about 0.3 ug/ml or lower. In some embodiments, binding to cynomolgus OX40 has an EC50 of about 1.5 ug/ml. In some embodiments, binding to cynomolgus OX40 has an EC50 of about 1.4 ug/ml.

In some embodiments, the OX40 agonist antibody does not bind to rat OX40 or mouse OX40.

In some embodiments, the OX40 agonist antibody does not induce apoptosis in OX40-expressing cells (e.g., Treg). In some embodiments, apoptosis is assayed using an antibody concentration of 30 ug/ml, e.g., by determining whether apoptosis has occurred using annexin V and proprodium iodide stained Treg.

In some embodiments, the OX40 agonist antibody increases memory T cell proliferation and/or increasing cytokine production by the memory cell. In some embodiments, the cytokine is IFN-γ. In some embodiments, the OX40 agonist antibody enhances memory T cell function, for example by increasing memory T cell proliferation and/or increasing cytokine production by the memory cell. In some embodiments, the cytokine is gamma interferon.

In some embodiments, the OX40 agonist antibody increases CD4+ effector T cell proliferation and/or increases cytokine production by the CD4+ effector T cell as compared to proliferation and/or cytokine production prior to treatment with the OX40 agonist antibody. In some embodiments, the cytokine is IFN-γ.

In some embodiments, the anti-human OX40 agonist antibody enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist antibody). In some embodiments, the cytokine is gamma interferon. In some embodiments, the anti-human OX40 agonist antibody increases number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with anti-human OX40 agonist antibody. In some embodiments, the anti-human OX40 agonist antibody increases number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment with anti-human OX40 agonist antibody.

In some embodiments, the number of CD4+ effector T cells is elevated relative to prior to administration of the OX40 agonist antibody. In some embodiments, CD4+ effector T cell cytokine secretion is elevated relative to prior to administration of the OX40 agonist antibody. In some embodiments of any of the methods, the CD8+ effector T cells in the individual have enhanced proliferation, cytokine secretion and/or cytolytic activity relative to prior to the administration of the OX40 agonist antibody. In some embodiments, the number of CD8+ effector T cells is elevated relative to prior to administration of the OX40 agonist antibody. In some embodiments, CD8+ effector T cell cytokine secretion is elevated relative to prior to administration of the OX40 agonist antibody.

In some embodiments, the anti-human OX40 agonist antibody increases number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment with anti-human OX40 agonist antibody. In some embodiments, the anti-human OX40 agonist antibody increases number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with anti-human OX40 agonist antibody.

In some embodiments, the number of intratumoral (infiltrating) CD8+ effector T cells (e.g., total number of CD8+ effector T cells, or e.g., percentage of CD8+ in CD45+ cells) is elevated relative to prior to administration of the OX40 agonist antibody. In some embodiments of any of the methods of the invention, number of intratumoral (infiltrating) CD8+ effector T cells that express gamma interferon (e.g., percentage of CD8+ cells that express gamma interferon in total CD8+ cells) is increased relative to prior to administration of the OX40 agonist antibody.

In some embodiments, the memory T cells in the individual have enhanced proliferation and/or cytokine secretion relative to prior to the administration of the OX40 agonist antibody. In some embodiments, the number of memory T cells is elevated relative to prior to administration of the OX40 agonist antibody. In some embodiments, memory T cell cytokine secretion (level) is elevated relative to prior to administration of the OX40 agonist antibody. In some embodiments of any of the methods, the Treg in the individual have decreased inhibition of effector T cell function (e.g., proliferation and/or cytokine secretion) relative to prior to the administration of the OX40 agonist antibody. In some embodiments, the number of effector T cells is elevated relative to prior to administration of the OX40 agonist antibody. In some embodiments, effector T cell cytokine secretion (level) is elevated relative to prior to administration of the OX40 agonist antibody.

In some embodiments, the OX40 agonist antibody inhibits Treg suppression of effector T cell function. In some embodiments, effector T cell function is effector T cell proliferation and/or cytokine production. In some embodiments, the effector T cell is a CD4+ effector T cell.

In some embodiments, the OX40 agonist antibody inhibits Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the OX40 agonist antibody reduces the number of intratumoral (infiltrating) Treg (e.g., total number of Treg or e.g., percentage of Fox3p+ cells in CD4+ cells).

In some embodiments, the number of intratumoral (infiltrating) Treg (e.g., total number of Treg or e.g., percentage of Fox3p+ cells in CD4+ cells) is reduced relative to prior to administration of the OX40 agonist antibody.

In some embodiments, the number of intratumoral (infiltrating) CD4+ effector T cells (e.g., total number of CD4+ effector T cells, or e.g., percentage of CD4+ cells in CD45+ cells) is elevated relative to prior to administration of the OX40 agonist antibody. In some embodiments of any of the methods of the invention, number of intratumoral (infiltrating) CD4+ effector T cells that express gamma interferon (e.g., total gamma interferon expressing CD4+ cells, or e.g., percentage of gamma interferon expressing CD4+ cells in total CD4+ cells) is elevated relative to prior to administration of the OX40 agonist antibody.

In some embodiments, the OX40 agonist antibody increases OX40 signal transduction in a target cell that expresses OX40. In some embodiments, OX40 signal transduction is detected by monitoring NFkB downstream signaling.

In some embodiments, the OX40 agonist antibody is stable after treatment at 40° C. for two weeks.

In some embodiments, the OX40 agonist antibody competes for binding to human OX40 with OX40L. In some embodiments, addition of OX40L does not enhance OX40 antibody function in an in vitro assay.

According to another embodiment, the OX40 agonist antibodies include any one, any combination, or all of the following properties: (1) binds human OX40 with an affinity of less than or equal to about 0.45 nM, in some embodiments, binds human OX40 with an affinity of less than or equal to about 0.4 nM, in some embodiments, binds human OX40 with an affinity of less than or equal to about 0.5 nM, in some embodiments, the binding affinity is determined using radioimmunoassay; (2) binds human OX40 and cynomolgus OX40, in some embodiments, binding is determined using a FACS assay, (3) binds human OX40 with an EC50 of about 0.2 ug/ml, in some embodiments, binds to human OX40 has an EC50 of about 0.3 ug/ml or lower, in some embodiments, binds to cynomolgus OX40 with an EC50 of about 1.5 ug/ml, in some embodiments, binds to cynomolgus OX40 has an EC50 of about 1.4 ug/ml, (4) does not substantially bind to rat OX40 or mouse OX40, (5) enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist antibody), (6) enhances memory T cell function, for example by increasing memory T cell proliferation and/or increasing cytokine production by the memory cell, (7) inhibits Treg function, for example, by decreasing Treg suppression of effector T cell function (e.g., effector T cell proliferation and/or effector T cell cytokine secretion). In some embodiments, the effector T cell is a CD4+ effector T cell, (8) increases OX40 signal transduction in a target cell that expresses OX40 (in some embodiments, OX40 signal transduction is detected by monitoring NFkB downstream signaling), and (9) is stable after treatment at 40° C. for two weeks.

TABLE A

OX40 Antibody Sequences

| Name | SEQUENCE | SEQ ID NO: |
|---|---|---|
| Human OX40 (lacking the signal peptide) | LHCVGDTYPSNDRCCHECRPGNGMVSRCSRSQNTVCR PCGPGFYNDVVSSKPCKPCTWCNLRSGSERKQLCTAT QDTVCRCRAGTQPLDSYKPGVDCAPCPPGHFSPGDNQ ACKPWTNCTLAGKHTLQPASNSSDAICEDRDPPATQPQ ETQGPPARPITVQPTEAWPRTSQGPSTRPVEVPGGRAV AAILGLGLVLGLLGPLAILLALYLLRRDQRLPPDAHKPP GGGSFRTPIQEEQADAHSTLAKI | 1 |
| HVR-H1-1A7.gr.1 1A7.gr.2 1A7.gr.3 1A7.gr.4 1A7.gr.5 1A7.gr.5' | DSYMS | 2 |

TABLE A-continued

OX40 Antibody Sequences

| Name | SEQUENCE | SEQ ID NO: |
|---|---|---|
| 1A7.gr.6 | | |
| 1A7.gr.7 | | |
| 1A7.gr.7' | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-H2- | DMYPDNGDSSYNQKFRE | 3 |
| 1A7.gr.1 | | |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-H3- | APRWYFSV | 4 |
| 1A7.gr.1 | | |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |

TABLE A-continued

OX40 Antibody Sequences

| Name | SEQUENCE | SEQ ID NO: |
|---|---|---|
| 1A7.Ala.3 | | |
| 1A7.Ala.4 | | |
| 1A7.Ala.5 | | |
| 1A7.Ala.6 | | |
| 1A7.Ala.7 | | |
| 1A7-Ala.15 | | |
| 1A7.Ala.16 | | |
| HVR-L1-1A7.gr.1 | RASQDISNYLN | 5 |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-L2-1A7.gr.1 | YTSRLRS | 6 |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |

TABLE A-continued

OX40 Antibody Sequences

| Name | SEQUENCE | SEQ ID NO: |
|---|---|---|
| 1A7.Ala.14 | | |
| 1A7.Ala.15 | | |
| 1A7.Ala.16 | | |
| HVR-L3-<br>1A7.gr.1<br>1A7.gr.2<br>1A7.gr.3<br>1A7.gr.4<br>1A7.gr.5<br>1A7.gr.5'<br>1A7.gr.6<br>1A7.gr.7<br>1A7.gr.7'<br>1A7.gr.DA<br>1A7.gr.ES<br>1A7.gr.NADS<br>1A7.gr.NADA<br>1A7.gr.NGDA<br>1A7.gr.SGDS<br>1A7.gr.NGSS<br>1A7.gr.DANADA<br>1A7.Ala.8<br>1A7.Ala.9<br>1A7.Ala.10<br>1A7.Ala.11<br>1A7.Ala.12<br>1A7.Ala.13<br>1A7.Ala.14<br>1A7.Ala.15<br>1A7.Ala.16 | QQGHTLPPT | 7 |
| HVR-H1-<br>1A7.gr.DA | DAYMS | 8 |
| HVR-H1-<br>1A7.gr.ES<br>1A7.gr.DANADA | ESYMS | 9 |
| HVR-H2-<br>1A7.gr.NADS | DMYPDNADSSYNQKFRE | 10 |
| HVR-H2-<br>1A7.gr.NADA<br>1A7.gr.DANADA | DMYPDNADASYNQKFRE | 11 |
| HVR-H2-<br>1A7.gr.NGDA | DMYPDNGDASYNQKFRE | 12 |
| HVR-H2-<br>1A7.gr.SGDS | DMYPDSGDSSYNQKFRE | 13 |
| HVR-H2-<br>1A7.gr.NGSS | DMYPDNGSSSYNQKFRE | 14 |
| HVR-H3-<br>1A7.Ala.8 | APRWYFSA | 15 |
| HVR-H3-<br>1A7.Ala.9 | APRWYASV | 16 |
| HVR-H3-<br>1A7.Ala.10 | APRWAFSV | 17 |
| HVR-H3-<br>1A7.Ala.11 | APAWYFSV | 18 |
| HVR-H3-<br>1A7.Ala.12 | APRWYFAV | 19 |
| HVR-H3-<br>1A7.Ala.13 | APRAYFSV | 20 |

TABLE A-continued

OX40 Antibody Sequences

| Name | SEQUENCE | SEQ ID NO: |
|---|---|---|
| HVR-H3-1A7.Ala.14 | AARWYFSV | 21 |
| HVR-L3-1A7.Ala.1 | QQGHTLPAT | 22 |
| HVR-L3-1A7.Ala.2 | QQGHTAPPT | 23 |
| HVR-L3-1A7.Ala.3 | QQGATLPPT | 24 |
| HVR-L3-1A7.Ala.4 | QQGHALPPT | 25 |
| HVR-L3-1A7.Ala.5 | QQAHTLPPT | 26 |
| HVR-L3-1A7.Ala.6 | QQGHTLAPT | 27 |
| HVR-L3-1A7.Ala.7 | QAGHTLPPT | 28 |
| HVR-H1-3C8.gr.1 3C8.gr.2 3C8.gr.3 3C8.gr.4 3C8.gr.5 3C8.gr.5.SG 3C8.gr.5.EG 3C8.gr.5.QG 3C9.gr.5.DQ 3C8.gr.5.DA 3C8.gr.6 3C8.gr.7 3C8.gr.8 3C8.gr.9 3C8.gr.10 3C8.gr.11 3C8.A.1 3C8.A.2 3C8.A.3 3C8.A.4 3C8.A.5 3C8.A.6 3C8.A.7 3C8.A.8 3C8.A.9 3C8.A.10 | NYLIE | 29 |
| HVR-H2-3C8.gr.1 3C8.gr.2 3C8.gr.3 3C8.gr.4 3C8.gr.5 3C8.gr.5.SG 3C8.gr.5.EG 3C8.gr.5.QG 3C8.gr.6 3C8.gr.7 3C8.gr.8 3C8.gr.9 3C8.gr.10 3C8.gr.11 3C8.A.1 3C8.A.2 3C8.A.3 3C8.A.4 3C8.A.5 3C8.A.6 | VINPGSGDTYYSEKFKG | 30 |

TABLE A-continued

OX40 Antibody Sequences

| Name | SEQUENCE | SEQ ID NO: |
|---|---|---|
| 3C8.A.7 | | |
| 3C8.A.8 | | |
| 3C8.A.9 | | |
| 3C8.A.10 | | |
| HVR-H2-3C8.gr.5.DA | VINPGSGDAYYSEKFKG | 31 |
| HVR-H2-3C8.gr.5.DQ | VINPGSGDQYYSEKFKG | 32 |
| HVR-H3-3C8.gr.1<br>3C8.gr.2<br>3C8.gr.3<br>3C8.gr.4<br>3C8.gr.5<br>3C8.gr.5.SG<br>3C8.gr.5.EG<br>3C8.gr.5.QG<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7 | DRLDY | 33 |
| HVR-H3-3C8.A.8 | ARLDY | 34 |
| HVR-H3-3C8.A.9 | DALDY | 35 |
| HVR-H3-3C8.A.10 | DRADY | 36 |
| HVR-L1-3C8.gr.1<br>3C8.gr.2<br>3C8.gr.3<br>3C8.gr.4<br>3C8.gr.5<br>3C8.gr.5.SG<br>3C8.gr.5.EG<br>3C8.gr.5.QG<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7<br>3C8.A.8<br>3C8.A.9<br>3C8.A.10 | HASQDISSYIV | 37 |

TABLE A-continued

OX40 Antibody Sequences

| Name | SEQUENCE | SEQ ID NO: |
|---|---|---|
| HVR-L2-<br>3C8.gr.1<br>3C8.gr.2<br>3C8.gr.3<br>3C8.gr.4<br>3C8.gr.5<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7<br>3C8.A.8<br>3C8.A.9<br>3C8.A.10 | HGTNLED | 38 |
| HVR-L2-<br>3C8.gr5.SG | HGTNLES | 39 |
| HVR-L2-<br>3C8.gr.5.EG | HGTNLEE | 40 |
| HVR-L2-<br>3C8.gr.5.QG | HGTNLEQ | 41 |
| HVR-L3<br>3C8.gr.1<br>3C8.gr.2<br>3C8.gr.3<br>3C8.gr.4<br>3C8.gr.5<br>3C8.gr.5.SG<br>3C8.gr.5.EG<br>3C8.gr.5.QG<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.8<br>3C8.A.9<br>3C8.A.10 | VHYAQFPYT | 42 |
| HVR-L3-<br>3C8.A.1 | AHYAQFPYT | 43 |
| HVR-L3-<br>3C8.A.2 | VAYAQFPYT | 44 |
| HVR-L3-<br>3C8.A.3 | VHAAQFPYT | 45 |
| HVR-L3-<br>3C8.A.4 | VHYAAFPYT | 46 |
| HVR-L3-<br>3C8.A.5 | VHYAQAPYT | 47 |
| HVR-L3-<br>3C8.A.6 | VHYAQFAYT | 48 |

TABLE A-continued

OX40 Antibody Sequences

| Name | SEQUENCE | SEQ ID NO: |
|---|---|---|
| HVR-L3-3C8.A.7 | VHYAQFPAT | 49 |
| HVR-H1-1D2.gr.1 1D2.gr.2 1D2.gr.3 | DYGVL | 50 |
| HVR-H2-1D2.gr.1 1D2.gr.2 1D2.gr.3 | MIWSGGTTDYNAAFIS | 51 |
| HVR-H3-1D2.gr.1 1D2.gr.2 1D2.gr.3 | EEMDY | 52 |
| HVR-L1-1D2.gr.1 1D2.gr.2 1D2.gr.3 | RASQDISNFLN | 53 |
| HVR-L2-1D2.gr.1 1D2.gr.2 1D2.gr.3 | YTSRLHS | 54 |
| HVR-L3-1D2.gr.1 1D2.gr.2 1D2.gr.3 | QQGNTLPWT | 55 |
| 1A7.gr.1 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVLAPRWYFSVWGQG TLVTVSS | 56 |
| 1A7.gr.1 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 57 |
| 1A7.gr.2 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 58 |
| 1A7.gr.2 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 59 |
| 1A7.gr.3 $V_H$ | EVQLVQSGAEVKKPGASVKVSCKASGYTFTDSYMSW VRQAPGQGLEWIGDMYPDNGDSSYNQKFRERVTLTV DTSTSTAYLELSSLRSEDTAVYYCVLAPRWYFSVWGQ GTLVTVSS | 60 |
| 1A7.gr.3 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 61 |
| 1A7.gr.4 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 62 |
| 1A7.gr.4 $V_L$ | DIQMTQSPSSLSASVGDRVTITCRASQDISNYLNWYQQ KPGKTVKLLIYYTSRLRSGVPSRFSGSGSGTDFTLTISSL QPEDFATYYCQQGHTLPPTFGQGTKVEIK | 63 |
| 1A7.gr.5 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 64 |

TABLE A-continued

OX40 Antibody Sequences

| Name | SEQUENCE | SEQ ID NO: |
| --- | --- | --- |
| 1A7.gr.5 $V_L$ | DIQMTQSPSSLSASVGDRVTITCRASQDISNYLNWYQQ KPGKTVKLLIYYTSRLRSGVPSRFSGSGSGTDFTLTISSL QPEDFATYYCQQGHTLPPTFGQGTKVEIK | 65 |
| 1A7.gr.6 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 66 |
| 1A7.gr.6 $V_L$ | DIQMTQSPSSLSASVGDRVTITCRASQDISNYLNWYQQ KPGKTVKLLIYYTSRLRSGVPSRFSGSGSGKDYTLTISS LQPEDFATYFCQQGHTLPPTFGQGTKVEIK | 67 |
| 1A7.gr.7 $V_H$ | EVQLVQSGAEVKKPGASVKVSCKASGYTFTDSYMSW VRQAPGQGLEWIGDMYPDNGDSSYNQKFRERVTITVD TSTSTAYLELSSLRSEDTAVYYCVLAPRWYFSVWGQG TLVTVSS | 68 |
| 1A7.gr.7 $V_L$ | DIQMTQSPSSLSASVGDRVTITCRASQDISNYLNWYQQ KPGKTVKLLIYYTSRLRSGVPSRFSGSGSGKDYTLTISS LQPEDFATYFCQQGHTLPPTFGQGTKVEIK | 69 |
| 1A7.gr.DA $V_H$ | EVQLVQSGAEVKKPGASVKVSCKASGYTFTDAYMSW VRQAPGQGLEWIGDMYPDNGDSSYNQKFRERVTITRD TSTSTAYLELSSLRSEDTAVYYCVLAPRWYFSVWGQG TLVTVSS | 70 |
| 1A7.gr.DA $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 71 |
| 1A7.gr.ES $V_H$ | EVQLVQSGAEVKKPGASVKVSCKASGYTFTESYMSW VRQAPGQGLEWIGDMYPDNGDSSYNQKFRERVTITRD TSTSTAYLELSSLRSEDTAVYYCVLAPRWYFSVWGQG TLVTVSS | 72 |
| 1A7.gr.ES $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 73 |
| 1A7.gr.NADS $V_H$ | EVQLVQSGAEVKKPGASVKVSCKASGYTFTDSYMSW VRQAPGQGLEWIGDMYPDNADSSYNQKFRERVTITRD TSTSTAYLELSSLRSEDTAVYYCVLAPRWYFSVWGQG TLVTVSS | 74 |
| 1A7.gr.NADS $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 75 |
| 1A7.gr.NADA $V_H$ | EVQLVQSGAEVKKPGASVKVSCKASGYTFTDSYMSW VRQAPGQGLEWIGDMYPDNADASYNQKFRERVTITRD TSTSTAYLELSSLRSEDTAVYYCVLAPRWYFSVWGQG TLVTVSS | 76 |
| 1A7.gr.NADA $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 77 |
| 1A7.gr.NGDA $V_H$ | EVQLVQSGAEVKKPGASVKVSCKASGYTFTDSYMSW VRQAPGQGLEWIGDMYPDNGDASYNQKFRERVTITRD TSTSTAYLELSSLRSEDTAVYYCVLAPRWYFSVWGQG TLVTVSS | 78 |
| 1A7.gr.NGDA $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 79 |
| 1A7.gr.SGDS $V_H$ | EVQLVQSGAEVKKPGASVKVSCKASGYTFTDSYMSW VRQAPGQGLEWIGDMYPDSGDSSYNQKFRERVTITRD TSTSTAYLELSSLRSEDTAVYYCVLAPRWYFSVWGQG TLVTVSS | 80 |

TABLE A-continued

OX40 Antibody Sequences

| Name | SEQUENCE | SEQ ID NO: |
|---|---|---|
| 1A7.gr.SGDS $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 81 |
| 1A7.gr.NGSS $V_H$ | EVQLVQSGAEVKKPGASVKVSCKASGYTFTDSYMSW VRQAPGQGLEWIGDMYPDNGSSSYNQKFRERVTITRD TSTSTAYLELSSLRSEDTAVYYCVLAPRWYFSVWGQG TLVTVSS | 82 |
| 1A7.gr.NGSS $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 83 |
| 1A7.gr.DANADA $V_H$ | EVQLVQSGAEVKKPGASVKVSCKASGYTFTDAYMSW VRQAPGQGLEWIGDMYPDNADASYNQKFRERVTITRD TSTSTAYLELSSLRSEDTAVYYCVLAPRWYFSVWGQG TLVTVSS | 84 |
| 1A7.gr.DANADA $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 85 |
| 1A7.Ala.1 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVLAPRWYFSVWGQG TLVTVSS | 86 |
| 1A7.Ala.1 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPATFGQGTKVEIK | 87 |
| 1A7.Ala.2 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVLAPRWYFSVWGQG TLVTVSS | 88 |
| 1A7.Ala.2 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTAPPTFGQGTKVEIK | 89 |
| 1A7.Ala.3 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVLAPRWYFSVWGQG TLVTVSS | 90 |
| 1A7.Ala.3 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGATLPPTFGQGTKVEIK | 91 |
| 1A7.Ala.4 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVLAPRWYFSVWGQG TLVTVSS | 92 |
| 1A7.Ala.4 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHALPPTFGQGTKVEIK | 93 |
| 1A7.Ala.5 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVLAPRWYFSVWGQG TLVTVSS | 94 |
| 1A7.Ala.5 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQAHTLPPTFGQGTKVEIK | 95 |
| 1A7.Ala.6 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVLAPRWYFSVWGQG TLVTVSS | 96 |

TABLE A-continued

OX40 Antibody Sequences

| Name | SEQUENCE | SEQ ID NO: |
|---|---|---|
| 1A7.Ala.6 V_L | DIQMTQSPSSLSASVGDRVTITCRASQDISNYLNWYQQKPGKAPKLLIYYTSRLRSGVPSRFSGSGSGTDFTLTISSLQPEDFATYYCQQGHTLAPTFGQGTKVEIK | 97 |
| 1A7.Ala.7 V_H | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS | 98 |
| 1A7.Ala.7 V_L | DIQMTQSPSSLSASVGDRVTITCRASQDISNYLNWYQQKPGKAPKLLIYYTSRLRSGVPSRFSGSGSGTDFTLTISSLQPEDFATYYCQAGHTLPPTFGQGTKVEIK | 99 |
| 1A7.Ala.8 V_H | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSAWGQGTLVTVSS | 100 |
| 1A7.Ala.8 V_L | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 101 |
| 1A7.Ala.9 V_H | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYASVWGQGTLVTVSS | 102 |
| 1A7.Ala.9 V_L | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 103 |
| 1A7.Ala.10 V_H | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWAFSVWGQGTLVTVSS | 104 |
| 1A7.Ala.10 V_L | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 105 |
| 1A7.Ala.11 V_H | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPAWYFSVWGQGTLVTVSS | 106 |
| 1A7.Ala.11 V_L | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 107 |
| 1A7.Ala.12 V_H | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFAVWGQGTLVTVSS | 108 |
| 1A7.Ala.12 V_L | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 109 |
| 1A7.Ala.13 V_H | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRAYFSVWGQGTLVTVSS | 110 |
| 1A7.Ala.13 V_L | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK | 111 |
| 1A7.Ala.14 V_H | EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAARWYFSVWGQGTLVTVSS | 112 |

TABLE A-continued

OX40 Antibody Sequences

| Name | SEQUENCE | SEQ ID NO: |
|---|---|---|
| 1A7.Ala.14 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 113 |
| 1A7.Ala.15 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCALAPRWYFSVWGQG TLVTVSS | 114 |
| 1A7.Ala.15 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 115 |
| 1A7.Ala.16 $V_H$ | EVQLVQSGAEVKKPGASVKVSCKASGYTFTDSYMSW VRQAPGQGLEWIGDMYPDNGDSSYNQKFRERVTITRD TSTSTAYLELSSLRSEDTAVYYCVAAPRWYFSVWGQG TLVTVSS | 116 |
| 1A7.Ala.16 $V_L$ | DIQMTQSPSSLSASVGDRVTITCRASQDISNYLNWYQQ KPGKAPKLLIYYTSRLRSGVPSRFSGSGSGTDFTLTISSL QPEDFATYYCQQGHTLPPTFGQGTKVEIK | 117 |
| 3C8.gr.1 $V_H$ | EVQLVQSGAEVKKPGASVKVSCKASGYAFTNYLIEWV RQAPGQGLEWIGVINPGSGDTYYSEKFKGRVTITRDTS TSTAYLELSSLRSEDTAVYYCARDRLDYWGQGTLVTV SS | 118 |
| 3C8.gr.1 $V_L$ | DIQMTQSPSSLSASVGDRVTITCHASQDISSYIVWYQQK PGKAPKLLIYHGTNLEDGVPSRFSGSGSGTDFTLTISSL QPEDFATYYCVHYAQFPYTFGQGTKVEIK | 119 |
| 3C8.gr.2 $V_H$ | EVQLVQSGAEVKKPGASVKVSCKASGYAFTNYLIEWV RQAPGQGLEWIGVINPGSGDTYYSEKFKGRVTITADTS TSTAYLELSSLRSEDTAVYYCARDRLDYWGQGTLVTV SS | 120 |
| 3C8.gr.2 $V_L$ | DIQMTQSPSSLSASVGDRVTITCHASQDISSYIVWYQQK PGKAPKLLIYHGTNLEDGVPSRFSGSGSGTDFTLTISSL QPEDFATYYCVHYAQFPYTFGQGTKVEIK | 121 |
| 3C8.gr.3 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 122 |
| 3C8.gr.3 $V_L$ | DIQMTQSPSSLSASVGDRVTITCHASQDISSYIVWYQQK PGKAPKLLIYHGTNLEDGVPSRFSGSGSGTDFTLTISSL QPEDFATYYCVHYAQFPYTFGQGTKVEIK | 123 |
| 3C8.gr.4 $V_H$ | EVQLVQSGAEVKKPGASVKVSCKASGYAFTNYLIEWV RQAPGQGLEWIGVINPGSGDTYYSEKFKGRVTITADTS TSTAYLELSSLRSEDTAVYYCARDRLDYWGQGTLVTV SS | 124 |
| 3C8.gr.4 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQFPYTFGQGTKVEIK | 125 |
| 3C8.gr.5 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 126 |
| 3C8.gr.5 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQFPYTFGQGTKVEIK | 127 |
| 3C8.gr.5.SG $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 128 |

TABLE A-continued

OX40 Antibody Sequences

| Name | SEQUENCE | SEQ ID NO: |
|---|---|---|
| 3C8.gr.5.SG $V_L$ | DIQMTQSPSSLSASVGDRVTITCHASQDISSYIVWYQQK PGKSFKGLIYHGTNLESGVPSRFSGSGSGTDFTLTISSLQ PEDFATYYCVHYAQFPYTFGQGTKVEIK | 129 |
| 3C8.gr.5.EG $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 130 |
| 3C8.gr.5.EG $V_L$ | DIQMTQSPSSLSASVGDRVTITCHASQDISSYIVWYQQK PGKSFKGLIYHGTNLEEGVPSRFSGSGSGTDFTLTISSLQ PEDFATYYCVHYAQFPYTFGQGTKVEIK | 131 |
| 3C8.gr.5.QG $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 132 |
| 3C8.gr.5.QG $V_L$ | DIQMTQSPSSLSASVGDRVTITCHASQDISSYIVWYQQK PGKSFKGLIYHGTNLEQGVPSRFSGSGSGTDFTLTISSL QPEDFATYYCVHYAQFPYTFGQGTKVEIK | 133 |
| 3C8.gr.6 $V_H$ | EVQLVQSGAEVKKPGASVKVSCKASGYAFTNYLIEWV RQAPGQGLEWIGVINPGSGDTYYSEKFKGRVTITADTS TSTAYLELSSLRSEDTAVYYCARDRLDYWGQGTLVTV SS | 134 |
| 3C8.gr.6 $V_L$ | DIQMTQSPSSLSASVGDRVTITCHASQDISSYIVWYQQK PGKSFKGLIYHGTNLEDGVPSRFSGSGSGADYTLTISSL QPEDFATYYCVHYAQFPYTFGQGTKVEIK | 135 |
| 3C8.gr.7 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 136 |
| 3C8.gr.7 $V_L$ | DIQMTQSPSSLSASVGDRVTITCHASQDISSYIVWYQQK PGKSFKGLIYHGTNLEDGVPSRFSGSGSGADYTLTISSL QPEDFATYYCVHYAQFPYTFGQGTKVEIK | 137 |
| 3C8.gr.8 $V_H$ | EVQLVQSGAEVKKPGASVKVSCKASGYAFTNYLIEWV RQAPGQGLEWIGVINPGSGDTYYSEKFKGRVTLTRDTS TSTAYLELSSLRSEDTAVYYCARDRLDYWGQGTLVTV SS | 138 |
| 3C8.gr.8 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQFPYTFGQGTKVEIK | 139 |
| 3C8.gr.9 $V_H$ | EVQLVQSGAEVKKPGASVKVSCKASGYAFTNYLIEWV RQAPGQGLEWIGVINPGSGDTYYSEKFKGRVTLTRDTS TSTAYLELSSLRSEDTAVYYCARDRLDYWGQGTLVTV SS | 140 |
| 3C8.gr.9 $V_L$ | DIQMTQSPSSLSASVGDRVTITCHASQDISSYIVWYQQK PGKSPKLLIYHGTNLEDGVPSRFSGSGSGTDFTLTISSLQ PEDFATYYCVHYAQFPYTFGQGTKVEIK | 141 |
| 3C8.gr.10 $V_H$ | EVQLVQSGAEVKKPGASVKVSCKASGYAFTNYLIEWV RQAPGQGLEWIGVINPGSGDTYYSEKFKGRVTLTRDTS TSTAYLELSSLRSEDTAVYYCARDRLDYWGQGTLVTV SS | 142 |
| 3C8.gr.10 $V_L$ | DIQMTQSPSSLSASVGDRVTITCHASQDISSYIVWYQQK PGKAFKLLIYHGTNLEDGVPSRFSGSGSGTDFTLTISSL QPEDFATYYCVHYAQFPYTFGQGTKVEIK | 143 |
| 3C8.gr.11 $V_H$ | EVQLVQSGAEVKKPGASVKVSCKASGYAFTNYLIEWV RQAPGQGLEWIGVINPGSGDTYYSEKFKGRVTLTRDTS TSTAYLELSSLRSEDTAVYYCARDRLDYWGQGTLVTV SS | 144 |

TABLE A-continued

OX40 Antibody Sequences

| Name | SEQUENCE | SEQ ID NO: |
|---|---|---|
| 3C8.gr.11 $V_L$ | DIQMTQSPSSLSASVGDRVTITCHASQDISSYIVWYQQK PGKAPKGLIYHGTNLEDGVPSRFSGSGSGTDFTLTISSL QPEDFATYYCVHYAQFPYTFGQGTKVEIK | 145 |
| 3C8.A.1 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 146 |
| 3C8.A.1 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCAHYAQFPYTFGQGTKVEIK | 147 |
| 3C8.A.2 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 148 |
| 3C8.A.2 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVAYAQFPYTFGQGTKVEIK | 149 |
| 3C8.A.3 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 150 |
| 3C8.A.3 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHAAQFPYTFGQGTKVEIK | 151 |
| 3C8.A.4 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 152 |
| 3C8.A.4 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAAFPYTFGQGTKVEIK | 153 |
| 3C8.A.5 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 154 |
| 3C8.A.5 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQAPYTFGQGTKVEIK | 155 |
| 3C8.A.6 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 156 |
| 3C8.A.6 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQFAYTFGQGTKVEIK | 157 |
| 3C8.A.7 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRLDYWGQGTLVTV SS | 158 |
| 3C8.A.7 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQFPATFGQGTKVEIK | 159 |
| 3C8.A.8 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARARLDYWGQGTLVTV SS | 160 |

TABLE A-continued

OX40 Antibody Sequences

| Name | SEQUENCE | SEQ ID NO: |
|---|---|---|
| 3C8.A.8 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQFPYTFGQGTKVEIK | 161 |
| 3C8.A.9 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDALDYWGQGTLVTV SS | 162 |
| 3C8.A.9 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQFPYTFGQGTKVEIK | 163 |
| 3C8.A.10 $V_H$ | EVQLVQSGAEVKKPGASVKVSCKASGYAFTNYLIEWV RQAPGQGLEWIGVINPGSGDTYYSEKFKGRVTLTADTS TSTAYLELSSLRSEDTAVYYCARDRADYWGQGTLVTV SS | 164 |
| 3C8.A.10 $V_L$ | DIQMTQSPSSLSASVGDRVTITCHASQDISSYIVWYQQK PGKSFKGLIYHGTNLEDGVPSRFSGSGSGTDFTLTISSL QPEDFATYYCVHYAQFPYTFGQGTKVEIK | 165 |
| 1D2.gr.1 $V_H$ | EVQLVESGPGLVKPSETLSLTCTVSGFSLTDYGVLWIR QPPGKGLEWIGMIWSGGTTDYNAAFISRVTISVDTSKN QFSLKLSSVTAADTAVYYCVREEMDYWGQGTLVTVSS | 166 |
| 1D2.gr.1 $V_L$ | DIQMTQSPSSLSASVGDRVTITCRASQDISNFLNWYQQ KPGKAPKLLIYYTSRLHSGVPSRFSGSGSGTDFTLTISSL QPEDFATYYCQQGNTLPWTFGQGTKVEIK | 167 |
| 1D2.gr.2 $V_H$ | EVQLVESGPGLVKPSETLSLTCTVSGFSLTDYGVLWIR QPPGKGLEWIGMIWSGGTTDYNAAFISRVTISKDTSKN QVSLKLSSVTAADTAVYYCVREEMDYWGQGTLVTVS S | 168 |
| 1D2.gr.2 $V_L$ | DIQMTQSPSSLSASVGDRVTITCRASQDISNFLNWYQQ KPGKAPKLLIYYTSRLHSGVPSRFSGSGSGTDFTLTISSL QPEDFATYYCQQGNTLPWTFGQGTKVEIK | 169 |
| 1D2.gr.3 $V_H$ | EVQLVESGPGLVKPSETLSLTCTVSGFSLTDYGVLWVR QPPGKGLEWLGMIWSGGTTDYNAAFISRLTISKDTSKN QVSLKLSSVTAADTAVYYCVREEMDYWGQGTLVTVS S | 170 |
| 1D2.gr.3 $V_L$ | DIQMTQSPSSLSASVGDRVTITCRASQDISNFLNWYQQ KPGKAPKLLIYYTSRLHSGVPSRFSGSGSGTDFTLTISSL QPEDFATYYCQQGNTLPWTFGQGTKVEIK | 171 |
| CON1 (1A7) HVR-H1 | $X_1X_2$YMS, wherein $X_1$ is D or E, and $X_2$ is S or A | 172 |
| CON1 (1A7) HVR-H2 | DMYPD$X_1X_2X_3X_4$SYNQKFRE, wherein $X_1$ is N or S, $X_1$ is A or G, $X_3$ is D or S, and $X_4$ is A or S | 173 |
| CON1 (1A7) HVR-H3 | APRW$X_1X_2X_3X_4$, wherein $X_1$ is Y or A, $X_2$ is A or F, $X_3$ is S or A, and $X_4$ is A or V. | 174 |
| CON1 (1A7) HVR-L3 | Q$X_1X_2X_3X_4X_5X_6X_7$T, wherein $X_1$ is A or Q, $X_2$ is A or G, $X_3$ is A or H, $X_4$ is A or T, $X_5$ is A or L, $X_6$ is A or P, and $X_7$ is A or P. | 175 |
| CON2 (3C8) HVR-H2 | VINPGSGD$X_1$YYSEKFKG, wherein $X_1$ is T, A or Q. | 176 |
| CON2 (3C8) HVR-L2 | HGTNLE$_1$, wherein $X_1$ is S, E, or Q. | 177 |
| CON2 (3C8) HVR-L3 | $X_1X_2$YAQFPY$X_3$, wherein $X_1$ is V or A, $X_2$ is H or A, and $X_3$ is Y or A. | 178 |
| 1A7 $V_L$ | DIQMTQTTSSLSASLGDRVTISCRASQDISNYLNWYQQ KPDGTVKLLIYYTSRLRSGVPSRFSGSGSGKDYFLTISN LEQEDVAAYFCQQGHTLPPTFGGGTKLEIK | 179 |

TABLE A-continued

OX40 Antibody Sequences

| Name | SEQUENCE | SEQ ID NO: |
|---|---|---|
| 1A7 V$_H$ | EVQLQQSGPELYKPGASYKISCKASGYTFTDSYMSWV KQSHGKTLEWIGDMYPDNGDSSYNQKFREKVTLTVD KSSTTAYMEFRSLTSEDSAVYYCVLAPRWYFSVWGTG TTVTVSS | 180 |
| 3C8 V$_L$ | DILMTQSPSSMSVSLGDTVSITCHASQDISSYIVWLQQK PGKSFRGLIYHGTNLEDGIPSRFSGSGSGADYSLTISSLE SEDFADYYCVHYAQFPYTFGGGTKLEIK | 181 |
| 3C8 V$_H$ | QVQLQQSGAELVRPGTSVKVSCKASGYAFTNYLIEWV KQRPGQGLEWIGVINPGSGDTYYSEKFKGKVTLTADK SSSTAYMQLSSLTSEDSAVYFCARDRLDYWGQGTTLT VSS | 182 |
| 1A7.gr.5' V$_H$ | EVQLVQSGAEVKKPGASVKVSCKASGYTFTDSYMSWVRQA PGQGLEWIGDMYPDNGDSSYNQKFRERVTLTVDTSTSTAYL ELSSLRSEDTAVYYCVLAPRWYFSVWGQGTLVTVSS | 183 |
| 1A7.gr.7' V$_H$ | EVQLVQSGAEVKKPGASVKVSCKASGYTFTDSYMSWVRQA PGQGLEWIGDMYPDNGDSSYNQKFRERVTLTVDTSTSTAYL ELSSLRSEDTAVYYCVLAPRWYFSVWGQGTLVTVSS | 184 |

In some embodiments, the OX40 agonist antibody is an anti-human OX40 agonist antibody described in U.S. Pat. No. 7,550,140. In some embodiments, the anti-human OX40 agonist antibody comprises a heavy chain comprising the sequence of EVQLVESGGGLVQPGGSLRLSCAASGFTFSNYTMNWVRQAPGKGLEWVSAISGSGGSTYYADSVKGRFTISRDNSKNTLYLQMNSLRAEDTAVYYCAKDRYSQVHYALDYW GQGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPKSCDK THTCPPCPAPELLGGPSVFLFPPKPKDTLMISRTPEVTCVVVD VSHEDPEVKFNWYVD GVEVHNAKTKPREEQYNSTYRVVSVLTVLHQDWLNGKEYKCKVSNKALPAPIEKTI SKAKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO:185) and/or a light chain comprising the sequence of DIVMTQSPDSLPVTPGEPASISCRSSQSLLHSNGYNYLDWYLQKAGQSPQLLIYLGSN RASGVPDRFSGSGSGTDFTLKISRVEAEDVGVYYCQQYYNHPTTFGQGTKLEIKRTV AAPSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC (SEQ ID NO:186). In some embodiments, the antibody comprises at least one, two, three, four, five, or six hypervariable region (HVR) sequences of antibody 008 as described in U.S. Pat. No. 7,550,140. In some embodiments, the antibody comprises a heavy chain variable region sequence and/or a light chain variable region sequence of antibody 008 as described in U.S. Pat. No. 7,550,140.

In some embodiments, the OX40 agonist antibody is an anti-human OX40 agonist antibody described in U.S. Pat. No. 7,550,140. In some embodiments, the anti-human OX40 agonist antibody comprises the sequence of DIQMTQSPD-SLPVTPGEPASISCRSSQSLLHSNGYNYLDWYLQK-AGQSPQLLIYLGSN RASGVPDRFSGSGSGTDFTLKIS-RVEAEDVGVYYCQQYYNHPTTFGQGTKLEIKRTV AAPSVFIFPPSDEQLKSGTASVVCLLNNFY-PREAKVQWKVDNALQSGNSQESVTEQD SKDSTYS-LSSTLTLSKADYEKHKVYACE-VTHQGLSSPVTKSFNRGEC (SEQ ID NO:187). In some embodiments, the antibody comprises at least one, two, three, four, five, or six hypervariable region (HVR) sequences of antibody SC02008 as described in U.S. Pat. No. 7,550,140. In some embodiments, the antibody comprises a heavy chain variable region sequence and/or a light chain variable region sequence of antibody SC02008 as described in U.S. Pat. No. 7,550,140.

In some embodiments, the OX40 agonist antibody is an anti-human OX40 agonist antibody described in U.S. Pat. No. 7,550,140. In some embodiments, the anti-human OX40 agonist antibody comprises a heavy chain comprising the sequence of EVQLVESGGGLVHPGGSLRLS-CAGSGFTFSSYAMHWVRQAPGKGLEWVSAIGTGGG TYYADSVMGRFTISRDNSKNTLYLQMNSLRAED-TAVYYCARYDNVMGLYWFDYW GQGTLVTVSSAS-TKGPSVFPLAPSSKSTSGGTAALGCLVKDYF-PEPVTVSWNSGALT SGVHTFPAVLQSSGLYS-LSSVVTVPSSSLGTQTYICNVNHKPSNTKVDKRVE-PKSCDK THTCPPCPA-PELLGGPSVFLFPPKPKDTLMISRTPEVTCVV VDVSHEDPEVKFNWYVD GVEVHNAKTKPREEQYN-STYRVVSVLTVLHQDWLNGKEYKCKVSNKALPA-PIEKTI SKAKGQPREPQVYTLPPSREEMTKNQVSLT-CLVKGFYPSDIAVEWESNGQPENNYKT TPPVLDSDGSFFLYSK-LTVDKSRWQQGNVFSCSVMHEALHNHYTQKSLSL-SPGK (SEQ ID NO:188) and/or a light chain comprising the sequence of EIVLTQSPATLSLSPGERATLSCRASQSVS-SYLAWYQQKPGQAPRLLIYDASNRATGI PARFSGSGSGTDFTLTISSLEPEDFAVYYCQQRSNWP- PAFGGGTKVEIKRTVAAPSVFI FPPSDEQLKSG-TASVVCLLNNFYPREAKVQWKVD-NALQSGNSQESVTEQDSKDSTY SLSSTLTLSKADYEKHKVYACE-VTHQGLSSPVTKSFNRGEC (SEQ ID NO:189). In some embodiments, the antibody comprises at least one, two, three, four, five, or six hypervariable region (HVR) sequences of antibody 023 as described in U.S. Pat. No. 7,550,140. In some embodiments, the antibody comprises a heavy chain variable region sequence and/or a light chain variable region sequence of antibody 023 as described in U.S. Pat. No. 7,550,140.

In some embodiments, the OX40 agonist antibody is an anti-human OX40 agonist antibody described in U.S. Pat. No. 7,960,515. In some embodiments, the anti-human OX40 agonist antibody comprises a heavy chain variable region comprising the sequence of EVQLVESGG-GLVQPGGSLRLSCAASGFTFSSYSMNWVRQAPGK-GLEWVSYISSSSST IDYADSVKGRFTISRDNAKNS-LYLQMNSLRDEDTAVYYCARESGWYLFDYWGQGT LVTVSS (SEQ ID NO:190) and/or a light chain variable region comprising the sequence of DIQMTQSPSSL-SASVGDRVTITCRASQGISSWLAWYQQK-PEKAPKSLIYAASSLQSGV PSRFSGSGSGTDFTLTISSLQPEDFATYYCQQYN-SYPPTFGGGTKVEIK (SEQ ID NO:191). In some embodiments, the antibody comprises at least one, two, three, four, five, or six hypervariable region (HVR) sequences of antibody 11D4 as described in U.S. Pat. No. 7,960,515. In some embodiments, the antibody comprises a heavy chain variable region sequence and/or a light chain variable region sequence of antibody 11D4 as described in U.S. Pat. No. 7,960,515.

In some embodiments, the OX40 agonist antibody is an anti-human OX40 agonist antibody described in U.S. Pat. No. 7,960,515. In some embodiments, the anti-human OX40 agonist antibody comprises a heavy chain variable region comprising the sequence of EVQLVESGG-GLVQPGRSLRLSCAASGFTFDDYAMHWVRQAPGK-GLEWVSGISWNS GSIGYADSVKGRFTISRDNAKNS-LYLQMNSLRAEDTALYYCAKDQSTADYYFYYGM DVWGQGTTVTVSS (SEQ ID NO:192) and/or a light chain variable region comprising the sequence of EIV-VTQSPATLSLSPGERATLSCRASQSVSSY-LAWYQQKPGQAPRLLIYDASNRATGI PARFSGSGSGTDFTLTISSLEPED-FAVYYCQQRSNWPTFGQGTKVEIK (SEQ ID NO:193). In some embodiments, the antibody comprises at least one, two, three, four, five, or six hypervariable region (HVR) sequences of antibody 18D8 as described in U.S. Pat. No. 7,960,515. In some embodiments, the antibody comprises a heavy chain variable region sequence and/or a light chain variable region sequence of antibody 18D8 as described in U.S. Pat. No. 7,960,515.

In some embodiments, the OX40 agonist antibody is an anti-human OX40 agonist antibody described in WO 2012/027328. In some embodiments, the anti-human OX40 agonist antibody comprises a heavy chain variable region comprising the sequence of QVQLVQSGSELKKPGASVKVSCK-ASGYTFTDYSMHWVRQAPGQGLKWMGWINTE TGEPTYADDFKGRFVFSLDTSVSTAYLQISSLKAED-TAVYYCANPYYDYVSYYAMD YWGQGTTVTVSS (SEQ ID NO:194) and/or a light chain variable region comprising the sequence of DIQMTQSPSSL-SASVGDRVTITCKASQDVSTA-VAWYQQKPGKAPKLLIYSASYLYTG VPSRFSGSGSGTDFTFTISSLQPEDIATYYCQQHYST-PRTFGQGTKLEIK (SEQ ID NO:195). In some embodiments, the antibody comprises at least one, two, three, four, five, or six hypervariable region (HVR) sequences of antibody hu106-222 as described in WO 2012/027328. In some embodiments, the antibody comprises a heavy chain variable region sequence and/or a light chain variable region sequence of antibody hu106-222 as described in WO 2012/027328.

In some embodiments, the OX40 agonist antibody is an anti-human OX40 agonist antibody described in WO 2012/027328. In some embodiments, the anti-human OX40 agonist antibody comprises a heavy chain variable region comprising the sequence of EVQLVESGGGLVQPGGSLRLSCAASEYEFP-SHDMSWVRQAPGKGLELVAAINSDGG STYYPDT-MERRFTISRDNAKNSLYLQMNSLRAEDTAVYYCAR-HYDDYYAWFAYWG QGTMVTVSS (SEQ ID NO:196) and/or a light chain variable region comprising the sequence of EIVLTQSPATLSLSPGERATLSCRASKSVST-SGYSYMHWYQQKPGQAPRLLIYLASNL ESGVPARFSGSGSGTDFTLTISSLEPEDFAVYYCQHS-RELPLTFGGGTKVEIK (SEQ ID NO:197). In some embodiments, the antibody comprises at least one, two, three, four, five or six hypervariable region (HVR) sequences of antibody Hu119-122 as described in WO 2012/027328. In some embodiments, the antibody comprises a heavy chain variable region sequence and/or a light chain variable region sequence of antibody Hu119-122 as described in WO 2012/027328.

In some embodiments, the OX40 agonist antibody is an anti-human OX40 agonist antibody described in WO 2013/028231. In some embodiments, the anti-human OX40 agonist antibody comprises a heavy chain comprising the sequence of MYLGLNYVFIVFLLNGVQSEVKLEESGG-GLVQPGGSMKLSCAASGFTFSDAWMDW VRQS-PEKGLEWVAEIRSKANNHATYYAESVNGRFTISRDD-SKSSVYLQMNSLRAED TGIYYCTWGEVFYFDYWGQGTTLTVSSAS-TKGPSVFPLAPSSKSTSGGTAALGCLVK DYF-PEPVTVSWNSGALTSGVHTFPAVLQSSGLYS-LSSVVTVPSSSLGTQTYITCNVNH KPSNTKVDKKVEPKSCDKTHTCPPCPA-PELLGGPSVFLFPPKPKDTLMISRTPEVTCV VVDVSHEDPEVKFNWYVDGVEVHNAKTKPRE-EQYNSTYRVVSVLTVLHQDWLNG KEYKCKVSNKA-LPAPIEKTISKAKGQPREPQVYTLPPSRDELT-KNQVSLTCLVKGFYP SDIAVEWESNGQPENNYKTTPPVLDSDGSFFLYSK-LTVDKSRWQQGNVFSCSVMHE ALHNHYTQKSLSL-SPGK (SEQ ID NO:198) and/or a light chain comprising the sequence of MRPSIQFLGLLL-FWLHGAQCDIQMTQSPSSLSASLGGKVTITCK-SSQDINKYIAWYQH KPGKGPRLLIHYTSTLQP-GIPSRFSGSGSGRDYSFSISNLEPEDIATYYC LQYDNLLTFG AGTKLELKRTVAAPSVFIFPPSD-EQLKSGTASVVCLLNNFYPREAKVQWKVDNALQS GNSQESVTEQDSKDSTYSLSSTLTLSKADYEKHKVY-ACEVTHQGLSSPVTKSFNRGE C (SEQ ID NO:199). In some embodiments, the anti-human OX40 agonist antibody comprises a heavy chain variable region comprising the sequence of MYLGLNYVFIVFLLNGVQSEVKLEESGG-GLVQPGGSMKLSCAASGFTFSDAWMDW VRQS-PEKGLEWVAEIRSKANNHATYYAESVNGRFTISRDD-SKSSVYLQMNSLRAED TGIYYCTWGEVFYFDYWGQGTTLTVSS (SEQ ID NO:214) and/or a light chain variable region comprising the sequence of MRPSIQFLGLLLFWLHGAQCDIQMTQSPSSLSASLGGKVTITCKSSQDINKYIAWYQH KPGKGPRLLIHYTSTLQPGIPSRFSGSGSGRDYSFSISNLEPEDIATYYCLQY DNLLTFG AGTKLELK (SEQ ID NO:215). In some embodiments, the antibody comprises at least one, two, three, four, five, or six hypervariable region (HVR) sequences of antibody Mab CH 119-43-1 as described in WO 2013/028231. In some embodiments, the antibody comprises a heavy chain variable region sequence and/or a light chain variable region sequence of antibody Mab CH 119-43-1 as described in WO 2013/028231.

In some embodiments, the OX40 agonist antibody is an anti-human OX40 agonist antibody described in WO 2013/038191. In some embodiments, the anti-human OX40 agonist antibody comprises a heavy chain variable region comprising the sequence of EVQLQQSGPELVKPGASVKMSCKASGYTFTSYVMHWVKQKPGQGLEWIGYINPYN DGTKYNEKFKGKATLTSDKSSSTAYMELSSLTSEDSAVYYCANYYGSSLSMDYWG QGTSVTVSS (SEQ ID NO:200) and/or a light chain variable region comprising the sequence of DIQMTQTTSSLSASLGDRVTISCRASQDISNYLNWYQQKPDGTVKLLIYYTSRLHSGV PSRFSGSGSGTDYSLTISNLEQEDIATYFCQQGNTLPWTFGGGTKLEIKR (SEQ ID NO:201). In some embodiments, the antibody comprises at least one, two, three, four, five, or six hypervariable region (HVR) sequences of antibody clone 20E5 as described in WO 2013/038191. In some embodiments, the antibody comprises a heavy chain variable region sequence and/or a light chain variable region sequence of antibody clone 20E5 as described in WO 2013/038191.

In some embodiments, the OX40 agonist antibody is an anti-human OX40 agonist antibody described in WO 2013/038191. In some embodiments, the anti-human OX40 agonist antibody comprises a heavy chain variable region comprising the sequence of EVQLQQSGPELVKPGASVKISCKTSGYTFKDYTMHWVKQSHGKSLEWIGGIYPNNG GSTYNQNFKDKATLTVDKSSSTAYMEFRSLTSEDSAVYYCARMGYHGPHLDFDVW GAGTTVTVSP (SEQ ID NO:202) and/or a light chain variable region comprising the sequence of DIVMTQSHKFMSTSLGDRVSITCKASQDVGAAVAWYQQKPGQSPKLLIYWASTRHT GVPDRFTGGGSGTDFTLTISNVQSEDLTDYFCQQYINYPLTFGGGTKLEIKR (SEQ ID NO:203). In some embodiments, the antibody comprises at least one, two, three, four, five, or six hypervariable region (HVR) sequences of antibody clone 12H3 as described in WO 2013/038191. In some embodiments, the antibody comprises a heavy chain variable region sequence and/or a light chain variable region sequence of antibody clone 12H3 as described in WO 2013/038191.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWMGYINPY NDGTKYNEKFKGRVTITSDTSASTAYMELSSLRSEDTAVYYCANYYGSSLSMDYWG QGTLVTVSS (SEQ ID NO:204) and/or a light chain variable region comprising the sequence of DIQMTQSPSSLSASVGDRVTITCRASQDISNYLNWYQQKPGKAPKLLIYYTSRLHSGV PSRFSGSGSGTDYTLTISSLQPEDFATYYCQQGNTLPWTFGQGTKVEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWMGYINPY NDGTKYNEKFKGRVTITSDTSASTAYMELSSLRSEDTAVYYCANYYGSSLSMDYWG QGTLVTVSS (SEQ ID NO:204) and/or a light chain variable region comprising the sequence of DIQMTQSPSSLSASVGDRVTITCRASQDISNYLNWYQQKPGKAVKLLIYYTSRLHSG VPSRFSGSGSGTDYTLTISSLQPEDFATYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWIGYINPYN DGTKYNEKFKGRATITSDTSASTAYMELSSLRSEDTAVYYCANYYGSSLSMDYWGQ GTLVTVSS (SEQ ID NO:207) and/or a light chain variable region comprising the sequence of DIQMTQSPSSLSASVGDRVTITCRASQDISNYLNWYQQKPGKAPKLLIYYTSRLHSGV PSRFSGSGSGTDYTLTISSLQPEDFATYYCQQGNTLPWTFGQGTKVEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWIGYINPYN DGTKYNEKFKGRATITSDTSASTAYMELSSLRSEDTAVYYCANYYGSSLSMDYWGQ GTLVTVSS (SEQ ID NO:207) and/or a light chain variable region comprising the sequence of DIQMTQSPSSLSASVGDRVTITCRASQDISNYLNWYQQKPGKAVKLLIYYTSRLHSG VPSRFSGSGSGTDYTLTISSLQPEDFATYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWIGYINPYN DGTKYNEKFKGRATLTSDKSASTAYMELSSLRSEDTAVYYCANYYGSSLSMDYWGQGTLVTVSS (SEQ ID NO:208) and/or a light chain variable region comprising the sequence of DIQMTQSPSSLSASVGDRVTITCRASQDISNYLNWYQQKPGKAPKLLIYYTSRLHSGVPSRFSGSGSGTDYTLTISSLQPEDFATYYCQQGNTLPWTFGQGTKVEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGASVKVSCKASGYTFTSYVMHWVRQAPGQRLEWIGYINPYN DGTKYNEKFKGRATLTSDKSASTAYMELSSLRSEDTAVYYCANYYGSSLSMDYWGQGTLVTVSS (SEQ ID NO:208) and/or a light chain variable region comprising the sequence of DIQMTQSPSSLSASVGDRVTITCRASQDISNYLNWYQQKPGKAVKLLIYYTSRLHSGVPSRFSGSGSGTDYTLTISSLQPEDFATYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSSVKVSCKASGYTFKDYTMHWVRQAPGQGLEWMGGIYPNNGGSTYNQNFKDRVTITADKSTSTAYMELSSLRSEDTAVYYCARMGYHGPHLDFDV WGQGTTVTVSS (SEQ ID NO:209) and/or a light chain variable region comprising the sequence of DIQMTQSPSSLSASVGDRVTITCKASQDVGAAVAWYQQKPGKAPKLLIYWASTRHTGVPSRFSGSGSGTDFTLTISSLQPEDFATYYCQQYINYPLTFGGGTKVEIKR (SEQ ID NO:210). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSSVKVSCKASGYTFKDYTMHWVRQAPGQGLEWMGGIYPNNGGSTYNQNFKDRVTITADKSTSTAYMELSSLRSEDTAVYYCARMGYHGPHLDFDV WGQGTTVTVSS (SEQ ID NO:209) and/or a light chain variable region comprising the sequence of DIQMTQSPSSLSASVGDRVTITCKASQDVGAAVAWYQQKPGKAPKLLIYWASTRHTGVPDRFSGGGSGTDFTLTISSLQPEDFATYYCQQYINYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSSVKVSCKASGYTFKDYTMHWVRQAPGQGLEWIGGIYPNNGGSTYNQNFKDRVTLTADKSTSTAYMELSSLRSEDTAVYYCARMGYHGPHLDFDV WGQGTTVTVSS (SEQ ID NO:212) and/or a light chain variable region comprising the sequence of DIQMTQSPSSLSASVGDRVTITCKASQDVGAAVAWYQQKPGKAPKLLIYWASTRHTGVPSRFSGSGSGTDFTLTISSLQPEDFATYYCQQYINYPLTFGGGTKVEIKR (SEQ ID NO:210 In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSSVKVSCKASGYTFKDYTMHWVRQAPGQGLEWIGGIYPNNGGSTYNQNFKDRVTLTADKSTSTAYMELSSLRSEDTAVYYCARMGYHGPHLDFDV WGQGTTVTVSS (SEQ ID NO:212) and/or a light chain variable region comprising the sequence of DIQMTQSPSSLSASVGDRVTITCKASQDVGAAVAWYQQKPGKAPKLLIYWASTRHTGVPDRFSGGGSGTDFTLTISSLQPEDFATYYCQQYINYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQS-GAEVKKPGSSVKVSCK-ASGYTFKDYTMHWVRQAPGQGLEWIGGIYPNN GGSTYNQNFKDRATLTVDKSTSTAYMELSSLRSED-TAVYYCARMGYHGPHLDFDV WGQGTTVTVSS (SEQ ID NO:213) and/or a light chain variable region comprising the sequence of DIQMTQSPSSLSASVGDRVTITCK-ASQDVGAAVAWYQQKPGKAPKLLIYWASTRHT GVPSRFSGSGSGTDFTLTISSLQPEDFATYYCQQYINY-PLTFGGGTKVEIKR (SEQ ID NO:210). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQS-GAEVKKPGSSVKVSCK-ASGYTFKDYTMHWVRQAPGQGLEWIGGIYPNN GGSTYNQNFKDRATLTVDKSTSTAYMELSSLRSED-TAVYYCARMGYHGPHLDFDV WGQGTTVTVSS (SEQ ID NO:213) and/or a light chain variable region comprising the sequence of DIQMTQSPSSLSASVGDRVTITCK-ASQDVGAAVAWYQQKPGKAPKLLIYWASTRHT GVPDRFSGGGSGTDFTLTISSLQPEDFATYYCQQY-INYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the agonist anti-human OX40 antibody is L106 BD (Pharmingen Product #340420). In some embodiments, the antibody comprises at least one, two, three, four, five or six hypervariable region (HVR) sequences of antibody L106 (BD Pharmingen Product #340420). In some embodiments, the antibody comprises a heavy chain variable region sequence and/or a light chain variable region sequence of antibody L106 (BD Pharmingen Product #340420).

In some embodiments, the agonist anti-human OX40 antibody is ACT35 (Santa Cruz Biotechnology, Catalog #20073). In some embodiments, the antibody comprises at least one, two, three, four, five or six hypervariable region (HVR) sequences of antibody ACT35 (Santa Cruz Biotechnology, Catalog #20073). In some embodiments, the antibody comprises a heavy chain variable region sequence and/or a light chain variable region sequence of antibody ACT35 (Santa Cruz Biotechnology, Catalog #20073).

In some embodiments, the OX40 agonist antibody is MEDI6469. In some embodiments, the antibody comprises at least one, two, three, four, five, or six hypervariable region (HVR) sequences of antibody MEDI6469. In some embodiments, the antibody comprises a heavy chain variable region sequence and/or a light chain variable region sequence of antibody MEDI6469.

In some embodiments, the OX40 agonist antibody is MEDI0562. In some embodiments, the antibody comprises at least one, two, three, four, five, or six hypervariable region (HVR) sequences of antibody MEDI0562. In some embodiments, the antibody comprises a heavy chain variable region sequence and/or a light chain variable region sequence of antibody MEDI0562.

Non-Antibody OX40 Agonists

In certain embodiments, the antigen binding polypeptides described herein comprise antigen binding regions comprising non-antibody OX40 agonists. Non-antibody OX40 agonists are well known in the art.

OX40L (also known as CD134L) serves as a ligand for OX40. As such, agonists that present part or all of OX40L may serve as OX40 agonists. In some embodiments, an OX40 agonist may include one or more extracellular domains of OX40L. Examples of extracellular domains of OX40L may include OX40-binding domains. In some embodiments, an OX40 agonist may be a soluble form of OX40L that includes one or more extracellular domains of OX40L but lacks other, insoluble domains of the protein, e.g., transmembrane domains. In some embodiments, an OX40 agonist is a soluble protein that includes one or more extracellular domains of OX40L able to bind OX40L.

In some embodiments, an OX40 agonist may be any one of the OX40 agonists described in U.S. Pat. No. 7,696,175 or European Patent No. EP0672141 B1. In some embodiments, an OX40 agonist may be any one of the OX40 agonists described in International Publication No. WO2006/121810, such as an OX40 immunoadhesin. In some embodiments, the OX40 agonist is MEDI6383.

Fc Variants that Promote Intermolecular Interactions Between Fc Domains

In certain embodiments, the antigen binding polypeptides described herein comprise a variant Fc region that enhances intermolecular interactions between Fc domains to form the agonist binding complexes provided herein. In exemplary embodiments, the antigen binding polypeptides described herein comprise a variant Fc region that enhances hexamer formation to produce the agonist antigen binding complexes provided herein. The variant Fc region may comprise a variant of an Fc region from a variety of species, including for example, human, rodent (e.g., mouse, rat, hamster, rabbit, etc.), dog, or non-human primate (e.g., old world monkeys such as macques (e.g., cynomolgus monkeys or rhesus monkeys), baboons, and chimpanzees, or new world monkeys such as marmosets, tamarins, howler, wooly, spider, owl, capuchins or squirrel monkeys). The Fc variant may be a variant of any antibody isotype, including Fc regions from IgG1, IgG2, IgG3, IgG4, IgA1, IgA2 or IgE antibodies. In an exemplary embodiment, the Fc region is a variant of a human Fc region sequence (e.g., a human IgG1, IgG2, IgG3 or IgG4 Fc region) comprising an amino acid modification (e.g. a substitution, deletion or insertion) at one or more amino acid positions.

The amino acid modifications described herein may directly or indirectly promote intermolecular interactions between Fc domains. For example, the amino acid modification may cause the effect itself, be involved in contacting the Fc domain of another molecule directly, or may be modified to interact with another Fc domain directly, or may indirectly affect the intermolecular Fc:Fc interaction. In certain embodiments, the amino acid modifications described herein may directly or indirectly enhance the binding strength between the Fc domains in the complex form, e g, enhancing the stability of the complex structure (e.g., a hexameric, pentameric, tetrameric, trimeric, or dimeric structure). In certain embodiments, the amino acid modifications described herein may promote or strengthen the formation of new intermolecular Fc:Fc bonds, such as, but not limited to, Van der Waals interactions, hydrogen bonds, charge-charge interactions, or aromatic stacking interactions, or promote increased entropy upon Fc:Fc interaction by release of water molecules. In certain embodiments, exemplary substitutions for producing the Fc variants described herein may be selected based on size and physicochemical properties engaging in or promoting intermolecular Fc:Fc interactions or intramolecular interactions (allosteric mutations).

Methods for determining whether an Fc variant promotes an intermolecular interaction between Fc domains and/or promotes complex formation (e.g., dimer, trimer, tetramer, pentamer, or hexamer formation) may be determined using assays well known in the art, for example, by determining the molecular weight of an Fc complex or antigen binding complex using size exclusive chromatography (SEC) as further described in the Examples section herein.

In certain embodiments, the Fc variant that promotes intermolecular interactions between Fc domains includes a substitution at one or more Fc region residues selected from E345, E430, and S440 (EU numbering). In certain embodiments, the Fc variant includes substitutions at two or more of amino acid positions E345, E430, and E440 (EU numbering). In an exemplary embodiment, the Fc variant comprises the following three modifications: E345R, E430G, and S440Y (EU numbering).

In other embodiments, the Fc variant may include any of the modifications described in WO 2013/004842, WO 2014/108198, WO 2014/006217, or Diebolder et al. SCIENCE, vol. 434, 1260-1263(2014).

In certain embodiments, the Fc variant may include modifications at 1, 2, 3, 4, 5, 6 or more of the amino acid positions described in Table 1 below. The modifications may be a deletion, insertion or substitution of one or more amino acid, or combinations thereof. Such a substitution of amino acids may be with any naturally occurring or non-naturally amino acid.

Such modifications are useful for promoting intermolecular interactions between Fc domains and complex formation (e.g., hexamer formation).

TABLE 1

Exemplary modification sites and amino acid substitutions for promoting intermolecular interactions between Fc domains and hexamer formation. Each amino acid residue is listed with numbering according to the EU index in a human IgG1 antibody, and shows the amino acid in the corresponding position in an IgG2, IgG3, and IgG4 parent antibody.

| Amino acid in IgG1/IgG2/IgG3/IgG4 | Exemplary substitutions | Preferred Substitutions |
|---|---|---|
| P247 | A, C, D, F, G, H, I, K, L, M, N, R, S, T, V, or W | G |
| I253 | A, D, K, L, M, N, R, S, or V, alternatively E, Q, or T | L or V, alternatively Q or N |
| S254 | E, F, G, H, I, K, L, P, T, V, or W | L |
| H310 | A, G, F, K, L, P, R, T, V, or W, alternatively N, Q, or Y | P or W, alternatively Q |
| Q311 | A, C, E, G, H, F, I, K, L, N, P, R, S, T, W, or Y | L or W, alternatively E or R |
| E345 | A, C, D, G, H, F, I, K, L, M, N, P, Q, R, S, T, V, W, or Y | A, D, G, H, F, I, K, L, M, N, P, Q, R, S, T, V, W, or Y |

TABLE 1-continued

Exemplary modification sites and amino acid substitutions for promoting intermolecular interactions between Fc domains and hexamer formation. Each amino acid residue is listed with numbering according to the EU index in a human IgG1 antibody, and shows the amino acid in the corresponding position in an IgG2, IgG3, and IgG4 parent antibody.

| Amino acid in IgG1/IgG2/IgG3/IgG4 | Exemplary substitutions | Preferred Substitutions |
|---|---|---|
| D/E356* | G, I, L, R, T, or V | R |
| T359 | G, N, P, or R | R |
| E382 | F, K, L, M, P, V, or W, alternatively D, H, N, Q, S, T, or Y | L or V, alternatively D, Q, K, or R |
| G385 | A, D, H, I, L, N, P, Q, R, S, T, or V, alternatively E, K, W, or Y | N or R, alternatively D, E, or K |
| Q386 | A, C, D, E, G, H, F, I, K, L, N, P, R, S, T, V, W, or Y | K |
| E430 | A, C, D, F, G, H, I, K, L, M, N, P, Q, R, S, T, V, W, or Y | A, D, G, H, F, I, K, L, M, N, P, Q, R, S, T, V, W, or Y |
| H433 | R | R |
| N434 | D, E, G, K, R, S, V, or W, alternatively H, Q, T, or Y | W, alternatively Q, H, K, or R |
| Y436 | I, K, L, R, S, T, V, or W, alternatively A, E, F, H, M, N, or Q | I or V, alternatively N, Q, S, or T |
| Q438 | C, E, I, K, L, S, T, V, W, or Y, alternatively A, G, H, N, Q, or R | C or L, alternatively N, S, or T |
| K439 | A, D, E, H, L, P, R, T, Y, alternatively Q or W | D, E, H, or R, alternatively Q |
| S440 | A, C, D, E, G, H, F, I, K, L, M, N, P, Q, R, T, V, W, or Y | W or Y, alternatively D, E, or Q |
| K447 | D, E, N, or Q, deletion | D, E, N, or Q, deletion |

*In IgG1, position 356 may be either D or E in the parent antibody. The reference to "D/E356" refers in the present context to allotypic variants in the sequence of human IgG1. In the IgG1m(za) allotype of human IgG1 the amino acid in position 356 is D, while in the IgG1m(f) allotype of human IgG1 the amino acid in position 356 is E.

In certain embodiments, the Fc variant comprises a modification in at least one amino acid residue selected from those corresponding to E345, E430, S440, Q386, P247, I253, S254, Q311, D/E356, T359, E382, Y436, and K447 in the Fc-region of a human IgG1 heavy chain. In certain embodiments, the Fc variant comprises a modification in at least one amino acid residue selected from those corresponding to H310, G385, H433, N434, Q438, and K439 in the Fc-region of a human IgG1 heavy chain.

In one embodiment, the Fc comprises a modification in at least one amino acid residue selected from those corresponding to E345X, E430X, S440W/Y, Q386K, P247G, I253V, S254L, Q311I/W, D/E356R, E382V, Y436I, and K447D/E/deletion in the Fc region of a human IgG1 heavy chain, wherein X is any amino acid (e.g., a natural occurring amino acid).

In one embodiment, the Fc variant comprises a modification in at least one amino acid residue selected from E345, E430, S440, and Q386 in the Fc-region of a human IgG1 heavy chain.

In another embodiment, the Fc variant comprises a modification in at least one amino acid residue selected from E345X, E430X, S440W/Y, Q386K, in the Fc region of a human IgG1 heavy chain, wherein X is any amino acid (e.g., a natural occurring amino acid).

In certain embodiments, the Fc variant comprises a modification in at least one amino acid residue selected from E345R, Q, N, K, A, C, D, F, G, H, I, L, M, P, S, T, V, W, Y;

E430T, S, G, A, C, D, F, H, I, L, K, M, N, P, Q, R, V, W, Y; S440W, Y, and Q386K in the Fc region of a human IgG1 heavy chain.

In certain embodiments, the Fc variant comprises a modification in at least one amino acid residue selected from E345R/Q/N/K, E430T/S/G, S440Y/W, and Q386K in the Fc-region of a human IgG1 heavy chain.

In certain embodiments, the Fc variant comprises a modification in at least one amino acid residue selected from E345R, E430G and S440Y in the Fc-region of a human IgG1 heavy chain. In one embodiment, the Fc variant comprises a E345R modification in the Fc-region of a human IgG1 heavy chain. In one embodiment, the Fc variant comprises a E430G modification in the Fc-region of a human IgG1 heavy chain. In one embodiment, the Fc variant comprises a S440Y modification in the Fc-region of a human IgG1 heavy chain.

In certain embodiments, the Fc variant comprises a modification in at least one amino acid residue selected from E382 and H433, including, for example, E345Y, D, W; E430F, H; E382D, Q, K, R; and H433R.

In another embodiment, the Fc variant comprises the following substitution: E345R.

In another embodiment, the Fc variant comprises at least one of the following amino acid residue substitutions: I253 to E, N, Q, S or T; H310 to N, Q, W or Y; Q311 to E or R; E382 to D, H, K, R, N, Q, S, T, W or Y; G385 to E, H, K, N, Q, R, S, T, W or Y; H433 to R; N434 to D, E, H, K, Q, R, S, T, W or Y; Y436 to A, E, F, H, I, K, L, M, N, Q, R, S, T or V; Q438 to A, E, G, H, K, N, Q, R, S, T, W or Y; K439 to D, H, Q, R, W or Y; or S440 to D, E, H, F, N, Q, W or Y.

In another embodiment, the Fc variant comprises at least one of the following amino acid residue substitutions: I253 to N or Q; H310 to Q; Q311 to E or R; E382 to D, Q, K, or R; G385 to D, E, K or R; H433 to R; N434 to H, K, Q or R; Y436 to N, Q, S or T; Q438 to N, S or T; K439 to Q; or S440 to D, E or Q.

In another embodiment, the Fc variant comprises at least one of the following amino acid residue substitutions: E382 to D, Q, K, or R; or H433 to R.

In another embodiment, the Fc variant comprises the following substitution: E382R.

In another embodiment, the Fc variant comprises the following substitution: H433R.

In another embodiment, the Fc variant comprises at least one of the following amino acid residue substitutions: P247G, I253V, S254L, Q311L, Q311W, E345A, E345C, E345D, E345F, E345G, E345H, E345I, E345K, E345L, E345M, E345N, E345P, E345Q, E345R, E345S, E345T, E345V, E345W, E345Y, D/E356G, D/E356R, T359R, E382L, E382V, Q386K, E430A, E430C, E430D, E430F, E430G, E430H, E430I, E430K, E430L, E430M, E430N, E430P, E430Q, E430R, E430S, E430T, E430V, E430W, E430Y, Y436I, S440Y or S440W.

In another embodiment, the Fc variant comprises at least one of the following amino acid residue substitutions: E382R, H433R, H435R, or H435A.

In another embodiment, the Fc variant comprises modifications in at least two of the following amino acid residue: E345, E382 or Q386 in the Fc-region of a human IgG1 heavy chain, wherein the at least two amino acid modifications are different.

In certain embodiments, where the Fc variant comprises modifications in two or more amino acid residues, the modifications may be present in each of the heavy chains of the Fc variant, or one of the amino acid modifications may be present in one of the heavy chains of the Fc domain and the other amino acid modification may be present in the other heavy chain of the Fc domain, respectively, or vice versa.

In one embodiment, the Fc variant comprises a modification in at least two amino acid residues selected from those corresponding to E345, E430, S440, Q386, P247, I253, S254, Q311, D/E356, T359, E382, Y436, and K447 in the Fc-region of a human IgG1 heavy chain. In one embodiment, the Fc variant comprises a modification in at least two amino acid residues selected from those corresponding to H310, G385, H433, N434, Q438, and K439. In an exemplary embodiment, the Fc variant comprises one or more of the following modifications: S440Y or S440W.

In one embodiment, the Fc variant comprises a modification in at least two amino acid residues selected from those corresponding to E345X, E430X, S440W/Y, Q386K, P247G, I253V, S254L, Q311L/W, D/E356R, E382V, and Y436I in the Fc region of a human IgG1 heavy chain, wherein X is any amino acid (e.g., a natural occurring amino acid).

In one embodiment, the Fc variant comprises a modification in at least one of E345, E430, S440, and Q386, such as two or all of E345, E430, S440, and Q386. In another embodiment, the Fc variant comprises a modification in at least one of E382 and H433, or both of E382 and H433. In certain embodiments, such variants may optionally comprise a further modification in one or more other amino acids listed in Table 1. In an exemplary embodiment, the Fc variant comprises a modification in at least two amino acid residues selected from the group of corresponding to E345X, E430X, S440W/Y, and Q386K in the Fc-region of a human IgG1 heavy chain, wherein X is any amino acid (e.g., a natural occurring amino acid).

Exemplary combinations of modifications in at least two amino acid residues are E345X/E430X, E345X/S440Y or W, E345X/Q386K, E430X/S440Y or W, and E430X/Q386K.

In certain embodiments, the Fc variant comprises a modification in at least two amino acid residues selected from the group consisting of P247G, I253V, S254L, Q311L, Q311W, E345A, E345C, E345D, E345F, E345G, E345H, E345I, E345K, E345L, E345M, E345N, E345P, E345Q, E345R, E345S, E345T, E345V, E345W, E345Y, D/E356G, D/E356R, T359R, E382L, E382V, Q386K, E430A, E430C, E430D, E430F, E430G, E430H, E430I, E430K E430L, E430M, E430N, E430P, E430Q, E430R, E430S, E430T, E430V, E430W, E430Y, Y436I, S440Y and S440W.

In an exemplary embodiment, the Fc variant comprises a modification in at least two amino acid residues, wherein the modifications are substitutions selected from the consisting of: E345R, Q, N, K, A, C, D, F, G, H, I, L, M, P, S, T, V, W, Y; E430T, S, G, A, C, D, F, H, I, L, K, M, N, P, Q, R, V, W, Y; S440W, Y; and Q386K, in the Fc region of a human IgG1 heavy chain.

In an exemplary embodiment, the Fc variant comprises a modification in at least two amino acid residues, wherein the modifications are amino acid substitutions selected from the consisting of: I253E, N, Q, S, T; H310N, Q, W, Y; Q311E, R; E382D, H, K, R, N, Q, S, T, W, Y; G385E, H, K, N, Q, R, S, T, W, Y; H433R; N434D, E, H, K, Q, R, S, T, W, Y; Y436, A, E, F, H, I, K, L, M, N, Q, R, S, T, V; Q438A, E, G, H, K, N, Q, R, S, T, W, Y; K439D, H, Q, R, W, Y; and S440D, E, H, F, N, Q, in the Fc region of a human IgG1 heavy chain.

In an exemplary embodiment, the Fc variant comprises modification in at least two amino acid residues, wherein the modifications are amino acid substitutions selected from the group consisting of E345R/Q/N/K, E430T/S/G, S440Y/W, and Q386K in the Fc-region of a human IgG1 heavy chain.

In an exemplary embodiment, the Fc variant comprises modification in at least two amino acid residues, wherein the modifications are amino acid substitutions selected from the group consisting of I253N, Q; H310Q; Q311E, R; E382D, Q, K, R; G385D, E, K, R; H433R; N434H, K, Q, R; Y436N, Q, S, T; Q438N, S, T; K439Q; and S440D, E, Q in the Fc-region of a human IgG1 heavy chain.

Exemplary combinations of modifications in at least two amino acid residues are E345R/E430T, E345R/S440Y, E345R/S440W, E345R/Q386K, E345R/E430G, E345Q/E430T, E345Q/S440Y, E345Q/S440W, E430T/S440Y, E430G/S440Y, E430T/S440W, E430T/Q386K, and S440Y/Q386K.

In another embodiment, the Fc variant comprises a modification in at least two amino acid residues selected from the group consisting of E345, E382 or Q386 in the Fc-region of a human IgG1 heavy chain, wherein the at least three amino acid modifications are different.

In an exemplary embodiment, the Fc variant comprises modifications in at least three amino acid residues, wherein the modifications are the following amino acid substitutions: E345R, Q396K and E430G, which may be in either one or both the heavy chains of the Fc variant.

The modifications in the at least three amino acid residues may be individually selected from the substitutions listed in Table 1. Exemplary combinations of modifications in at least three amino acid residues are: E345R/E430G/S440Y, E345R/E430G/S440W, E345K/E430G/S440Y, E345K/E430G/S440W, E345Q/E430G/S440Y, E345Q/E430G/S440W, E345N/E430G/S440Y, E345N/E430G/S440W, E345R/E430T/S440Y, E345R/E430T/S440W, E345K/E430T/S440Y, E345K/E430T/S440W, E345Q/E430T/S440Y, E345Q/E430T/S440W, E345N/E430T/S440Y, E345N/E430T/S440W, E345R/E430S/S440Y, E345R/E430S/S440W, E345K/E430S/S440Y, E345K/E430S/S440W, E345Q/E430S/S440Y, E345Q/E430S/S440W, E345N/E430S/S440Y, E345N/E430S/S440W, E345R/E430F/S440Y, E345R/E430F/S440W, E345K/E430F/S440Y, E345K/E430F/S440W, E345Q/E430F/S440Y, E345Q/E430F/S440W, E345N/E430F/S440Y, and E345N/E430F/S440W.

In another embodiment, an Fc variant may comprise two modifications in the specific amino acid residue interaction pair K439 and S440, as set forth below in Table 2.

TABLE 2

Exemplary double modifications for Fc variants.

| Amino Acid Pair (IgG1, 2, 3, 4) | Exemplary Substitutions | Preferred Substitutions |
|---|---|---|
| K439/S440 | K439ED, alternatively R; S440KR, alternatively ED | K439E/S440K |
| K447/K448/K449 | K447ED; K448RH; K448P | K447E/K448K/K449P |
| K447/K448 | K447KRH; K448ED | K447K/K448E |

In one embodiment, the application provides an Fc variant wherein the variant comprises a modification:

(i) in at least one amino acid residue selected from those corresponding to K439 and S440 in the Fc-region of a human IgG1 heavy chain, with the proviso that the modification in S440 is not S440Y or S440W, such as, e.g., wherein the modification in the position corresponding to K439 in the Fc-region of human IgG1 heavy chain is K439D/E, and/or the modification in the position corresponding to S440 in the Fc-region of human IgG1 heavy chain is S440K/H/R;

(ii) in at least one amino acid residue corresponding to K447D/E or corresponding to K447K/R/H and 448P in the Fc region of a human IgG1 heavy chain; or (iii) in at least one amino acid residue corresponding to K447D/E or corresponding to K447K/R/H and 448K/R/H and 449P in the Fc region of a human IgG1 heavy chain.

In one embodiment, wherein the Fc variant comprises a modification that is in position(s) other than S440 and/or K447, the variant may further comprise a modification:

(i) in at least one amino acid residue corresponding to K439 or S440 in the Fc-region of a human IgG1 heavy chain, with the proviso that the modification in S440 is not S440W or S440Y;

(ii) in at least one amino acid residue corresponding to K447D/E or corresponding to K447K/R/H and 448P in the Fc region of a human IgG1 heavy chain; or (iii) in at least one amino acid residue corresponding to K447D/E or corresponding to K447K/R/H and 448K/R/H and 449P in the Fc region of a human IgG1 heavy chain.

In certain embodiments, the Fc variant may also comprise only one of the amino acid residue substitutions, such as either K439E or S440K, for example the variant may comprise a modification in K439, optionally with no modification in S440.

In one embodiment, the Fc variant comprises a modification in amino acid residue K439, wherein the modification is an amino acid substitution selected from E and D, such as K439E or K439D.

In another embodiment, the Fc variant comprises a modification in S440, optionally with no modification in K439.

In one embodiment, the Fc variant comprises a modification in amino acid residue S440, wherein the modification is an amino acid substitution selected from K, R and H, such as S440K, S440R or S440H.

In one embodiment, the Fc variant comprises modifications in both K439 and S440.

In another embodiment, the Fc variant comprises a modification in K439, wherein the modification is an amino acid substitution selected from K439 to D, E or R, and the modification in S440 is selected from S440 to D, E, K, H or R.

In another embodiment, the Fc variant comprises a modification in K439 that is selected from K439D and K439E, and a modification in S440 selected from S440K, S440R, and S440H.

In another embodiment, the Fc variant comprises K439E and S440K modifications.

In another embodiment, the Fc variant comprises a combination of modifications, wherein the combination comprises (i) an amino acid residue corresponding to E345, E382 or Q386 in the Fc-region of a human IgG1 heavy chain, and a further modification selected from the group consisting of:

(a) in at least one amino acid residue corresponding to K439 or S440 in the Fc-region of a human IgG1 heavy chain, with the proviso that the modification in S440 is not S440W or S440Y;

(b) in at least one amino acid residue corresponding to K447D/E or corresponding to K447K/R/H and 448P in the Fc region of a human IgG1 heavy chain; and (c) in at least one amino acid residue corresponding to K447D/E or corresponding to K447K/R/H and 448K/R/H and 449P in the Fc region of a human IgG1 heavy chain.

In another embodiment, the Fc variant comprises a combination of modifications, wherein the combination comprises (i) an amino acid residue corresponding to E345, E382 or Q386 in the Fc-region of a human IgG1 heavy chain, and a further modification selected from the group consisting of:

(a) in at least one amino acid residue corresponding to K439 or S440 in the Fc-region of a human IgG1 heavy chain, with the proviso that the modification in S440 is not S440W or S440Y, (b) in at least one amino acid residue corresponding to K447D/E or corresponding to K447K/R/H and 448P in the Fc region of a human IgG1 heavy chain; and (c) in at least one amino acid residue corresponding to K447D/E or corresponding to K447K/R/H and 448K/R/H and 449P in the Fc region of a human IgG1 heavy chain.

In another embodiment, the Fc variant comprises a combination of modifications, wherein the combination comprises (i) a modification in at least an amino acid residue selected from those corresponding to E345, E430, S440, Q386, P247, I253, S254, Q311, D/E356, T359, E382, Y436, and K447 in the Fc-region of a human IgG1 heavy chain, and (ii) a further modification in at least one amino acid residue corresponding to K439 or S440 in the Fc-region of a human IgG1 heavy chain.

In another embodiment, the Fc variant comprises a combination of modifications, wherein the combination comprises (i) an amino acid substitution selected from those corresponding to E345X, E430X, S440W/Y, Q386K, in the Fc region of a human IgG1 heavy chain, wherein X is any amino acid (e.g., a natural occurring amino acid), and (ii) a further modification in at least one amino acid residue corresponding to K439 or S440 in the Fc-region of a human IgG1 heavy chain, with the proviso that the modification in S440 is not S440W or S440Y.

In one embodiment, the Fc variant comprises an amino acid modification in both of the positions corresponding to K439 and S440 in the Fc-region of an IgG1 heavy chain.

In certain embodiments, the modification in the position corresponding to K439 in the Fc-region of human IgG1 heavy chain is K439D/E, and/or the modification in the position corresponding to S440 in the Fc-region of human IgG1 heavy chain is S440K/H/R.

In certain embodiments, the Fc variant comprises a combination of modifications, wherein the first modification is in an amino acid residues selected from those corresponding to E345, E430, Q386, and S440 in the Fc-region of a human IgG1 heavy chain, with the proviso that the modification in S440 is not S440Y or S440W; and the second and third modifications are an amino acid substitution in position K439E or S440K.

In a further embodiment, the Fc variant comprises a combination of modifications, wherein the first modification is selected from the group of E345R, Q, N, K, A, F, G, H, I, L, M, P, S, T, V, W, Y, C, D; E430T, S, G, A, F, H, L, P, R, V, C, D, I, K, M, N, Q, W, Y; and S440W, Y, D; and each of the second and third modifications is an amino acid substitution in position K439E or S440K.

In another embodiment, the Fc variant comprises a combination of modifications, wherein the first modification is selected from the group of E345R, Q, N, K, Y; E430T, S, G, F, H; S440W, Y; and Q386K.

In another embodiment, the Fc variant comprises E345R, K439E and S440K amino acid substitutions.

In one embodiment, the Fc variant comprises a modification in at least two amino acid residues selected from those corresponding to E345, E430, S440, Q386, P247, I253, S254, Q311, D/E356, T359, E382, Y436, and K447 in the Fc-region of a human IgG1 heavy chain, with the proviso that the modification in S440 is not S440Y or S440W, and the Fc variant comprises a further modification in at least one amino acid residue corresponding to K439 or S440 in the Fc-region of a human IgG1 heavy chain, with the proviso that the modification in S440 is not S440W or S440Y.

In a further embodiment, the Fc variant comprises a modification in at least two amino acid residues, wherein the modifications are amino acid substitutions selected from those corresponding to E345X, E430X, S440W/Y, and Q386K, in the Fc region of a human IgG1 heavy chain, wherein X is any amino acid (e.g., a natural occurring amino acid), and the Fc variant comprises a further modification in at least one amino acid residue corresponding to K439 or S440 in the Fc-region of a human IgG1 heavy chain, with the proviso that the modification in S440 is not S440W or S440Y.

In one embodiment, the Fc variant comprises an amino acid modification in both of the positions corresponding to K439 and S440 in the Fc-region of an IgG1 heavy chain, with the proviso that the modification in S440 is not S440Y or S440W.

In a further embodiment, the modification in the position corresponding to K439 in the Fc-region of human IgG1 heavy chain is K439D/E, and/or the modification in the position corresponding to S440 in the Fc-region of human IgG1 heavy chain is S440K/H/R.

In a further embodiment, the Fc variant comprises a combination of modifications, wherein the first and second modification are amino acid substitutions selected from the group consisting of E345, E430, Q386, and S440 in the Fc-region of a human IgG1 heavy chain, with the proviso that the modification in S440 is not S440Y or S440W; and the third and fourth modification are amino acid substitution in position K439E or S440K.

In another embodiment, the complexes described herein may contain a mixture of Fc variants wherein any given Fc variant does not promote intermolecular interactions with another Fc variant having the same mutation, but intermolecular interactions are promoted between two or more Fc variants each having a different modification in the Fc region. For example, a first antigen binding protein comprises an Fc variant comprising a modification at amino acid residue K439 and a second antigen binding protein comprises an Fc variant comprising a modification at amino acid residue S440. Such embodiments typically lead to a reduced or much reduced Fc:Fc interaction between identical Fc-molecules and may be used to ensure pairing of two different antigen binding proteins. For example, antigen binding proteins all having a modification at K439 or S440 may not form intermolecular interactions, but a first antigen binding protein having a K439 modification and a second antigen binding protein having a S440 modification will form intermolecular interactions. Exemplary modification sites for mixtures of Fc variants are shown in Table 3 below.

TABLE 3

Exemplary mixed modifications.

| Amino Acid Pair (IgG1) | Exemplary Substitutions | Preferred Substitutions |
|---|---|---|
| K439 + S440 | K439ER + S440DEKR | K439E + S440K |
| K447 + K4487/K448 | K447DE + K447KRH/K448P | K447E + K447K/K448P |

TABLE 3-continued

Exemplary mixed modifications.

| Amino Acid Pair (IgG1) | Exemplary Substitutions | Preferred Substitutions |
|---|---|---|
| K447 + K447/K448/K449 | K447DE + K447KRH/K448KRH/K449P | K447E + K447K/K448K/K449PE |

Fc Modifications that Reduce Effector Function

In certain embodiments, the Fc variants described herein further comprises one or more amino acid modifications for attenuating effector function (such as CDC and/or ADCC). In exemplary embodiments, the modification to attenuate effector function is a modification that does not alter the glycosylation pattern of the Fc region. In certain embodiments, the modification to attenuate effector function reduces or eliminates binding to human effector cells, binding to one or more Fc receptors, and/or binding to cells expressing an Fc receptor. In an exemplary embodiment, the Fc variants described herein comprise the following modifications: L234A, L235A and P329G in the Fc region of human IgG1, that result in attenuated effector function.

In various embodiments, Fc variants having reduced effector function refer to Fc variants that reduce effector function (e.g., CDC, ADCC, and/or binding to FcR, etc. activities) by at least 10%, 20%, 30%, 40%, 50%, 60%, 70%, 80%, 90%, 95%, 97%, 98%, 99% or more as compared to the effector function achieved by a wild-type Fc region (e.g., an Fc region not having a mutation to reduce effector function, although it may have other mutations). In certain embodiments, Fc variants having reduced effector function refer to Fc variants that eliminate all detectable effector function as compared to a wild-type Fc region. Assays for measuring effector function are known in the art and described below.

In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity). The primary cells for mediating ADCC, NK cells, express FcγRIII only, whereas monocytes express FcγRI, FcγRII and FcγRIII. FcR expression on hematopoietic cells is summarized in Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)).

Fc variants with reduced effector function include those having amino acid substitutions at one or more of the following amino acid residues: 238, 265, 269, 270, 297, 327 and 329 (U.S. Pat. No. 6,737,056). Such Fc variants include Fc variants with substitutions at two or more of amino acid positions 265, 269, 270, 297 and 327, including the so-called "DANA" Fc variant with substitution of residues 265 and 297 to alanine (U.S. Pat. No. 7,332,581).

Certain antibody variants with improved or diminished binding to FcRs are described (see, e.g., U.S. Pat. No. 6,737,056; WO 2004/056312, and Shields et al., J. Biol. Chem. 9(2): 6591-6604 (2001)).

In certain embodiments, Fc variants described herein can comprise one or more modifications in the Fc region that result in diminished C1q binding and/or Complement Dependent Cytotoxicity (CDC), e.g., as described in U.S. Pat. No. 6,194,551, WO 99/51642, and Idusogie et al. J. Immunol. 164: 4178-4184 (2000). In exemplary embodiments, the Fc variants described herein comprise a modification at lysine 322 in the Fc region of human IgG1 (EU numbering of residues). In some embodiments, the modification(s) result in diminished C1q binding and/or CDC, e.g., as compared to an Fc region without the modification(s). For example, in certain embodiments, Fc variants described herein comprise a K322A modification in the Fc region of human IgG1 (EU numbering of residues), e.g., as described in U.S. Pat. No. 6,194,551, WO 99/51642, and Idusogie et al. J. Immunol. 164: 4178-4184 (2000). Other such exemplary modifications (in the Fc region of human IgG1, and according to EU numbering of residues) include but are not limited to D270K, D270V, P329A, and P331A.

In some embodiments, any of the Fc variants described herein can comprise a K322A modification in the Fc region of human IgG1 (EU numbering of residues) and one or more amino acid substitutions selected from E345R, E430G and S440Y in the Fc region of a human IgG1 (EU numbering). For example, in some embodiments, any of the Fc variants described herein can comprise a K322A modification in the Fc region of human IgG1 (EU numbering of residues) and a single amino acid substitution selected from E345R, E430G and S440Y in the Fc region of a human IgG1 (EU numbering). In some embodiments, any of the Fc variants described herein can comprise a K322A modification in the Fc region of human IgG1 (EU numbering of residues) and a set of amino acid substitutions selected from (a) E345R and E430G, (b) E345R and S440Y, and (c) E430G and S440Y in the Fc region of a human IgG1 (EU numbering). In some embodiments, any of the Fc variants described herein can comprise K322A, E345R, E430G, and S440Y substitutions in the Fc region of human IgG1 (EU numbering of residues).

In some embodiments, any of the Fc variants described herein can comprise one or more amino acid substitutions selected from Table 4 in the Fc region of human IgG1 (EU numbering of residues). In some embodiments, any of the Fc variants described herein can comprise a K322A modification and one or more amino acid substitutions selected from Table 4 in the Fc region of human IgG1 (EU numbering of residues).

In certain embodiments, an Fc variant encompassed herein (an Fc variant comprising a modified Fc region that enhances hexamer formation, wherein the formed hexameric antigen binding complex has agonist activity, that is enhanced agonist activity compared to the agonist activity of the parental antibody without the modification in the Fc region) is an Fc variant comprising any one or more of the Fc modifications described in International Patent Publication numbers WO 2013/004842, WO 2014/108198 and/or WO 2014/006217. In certain embodiments, the Fc variants comprising one or more of the Fc modifications are further modified to have reduced, including abrogated, CDC. For example, and without limitation, in some embodiments, the Fc variant comprises a K322A modification.

In certain embodiments, the Fc variants described herein comprise modifications to the Fc region that reduce effector function as described in Strohl, Current Opinion in Biotechnology, 20; 685-691 (2009). In exemplary embodiments, the Fc variants described herein comprise modifications at one or more amino acid residues selected from the following (EU numbering of residues):

(a) N297A in the Fc region of human IgG1;
(b) 234 and 235 in the Fc region of human IgG1,
(c) 234, 235 and 329 in the Fc region of human IgG1,
(d) 234 and 237 in the Fc region of human IgG2,
(e) 235, 237 and 318 in the Fc region of human IgG4,
(f) 228 and 236 in the Fc region of human IgG4,
(g) 268, 309, 330 and 331 in the Fc region of human IgG2,
(h) 220, 226, 229 and 238 in the Fc region of human IgG1,
(i) 226, 229, 233, 234 and 235 in the Fc region of human IgG1,
(j) 234, 235 and 331 in the Fc region of human IgG1,
(k) 226 and 230 in the Fc region of human IgG1, and
(l) 267 and 328 in the Fc region of human IgG1,
wherein the modifications reduce effector function of the Fc domain.

In other exemplary embodiments, the Fc variants described herein comprise modifications that attenuate effector function selected from the following (EU numbering of residues):

(a) N297A in the Fc region of human IgG1;
(b) L234A and L235A in the Fc region of human IgG1,
(c) L234A, L235A and P329G in the Fc region of human IgG1,
(d) V234A and G237A in the Fc region of human IgG2,
(e) L235A, G237A and E318A in the Fc region of human IgG4,
(f) S228P and L236E in the Fc region of human IgG4,
(g) 118 to 260 in the Fc region of human IgG2 or 261 to 447 in the Fc region of human IgG4,
(h) H268Q, V309L, A330S and A331S in the Fc region of human IgG2,
(i) C220S, C226S, C229S and P238S in the Fc region of human IgG1,
(j) C226S, C229S, E233P, L234V and L235A in the Fc region of human IgG1,
(k) L234F, L235E and P331S in the Fc region of human IgG1,
(l) C226S and P230S in the Fc region of human IgG1, and
(m) S267E and L328F in the Fc region of human IgG1.

In certain embodiments, the Fc variants described herein do not comprise an N297A modification to attenuate effector function.

In an exemplary embodiment, an agonist antigen binding complex provided herein binds to and agonizes OX40 in the absence of FcR binding. In an exemplary embodiment, the agonist antigen binding complex provided herein binds to and agonizes OX40 while having reduced FcR binding as compared to the equivalent antigen binding complex that does not contain a mutation in the Fc region to attenuate effector function. In various embodiments, the agonist antigen binding complex provided herein binds to and agonizes OX40 while having FcR binding that is reduced by at least 10%, 20%, 30%, 40%, 50%, 60%, 70%, 80%, 90%, 95% or more as compared to the equivalent antigen binding complex that does not contain a mutation in the Fc region to attenuate effector function. In certain embodiments, the agonist antigen binding complex provided herein binds to and agonizes OX40 while having FcR binding that is reduced by at least 50%, 75%, 80%, 85%, 90, 95%, 97%, 98% or more as compared to the equivalent antigen binding complex that does not contain a mutation in the Fc region to attenuate effector function.

Vectors, Host Cells and Recombinant Methods

For recombinant production of an antigen binding polypeptide provided herein, the nucleic acid encoding it is isolated and inserted into a replicable vector for further cloning (amplification of the DNA) or for expression. DNA encoding the antigen binding polypeptide is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian, but also including fungi (e.g., yeast), insect, plant, and nucleated cells from other multicellular organisms) origin. In some embodiments, the host cell is an isolated host cell, e.g., a host cell derived from a multicellular organism that is grown as an isolated cell, such as a cell line derived from an invertebrate (e.g., insect) or vertebrate (e.g., mouse, human, Chinese hamster ovary (CHO) cell, etc.) organism that is grown in cell culture. In cases where an antigen binding polypeptide is an antibody, it will be appreciated that constant regions of any isotype can be used for this purpose, including IgG, IgM, IgA, IgD, and IgE constant regions, and that such constant regions can be obtained from any human or animal species.

a. Generating Antigen Binding Polypeptides Using Prokaryotic Host Cells i. Vector Construction Polynucleotide sequences encoding polypeptide components of the antigen binding polypeptides (such as, for example, an antibody) provided herein can be obtained using standard recombinant techniques. Desired polynucleotide sequences may be isolated and sequenced from, for example, antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding, for example, the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of the expressed target gene as compared to the native target polypeptide promoter.

Promoters suitable for use with prokaryotic hosts include the PhoA promoter, the (3-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to operably ligate them to cistrons encoding the genes of the antigen binding polypeptide protein, e.g., the target light and heavy chains (Siebenlist et al., (1980) Cell 20: 269), using linkers or adaptors to supply any required restriction sites.

In one embodiment, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected should be one that is recognized and processed {i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another embodiment, the production of the immunoglobulins can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. See Proba and Pluckthun Gene, 159:203 (1995).

Prokaryotic host cells suitable for expressing antigen binding polypeptides (e.g., antibodies) of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E coli* strains include strain W31 10 (Bachmann, Cellular and Molecular Biology, vol. 2 (Washington, D.C.: American Society for Microbiology, 1987), pp. 1 190-1219; ATCC Deposit No. 27,325) and derivatives thereof, including strain 33D3 having genotype W31 10 AfhuA (AtonA) ptr3 lac Iq lacL8 AompTA(nmpc-fepE) degP41 kanR (U.S. Pat. No. 5,639,635). Other strains and derivatives thereof, such as *E coli* 294 (ATCC 31,446), *E coli* B, E colix 1776 (ATCC 31,537) and *E coli* RV308 (ATCC 31,608) are also suitable. In one embodiment, *E coli* Alpp finds particular use. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Polypeptide Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one embodiment of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment of the invention, antigen binding polypeptides (such as, for example, an antibody) production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To minimize proteolysis of expressed antigen binding polypeptides (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), Proc. Natl. Acad. Sci. USA 95:2773-2777; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention. In a second embodiment, the *E. coli* strain is deficient for a lipoprotein of the outer membrane (Alpp).

iii. Antigen Binding Polypeptide Purification

In one embodiment, the antigen binding polypeptide produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one embodiment, Protein A immobilized on a solid phase is used for immunoaffinity purification of, for example, antigen binding polypeptides of the invention. Protein A is a 41 kD cell wall protein from *Staphylococcus aureus* which binds with a high affinity to the Fc region of antigen binding polypeptides. Lindmark et al. (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antigen binding polypeptide of interest to Protein A. The solid phase is then washed to remove contaminants non-specifically bound to the solid phase. The antigen binding polypeptide (such as, for example, an antibody) is recovered from the solid phase by elution.

b. Generating Antigen Binding Polypeptides Using Eukaryotic Host Cells

The vector components generally include, but are not limited to, one or more of the following: a signal sequence, an origin of replication, one or more marker genes, an enhancer element, a promoter, and a transcription termination sequence.

i. Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the desired antigen binding polypeptide(s) (e.g., antibodies).

ii. Origin of Replication

Generally, an origin of replication component is not needed for mammalian expression vectors. For example, the SV40 origin may typically be used, but only because it contains the early promoter.

iii. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-1 and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHI-K is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

iv. Promoter Component

Expression and cloning vectors usually contain a promoter that is recognized by the host organism and is operably linked to the desired Fc-containing polypeptide(s) (e.g., antibody) nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

For production of Fc-containing polypeptide(s) (such as, for example, an antibody) transcription from vectors in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a Hind 111 E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

v. Enhancer Element Component

Transcription of DNA encoding an antigen binding polypeptide(s) (such as, for example, an antibody) by higher eukaryotes can be increased by inserting an enhancer sequence into the vector. Many enhancer sequences are now known from mammalian genes (e.g., globin, elastase, albumin, a-fetoprotein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) for a description of elements for enhancing activation of eukaryotic promoters. The enhancer may be spliced into the vector at a position 5' or 3' to the antibody polypeptide-encoding sequence, provided that enhancement is achieved, but is generally located at a site 5' from the promoter.

vi. Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/1 1026 and the expression vector disclosed therein.

vii. Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N. Y. Acad. Sci. 383:44-68 (1982)); MRC 5 cells; FS4 cells; and a human hepatoma line (Hep G2).

Host cells are transformed with the above-described expression or cloning vectors for desired antigen binding polypeptide(s) (such as, for example, an antibody) production and cultured in conventional nutrient media modified as appropriate for inducing promoters, selecting transformants, or amplifying the genes encoding the desired sequences.

viii. Culturing the Host Cells

The host cells used to produce a desired antigen binding polypeptide(s) (such as, for example, an antibody) of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix. Purification of Antigen Binding Polypeptides

When using recombinant techniques, the antigen binding polypeptides can be produced intracellularly, or directly secreted into the medium. If the antigen binding polypeptide is produced intracellularly, as a first step, the particulate debris, either host cells or lysed fragments, are removed, for example, by centrifugation or ultrafiltration. Where the antigen binding polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antigen binding polypeptide composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62: 1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt). The production of the antigen binding polypeptides can alternatively or additionally (to any of the foregoing particular methods) comprise dialyzing a solution comprising a mixture of the polypeptides.

x. Antigen Binding Polypeptide Production Using Baculovirus

Recombinant baculovirus may be generated by co-transfecting a plasmid encoding an antigen binding polypeptide and BaculoGold™ virus DNA (Pharmingen) into an insect cell such as a *Spodoptera frugiperda* cell (e.g., Sf9 cells; ATCC CRL 1711) or a *Drosophila melanogaster* S2 cell using, for example, lipofectin (commercially available from GIBCO-BRL). In a particular example, an antigen binding polypeptide sequence is fused upstream of an epitope tag contained within a baculovirus expression vector. Such epitope tags include poly-His tags. A variety of plasmids may be employed, including plasmids derived from commercially available plasmids such as pVL1393 (Novagen) or pAcGP67B (Pharmingen). Briefly, the sequence encoding an antigen binding polypeptide may be amplified by PCR with primers complementary to the 5' and 3' regions. The 5' primer may incorporate flanking (selected) restriction enzyme sites. The product may then be digested with the selected restriction enzymes and subcloned into the expression vector.

After transfection with the expression vector, the host cells (e.g., Sf9 cells) are incubated for 4-5 days at 28° C. and the released virus is harvested and used for further amplifications. Viral infection and protein expression may be performed as described, for example, by O'Reilley et al. (Baculovirus expression vectors: A Laboratory Manual. Oxford: Oxford University Press (1994)).

Expressed poly-His tagged antigen binding polypeptide can then be purified, for example, by Ni2+-chelate affinity chromatography as follows. Extracts can be prepared from recombinant virus-infected Sf9 cells as described by Rupert et al. (Nature 362:175-179 (1993)). Briefly, Sf9 cells are washed, resuspended in sonication buffer (25 mL HEPES pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 μm filter. A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline A280 with loading buffer, at which point fraction collection is started. Next, the column is washed with a secondary wash buffer (50 mM phosphate; 300 mM NaI; 10% glycerol pH 6.0), which elutes nonspecifically bound protein. After reaching A280 baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted His10-tagged antigen binding polypeptide are pooled and dialyzed against loading buffer.

Alternatively, purification of the antigen binding polypeptide can be performed using known chromatography techniques, including for instance, Protein A or protein G column chromatography. In one embodiment, the antigen binding polypeptide of interest may be recovered from the solid phase of the column by elution into a solution containing a chaotropic agent or mild detergent. Exemplary chaotropic agents and mild detergents include, but are not limited to, Guanidine-HCl, urea, lithium perclorate, Arginine, Histidine, SDS (sodium dodecyl sulfate), Tween, Triton, and NP-40, all of which are commercially available.

Target Molecules & Methods of Use

The antigen binding polypeptides or antigen binding complexes of the present disclosure can be used to interact with a target to activate a signal transduction pathway. In certain embodiments, the target can be any target that activates, initiates, modulates and/or regulates a signal transduction pathway. Examples of molecules that may be targeted by an antigen binding polypeptide or an antigen binding complex as described herein include, but are not limited to, cell surface receptors. In certain embodiments, the cell surface receptor may be a receptor that oligomerizes, e.g. dimerizes (homodimerizes or heterodimerizes), by combining with the ligand and thereby transduce a signal into cells.

In certain embodiments, the target can be any target that oligomerizes, e.g., upon interaction with its ligand, to activate a signal transduction pathway. In certain embodiments, the target can be a multimeric receptor. The term "multimeric receptor," as used herein, refers to a receptor that requires the oligomerization of two or more, three or more, four or more, five or more or six or more receptors, e.g., of the same type and/or from the same family, for signaling activity. See, e.g., Heidin (1995) Cell 80:213-223.

In certain embodiments, the target receptor can be "dimeric" and require oligomerization of two receptors for activity. Non-limiting examples of dimeric receptors include neurotrophic receptors, nerve growth factors, growth factors, serine/threonine kinase receptors and receptor tyrosine kinases (RTKs). See, e.g., Li and Hristova (2010) Cell Adhesion and Migration 4(2):249-254.

In certain embodiments, the target receptor can be "trimeric" and require oligomerization of three receptors for activity. Non-limiting examples of trimeric receptors include Tumor necrosis factor receptors (TNFRs). See, e.g., Brazil (2006) Nature Reviews Drug Discovery 5:20.

In certain embodiments, the target can be any target that results in "agonism," as defined above, when interacting with an antigen binding polypeptide or antigen binding complex of the present disclosure, wherein the agonism is enhanced over the monomeric parental antibody.

Cell surface receptors include, for example, receptors that belong to receptor families such as the hematopoietic factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. Various references that relate to receptors belonging to these receptor families and their characteristics are available and include, for example, Cooke B A., King R J B., van der Molen H J. ed. New Comprehensive Biochemistry Vol. 18B "Hormones and their Actions Part II" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim Biophys. Acta, 1422: 207-234; and M. Miyasaka ed., Cell Technology, supplementary volume, Handbook series, "Handbook for Adhesion Factors" (1994) (Shujunsha, Tokyo, Japan).

In certain embodiments, cell surface receptors include, for example, hormone receptors and cytokine receptors. An exemplary hormone receptor includes, for example, estrogen receptor. Exemplary cytokine receptors include, for example, hematopoietic factor receptor, lymphokine receptor, growth factor receptor, differentiation control factor receptor and the like. Examples of cytokine receptors are erythropoietin (EPO) receptor, thrombopoietin (TPO) receptor, granulocyte colony stimulating factor (G-CSF) receptor, macrophage colony stimulating factor (M-CSF) receptor, granular macrophage colony stimulating factor (GM-CSF) receptor, tumor necrosis factor (TNF) receptor, interleukin-1 (IL-1) receptor, interleukin-2 (IL-2) receptor, interleukin-3 (IL-3) receptor, interleukin-4 (IL-4) receptor, interleukin-5 (IL-5) receptor, interleukin-6 (IL-6) receptor, interleukin-7 (IL-7) receptor, interleukin-9 (IL-9) receptor, interleukin-10 (IL-10) receptor, interleukin-11 (IL-11) receptor, interleukin-12 (IL-12) receptor, interleukin-13 (IL-13) receptor, interleukin-15 (IL-15) receptor, interferon-alpha (IFN-alpha) receptor, interferon-beta (IFN-beta) receptor, interferon-gamma (IFN-gamma) receptor, growth hormone (GH) receptor, insulin receptor, blood stem cell proliferation factor (SCF) receptor, vascular epidermal growth factor (VEGF) receptor, epidermal cell growth factor (EGF) receptor, nerve growth factor (NGF) receptor, fibroblast growth factor (FGF) receptor, platelet-derived growth factor (PDGF) receptor, transforming growth factor-beta (TGF-beta) receptor, leukocyte migration inhibitory factor (LIF) receptor, ciliary neurotrophic factor (CNTF) receptor, oncostatin M (OSM) receptor, and Notch family receptor. Additional non-limiting examples of cytokine receptors are disclosed in Wang et al. (2009) Ann. Rev. Immunol. 27:29-60.

In certain embodiments, the target can include members of the tumor necrosis factor receptor (TNFR) family Non-limiting examples of TNFRs include TNFR1, TNFR2, lymphotoxin β receptor, OX40, CD40, Fas, decoy receptor 3, CD27, CD70, CD226, CD137, ICOS, 2B4, CD30, 4-1BB, death receptor 3 (DR3), death receptor 4 (DR4), death receptor 5 (DR5), death receptor 6 (DR6), decoy receptor 1, decoy receptor 2, receptor activator of NF-kappa B (RANK), osteoprotegerin (OPG), TWEAK receptor, TACI, BAFF receptor (BAFF-R), HVEM (herpes virus entry mediator, nerve growth factor receptor, B cell maturation antigen (BCMA), glucocorticoid-induced TNF receptor (GITR), toxicity and JNK inducer (TAJ), RELT, TNFRSF22, TNFRSF23, ectodysplasin A2 isoform receptor and ectodysplasin 1, anihidrotic receptor. Additional non-limiting examples of TNFRs are disclosed in Naismith and Sprang (1998) Trends in Biochemical Sciences 23(2):74-79.

In certain embodiments, the target can include members of the low density lipoprotein receptor (LDLR) family Non-limiting examples of LDLRs include LDLR, Low-density lipoprotein receptor-related protein (LRP)1, LRP10, LRP1B, LRP2, LRP4, LRP5, LRP5L, LRP6, LRP8, Nidogen (NID)-1, NID2, Sortilin-related receptor, L (SORL1) and Very-low-density-lipoprotein receptor (VLDLR).

In certain embodiments, the target can include members of the receptor tyrosine kinases (RTK) family Non-limiting examples of RTKs include Leukocyte receptor tyrosine kinase (LTK), Receptor tyrosine kinase-like orphan receptors (RORs), Ephrin receptors (Ephs), Trk receptor, insulin receptor (IR) and Tie2. Additional non-limiting examples of RTKs are disclosed in Alexander et al. (2013) The Concise Guide to Pharmacology 2013/14: Enzymes. Br. J. Pharmacol. 170: 1797-1867; Li and Hristova (2010); and Lemmon and Schlessinger (2010) Cell 141(7):1117-1134.

In other embodiments, the cell surface receptor may be a growth hormone receptor, an insulin receptor, a leptin receptor, a Flt-3 ligand receptor, or an insulin-like growth factor (IGF)-I receptor. Exemplary receptors include, for example, hEPOR (Simon, S. et al. (1990) Blood 76, 31-3); mEPOR (D'Andrea, A D. et al. (1989) Cell 57, 277-285); hG-CSFR (Fukunaga, R. et al. (1990) Proc. Natl. Acad. Sci. USA. 87, 8702-8706); mG-CSFR (Fukunaga, R. et al. (1990) Cell 61, 341-350); hTPOR (Vigon, I. et al. (1992) 89, 5640-5644); mTPOR (Skoda, R C. et al. (1993) 12, 2645-2653); hInsR (Ullrich, A. et al. (1985) Nature 313, 756-761); hFlt-3 (Small, D. et al. (1994) Proc. Natl. Acad. Sci. USA. 91, 459-463); hPDGFR (Gronwald, R G K. et al. (1988) Proc. Natl. Acad. Sci. USA. 85, 3435-3439); hIFNa/b R (Uze, G. et al. (1990) Cell 60, 225-234; and Novick, D. et al. (1994) Cell 77, 391-400).

In certain embodiments, the target can include members of the nerve growth factor receptor family and/or the neurotrophin receptor family Non-limiting examples of nerve growth factor receptors and neurotrophin receptors include p75 (also referred to as low affinity nerve growth factor receptor (LNGFR)), TrkA, TrkB and TrkC. Additional non-limiting examples of nerve growth factor receptors and neurotrophin receptors are disclosed in Lotz et al. (1996) J. of Leukocyte Biology 60(1):1-7.

In certain embodiments, the target can include members of the growth factor receptor family. For example, and not by way of limitation, a growth factor receptor can be a receptor that signals through the JAK/STAT, MAP kinase and PI3 kinase pathways. Non-limiting examples of growth factor receptors include fibroblast growth factor receptors (FGFRs), ErbB family of receptors (e.g., epidermal growth factor receptor (EGFR)), vascular endothelial growth factor receptors (VEGFR) and Platelet-derived growth factor receptors (PDGFRs).

In certain embodiments, the target can include receptors that form heterodimers or heterotrimers to induce a cell signal. For example, and not by way of limitation, the target can be a member of the serine/threonine kinase receptor family Non-limiting examples of serine/threonine kinase receptors include activin A receptor type II-like I (ALK1), activin A receptor, type I (ALK2), bone morphogenetic protein receptor, type IA (BMPR1A), activin A receptor, type IB (ALK4), activin A receptor, type IC (ALK7), transforming growth factor, beta receptor 1 (TGFBR1), bone morphogenetic protein receptor, type IB (BMPR1B), transforming growth factor, beta receptor II (TGFBR2), bone morphogenetic protein receptor, type II (BMPR2), anti-Mullerian hormone receptor, type II (MISR2), activin A receptor, type HA (ActR2), activin A receptor, type JIB (ActR2B) and transforming growth factor, beta receptor III (TGFBR3).

In certain embodiments, potential targets exclude the following: 5T4; ADAM-10; ADAM-12; ADAM 17; AFP; AXL; ANGPT2 anthrax antigen; BSG; CAIX; CAXII; CA 72-4; carcinoma associated antigen CTAA16.88; CCL11; CCL2; CCR4; CCR5; CCR6; CD2; CD3E; CD4; CD5; CD6; CD15; CD18; CD19; CD20; CD22; CD24; CD25; CD29; CD30; CD32B; CD33; CD37; CD38; CD40; CD40LG; CD44; CD47; CD52; CD56; CD66E; CD72; CD74; CD79a; CD79b; CD80; CD86; CD98; CD137; CD147; CD138; CD168; CD200; CD248; CD254; CD257; CDH3; CEA; CEACAM5; CEACAM6; CEACAM8; Claudin4; CS-1; CSF2RA; CSPG-4; CTLA4; Cripto; DLL4; ED-B; EFNA2; EGFR; Endothelin B receptor; ENPP3; EPCAM; ERBB2; ERBB3; FAP alpha; Fc gamma RI; FCER2; FGFR3; fibrin II beta chain; FLT1; FOLH1; FOLR1; FRP-1; GD3 ganglioside; GDF2; GLP1R; Glypican-3; GPNM B; HBV (hepatitis B virus); HCMV (human cytomegalovirus); heat shock protein 90 homolog [*Candida albicans*]; herpes simplex virus gD glycoprotein; HGF; HIV-1; HIV-1 IIIB gp120 V3 loop; HLA-DRB (HLA-DR beta); human respiratory syncytial virus, glycoprotein F; ICAM 1; IFNA1; IFNA1; IFNB1 bispecific; IgE Fc; IGF1R; IGHE connecting region; IL12B; IL13; IL15; IL17A; ILIA; IL1B; IL2RA; IL4; IL5; IL5RA; IL6; IL6R; IL9; interleukin-2 receptor beta subunit; ITGA2; ITGA2B ITGB3; ITGA4 ITGB7; ITGA5; ITGAL; ITGAV_ITGB3; ITGB2; KDR; L1CAM; Lewis-y; lipid A, domain of lipopolyaccharide LPS; LTA; MET; MM P14; MMpl5; MST1R; MSTN; MUC1; MUC4; MUC16; MUC5AC; NCA-90 granulocyte cell antigen; Nectin 4; NGF; NRP; NY-ESO-1; OX40L; PLAC-1; PLGF; PDGFRA; PD1; PDL1; PSCA; phosphatidylserine; PTK-7; *Pseudomonas aeruginosa* serotype IATS Oil; RSV (human respiratory syncytial virus, glycoprotein F); ROR1; RTN4; SELL; SELP; STEAP1; Shiga-like toxin II B subunit [*Escherichia coli*]; SLAM7; SLC44A4; SOST; *Staphylococcus epidermidis* lipoteichoic acid; T cell receptor alpha_beta; TF; TGFB1; TGFB2; TMEFF2; TNC; TNF; TNFRSF10A; TNFRSF10B; TNFRSF12A; TNFSF13; TNFSF14; TNFSF2; TNFSF7; TRAILR2; TROP2; TYRP1; VAP-1; and Vimentin.

In an exemplary embodiment, the cell surface receptor is OX40.

In another exemplary embodiment, the cell surface receptor is DR5.

In another exemplary embodiment, the cell surface receptor is Tie2.

In certain embodiments, the antigen binding polypeptides or antigen binding complexes described herein may be used for agonizing a cell surface receptor in a subject comprising administering to the subject the complex or the antigen binding polypeptide described herein.

In certain embodiments, the antigen binding polypeptides or antigen binding complexes described herein may be used for treating or preventing various diseases or disorders that would benefit from receptor agonism, including, for example, tumors, including pre-cancerous, non-metastatic, metastatic, and cancerous tumors (e.g., early stage cancer), cancers, allergic or inflammatory disorders, autoimmune disease, hormone disorders, or for the treatment of a subject at risk for developing cancer (for example, breast cancer, colorectal cancer, lung cancer, renal cell carcinoma, glioma, or ovarian cancer), an allergic or inflammatory disorder, or an autoimmune disease.

Uses of OX40 Agonists

In certain embodiments, an agonist antigen binding complex that binds to OX40 as described herein may be used for enhancing an immune response, treating cancer, preventing cancer, enhancing efficacy of other cancer therapy, enhancing vaccine efficacy, treating a viral or bacterial disease or disorder, or modulating a T cell response in a subject.

In one aspect, provided is a method for enhancing immune function (e.g., by upregulating cell-mediated immune responses) in an individual having cancer comprising administering to the individual an effective amount of an agonist antigen binding complex that binds to OX40 as described herein. In one aspect, provided is a method for enhancing T cell function in an individual having cancer comprising administering to the individual an effective amount of an agonist antigen binding complex that binds to OX40 as described herein.

In some embodiments, "enhancing T cell function" includes inducing, causing or stimulating an effector or memory T cell to have a renewed, sustained or amplified biological function. Examples of enhancing T-cell function include: increased secretion of γ-interferon from CD8+ effector T cells, increased secretion of γ-interferon from CD4+ memory and/or effector T-cells, increased proliferation of CD4+ effector and/or memory T cells, increased proliferation of CD8+ effector T-cells, increased antigen responsiveness (e.g., clearance), relative to such levels before the intervention. In one embodiment, the level of enhancement is at least 50%, alternatively 60%, 70%, 80%, 90%, 100%, 120%, 150%, 200%. The manner of measuring this enhancement is known to one of ordinary skill in the art.

In one aspect, provided is a method for enhancing immune function (e.g., by reducing immune dysfunction and/or a dysfunctional immune response or immune cell) in an individual having cancer comprising administering to the individual an effective amount of an agonist antigen binding complex that binds to OX40 as described herein. In some embodiments, "dysfunction" in the context of immune dysfunction refers to a state of reduced immune responsiveness to antigenic stimulation. In some embodiments, "dysfunctional" also includes refractory or unresponsive to antigen recognition, specifically, impaired capacity to translate antigen recognition into downstream T-cell effector functions, such as proliferation, cytokine production (e.g., gamma interferon) and/or target cell killing.

In one aspect, provided is a method for treating tumor immunity and/or enhancing tumor immunogenicity in an individual having cancer comprising administering to the individual an effective amount of an agonist antigen binding complex that binds to OX40 as described herein. In some embodiments, "tumor immunity" refers to the process in which tumors evade immune recognition and clearance. Thus, in some embodiments, as a therapeutic concept, tumor immunity is "treated" when such evasion is attenuated, and the tumors are recognized and attacked by the immune system. Examples of tumor recognition include tumor binding, tumor shrinkage and tumor clearance. In some embodiments, "immunogenicity" refers to the ability of a particular substance to provoke an immune response. Tumors are immunogenic and enhancing tumor immunogenicity aids in the clearance of the tumor cells by the immune response.

In some embodiments, an agonist antigen binding complex that binds to OX40 as described herein enhances CD4+ effector T cell function, for example, by increasing CD4+ effector T cell proliferation and/or increasing gamma interferon production by the CD4+ effector T cell (for example, as compared to proliferation and/or cytokine production prior to treatment with an agonist antigen binding complex that binds to OX40). In some embodiments, the cytokine is gamma interferon. In some embodiments, an agonist antigen binding complex that binds to OX40 as described herein increases number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with an agonist antigen binding complex that binds to OX40. In some embodiments, an agonist antigen binding complex that binds to OX40 as described herein increases number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment with an agonist antigen binding complex that binds to OX40.

In some embodiments, an agonist antigen binding complex that binds to OX40 as described herein increases number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment with anti-human OX40 agonist antibody. In some embodiments, an agonist antigen binding complex that binds to OX40 as described herein increases the number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with an agonist antigen binding complex that binds to OX40.

In some embodiments, an agonist antigen binding complex that binds to OX40 as described herein enhances memory T cell function, for example by increasing memory T cell proliferation and/or increasing cytokine production by the memory cell. In some embodiments, the cytokine is gamma interferon.

In some embodiments, an agonist antigen binding complex that binds to OX40 as described herein inhibits Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the anti-human OX40 agonist antibody reduces the number of intratumoral (infiltrating) Treg (e.g., total number of Treg or e.g., percentage of Fox3p+ cells in CD4+ cells).

In one embodiment, the application provides methods for enhancing an immune response in a mammal, comprising administering to the mammal a therapeutically effective amount of an agonist antigen binding complex that binds to OX40. In certain embodiments, the methods involve stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased CD4+ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production), regression of tumors, survival of tumor bearing animals, antibody production, immune cell proliferation, expression of cell surface markers, and cytotoxicity. Typically, methods of the disclosure enhance the immune response by a mammal when compared to the immune response by an untreated mammal or an animal not treated using the claimed methods. In one embodiment, the method enhances a cellular immune response, particularly a cytotoxic T cell response. In another embodiment, the cellular immune response is a T helper cell response. In still another embodiment, the immune response is a cytokine production, particularly IL-2 production.

In another embodiment, the application provides method of treating cancer in a mammal, comprising administering to the mammal a therapeutically effective amount of an agonist antigen binding complex that binds to OX40. In certain embodiments, the methods involve causing a desirable or beneficial effect in a mammal diagnosed with a cancer. The desirable or beneficial effect may include inhibition of further growth or spread of cancer cells, death of cancer cells, inhibition of reoccurrence of cancer, reduction of pain associated with the cancer, or improved survival of the animal. Inhibition of reoccurrence of cancer contemplates cancer sites and surrounding tissue which have previously been treated by radiation, chemotherapy, surgery, or other techniques. The effect can be either subjective or objective. For example, if the animal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

In one embodiment, the application provides methods for preventing cancer in a mammal, comprising administering to the mammal a therapeutically effective amount of an agonist antigen binding complex that binds to OX40. In certain embodiments, the method involves delaying, inhibiting, or preventing the onset of a cancer in a mammal in which the onset of oncogenesis or tumorigenesis is not evidenced but a predisposition for cancer is identified whether determined by genetic screening or otherwise. The term also encompasses treating a mammal having premalignant conditions to stop the progression of, or cause regression of, the premalignant conditions towards malignancy. Examples of premalignant conditions include hyperplasia, dysplasia, and metaplasia.

In certain embodiments, cancers that are amenable to treatment by the agonist antigen binding complexes that bind to OX40 as described herein include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: non-small cell lung cancer, glioblastoma, neuroblastoma, melanoma, breast carcinoma (e.g. triple-negative breast cancer), gastric cancer, colorectal cancer (CRC), and hepatocellular carcinoma. Yet, in some embodiments, the cancer is selected from: non-small cell lung cancer, colorectal cancer, glioblastoma and breast carcinoma (e.g. triple-negative breast cancer), including metastatic forms of those cancers.

In some embodiments, examples of cancer further include, but are not limited to, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), B-cell proliferative disorders, and Meigs' syndrome. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B-cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B-cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

In some embodiments, examples of cancer further include, but are not limited to, B-cell proliferative disorders, which further include, but are not limited to, lymphomas (e.g., B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B-cell lymphoma (Mucosa-associated lymphatic tissue lymphomas, MALT), nodal marginal zone B-cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B cell prolymphocytic leukemia, i) plasma cell neoplasms, plasma cell myeloma, multiple myeloma, plasmacytoma, and/or j) Hodgkin's disease.

In some embodiments of any of the methods, the cancer is a B-cell proliferative disorder. In some embodiments, the B-cell proliferative disorder is lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), or mantle cell lymphoma. In some embodiments, the B-cell proliferative disorder is NHL, such as indolent NHL and/or aggressive NHL. In some embodiments, the B-cell proliferative disorder is indolent follicular lymphoma or diffuse large B-cell lymphoma.

In some embodiments of any of the methods of the invention, the cancer displays human effector cells (e.g., is infiltrated by human effector cells). Methods for detecting human effector cells are well known in the art, including, e.g., by IHC. In some embodiments, the cancer display high levels of human effector cells. In some embodiments, human effector cells are one or more of NK cells, macrophages, monocytes. In some embodiments, the cancer is any cancer described herein. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma.

Antigen binding polypeptides (e.g., antibodies) or complexes described herein can be used either alone or in combination with other agents in a therapy. For instance, an antigen binding polypeptide (e.g., antibody) or complex described herein may be co-administered with at least one additional therapeutic agent.

Such combination therapies noted above encompass combined administration (where two or more therapeutic agents are included in the same or separate formulations), and separate administration, in which case, administration of the antigen binding polypeptide (e.g., antibody) or complex described herein can occur prior to, simultaneously, and/or following, administration of the additional therapeutic agent or agents. In one embodiment, administration of the antigen binding polypeptide (e.g., antibody) or complex described herein and administration of an additional therapeutic agent occur within about one month, or within about one, two or three weeks, or within about one, two, three, four, five, or six days, of each other. Antigen binding polypeptides (e.g., antibodies) or complexes described herein can also be used in combination with radiation therapy.

In some embodiments, an antigen binding polypeptide (e.g., antibody) or complex described herein may be administered in conjunction with a chemotherapy or chemotherapeutic agent. In some embodiments, an antigen binding polypeptide (e.g., antibody) or complex described herein may be administered in conjunction with a radiation therapy or radiotherapeutic agent. In some embodiments, an antigen binding polypeptide (e.g., antibody) or complex described herein may be administered in conjunction with a targeted therapy or targeted therapeutic agent. In some embodiments, an antigen binding polypeptide (e.g., antibody) or complex described herein may be administered in conjunction with an immunotherapy or immunotherapeutic agent, for example a monoclonal antibody.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1 λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-

3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., At211, I131, I125, Y90, Re186, Re188, Sm153, Bi212, P32, Pb212 and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In some embodiments, an antigen binding polypeptide (e.g., antibody) or complex described herein may be administered in conjunction with a PARP inhibitor (e.g., Olaparanib, Rucaparib, Niraparib, Cediranib, BMN673, Veliparib), Trabectedin, nab-paclitaxel (albumen-bound paclitaxel, ABRAXANE), Trebananib, Pazopanib, Cediranib, Palbociclib, everolimus, fluoropyrimidine (e.g., FOLFOX, FOLFIRI), IFL, regorafenib, Reolysin, Alimta, Zykadia, Sutent, Torisel (temsirolimus), Inlyta (axitinib, Pfizer), Afinitor (everolimus, Novartis), Nexavar (sorafenib, Onyx/Bayer), Votrient, Pazopanib, axitinib, IMA-901, AGS-003, cabozantinib, Vinflunine, Hsp90 inhibitor (e.g., apatorsin), Ad-GM-CSF (CT-0070), Temazolomide, IL-2, IFNa, vinblastine, Thalomid, dacarbazine, cyclophosphamide, lenalidomide, azacytidine, lenalidomide, bortezomid (VELCADE), amrubicine, carfilzomib, pralatrexate, and/or enzastaurin.

In some embodiments, an antigen binding polypeptide (e.g., antibody) or complex described herein may be administered in conjunction with a PD-1 axis binding antagonist. A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of MDX-1106 (nivolumab, OPDIVO), Merck 3475 (MK-3475, pembrolizumab, KEYTRUDA), CT-011 (Pidilizumab), MEDI-0680 (AMP-514), PDR001, REGN2810, BGB-108, and BGB-A317. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A (atezolizumab), MEDI4736 (durvalumab), MDX-1105, and MSB0010718C (avelumab). MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1106, also known as MDX-1106-04, ONO-4538, BMS-936558 or nivolumab, is an anti-PD-1 antibody described in WO2006/121168. Merck 3475, also known as MK-3475, SCH-900475 or pembrolizumab, is an anti-PD-1 antibody described in WO2009/114335. CT-011, also known as hBAT, hBAT-1 or pidilizumab, is an anti-PD-1 antibody described in WO2009/101611. AMP-224, also known as B7-DCIg, is a PD-L2-Fc fusion soluble receptor described in WO2010/027827 and WO2011/066342. In some embodiments, the anti-PD-1 antibody is MDX-1106. Alternative names for "MDX-1106" include MDX-1 106-04, ONO-4538, BMS-936558 or nivolumab. In some embodiments, the anti-PD-1 antibody is nivolumab (CAS Registry Number: 946414-94-4).

In some embodiments, an antigen binding polypeptide (e.g., antibody) or complex described herein may be administered in conjunction with an agonist directed against an activating co-stimulatory molecule. In some embodiments, an activating co-stimulatory molecule may include CD40, CD226, CD28, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, an antigen binding polypeptide (e.g., antibody) or complex described herein may be administered in conjunction with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3 (e.g., LAG-3-IgG fusion protein (IMP321)), B7-H3, B7-H4, IDO, TIGIT, MICA/B, or arginase.

In some embodiments, an antigen binding polypeptide (e.g., antibody) or complex described herein may be administered in conjunction with an antagonist directed against CTLA-4 (also known as CD152), e.g., a blocking antibody. In some embodiments, an antigen binding polypeptide (e.g., antibody) or complex described herein may be administered in conjunction with ipilimumab (also known as MDX-010, MDX-101, or Yervoy®). In some embodiments, an antigen binding polypeptide (e.g., antibody) or complex described herein may be administered in conjunction with tremelimumab (also known as ticilimumab or CP-675,206). In some embodiments, an antigen binding polypeptide (e.g., antibody) or complex described herein may be administered in conjunction with an antagonist directed against B7-H3 (also known as CD276), e.g., a blocking antibody. In some embodiments, an antigen binding polypeptide (e.g., antibody) or complex described herein may be administered in conjunction with MGA271. In some embodiments, an antigen binding polypeptide (e.g., antibody) or complex described herein may be administered in conjunction with an antagonist directed against a TGF beta, e.g., metelimumab (also known as CAT-192), fresolimumab (also known as GC1008), or LY2157299.

In some embodiments, an antigen binding polypeptide (e.g., antibody) or complex described herein may be administered in conjunction with a treatment comprising adoptive transfer of a T cell (e.g., a cytotoxic T cell or CTL) expressing a chimeric antigen receptor (CAR). In some embodiments, an antigen binding polypeptide (e.g., antibody) or complex described herein may be administered in conjunction with UCART19. In some embodiments, an antigen binding polypeptide (e.g., antibody) or complex described herein may be administered in conjunction with WT128z. In some embodiments, an antigen binding polypeptide (e.g., antibody) or complex described herein may be administered in conjunction with KTE-C19 (Kite). In some embodiments, an antigen binding polypeptide (e.g., antibody) or complex described herein may be administered in conjunction with CTL019 (Novartis). In some embodiments, an antigen binding polypeptide (e.g., antibody) or complex described herein may be administered in conjunction with a treatment comprising adoptive transfer of a T cell comprising a dominant-negative TGF beta receptor, e.g, a dominant-negative TGF beta type II receptor. In some embodiments, an antigen binding polypeptide (e.g., antibody) or complex described herein may be administered in conjunction with a treatment comprising a HERCREEM protocol (see, e.g., ClinicalTrials.gov Identifier NCT00889954).

In some embodiments, an antigen binding polypeptide (e.g., antibody) or complex described herein may be administered in conjunction with an antagonist directed against CD19. In some embodiments, an antigen binding polypeptide (e.g., antibody) or complex described herein may be administered in conjunction with MOR00208. In some embodiments, an antigen binding polypeptide (e.g., antibody) or complex described herein may be administered in conjunction with an antagonist directed against CD38. In some embodiments, an antigen binding polypeptide (e.g., antibody) or complex described herein may be administered in conjunction with daratumumab.

In some embodiments, an antigen binding polypeptide (e.g., antibody) or complex described herein may be administered in conjunction with an agonist directed against CD137 (also known as TNFRSF9, 4-1BB, or ILA), e.g., an activating antibody. In some embodiments, an antigen binding polypeptide (e.g., antibody) or complex described herein may be administered in conjunction with urelumab (also known as BMS-663513). In some embodiments, an antigen binding polypeptide (e.g., antibody) or complex described herein may be administered in conjunction with an agonist directed against CD40, e.g., an activating antibody. In some embodiments, an antigen binding polypeptide (e.g., antibody) or complex described herein may be administered in conjunction with CP-870893. In some embodiments, an antigen binding polypeptide (e.g., antibody) or complex described herein may be administered in conjunction with an agonist directed against OX40 (also known as CD134), e.g., an activating antibody. In some embodiments, an antigen binding polypeptide (e.g., antibody) or complex described herein may be administered in conjunction with a different anti-OX40 antibody (e.g., AgonOX). In some embodiments, an antigen binding polypeptide (e.g., antibody) or complex described herein may be administered in conjunction with an agonist directed against CD27, e.g., an activating antibody. In some embodiments, an antigen binding polypeptide (e.g., antibody) or complex described herein may be administered in conjunction with CDX-1127. In some embodiments, an antigen binding polypeptide (e.g., antibody) or complex described herein may be administered in conjunction with an antagonist directed against indoleamine-2,3-dioxygenase (IDO). In some embodiments, with the IDO antagonist is 1-methyl-D-tryptophan (also known as 1-D-MT).

In some embodiments, an antigen binding polypeptide (e.g., antibody) or complex described herein may be administered in conjunction with an agonist directed against CD137 (also known as TNFRSF9, 4-1BB, or ILA), e.g., an activating antibody. In some embodiments, an antigen binding polypeptide (e.g., antibody) or complex described herein may be administered in conjunction with urelumab (also known as BMS-663513). In some embodiments, an antigen binding polypeptide (e.g., antibody) or complex described herein may be administered in conjunction with an agonist directed against CD40, e.g., an activating antibody. In some embodiments, an antigen binding polypeptide (e.g., antibody) or complex described herein may be administered in conjunction with CP-870893 or RO7009789. In some embodiments, an antigen binding polypeptide (e.g., antibody) or complex described herein may be administered in conjunction with an agonist directed against OX40 (also known as CD134), e.g., an activating antibody.). In some embodiments, an antigen binding polypeptide (e.g., antibody) or complex described herein may be administered in conjunction with an agonist directed against CD27, e.g., an activating antibody. In some embodiments, an antigen binding polypeptide (e.g., antibody) or complex described herein may be administered in conjunction with CDX-1127 (also known as varlilumab). In some embodiments, an antigen binding polypeptide (e.g., antibody) or complex described herein may be administered in conjunction with an antagonist directed against indoleamine-2,3-dioxygenase (IDO). In some embodiments, with the IDO antagonist is 1-methyl-D-tryptophan (also known as 1-D-MT). In some embodiments, the IDO antagonist is an IDO antagonist shown in WO2010/005958 (the contents of which are expressly incorporated by record herein). In some embodiments the IDO antagonist is 4-({2-[(Aminosulfonyl)amino]ethyl}amino)-N-(3-bromo-4-fluorophenyl)-N'-hydroxy-1,2,5-oxadiazole-3-carboximidamide (e.g., as described in Example 23 of WO2010/005958). In some embodiments the IDO antagonist is

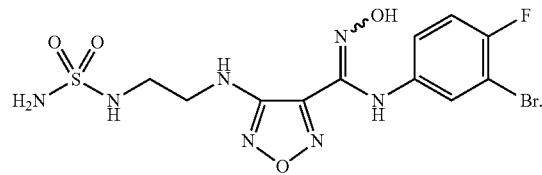 [SMILES: NS(=O)(=O)NCCNc1nonc1C(=NO)Nc1ccc(F)c(Br)c1]

In some embodiments, the IDO antagonist is INCB24360. In some embodiments, the IDO antagonist is Indoximod (the D isomer of 1-methyl-tryptophan). In some embodiments, an antigen binding polypeptide (e.g., antibody) or complex described herein may be administered in conjunction with an antibody-drug conjugate. In some embodiments, the antibody-drug conjugate comprises mertansine or monomethyl auristatin E (MMAE). In some embodiments, an antigen binding polypeptide (e.g., antibody) or complex described herein may be administered in conjunction with an anti-NaPi2b antibody-MMAE conjugate (also known as DNIB0600A, RG7599 or lifastuzumab vedotin). In some embodiments, an antigen binding polypeptide (e.g., antibody) or complex described herein may be administered in conjunction with trastuzumab emtansine (also known as T-DM1, ado-trastuzumab emtansine, or KADCYLA®, Genentech). In some embodiments, an antigen binding polypeptide (e.g., antibody) or complex described herein may be administered in conjunction with an anti-MUC16 antibody-MMAE conjugate, DMUC5754A. In some embodiments, an antigen binding polypeptide (e.g., antibody) or complex described herein may be administered in conjunction with an anti-MUC16 antibody-MMAE conjugate, DMUC4064A. In some embodiments, an antigen binding polypeptide (e.g., antibody) or complex described herein may be administered in conjunction with an antibody-drug conjugate targeting the endothelin B receptor (EDNBR), e.g., an antibody directed against EDNBR conjugated with MMAE. In some embodiments, an antigen binding polypeptide (e.g., antibody) or complex described herein may be administered in conjunction with an antibody-drug conjugate targeting the lymphocyte antigen 6 complex, locus E (Ly6E), e.g., an antibody directed against Ly6E conjugated with MMAE, (also known as DLYE5953A). In some embodiments, an antigen binding polypeptide (e.g., antibody) or complex described herein may be administered in conjunction with polatuzumab vedotin. In some embodiments, an antigen binding polypeptide (e.g., antibody) or complex described herein may be administered in conjunction with an antibody-drug conjugate targeting CD30. In some embodiments, an antigen binding polypeptide (e.g., antibody) or complex described herein may be administered in conjunction with ADCETRIS (also known as brentuximab vedotin). In some embodiments, an antigen binding polypeptide (e.g., antibody) or complex described herein may be administered in conjunction with polatuzumab vedotin.

In some embodiments, an antigen binding polypeptide (e.g., antibody) or complex described herein may be administered in conjunction with an angiogenesis inhibitor. In some embodiments, an antigen binding polypeptide (e.g., antibody) or complex described herein may be administered in conjunction with an antibody directed against a VEGF, e.g., VEGF-A. In some embodiments, an antigen binding polypeptide (e.g., antibody) or complex described herein may be administered in conjunction with bevacizumab (also known as AVASTIN®, Genentech). In some embodiments, an antigen binding polypeptide (e.g., antibody) or complex described herein may be administered in conjunction with an antibody directed against angiopoietin 2 (also known as Ang2). In some embodiments, an antigen binding polypeptide (e.g., antibody) or complex described herein may be administered in conjunction with MEDI3617. In some embodiments, an antigen binding polypeptide (e.g., antibody) or complex described herein may be administered in conjunction with an antibody directed against VEGFR2. In some embodiments, an antigen binding polypeptide (e.g., antibody) or complex described herein may be administered in conjunction with ramucirumab. In some embodiments, an antigen binding polypeptide (e.g., antibody) or complex described herein may be administered in conjunction with a VEGF Receptor fusion protein. In some embodiments, an antigen binding polypeptide (e.g., antibody) or complex described herein may be administered in conjunction with aflibercept. In some embodiments, an antigen binding polypeptide (e.g., antibody) or complex described herein may be administered in conjunction with ziv-aflibercept (also known as VEGF Trap or Zaltrap®). In some embodiments, an antigen binding polypeptide (e.g., antibody) or complex described herein may be administered in conjunction with a bispecific antibody directed against VEGF and Ang2. In some embodiments, an antigen binding polypeptide (e.g., antibody) or complex described herein may be administered in conjunction with RG7221 (also known as vanucizumab).

In some embodiments, an antigen binding polypeptide (e.g., antibody) or complex described herein may be administered in conjunction with an angiogenesis inhibitor and in conjunction with a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, an antigen binding polypeptide (e.g., antibody) or complex described herein may be administered in conjunction with bevacizumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, an antigen binding polypeptide (e.g., antibody) or complex described herein may be administered in conjunction with bevacizumab and MDX-1106 (nivolumab, OPDIVO). In some embodiments, an antigen binding polypeptide (e.g., antibody) or complex described herein may be administered in conjunction with bevacizumab and Merck 3475 (MK-3475, pembrolizumab, KEYTRUDA). In some embodiments, an antigen binding polypeptide (e.g., antibody) or complex described herein may be administered in conjunction with bevacizumab and CT-011 (Pidilizumab). In some embodiments, an antigen binding polypeptide (e.g., antibody) or complex described herein may be administered in conjunction with bevacizumab and MEDI-0680 (AMP-514). In some embodiments, an antigen binding polypeptide (e.g., antibody) or complex described herein may be administered in conjunction with bevacizumab and PDR001. In some embodiments, an antigen binding polypeptide (e.g., antibody) or complex described herein may be administered in conjunction with bevacizumab and REGN2810. In some embodiments, an antigen binding polypeptide (e.g., antibody) or complex described herein may be administered in conjunction with bevacizumab and BGB-108. In some embodiments, an antigen binding polypeptide (e.g., antibody) or complex described herein may be administered in conjunction with bevacizumab and BGB-A317. In some embodiments, an antigen binding polypeptide (e.g., antibody) or complex described herein may be administered in conjunction with bevacizumab and YW243.55.S70. In some embodiments, an antigen binding polypeptide (e.g., antibody) or complex described herein may be administered in conjunction with bevacizumab and MPDL3280A. In some embodiments, an antigen binding polypeptide (e.g., antibody) or complex described herein may be administered in conjunction with bevacizumab and MEDI4736. In some embodiments, an antigen binding polypeptide (e.g., antibody) or complex described herein may be administered in conjunction with bevacizumab and MDX-1105. In some embodiments, an antigen binding polypeptide (e.g., antibody) or complex described herein may be administered in conjunction with bevacizumab and MSB0010718C (avelumab).

In some embodiments, an antigen binding polypeptide (e.g., antibody) or complex described herein may be administered in conjunction with an antineoplastic agent. In some embodiments, an antigen binding polypeptide (e.g., antibody) or complex described herein may be administered in conjunction with an agent targeting CSF-1R (also known as M-CSFR or CD115). In some embodiments, an antigen binding polypeptide (e.g., antibody) or complex described herein may be administered in conjunction with anti-CSF-1R antibody (also known as IMC-CS4 or LY3022855) In some embodiments, an antigen binding polypeptide (e.g., antibody) or complex described herein may be administered in conjunction with anti-CSF-1R antibody, RG7155 (also known as RO5509554 or emactuzumab). In some embodiments, an antigen binding polypeptide (e.g., antibody) or complex described herein may be administered in conjunction with an interferon, for example interferon alpha or interferon gamma. In some embodiments, an antigen binding polypeptide (e.g., antibody) or complex described herein may be administered in conjunction with Roferon-A (also known as recombinant Interferon alpha-2a). In some embodiments, an antigen binding polypeptide (e.g., antibody) or complex described herein may be administered in conjunction with GM-CSF (also known as recombinant human granulocyte macrophage colony stimulating factor, rhu GM-CSF, sargramostim, or Leukine®). In some embodiments, an antigen binding polypeptide (e.g., antibody) or complex described herein may be administered in conjunction with IL-2 (also known as aldesleukin or Proleukin®). In some embodiments, an antigen binding polypeptide (e.g., antibody) or complex described herein may be administered in conjunction with IL-12. In some embodiments, an antigen binding polypeptide (e.g., antibody) or complex described herein may be administered in conjunction with IL27. In some embodiments, an antigen binding polypeptide (e.g., antibody) or complex described herein may be administered in conjunction with IL-15. In some embodiments, an antigen binding polypeptide (e.g., antibody) or complex described herein may be administered in conjunction with ALT-803. In some embodiments, an antigen binding polypeptide (e.g., antibody) or complex described herein may be administered in conjunction with an antibody targeting CD20. In some embodiments, the antibody targeting CD20 is obinutuzumab (also known as GA101 or Gazyva®) or rituximab. In some embodiments, an antigen binding polypeptide (e.g., antibody) or complex described herein may be administered in conjunction with an antibody targeting GITR. In some embodiments, the antibody targeting GITR is TRX518. In some embodiments, the antibody targeting GITR is MK04166 (Merck).

In some embodiments, an antigen binding polypeptide (e.g., antibody) or complex described herein may be administered in conjunction with an inhibitor of Bruton's tyrosine kinase (BTK). In some embodiments, an antigen binding polypeptide (e.g., antibody) or complex described herein may be administered in conjunction with ibrutinib. In some embodiments, an antigen binding polypeptide (e.g., antibody) or complex described herein may be administered in conjunction with an inhibitor of Isocitrate dehydrogenase 1 (IDH1) and/or Isocitrate dehydrogenase 2 (IDH2). In some embodiments, an antigen binding polypeptide (e.g., antibody) or complex described herein may be administered in conjunction with AG-120 (Agios).

In some embodiments, an antigen binding polypeptide (e.g., antibody) or complex described herein may be administered in conjunction with obinutuzumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody).

In some embodiments, an antigen binding polypeptide (e.g., antibody) or complex described herein may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, an antigen binding polypeptide (e.g., antibody) or complex described herein may be administered in conjunction with an adjuvant. In some embodiments, an antigen binding polypeptide (e.g., antibody) or complex described herein may be administered in conjunction with a treatment comprising a TLR agonist, e.g., Poly-ICLC (also known as Hiltonol®), LPS, MPL, or CpG ODN. In some embodiments, an antigen binding polypeptide (e.g., antibody) or complex described herein may be administered in conjunction with tumor necrosis factor (TNF) alpha. In some embodiments, an antigen binding polypeptide (e.g., antibody) or complex described herein may be administered in conjunction with IL-1. In some embodiments, an antigen binding polypeptide (e.g., antibody) or complex described herein may be administered in conjunction with HMGB1. In some embodiments, an antigen binding polypeptide (e.g., antibody) or complex described herein may be administered in conjunction with an IL-10 antagonist. In some embodiments, an antigen binding polypeptide (e.g., antibody) or complex described herein may be administered in conjunction with an IL-4 antagonist. In some embodiments, an antigen binding polypeptide (e.g., antibody) or complex described herein may be administered in conjunction with an IL-13 antagonist. In some embodiments, an antigen binding polypeptide (e.g., antibody) or complex described herein may be administered in conjunction with an IL-17 antagonist. In some embodiments, an antigen binding polypeptide (e.g., antibody) or complex described herein may be administered in conjunction with an HVEM antagonist. In some embodiments, an antigen binding polypeptide (e.g., antibody) or complex described herein may be administered in conjunction with an ICOS agonist, e.g., by administration of ICOS-L, or an agonistic antibody directed against ICOS. In some embodiments, an antigen binding polypeptide (e.g., antibody) or complex described herein may be administered in conjunction with a treatment targeting CX3CL1. In some embodiments, an antigen binding polypeptide (e.g., antibody) or complex described herein may be administered in conjunction with a treatment targeting CXCL9. In some embodiments, an antigen binding polypeptide (e.g., antibody) or complex described herein may be administered in conjunction with a treatment targeting CXCL10. In some embodiments, an antigen binding polypeptide (e.g., antibody) or complex described herein may be administered in conjunction with a treatment targeting CCL5. In some embodiments, an antigen binding polypeptide (e.g., antibody) or complex described herein may be administered in conjunction with an LFA-1 or ICAM1 agonist. In some embodiments, an antigen binding polypeptide (e.g., antibody) or complex described herein may be administered in conjunction with a Selectin agonist.

In some embodiments, an antigen binding polypeptide (e.g., antibody) or complex described herein may be administered in conjunction with an inhibitor of B-Raf. In some embodiments, an antigen binding polypeptide (e.g., antibody) or complex described herein may be administered in conjunction with vemurafenib (also known as Zelboraf®). In some embodiments, an antigen binding polypeptide (e.g., antibody) or complex described herein may be administered in conjunction with dabrafenib (also known as Tafinlar®). In some embodiments, an antigen binding polypeptide (e.g., antibody) or complex described herein may be administered in conjunction with encorafenib (LGX818).

In some embodiments, an antigen binding polypeptide (e.g., antibody) or complex described herein may be administered in conjunction with an EGFR inhibitor. In some embodiments, an antigen binding polypeptide (e.g., antibody) or complex described herein may be administered in conjunction with erlotinib (also known as Tarceva®). In some embodiments, an antigen binding polypeptide (e.g., antibody) or complex described herein may be administered in conjunction with an inhibitor of EGFR-T790M. In some embodiments, an antigen binding polypeptide (e.g., antibody) or complex described herein may be administered in conjunction with gefitinib. In some embodiments, an antigen binding polypeptide (e.g., antibody) or complex described herein may be administered in conjunction with afatinib. In some embodiments, an antigen binding polypeptide (e.g., antibody) or complex described herein may be administered in conjunction with cetuximab (also known as Erbitux®). In some embodiments, an antigen binding polypeptide (e.g., antibody) or complex described herein may be administered in conjunction with panitumumab (also known as Vectibix®). In some embodiments, an antigen binding polypeptide (e.g., antibody) or complex described herein may be administered in conjunction with rociletinib. In some embodiments, an antigen binding polypeptide (e.g., antibody) or complex described herein may be administered in conjunction with AZD9291. In some embodiments, an antigen binding polypeptide (e.g., antibody) or complex described herein may be administered in conjunction with an inhibitor of a MEK, such as MEK1 (also known as MAP2K1) and/or MEK2 (also known as MAP2K2). In some embodiments, an antigen binding polypeptide (e.g., antibody) or complex described herein may be administered in conjunction with cobimetinib (also known as GDC-0973 or XL-518). In some embodiments, an antigen binding polypeptide (e.g., antibody) or complex described herein may be administered in conjunction with trametinib (also known as Mekinist®). In some embodiments, an antigen binding polypeptide (e.g., antibody) or complex described herein may be administered in conjunction with binimetinib.

In some embodiments, an antigen binding polypeptide (e.g., antibody) or complex described herein may be administered in conjunction an inhibitor of B-Raf (e.g., vemurafenib or dabrafenib) and an inhibitor of MEK (e.g., MEK1 and/or MEK2 (e.g., cobimetinib or trametinib). In some embodiments, an antigen binding polypeptide (e.g., antibody) or complex described herein may be administered in conjunction with an inhibitor of ERK (e.g., ERK1/2). In some embodiments, an antigen binding polypeptide (e.g., antibody) or complex described herein may be administered in conjunction with GDC-0994). In some embodiments, an antigen binding polypeptide (e.g., antibody) or complex described herein may be administered in conjunction with an inhibitor of B-Raf, an inhibitor of MEK, and an inhibitor of ERK1/2. In some embodiments, an antigen binding polypeptide (e.g., antibody) or complex described herein may be administered in conjunction with an inhibitor of EGFR, an inhibitor of MEK, and an inhibitor of ERK1/2. In some embodiments, an antigen binding polypeptide (e.g., antibody) or complex described herein may be administered in conjunction with one or more MAP kinase pathway inhibitor. In some embodiments, an antigen binding polypeptide (e.g., antibody) or complex described herein may be administered in conjunction with CK127. In some embodiments, an antigen binding polypeptide (e.g., antibody) or complex described herein may be administered in conjunction with an inhibitor of K-Ras.

In some embodiments, an antigen binding polypeptide (e.g., antibody) or complex described herein may be administered in conjunction with an inhibitor of c-Met. In some embodiments, an antigen binding polypeptide (e.g., antibody) or complex described herein may be administered in conjunction with onartuzumab (also known as MetMAb). In some embodiments, an antigen binding polypeptide (e.g., antibody) or complex described herein may be administered in conjunction with an inhibitor of anaplatic lymphoma kinase (ALK). In some embodiments, an antigen binding polypeptide (e.g., antibody) or complex described herein may be administered in conjunction with AF802 (also known as CH5424802 or alectinib). In some embodiments, an antigen binding polypeptide (e.g., antibody) or complex described herein may be administered in conjunction with crizotinib. In some embodiments, an antigen binding polypeptide (e.g., antibody) or complex described herein may be administered in conjunction with ceritinib. In some embodiments, an antigen binding polypeptide (e.g., antibody) or complex described herein may be administered in conjunction with an inhibitor of a phosphatidylinositol 3-kinase (PI3K). In some embodiments, an antigen binding polypeptide (e.g., antibody) or complex described herein may be administered in conjuction with buparlisib (BKM-120). In some embodiments, an antigen binding polypeptide (e.g., antibody) or complex described herein may be administered in conjunction with pictilisib (also known as GDC-0941). In some embodiments, an antigen binding polypeptide (e.g., antibody) or complex described herein may be administered in conjunction with buparlisib (also known as BKM-120). In some embodiments, an antigen binding polypeptide (e.g., antibody) or complex described herein may be administered in conjunction with perifosine (also known as KRX-0401). In some embodiments, an antigen binding polypeptide (e.g., antibody) or complex described herein may be administered in conjunction with a delta-selective inhibitor of a phosphatidylinositol 3-kinase (PI3K). In some embodiments, an antigen binding polypeptide (e.g., antibody) or complex described herein may be administered in conjunction with idelalisib (also known as GS-1101 or CAL-101). In some embodiments, an antigen binding polypeptide (e.g., antibody) or complex described herein may be administered in conjunction with taselisib (also known as GDC-0032). In some embodiments, an antigen binding polypeptide (e.g., antibody) or complex described herein may be administered in conjunction with BYL-719. In some embodiments, an antigen binding polypeptide (e.g., antibody) or complex described herein may be administered in conjunction with an inhibitor of an Akt. In some embodiments, an antigen binding polypeptide (e.g., antibody) or complex described herein may be administered in conjunction with MK2206. In some embodiments, an antigen binding polypeptide (e.g., antibody) or complex described herein may be administered in conjunction with GSK690693. In some embodiments, an antigen binding polypeptide (e.g., antibody) or complex described herein may be administered in conjunction with ipatasertib (also known as GDC-0068). In some embodiments, an antigen binding polypeptide (e.g., antibody) or complex described herein may be administered in conjunction with an inhibitor of mTOR. In some embodiments, an antigen binding polypeptide (e.g., antibody) or complex described herein may be administered in conjunction with sirolimus (also known as rapamycin). In some embodiments, an antigen binding polypeptide (e.g., antibody) or complex described herein may be administered in conjunction with temsirolimus (also known as CCI-779 or Torisel®). In some embodiments, an antigen binding polypeptide (e.g., antibody) or complex described herein may be administered in conjunction with everolimus (also known as RAD001). In some embodiments, an antigen binding polypeptide (e.g., antibody) or complex described herein may be administered in conjunction with ridaforolimus (also known as AP-23573, MK-8669, or deforolimus). In some embodiments, an antigen binding polypeptide (e.g., antibody) or complex described herein may be administered in conjunction with OSI-027. In some embodiments, an antigen binding polypeptide (e.g., antibody) or complex described herein may be administered in conjunction with AZD8055. In some embodiments, an antigen binding polypeptide (e.g., antibody) or complex described herein may be administered in conjunction with INK128. In some embodiments, an antigen binding polypeptide (e.g., antibody) or complex described herein may be administered in conjunction with a dual PI3K/mTOR inhibitor. In some embodiments, an antigen binding polypeptide (e.g., antibody) or complex described herein may be administered in conjunction with XL765. In some embodiments, an antigen binding polypeptide (e.g., antibody) or complex described herein may be administered in conjunction with GDC-0980. In some embodiments, an antigen binding polypeptide (e.g., antibody) or complex described herein may be administered in conjunction with BEZ235 (also known as NVP-BEZ235). In some embodiments, an antigen binding polypeptide (e.g., antibody) or complex described herein may be administered in conjunction with BGT226. In some embodiments, an antigen binding polypeptide (e.g., antibody) or complex described herein may be administered in conjunction with GSK2126458. In some embodiments, an antigen binding polypeptide (e.g., antibody) or complex described herein may be administered in conjunction with PF-04691502. In some embodiments, an antigen binding polypeptide (e.g., antibody) or complex described herein may be administered in conjunction with PF-05212384 (also known as PKI-587).

In some embodiments, an antigen binding polypeptide (e.g., antibody) or complex described herein may be administered in conjunction with an agent that selectively degrades the estrogen receptor. In some embodiments, an antigen binding polypeptide (e.g., antibody) or complex described herein may be administered in conjunction with GDC-0927. In some embodiments, an antigen binding polypeptide (e.g., antibody) or complex described herein may be administered in conjunction with an inhibitor of HER3. In some embodiments, an antigen binding polypeptide (e.g., antibody) or complex described herein may be administered in conjunction with duligotuzumab. In some embodiments, an antigen binding polypeptide (e.g., antibody) or complex described herein may be administered in conjunction with an inhibitor of LSD1. In some embodiments, an antigen binding polypeptide (e.g., antibody) or complex described herein may be administered in conjunction with an inhibitor of MDM2. In some embodiments, an antigen binding polypeptide (e.g., antibody) or complex described herein may be administered in conjunction with an inhibitor of BCL2. In some embodiments, an antigen binding polypeptide (e.g., antibody) or complex described herein may be administered in conjunction with venetoclax. In some embodiments, an antigen binding polypeptide (e.g., antibody) or complex described herein may be administered in conjunction with an inhibitor of CHK1. In some embodiments, an antigen binding polypeptide (e.g., antibody) or complex described herein may be administered in conjunction with GDC-0575. In some embodiments, an antigen binding polypeptide (e.g., antibody) or complex described herein may be administered in conjunction with an inhibitor of activated hedgehog signaling pathway. In some embodiments, an antigen binding polypeptide (e.g., antibody) or complex described herein may be administered in conjunction with ERIVEDGE.

In some embodiments, an antigen binding polypeptide (e.g., antibody) or complex described herein may be administered in conjunction with radiation therapy. In some embodiments, an antigen binding polypeptide (e.g., antibody) or complex described herein may be administered in conjunction with gemcitabine. In some embodiments, an antigen binding polypeptide (e.g., antibody) or complex described herein may be administered in conjunction with nab-paclitaxel (ABRAXANE). In some embodiments, an antigen binding polypeptide (e.g., antibody) or complex described herein may be administered in conjunction with trastuzumab. In some embodiments, an antigen binding polypeptide (e.g., antibody) or complex described herein may be administered in conjunction with TVEC. In some embodiments, an antigen binding polypeptide (e.g., antibody) or complex described herein may be administered in conjunction with IL27. In some embodiments, an antigen binding polypeptide (e.g., antibody) or complex described herein may be administered in conjunction with cyclophosphamide. In some embodiments, an antigen binding polypeptide (e.g., antibody) or complex described herein may be administered in conjunction with an agent that recruits T cells to the tumor. In some embodiments, an antigen binding polypeptide (e.g., antibody) or complex described herein may be administered in conjunction with lirilumab (IPH2102/BMS-986015). In some embodiments, an antigen binding polypeptide (e.g., antibody) or complex described herein may be administered in conjunction with Idelalisib. In some embodiments, an antigen binding polypeptide (e.g., antibody) or complex described herein may be administered in conjunction with an antibody that targets CD3 and CD20. In some embodiments, an antigen binding polypeptide (e.g., antibody) or complex described herein may be administered in conjunction with REGN1979. In some embodiments, an antigen binding polypeptide (e.g., antibody) or complex described herein may be administered in conjunction with an antibody that targets CD3 and CD19. In some embodiments, an antigen binding polypeptide (e.g., antibody) or complex described herein may be administered in conjunction with blinatumomab.

In some embodiments, an antigen binding polypeptide (e.g., antibody) or complex described herein may be administered in conjunction with an oncolytic virus. In some embodiments, an antigen binding polypeptide (e.g., antibody) or complex described herein may be administered in conjunction with carboplatin and nab-paclitaxel. In some embodiments, an antigen binding polypeptide (e.g., antibody) or complex described herein may be administered in conjunction with carboplatin and paclitaxel. In some embodiments, an antigen binding polypeptide (e.g., antibody) or complex described herein may be administered in conjunction with cisplatin and pemetrexed. In some embodiments, an antigen binding polypeptide (e.g., antibody) or complex described herein may be administered in conjunction with cisplatin and gemcitabine. In some embodiments, an antigen binding polypeptide (e.g., antibody) or complex described herein may be administered in conjunction with FOLFOX. In some embodiments, an antigen binding polypeptide (e.g., antibody) or complex described herein may be administered in conjunction with FOLFIRI.

Such combination therapies noted above encompass combined administration (where two or more therapeutic agents are included in the same or separate formulations), and separate administration, in which case, administration of the antigen binding polypeptide (e.g., antibody) or complex described herein can occur prior to, simultaneously, and/or following, administration of the additional therapeutic agent and/or adjuvant. Antibodies or complexes of the invention can also be used in combination with radiation therapy.

An antibody or complex of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or complexes of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or complex need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or complex of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody or complex is suitably administered to the patient at one time or over a series of treatments. Depending on the type and severity of the disease, about 1 µg/kg to 40 mg/kg of antibody or complex can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Use of Tie2 Agonists

In certain embodiments, the application provides methods for treating or preventing a disease or disorder in a mammal, comprising administering to the mammal a therapeutically effective amount of an agonist antigen binding complex that binds to Tie 2. In certain embodiments, a Tie2 agonist as described herein may be used to stimulate angiogenesis, and can be used in a variety of clinical situations in which promotion of angiogenesis is desirable. Non-limiting examples of such indications include vascularization of regenerative tissues, ischemic limb disease, cerebral ischemia, conditions of vascular inflammation including arteriosclerosis, avascular necrosis, stimulation of hair growth and erectile dysfunction. In certain embodiments, a Tie2 agonist as described herein may be used for decreasing vascular permeability, e.g. at a site of leaky vessels. Such a method can be used in a variety of clinical situations, non-limiting examples of which include stroke, macular degeneration, macular edema, lymph edema, breakdown of the blood-retinal barrier, breakdown of the blood-brain barrier (e.g., during chemotherapeutic treatment) and normalization of tumor vasculature to facilitate drug delivery and increase radiation sensitivity. In certain embodiments, a Tie2 agonist as described herein may be used to inhibit apoptosis of endothelial cells. Such a method can be used in a variety of clinical situations, non-limiting examples of which include kidney fibrosis, stroke, macular degeneration and diabetic complications (e.g., in the kidney, eye, skin and/or limbs). In other embodiments, a Tie2 agonist as described herein may be used in stimulating wound healing.

Screening Assays

Also provided herein are methods for identifying polypeptides that have agonist activity. In particular, an antigen binding polypeptide may not have agonist activity when expressed as an individual polypeptide (e.g., an individual antibody, antibody fragment, ligand, etc.), however, when the same polypeptide is presented in the context of a multimeric complex as described herein, the complex may exhibit agonist activity. Therefore, by screening for agonist activity of individual polypeptides, there may be a number of candidates that are discarded as false negatives, e.g., polypeptides that have the ability to act as an agonist when contained in a complex but do not exhibit such activity when presented in isolated form. Therefore, the antigen binding complexes as described herein may be used in an initial screen of candidate polypeptides to identify those having agonist activity.

Accordingly, in certain embodiments, the application provides novel methods for identifying an antigen binding polypeptide (or antigen binding complex) having agonist activity. The methods include providing a plurality of antigen binding complexes as described herein, screening the antigen binding complexes against a cell surface receptor, and selecting antigen binding complexes having agonist activity for the cell surface receptor. In certain embodiments, the antigen binding complexes may be provided as libraries of antigen binding complexes whose amino acid sequences differ from each other. Such libraries provide a tremendously useful resource for identifying antigen binding complex which bind to the cell surface receptor and has agonist activity for the cell surface receptor.

In certain embodiments, the antigen binding complexes useful in such a screening assay may be a library wherein each antigen binding complex comprises a hexamer of monospecific bivalent antibodies, wherein each antibody in a given complex is the same, and each hexameric complex contains a different antibody that binds to the same target, e.g., essentially a library of hexameric complexes of monospecific antibodies raised to a given cell surface target. Such libraries would be useful, for example, for identifying an antibody (or antigen binding complex) that binds to cell surface receptor and agonizes the receptor.

In certain embodiments, the antigen binding complexes useful in such a screening assay may be a library wherein each antigen binding complex comprises a hexamer of bivalent antibodies, wherein each complex comprises at least two different antibodies that bind to two different targets, and each complex contains different antibodies that bind to the same two targets. For example, such a library could contain a mix of antibodies that bind to cell surface receptor 1 and a mix of antibodies that bind to cell surface receptor 2. Screening this type of library would be useful, for example, for identifying a combination of antibodies that would agonize a heterodimeric cell surface receptor and could inform development of a bispecific antibody that would agonize the receptor pair.

In other embodiments, the application provides a method for increasing agonist activity of an antigen binding polypeptide. In certain embodiments, the method comprises providing an antigen binding polypeptide which comprises an antigen binding region for a cell surface receptor and a Fc region, and introducing a modification into the Fc region, wherein the modification enhances complex formation (including, for example, hexamer formation) of the antigen binding polypeptide, and wherein the complex has increased agonist activity for a cell surface receptor bound by the antigen binding polypeptide as compared to an individual subunit of the complex.

The antigen binding complexes or the antigen binding polypeptides described herein can be characterized for their physical/chemical properties and biological functions by various assays known in the art. For example, as exemplified herein, hexamer formation may be assayed, e.g., using Size Exclusion Chromatography (SEC) to monitor the differential retention time of monomeric and multimeric (e.g., hexameric) complexes.

In some embodiments, a composition comprising antigen binding polypeptides of the present disclosure may comprise the antigen binding polypeptides in monomeric and multimeric (e.g., hexameric) forms. As described herein, certain modified antigen binding polypeptides may comprise a percentage of multimeric species (e.g., hexamers) in solution. However, as exemplified herein, certain modified antigen binding polypeptides may promote strong T cell proliferation (e.g., a stronger proliferative response as compared to a control, such as an antigen binding polypeptide without the modification(s)) in the absence of FcR-mediated cross-linking despite forming predominantly or exclusively monomeric species in solution.

In certain embodiments, antigen binding complexes or antigen binding polypeptides can be characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments, antigen binding complexes or antigen binding polypeptides may be analyzed for biological activity, such as, for example, antigen binding activity. Antigen binding assays are known in the art and can be used herein including, for example, any direct or competitive binding assays using techniques such as western blots, radioimmunoassays, ELISA (enzyme linked immnosorbent assay), "sandwich" immunoassays, immunoprecipitation assays, fluorescent immunoassays, and protein A immunoassays.

In other embodiments, the antigen binding complexes or antigen binding polypeptides described herein may be analyzed for agonist activity. In certain embodiments, agonist activity of the antigen binding complexes or antigen binding polypeptides described herein can be determined by analyzing whether or not a cell that is depending on a ligand for growth will grow in the same way when an antigen binding complex or polypeptide is added during cell culture as compared to when a ligand is added. If the cell grows in the same or in a similar manner, then the antigen binding complex or polypeptide is determined to have agonistic activity. In certain embodiments, agonist activity of the antigen binding complexes or antigen binding polypeptides described herein can be determined by analyzing whether or not a cell line having intrinsic ligand-dependent activities (not limited to growth) shows the same reaction when an antigen binding complex or polypeptide is added during cell culture as compared to when the ligand is added. If the cell line shows the same or a similar reaction as for the ligand, then the antigen binding complex or polypeptide is determined to have agonistic activity.

In certain embodiments, cells capable of transducing the above-mentioned cell growth signals express the receptors responsive to the ligand on the cell surface. These cells transduce cell growth signals when the ligand (or agonist antigen binding complex or polypeptide) binds to the receptor. In certain embodiments, cells useful for screening for agonist activity proliferate or transduce a signal upon binding of a ligand to a cell surface receptor on the cell. In other embodiments, when the cell surface receptor is one that does not transduce a signal into the cell, then chimeric receptors made by fusing the extracellular domain (e.g., ligand binding domain) of a non-transducing receptor to the intracellular domain of a receptor that does transduce a signal into the cell. Receptors suitable for constructing chimeric receptors by fusion with ligand-binding receptors include any receptor that transduces a signal, including, for example, the G-CSF receptor, mpl, neu, GM-CSF receptor, EPO receptor, c-Kit, and FLT-3 receptors. Cells used to express such receptors include, for example, BaF3, NFS60, FDCP-1, FDCP-2, CTLL-2, DA-1, and KT-3.

In certain embodiments, agonistic activity refers to any activity caused by ligand (or antigen binding complex or polypeptide) binding that induces a specific reaction in a cell, such as, for example, inducing a change in a certain physiological activity by transmitting a signal into a cell. Such physiological activities include, for example, growth activities, growth-inducing activities, survival activities, differentiation activities, differentiation-inducing activities, transcriptional activities, membrane transport activities, binding activities, proteolytic activities, phosphorylation/dephosphorylation activities, oxidation-reduction activities, transfer activities, nucleolytic activities, dehydration activities, cell death-inducing activities, and apoptosis-inducing activities.

The agonistic activities described herein can be determined by methods known to those skilled in the art. For example, agonistic activity can be evaluated by methods which use cell growth as an indicator. More specifically, an antigen binding complex or polypeptide whose agonistic activity is to be determined is added to cells that show agonist-dependent growth, and the cells are cultured. Next, a reagent that shows a color reaction at a particular wavelength depending on viable cell count, such as WST-8, is added, and the absorbance is measured. The agonistic activity can be determined using the measured absorbance as an indicator.

In certain embodiments, agonist activity is determined using an indicator that can monitor quantitative and/or qualitative changes in the cell upon exposure to a ligand (or antigen binding complex or polypeptide). For example, it is possible to use cell-free assay indicators, cell-based assay indicators, tissue-based assay indicators, and in vivo assay indicators. Indicators that can be used in cell-free assays include enzymatic reactions, quantitative and/or qualitative changes in proteins, DNAs, or RNAs. Such enzymatic reactions include, for example, amino acid transfers, sugar transfers, dehydrations, dehydrogenations, and substrate cleavages. Alternatively, protein phosphorylations, dephosphorylations, dimerizations, multimerizations, hydrolyses, and dissociations; DNA or RNA amplifications, cleavages, and extensions can be used as the indicator in cell-free assays. For example, protein phosphorylations downstream of a signal transduction pathway may be used as a detection indicator. Alterations in cell phenotype, for example, quantitative and/or qualitative alterations in products, alterations in growth activity, alterations in cell number, morphological alterations, or alterations in cellular properties, can be used as the indicator in cell-based assays. The products include, for example, secretory proteins, surface antigens, intracellular proteins, and mRNAs. The morphological alterations include, for example, alterations in dendrite formation and/or dendrite number, alteration in cell flatness, alteration in cell elongation/axial ratio, alterations in cell size, alterations in intracellular structure, heterogeneity/homogeneity of cell populations, and alterations in cell density. Such morphological alterations can be observed under a microscope. Cellular properties to be used as the indicator include anchor dependency, cytokine-dependent response, hormone dependency, drug resistance, cell motility, cell migration activity, pulsatory activity, and alteration in intracellular substances. Cell motility includes cell infiltration activity and cell migration activity. The alterations in intracellular substances include, for example, alterations in enzyme activity, mRNA levels, levels of intracellular signaling molecules such as $Ca^{2+}$ and cAMP, and intracellular protein levels. When a cell membrane receptor is used, alterations in the cell proliferating activity induced by receptor stimulation can be used as the indicator. The indicators to be used in tissue-based assays include functional alterations adequate for the subject tissue. In in vivo assays, alterations in tissue weight, alterations in the blood system (for example, alterations in blood cell counts, protein contents, or enzyme activities), alterations in electrolyte levels, and alterations in the circulating system (for example, alterations in blood pressure or heart rate).

Any suitable method for measuring such detection indicators may be used in connection with the methods described herein. For example, absorbance, luminescence, color development, fluorescence, radioactivity, fluorescence polarization, surface plasmon resonance signal, time-resolved fluorescence, mass, absorption spectrum, light scattering, and fluorescence resonance energy transfer may be used. These measurement methods are known to those skilled in the art and may be selected appropriately depending on the purpose. For example, absorption spectra can be obtained by using a conventional photometer, plate reader, or such; luminescence can be measured with a luminometer or such; and fluorescence can be measured with a fluorometer or such. Mass can be determined with a mass spectrometer. Radioactivity can be determined with a device such as a gamma counter depending on the type of radiation. Fluorescence polarization can be measured with BEACON (TaKaRa). Surface plasmon resonance signals can be obtained with BIACORE. Time-resolved fluorescence, fluorescence resonance energy transfer, or such can be measured with ARVO or such. Furthermore, a flow cytometer can also be used for measurements. It is possible to use one of the above methods to measure two or more different types of detection indicators. A greater number of detection indicators may also be examined by using two or more measurement methods simultaneously and/or consecutively. For example, fluorescence and fluorescence resonance energy transfer can be measured at the same time with a fluorometer.

OX40 Assays

As described above, certain aspects of the present disclosure relate to agonist activity for a cell surface receptor. As will be recognized by one of skill in the art, the particular assay(s) used to determine agonist activity for a cell surface receptor may depend upon the particular cell surface receptor. Exemplary assays related to determining OX40 activity are provided below. Based on this guidance and common knowledge in the art, one of skill in the art may suitably identify assays for other cell surface receptors described herein.

In one aspect, assays are provided for identifying an agonist antigen binding complex that binds to OX40 having biological activity. Biological activity may include, e.g., binding OX40 (e.g., binding human and/or cynomolgus OX40), increasing OX40-mediated signal transduction (e.g., increasing NFkB-mediated transcription), depleting cells that express human OX40 (e.g., T cells), depleting cells that express human OX40 by ADCC and/or phagocytosis, enhancing T effector cell function (e.g., CD4+ effector T cell), e.g., by increasing effector T cell proliferation and/or increasing cytokine production (e.g., gamma interferon) by effector T cells, enhancing memory T cell function (e.g., CD4+ memory T cell), e.g., by increasing memory T cell proliferation and/or increasing cytokine production by memory T cells (e.g., gamma interferon), or inhibiting regulatory T cell function (e.g., by decreasing Treg suppression of effector T cell function (e.g., CD4+ effector T cell function). In certain embodiments, the agonist antigen binding complex that binds to OX40 has one or more of the listed biological activities in the absence of binding to human effector cells. In certain embodiments, the agonist antigen binding complex that binds to OX40 has one or more of the listed biological activities and does bind to human effector cells. Antibodies having such biological activity in vivo and/or in vitro are also provided.

In certain embodiments, an antibody of the invention is tested for such biological activity.

T cell costimulation may be assayed using methods known in the art and exemplary methods are disclosed herein. For example, T cells (e.g., memory or effector T cells) may be obtained from peripheral white blood cells (e.g., isolated from human whole blood using Ficoll gradient centrifugation). Memory T cells (e.g., CD4+ memory T cells) or effector T cells (e.g. CD4+ Teff cells) may be isolated from PBMC using methods known in the art. For example, the Miltenyi CD4+ memory T cell isolation kit or Miltenyi naïve CD4+ T cell isolation kit may be used. Isolated T cells are cultured in the presence of antigen presenting cells (e.g., irradiated L cells that express CD32 and CD80), and activated by addition of anti-CD3 antibody in the presence or absence of an agonist antigen binding complex that binds to OX40. The effect of an agonist antigen binding complex that binds to OX40 antibody on T cell proliferation may be measured using methods well known in the art. For example, the CellTiter Glo kit (Promega) may be used, and results read on a Multilabel Reader (Perkin Elmer). The effect of an agonist antigen binding complex that binds to OX40 on T cell function may also be determined by analysis of cytokines produced by the T cell. In one embodiment, production of interferon gamma by CD4+ T cells is determined, e.g., by measurement of interferon gamma in cell culture supernatant. Methods for measuring interferon gamma are well-known in the art.

Treg cell function may be assayed using methods known in the art and exemplary methods are disclosed herein. In one example, the ability of Treg to suppress effector T cell proliferation is assayed. T cells are isolated from human whole blood using methods known in the art (e.g., isolating memory T cells or naïve T cells). Purified CD4+ naïve T cells are labeled (e.g., with CFSE) and purified Treg cells are labeled with a different reagent. Irradiated antigen presenting cells (e.g., L cells expressing CD32 and CD80) are co-cultured with the labeled purified naïve CD4+ T cells and purified Tregs. The co-cultures are activated using anti-CD3 antibody and tested in the presence or absence of an agonist antigen binding complex that binds to OX40. Following a suitable time (e.g., 6 days of coculture), the level of CD4+ naïve T cell proliferation is tracked by dye dilution in reduced label staining (e.g., reduced CFSE label staining) using FACS analysis.

OX40 signaling may be assayed using methods well known in the art and exemplary methods are disclosed herein. In one embodiment, transgenic cells are generated that express human OX40 and a reporter gene comprising the NFkB promoter fused to a reporter gene (e.g., beta luciferase). Addition of an agonist antigen binding complex that binds to OX40 to the cells results in increased NFkB transcription, which is detected using an assay for the reporter gene.

Phagocytosis may be assayed, e.g., by using monocyte-derived macrophages, or U937 cells (a human histiocytic lymphoma cells line with the morphology and characteristics of mature macrophages). OX40 expressing cells are added to the monocyte-derived macrophages or U937 cells in the presence or absence of an agonist antigen binding complex that binds to OX40. Following culturing of the cells for a suitable period of time, the percentage of phagocytosis is determined by examining percentage of cells that double stain for markers of 1) the macrophage or U937 cell and 2) the OX40 expressing cell, and dividing this by the total number of cells that show markers of the OX40 expressing cell (e.g., GFP). Analysis may be done by flow cytometry. In another embodiment, analysis may be done by fluorescent microscopy analysis.

Cells for use in any of the above in vitro assays include cells or cell lines that naturally express OX40 or that have been engineered to express OX40. Such cells include activated T cells, Treg cells and activated memory T cells that naturally express OX40. Such cells also include cell lines that express OX40 and cell lines that do not normally express OX40 but have been transfected with nucleic acid encoding OX40. Exemplary cell lines provided herein for use in any of the above in vitro assays include transgenic BT474 cells (a human breast cancer cell line) that express human OX40.

III. Pharmaceutical Compositions

The antigen binding complexes and polypeptides as described herein may be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The "therapeutically effective amount" of the complexes or proteins to be administered will be governed by such considerations, and is the minimum amount necessary to prevent, ameliorate, or treat a particular disorder (for example, a cancer, allergic or inflammatory disorder, or autoimmune disorder). In certain embodiments, the complexes and proteins described herein may optionally be formulated with one or more agents currently used to prevent or treat the disorder. The effective amount of such other agents depends on the amount of complexes or proteins present in the formulation, the type of disorder or treatment, and other factors discussed above.

Therapeutic formulations are prepared using standard methods known in the art by mixing the active ingredient having the desired degree of purity with optional physiologically acceptable carriers, excipients or stabilizers (Remington's Pharmaceutical Sciences (20th edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

In certain embodiments, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antigen binding complex or the antigen binding polypeptide, which matrices are in the form of shaped articles, e.g., films, or microcapsule. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antigen binding complex(es) or antigen binding polypeptide(s) remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The complexes or the polypeptides described herein may be administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with antagonism to the target molecule recognized by the proteins. An ex vivo strategy can also be used for therapeutic applications. Ex vivo strategies involve transfecting or transducing cells obtained from the subject with a polynucleotide encoding a protein or complex of this invention. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratin ocytes, or muscle cells.

IV. Articles of Manufacture

Another embodiment of the invention is an article of manufacture containing one or more antigen binding complex or polypeptide as described herein, and materials useful for the treatment or diagnosis of a disorder (for example, an autoimmune disease or cancer). The article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is an antigen binding complex or polypeptide as described herein. The label or package insert indicates that the composition is used for treating the particular condition. The label or package insert will further comprise instructions for administering the antigen binding complex or polypeptide composition to the subject. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1. Engineering and Characterization of Variant Hexameric Antibodies

There is growing interest in discovering antibodies that mediate agonist activity against target receptors. Agonist antibodies engage a receptor in a manner that is productive for signaling, in effect acting as a surrogate ligand. For some targets antibody-mediated agonism may be possible via bivalent engagement of the receptor, taking advantage of the homodimeric nature of IgG. However some receptor systems require multivalent cross-linking to elicit activity, whereby receptors are pulled together into a cluster to elicit optimal signaling. For these receptors, antibody cross-linking in vivo is typically enabled by engagement of antibody Fc with Fc receptors (Wilson et al., 2011, Cancer Cell 19:101-13; Kim & Ashkenazi, 2013, J Exp Med 210:1647-51; Stewart et al., 2014 Journal for ImmunoTherapy of Cancer 2:1-10).

We explored whether antibody hexamerization could 1) promote antibody agonist activity and 2) enable agonist activity in the absence of effector-mediated cross-linking. Recent work has suggested that inter-Fc interactions mediate disposition for hexamerization of native human IgG antibodies (Diebolder et al., 2014, Science 343:1260-1263; Davies et al, 2014, Molecular Immunology 62:46-53), and that engineered variants can promote hexamer formation (Diebolder et al., 2014, Science 343:1260-1263; PCT/EP2012/063339). In this work, a triple-substitution variant is described, E345R/E430G/S440Y herein referred to as RGY, that promotes antibody hexamerization in solution.

The RGY substitutions were engineered into the Fc region of the anti-OX40 humanized antibody (hu1A7) (SEQ ID NOs: 56 and 57). OX40 is a TNFRSF on the surface of T cells, and agonist antibodies to OX40 have been shown to provide costimulatory activity similar to the natural ligand OX40L in a cross-link-dependent manner (Voo et al., 2013, J. Immunol, 191:3641-50). The RGY substitutions were also engineered into the Fc region of the anti-Her2 antibody trastuzumab (herein referred to as hu4D5 or 4D5) as a comparator.

Figure 2:
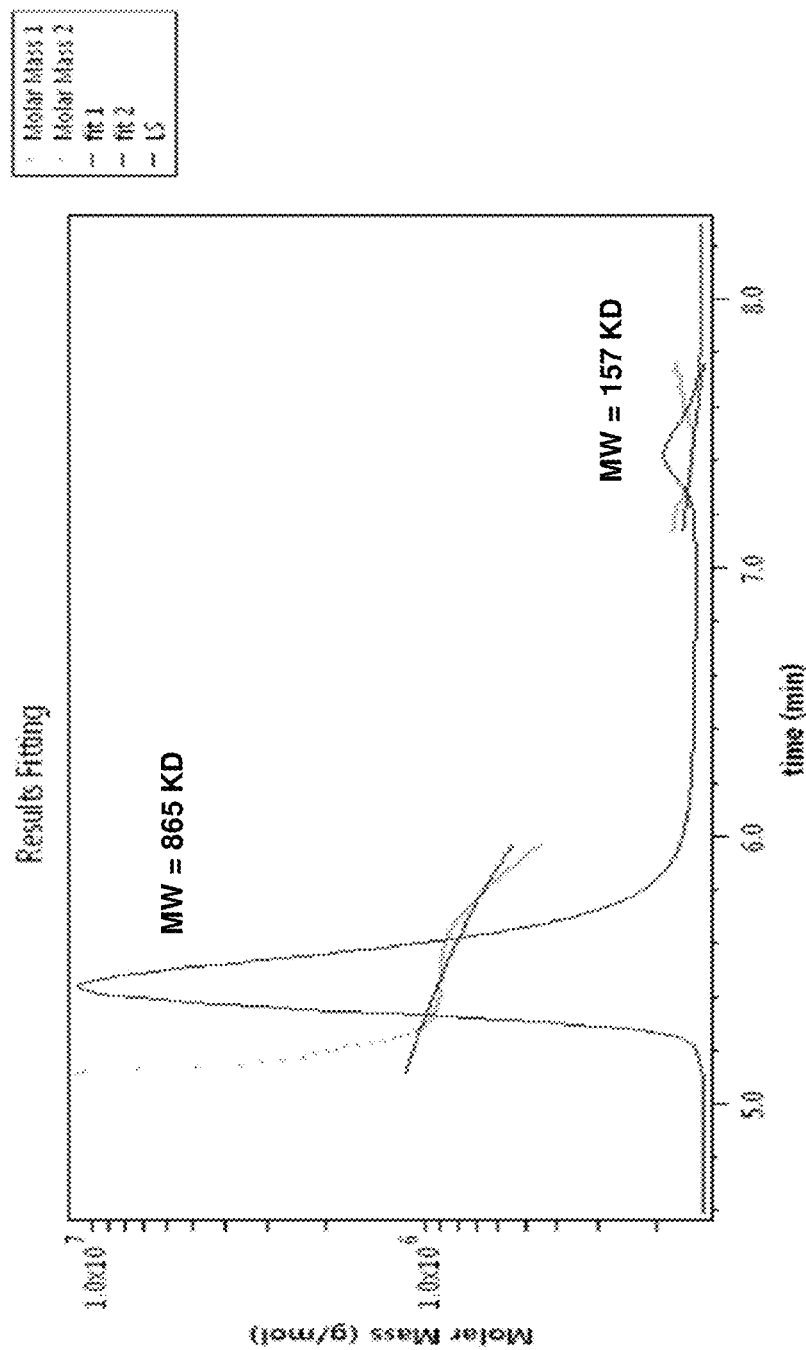
FIG. 2 shows size Exclusion Chromatography-Multiple Angle Light Scattering (SEC-MALS) data of RGY hu4D5 antibody confirming the presence of predominantly hexameric (865 kDa) species. A smaller population of monomeric (157 kDa) antibody is also observed.

The RGY substitutions were engineered into the heavy chains of anti-OX40 hu1A7 IgG1 and anti-Her2 trastuzumab IgG1 in the pRK mammalian expression vector (Eaton et al., 1986, Biochemistry 25:8343-8347) using standard molecular biology techniques. pRK vector DNA encoding heavy and light chains for each antibody were cotransfected into HEK293 cells for expression, and resulting protein was purified from the supernatant using protein A affinity chromatography. Purified antibodies were run on an analytical size exclusion column (SEC) to characterize their apparent molecular weight. The data are shown in FIG. 1. Whereas IgG standard runs at a retention time on the column of an approximate monomer (~150 kDa), the RGY variant versions of both hu1A7 and hu4D5 demonstrate an equilibrium between monomeric (~150 kDa) and hexameric (~900 kDa) species with hexamer being the dominant population. A more accurate measurement of the size of the variant antibody was obtained using Size Exclusion Chromatography coupled with Multiple Angle Light Scattering (SEC-MALS). The data, shown in FIG. 2, confirm the presence of hexameric (865 kDa) species and a smaller population of monomeric (157 kDa) antibody.

Figure 3:
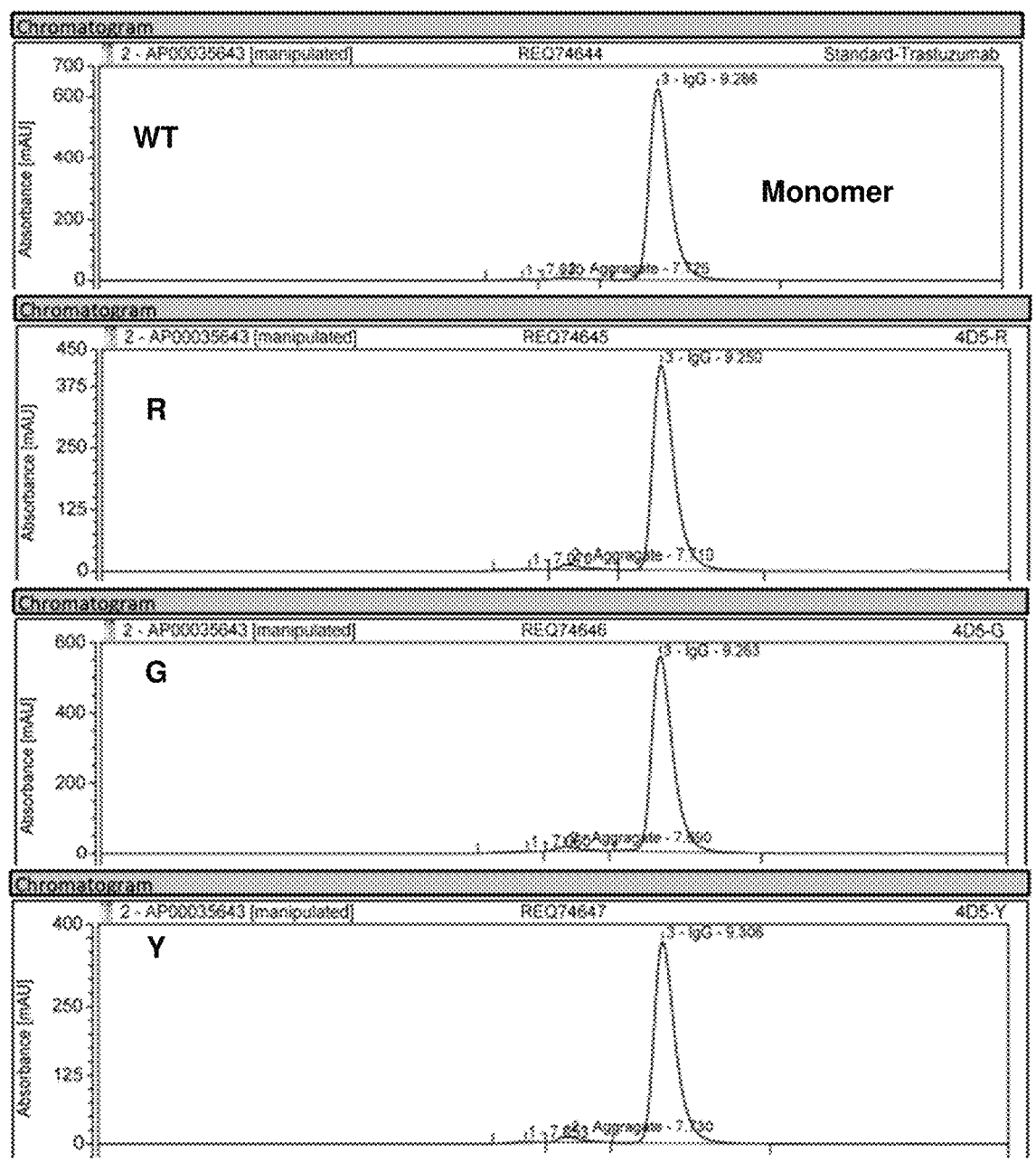
FIG. 3 shows analytical SEC chromatograms demonstrating that all three RGY substitutions are necessary to promote hexamer formation in solution. All antibodies were constructed, produced, and tested in the context of hu4D5 IgG1. WT=native IgG1, RGY=E345R/E430G/S440Y, R=E345R, G=E430G, Y=S440Y, RG=E345R/E430G, RY=E345R/S440Y, and GY=E430G/S440Y.

A series of variants were constructed to explore the contribution of the individual RGY substitutions to antibody hexamer formation. Single and double substitution variants were constructed in the Fc region of hu4D5 using standard molecular biology methods. pRK vector DNA encoding heavy and light chains were co-transfected into HEK293 cells for expression, and resulting protein was purified from the supernatant using protein A affinity chromatography. Purified antibodies were run on an analytical SEC to characterize their apparent molecular weight. The data, shown in FIG. 3, indicate that only the triple substitution variant RGY (E345R/E430G/S440Y) results in appreciable hexamer formation. All of the single variants R (E345R), G (E430G), and Y (S440Y), as well as the double variants RG (E345R/E430G), RY (E345R/S440Y), and GY (E430G/S440Y) resulted in chromatographic peaks that had retention times of only antibody monomer.

Example 2. Engineering of Variant Hexameric Antibodies with Attenuated Effector Engagement Previous characterization of the RGY variant focused entirely on the role of hexamerization in promoting complement activity (Diebolder et al., 2014, Science 343:1260-1263; PCT/EP2012/063339). In contrast, the current work explores the utility of Fc-engineered hexamerization to enhance antibody agonism, or potentially enable receptor agonism activity in the absence of effector-mediated cross-linking. The reliance of Fc receptor engagement for in vivo antibody cross-linking (typically referred to as "cross-link dependent activity") may be counter-productive to the desired therapeutic effect because Fc receptor or complement engagement can lead to effector-mediated depletion of the same target cells that are being agonized.

Figure 4:
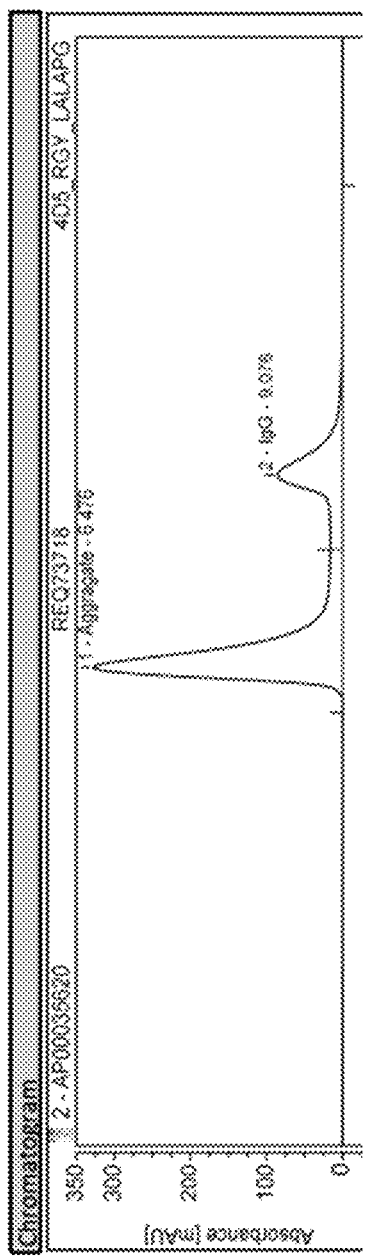
FIG. 4 shows analytical SEC chromatograms on hu4D5 antibodies containing combination of hexamer-promoting substitutions RGY with effector-attenuation substitutions N297G or LALAPG. The data demonstrate that the use N297G for effector attenuation does not permit hexamerization, whereas LALAPG does.
Figure 4:
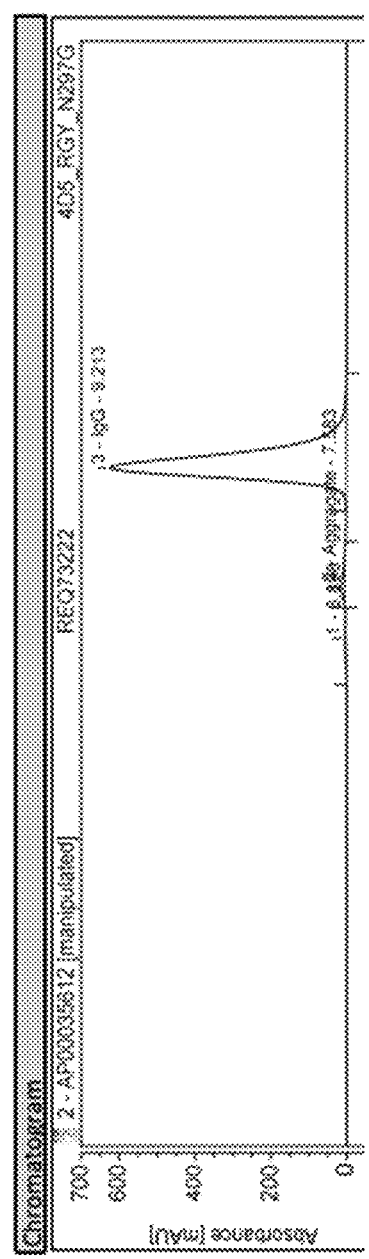
Figure 5:
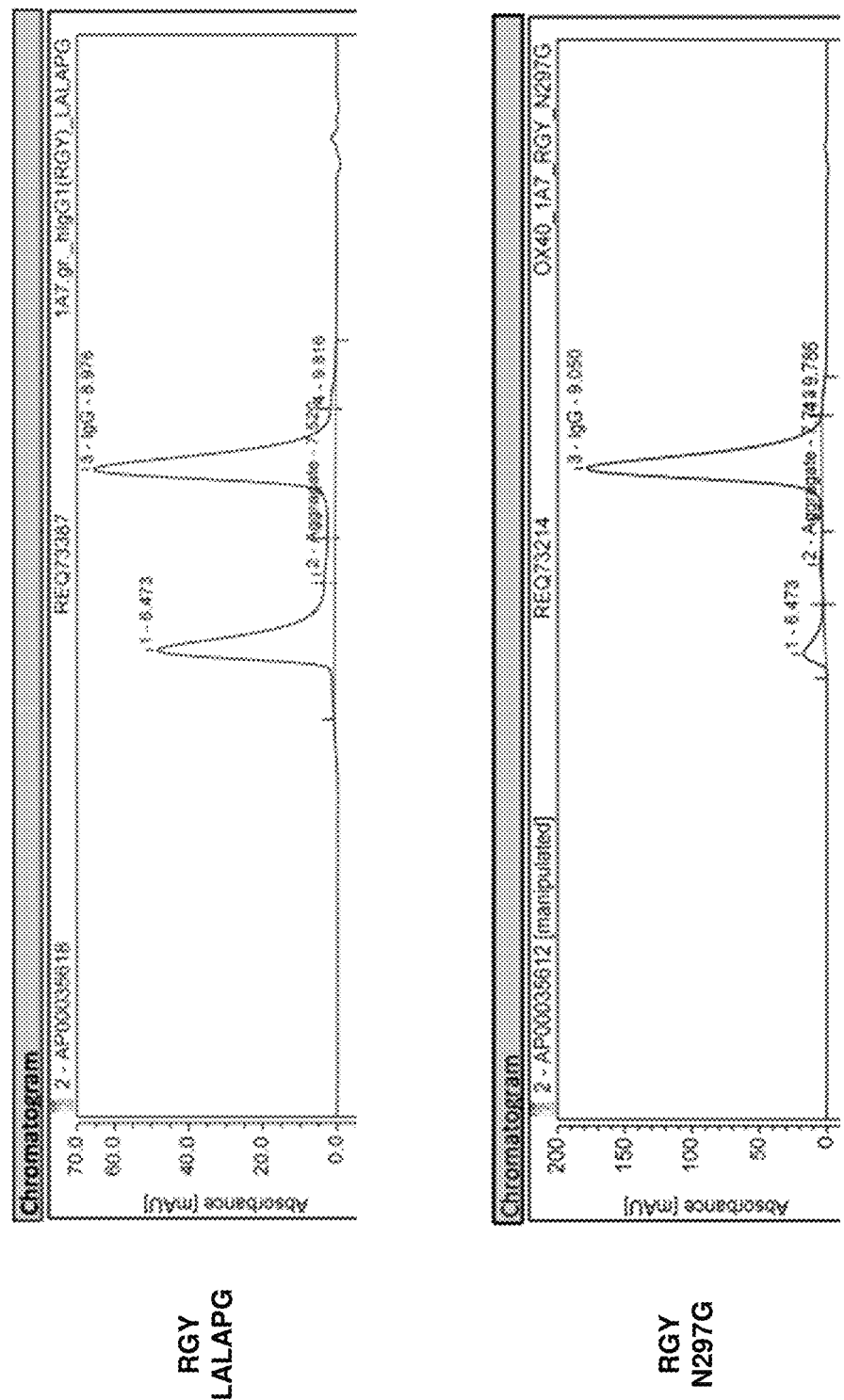
FIG. 5 shows analytical SEC chromatograms on hu1A7 antibodies containing combination of hexamer-promoting substitutions RGY with effector-attenuation substitutions N297G or LALAPG. The data demonstrate that the use N297G for effector attenuation does not permit hexamerization, whereas LALAPG does.

A variety of mutational strategies have been described for reducing the effector function properties of monoclonal antibodies (Strohl, 2009, Curr Opin in Biotech 20:685-691). Two approaches were used to engineer an effector-attenuated version of hexameric antibodies. First, the RGY substitutions were constructed in the context of an aglycosylated Fc region by combining them with the substitution N297G, which removes the conserved N-linked glycosylation site at position 297 of the Fc region. The second approach combined the RGY substitutions with substitutions L234A, L235A, and P329G (the L234A/L235A/P329G triple variant is referred to as LALAPG), which has previously been shown to reduce binding to Fc receptors and complement (see e.g., US Publication No. 2012/0251531). Variants were constructed in both hu4D5 and hu1A7 using mutagenesis techniques, and antibodies were expressed and purified as described above. Purified antibodies were run on analytical SEC to characterize their apparent molecular weight. The data are shown in FIG. 4 for hu4D5 and FIG. 5 for hu1A7. Surprisingly, whereas the RGY/LALAPG variant hexamerized comparably to RGY alone, the RGY/N297G variant did not hexamerize. While not wishing to be bound by theory, these data suggest that glycosylation is important for the formation of hexamer. This result is in contrast to the hexameric arrangement observed by crystal packing in the crystal structure of deglycosylated human IgG4 Fc (Davies et al, 2014, Molecular Immunology 62:46-53). Nonetheless, the results for the RGY/LALAPG combination variant demonstrate for the first time the successful engineering of an effector-attenuated hexameric antibody.

Example 3. Agonist Activity of Hexameric Anti-OX40 Antibodies

OX40 is a TNFRSF member co-stimulatory molecule expressed on antigen experienced effector T (Teff) and regulatory T (Treg) cells, including infiltrating cells in mouse and human tumors. Activation of OX40 by agonist antibodies has been shown to promote anti-tumor immunity by enhancing Teff activation and inhibiting Treg mediated suppression (Voo et al., 2013, J. Immunol, 191:3641-50). OX40 is a TNFRSF member, and agonism by anti-OX40 antibodies has been demonstrated to require cross-linking and be dependent on interactions with FcγRs in vivo.

Variant anti-OX40 antibodies were tested for their ability to agonize OX40 receptor. CD4+ memory T cells (CD4+ CD45RO+) were sorted from buffy coat, and L cells expressing CD80 (B7-1) and CD32a (FcγRIIa) were used as surrogate antigen presenting cells (APCs). CD4+ memory T cells were incubated with L cells, stimulated with soluble anti-CD3 antibody (mouse anti-human CD3 clone SP34) and increasing concentrations of anti-OX40 antibodies or anti-Her2 antibodies as control. Cells were cultured for 7 days, harvested, and assayed for T cell proliferation by cell titer glow (Promega) and cytokine release by ELISA.

Figure 6:
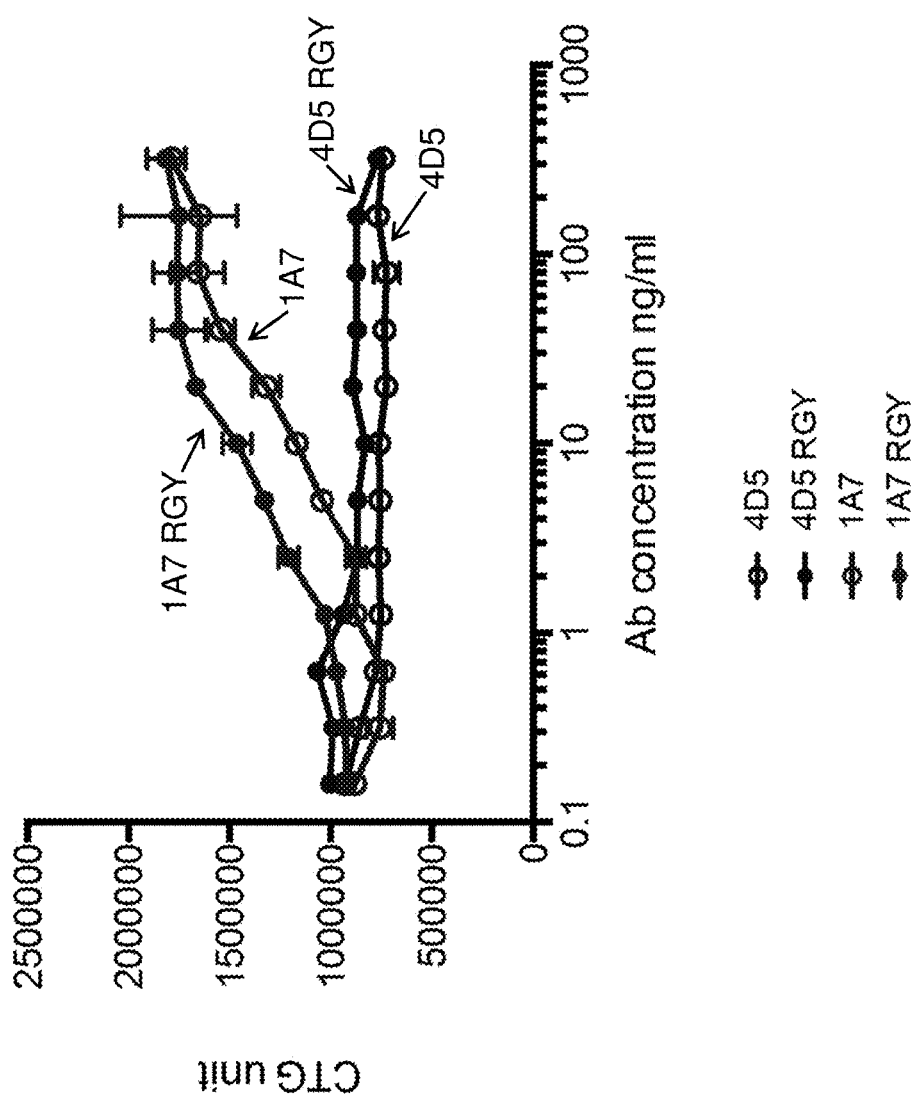
FIG. 6 shows co-stimulation of CD4+ memory T cells proliferation by anti-OX40 or control antibodies in the presence of anti-CD3 antibody and CD80+ FcγRIIa+ L cells. T cell proliferation was monitored by cell titer glo (Promega). Antibodies are as follows: 1A7=humanized 1A7 native IgG1, 1A7 RGY=humanized 1A7 RGY IgG1, 4D5=humanized 4D5 native IgG1, 4D5 RGY=humanized 4D5 RGY IgG1.

T cell proliferation data are shown in FIG. 6. The hexameric RGY variant of hu1A7 anti-OX40 antibody provided an enhanced level of T cell co-stimulation relative to native IgG1. Anti-Her2 antibodies, either RGY or native IgG1, showed no activity. A more dramatic level of enhancement of T cell activation was observed by measuring release of IL-13 and L-5 (FIG. 7).

Figure 7:
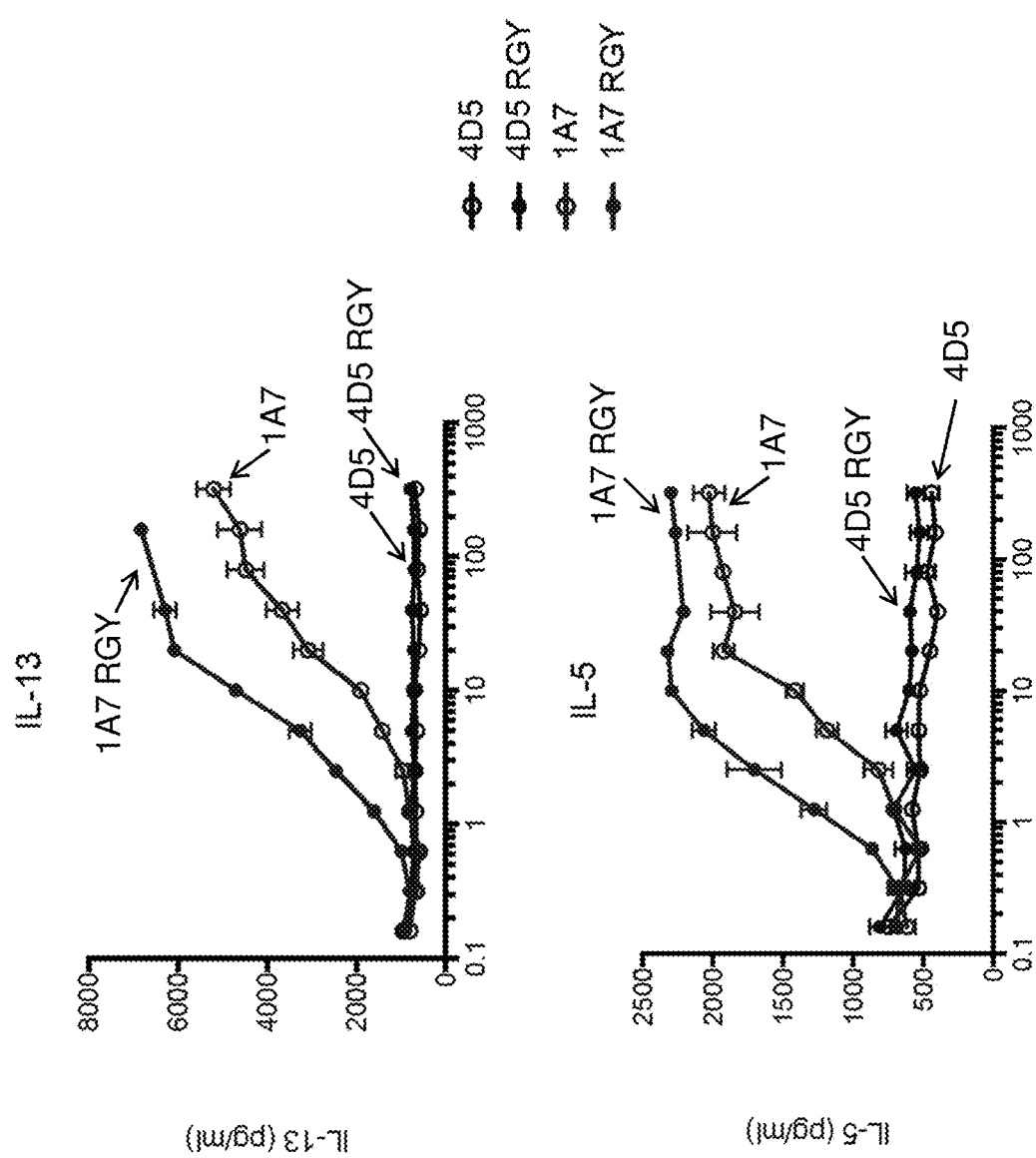
FIG. 7 shows co-stimulation of CD4+ memory T cells activation by anti-OX40 or control antibodies as measured by release of IL-13 and IL-5. Antibodies are as described in FIG. 6.
Figure 8:
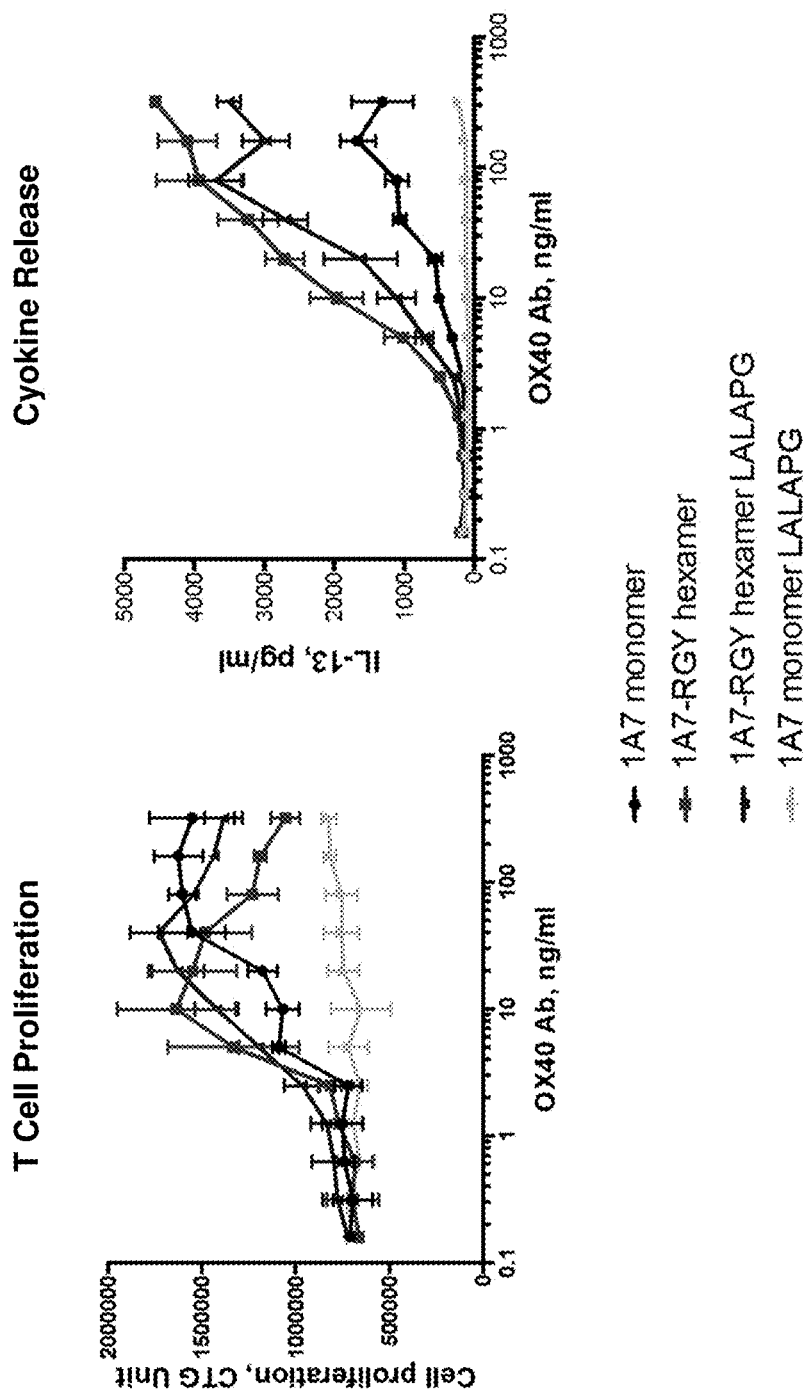
FIG. 8 shows co-stimulation of CD4+ memory T cells by anti-OX40 or control antibodies in the presence of anti-CD3 antibody and CD80+ and FcγRIIa+ L cells. T cell proliferation and activation was monitored by cell titer glo (upper graph) and release of IL-13 (lower graph).
Figure 9:
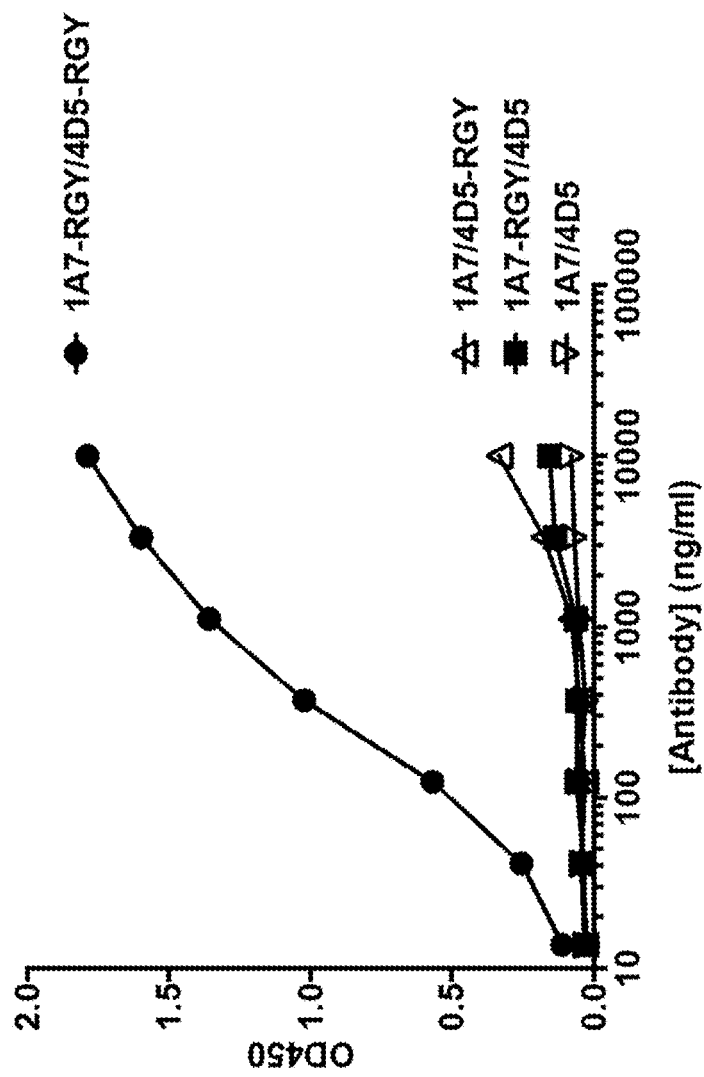
FIG. 9 shows enzyme-linked immunosorbent assay (ELISA) data demonstrating that mixed RGY variant antibodies exchange with each other to form multispecific hexamer complexes. The indicated anti-OX40 (1A7) and anti-Her2 (4D5) antibodies were mixed and captured on plates bearing OX40 antigen. After washing antibody complexes were detected with biotinylated Her2 and HRP-streptavidin.

Because both anti-OX40 antibodies in this experiment have uncompromised Fc receptor engagement, the data in FIG. 6 and FIG. 7 indicate that hexameric antibodies can enhance T cell activation and proliferation in the presence of FcγR-mediated crosslinking (provided by FcγRIIa on the L cells). Effector-attenuated antibodies, engineered via the LALAPG substitutions, were tested in the same assay. FIG. 8 shows T cell proliferation and cytokine release data for this experiment. In contrast to hu1A7 native IgG1, the effector-attenuated variant (LALAPG) provided no co-stimulation of T cell proliferation or cytokine release. This is consistent with previous work demonstrating that cross-linking is necessary for activity of anti-OX40 antibodies (Voo et al., 2013, J. Immunol, 191:3641-50). Strikingly, effector-attenuated hexameric hu1A7 (RGY LALAPG) mediates potent co-stimulatory activity as monitored by both T cell proliferation and cytokine release. Activity of hexameric RGY LALAPG was comparable or slightly less than hexameric RGY alone, and greater than native IgG1 hu1A7. These results demonstrate that engineering anti-OX40 antibodies for higher-order oligomeric structures can enable OX40 agonist activity without the reliance on cross-linking by Fc receptor engagement. Because RGY variant antibodies appears to exist in equilibrium between monomeric and hexameric species, we investigated the possibility that different RGY variants would exchange with each other. hu1A7_hIgG1 (RGY), hu4D5_hIgG1(RGY), and control antibodies were mixed in 1:1 ratio and incubated at 4° C. for a few days. Ni-NTA HisSorb strips were coated with 1 ug/ml human his-OX40 antigen. After washing, varying concentrations of mixed antibodies were added. After washing, 1 ug/ml biotinylated-Her2-ECD was added, HRP-streptavidin was added, and plates were read with and Envision plate reader. The results (FIG. 9) indicate that RGY antibodies selectively exchange with each other to form mixed hexamers with dual specificity. It is contemplated that this exchange equilibrium could be used to generate hexameric complexes with double or greater specificity. For example, mixed hexamers could be generated that target two different antigens or two different epitopes within the same antigen.

Example 4. In Vivo Anti-Tumor Activity of Hexameric Anti-OX40 Antibodies

Wishing to test the activity of hexameric anti-OX40 antibodies in vivo we first tested whether RGY hexameric antibody complexes would be competed by serum. Results indicated that RGY hexameric complexes were not competed by either 10 mg/ml recombinant IgG or human bovine serum (data not shown). We also demonstrated using analytical SEC that the RGY variant does not hexamerize mouse IgG2a (data not shown). We therefore engineered the RGY variants into a chimeric antibody comprising a rat anti-murine OX40 (mOX40) variable region (referred to herein as 2D2) and native or variant human Ckappa and human IgG1 (hIgG1) constant regions. Analytical SEC data confirmed that all RGY and RGY/LALAPG variants formed hexamers in solution (data not shown).

Hexameric variant antibodies were tested for anti-tumor activity in a syngeneic EMT6/Luc breast cancer model in Balb/c mice. Mice were inoculated into the 4th mammary fat pad with 0.1 million EMT6/Luc cells in 100 microliters of HBSS+matrigel. Mice were allowed to grow tumors until they achieved a mean tumor volume of ~150 mm³ (around 7 days after inoculation). At this point (Day 0), mice were recruited into the following groups: 1. anti-gD_hIgG1; 2. anti-gD_hIgG1(RGY); 3. anti-gD_hIgG1(RGY/LALAPG); 4. anti-mOX40_hIgG1; 5. anti-mOX40_hIgG1(RGY); 6. anti-mOX40_hIgG1(LALAPG); 7. anti-mOX40_hIgG1 (RGY/LALAPG). n=10 for all groups. Anti-gD binds to glycoprotein D of Herpes Simplex Virus and serves as a negative control. Antibodies were diluted in sterile PBS and dose volume was 100 ul. All groups were given a single 10 mg/kg dose intravenously on day 0. Blood was collected 24 hrs post dose and 13 days post dose from 5 mice/group/timepoint. Eyes were alternated between timepoints. Blood was collected 6 days post dose from the other 5 mice/group. Blood was collected by orbital bleed (collection volume did not exceed 100 ul), under isofluorane-induced anesthesia (inhalation to effect). Serum was harvested from the blood for PK analysis. Measurements and weights were collected 2x/week. Animals exhibiting weight loss of >15% were weighed daily and euthanized if they lost >20% body weight. Animals showing adverse clinical issues were observed more frequently, up to daily depending on severity, and euthanized if moribund. Mice were euthanized if tumor volumes exceeded 3,000 mm³, or after 3 months if tumors did not form. These remaining tumors were measured and weighed 1x/week. For any large or aggressively growing tumors present after 8 weeks, measurements and weights for these specific mice were collected 2x/week. Throughout the entire study, clinical observations of all mice were performed 2x/week.

Figure 10:
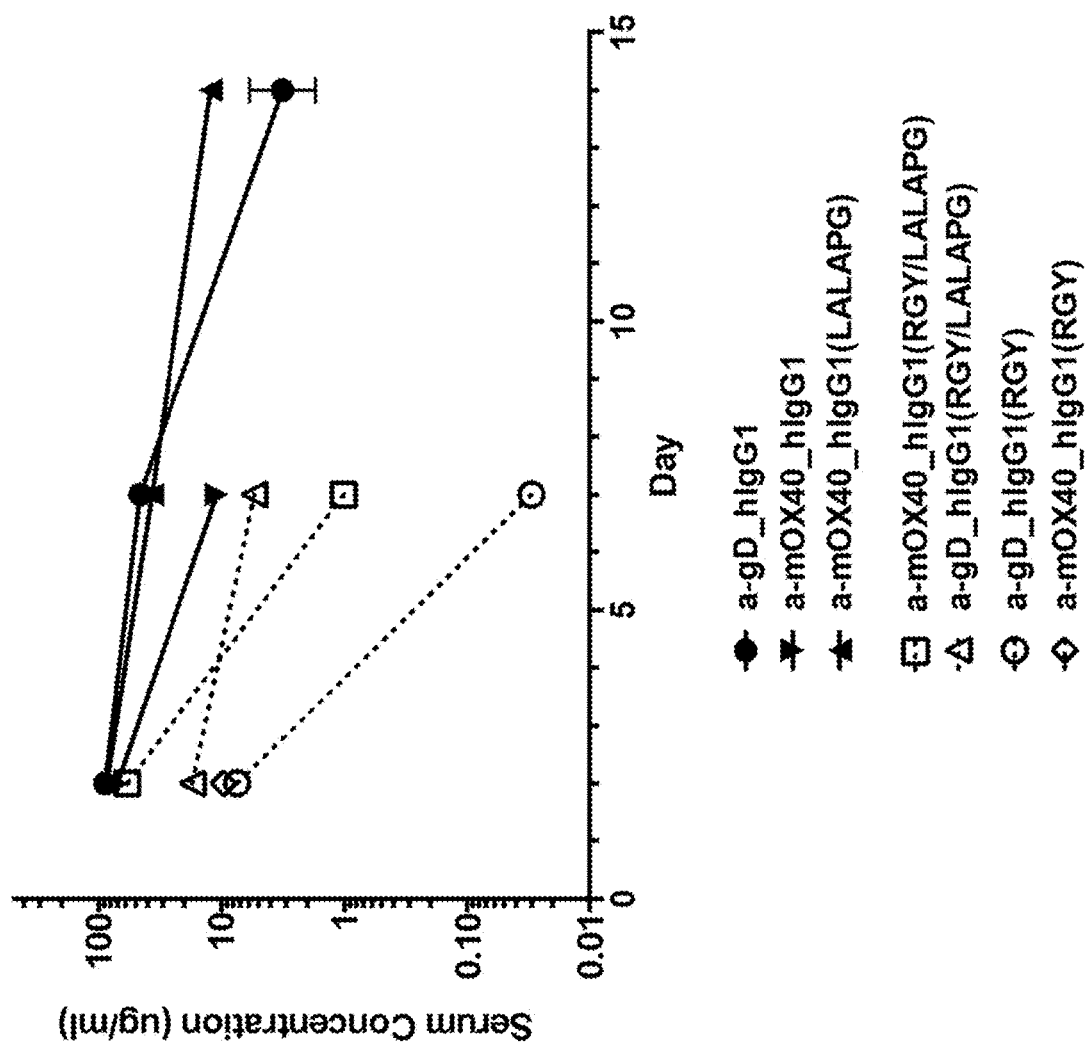
FIG. 10 shows pharmacokinetic (PK) data from a syngeneic EMT6 mouse cancer model demonstrating that RGY variant antibodies (open symbols and dotted lines) clear rapidly relative to native human IgG1 antibodies (solid symbols and solid lines). The PK ELISA used a sheep anti-human IgG antibody to capture test articles from serum and goat anti-human IgG-HRP to detect. The absence of day 7 and 14 timepoints for some test articles indicates that data were below limit of detection.

The pharmacokinetics of the antibodies were tested using a standard ELISA with a sheep anti-human IgG antibody to capture and goat anti-human IgG-HRP to detect. Pharmacokinetic data are shown in FIG. 10. Results demonstrated that RGY and RGY/LALAPG variants cleared much more rapidly than native human IgG1 antibodies.

Figure 11:
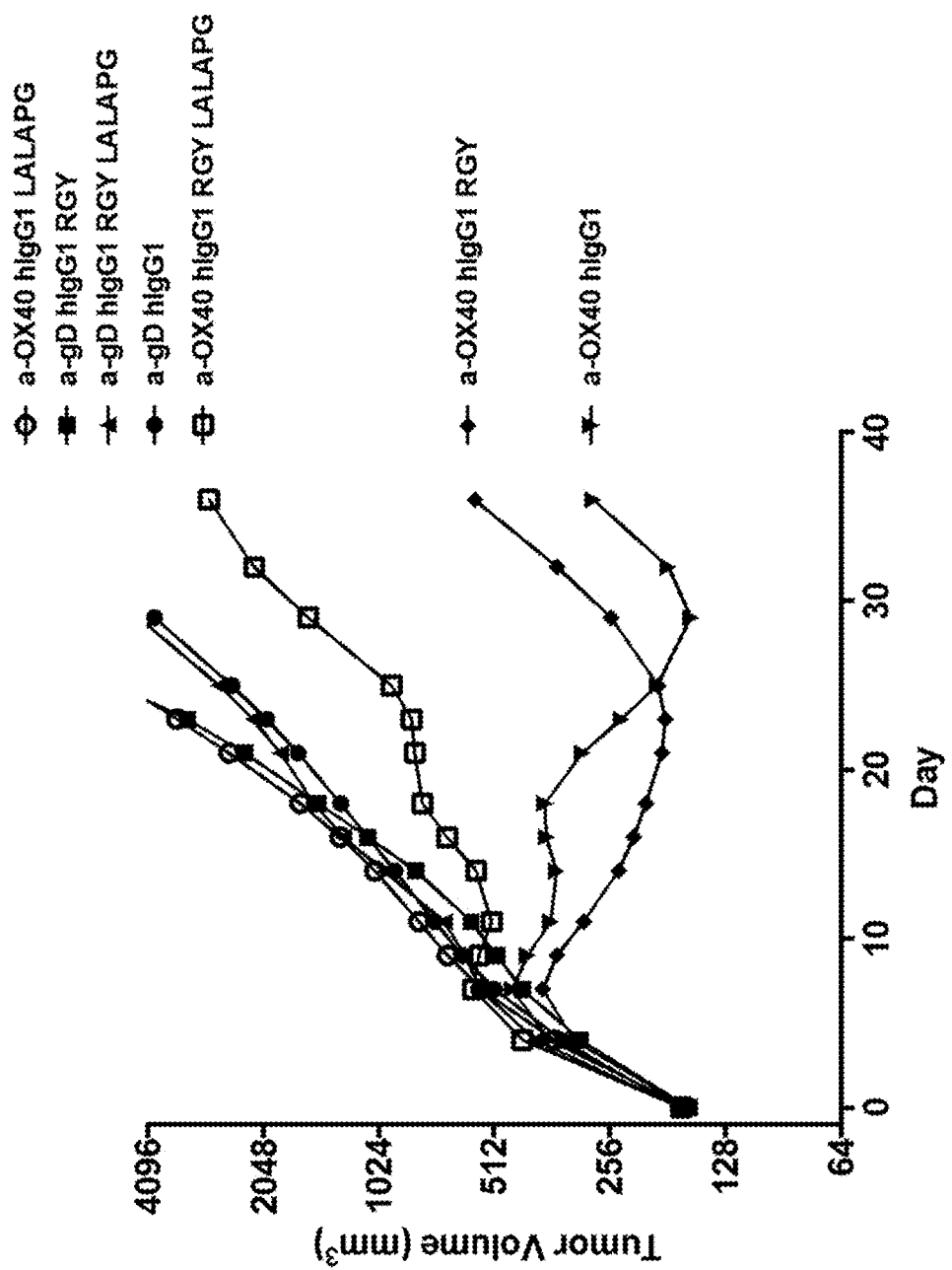
FIG. 11 shows tumor volume data from the syngeneic EMT6 mouse cancer model demonstrating that despite their rapid clearance the RGY variant antibodies enhance anti-tumor activity relative to their parental antibodies, and moreover promote agonist activity of the OX40 receptor in the absence of Fc receptor-mediated crosslinking.

Tumor volume data are shown in FIG. 11. Despite their rapid clearance, the RGY variant antibodies enhanced anti-tumor activity relative to their parental antibodies. The hIgG1(RGY) variant enhanced tumor killing relative to native hIgG1. Moreover, the hIgG1(RGY/LALAPG) variant provided some anti-tumor activity relative to hIgG1(LALAPG) which showed no anti-tumor activity. These results demonstrated that the hexameric antibodies could promote agonist activity of OX40 receptor in the absence of Fc receptor-mediated crosslinking.

Example 5. Non-Solution Hexamer Variants

Figure 12:
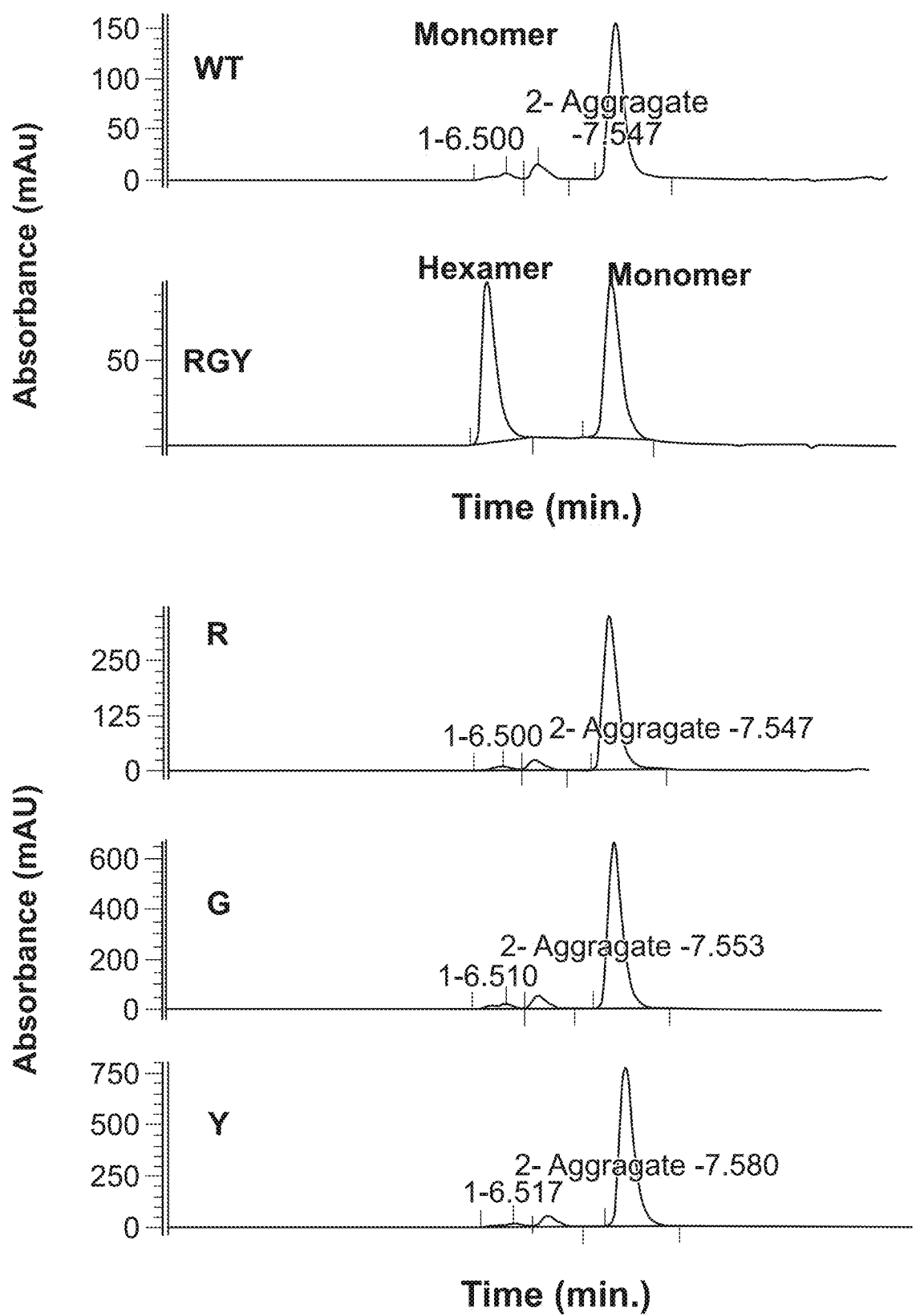
FIG. 12 shows analytical SEC chromatograms demonstrating that all three RGY substitutions are necessary to promote hexamer formation in solution. All antibodies were constructed, produced, and tested in the context of hu1A7 IgG1. WT=native IgG1, RGY=E345R/E430G/S440Y, R=E345R, G=E430G, Y=S440Y, RG=E345R/E430G, RY=E345R/S440Y, and GY=E430G/S440Y.
Figure 12:
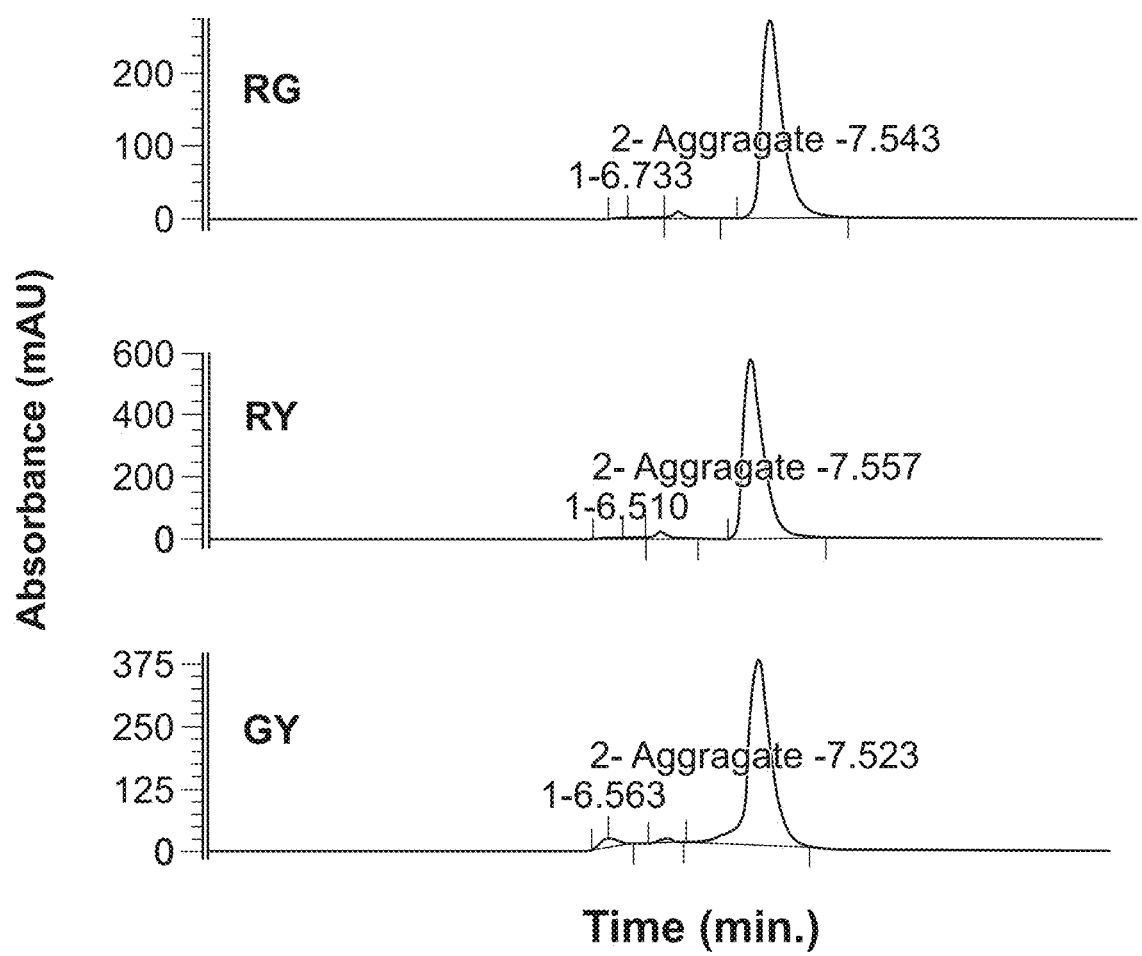

We hypothesized that the rapid clearance of the RGY variants in vivo was due to its size and accordingly its behavior was similar to that of an antibody immune complex. We explored whether the individual substitution components of the RGY variant could provide more favorable solution properties yet still enable enhanced and/or Fc-independent crosslinking. Single and double substitution variants were constructed and produced in the anti-hOX40 antibody hu1A7 as described above, in the context of both native hIgG1 and LALAPG hIgG1. In addition, variants were also constructed and produced in a different antibody hu3C8 that targets a separate epitope on human OX40 relative to hu1A7. Biacore data (not shown) demonstrated that binding affinities for these antibodies were similar. hu1A7 KD=0.5 nM, whereas hu3C8 KD=1.4 nm. Purified antibodies were run on an analytical SEC to characterize their apparent molecular weight. The data, shown in FIG. 12, confirmed previous data with hu4D5 antibodies (FIG. 3), namely that only the triple substitution variant RGY (E345R/E430G/S440Y) results in appreciable hexamer formation. All of the single variants R (E345R), G (E430G), and Y (S440Y), as well as the double variants RG (E345R/E430G), RY (E345R/S440Y), and GY (E430G/S440Y) resulted in chromatographic peaks that had retention times of only antibody monomer. Similar results were observed for the hu3C8 anti-hOX40 antibody (data not shown).

Figure 13:
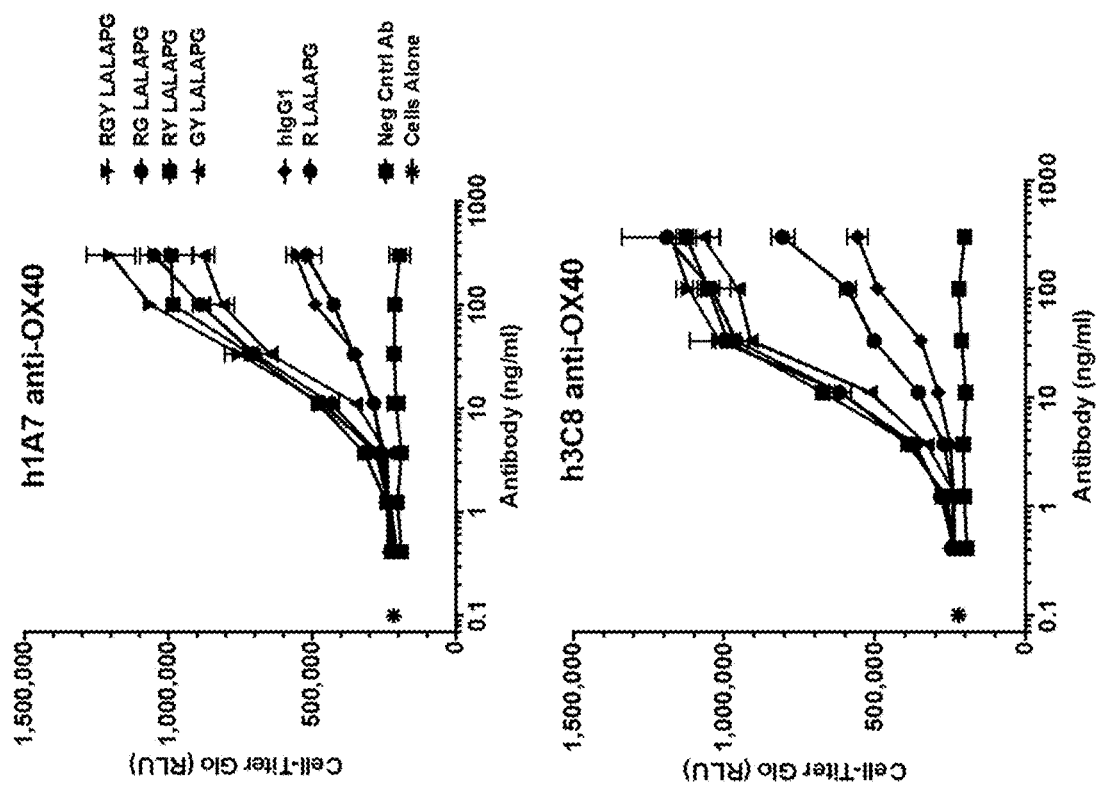
FIG. 13 shows co-stimulation of CD4+ memory T cell proliferation by anti-OX40 or control antibodies in the presence of anti-CD3 antibody and CD80+ FcγRIIa+ L cells. T cell proliferation was monitored by cell titer glo (Promega). The top graph shows data on hu1A7 antibodies while the bottom graph shows data on hu3C8 antibodies. The hIgG1 in both graphs (solid diamond) is hu1A7_hIgG1 antibody. Negative control antibody (Neg Cntrl Ab) in both graphs is anti-Her2 4D5 hIgG1 (RGY/LALAPG).

T cell activation activity of single and double variant hIgG1(LALAPG) antibodies was tested in the in vitro human primary T cell assay described above. T cell proliferation data are shown in FIG. 13. The results demonstrate that despite forming only monomeric species in solution, the three double variants (RG, RY, and GY) and single R variant promoted strong T cell proliferation in the absence of FcR-mediated crosslinking. The G and Y variants were also tested but showed no enhancements in activity (data not shown). FcR-independent activity was observed in the context of both hu1A7 and hu3C8 antibodies, indicating that at least two independent epitopes on human OX40 can be targeted with antibodies to promote T cell activation. Negative control Ab in this assay was anti-Her2 trastuzumab hIgG1(RGY/LALAPG).

The anti-tumor activity of the variant antibodies was tested in the syngeneic EMT6/Luc breast cancer model in Balb/c mice, as described above. Groups were: 1. anti-gD_hIgG1; 2. anti-mOX40_hIgG1(LALAPG); 3. anti-mOX40_hIgG1(RG/LALAPG); 4. anti-mOX40_hIgG1 (RY/LALAPG); 5. anti-mOX40_hIgG1(GY/LALAPG); 6. anti-mOX40_hIgG1(R/LALAPG); 7. anti-mOX40_hIgG1

(RG); 8. anti-mOX40_hIgG1(RGY/LALAPG). n=10 mice for all groups. All groups were dosed 10 mg/kg biweekly, intravenously on day 1 and then intraperitoneally therafter. Antibodies were diluted in sterile PBS and dose volume was 100-200 uL/mouse. Blood was collected 24 hrs post 1st dose and 14 days post 1st dose (Day 2 and 15 of study) from 5 mice/group/timepoint. Serum was harvested from the blood for PK analysis and tumor measurements were acquired as described above.

Figure 14:
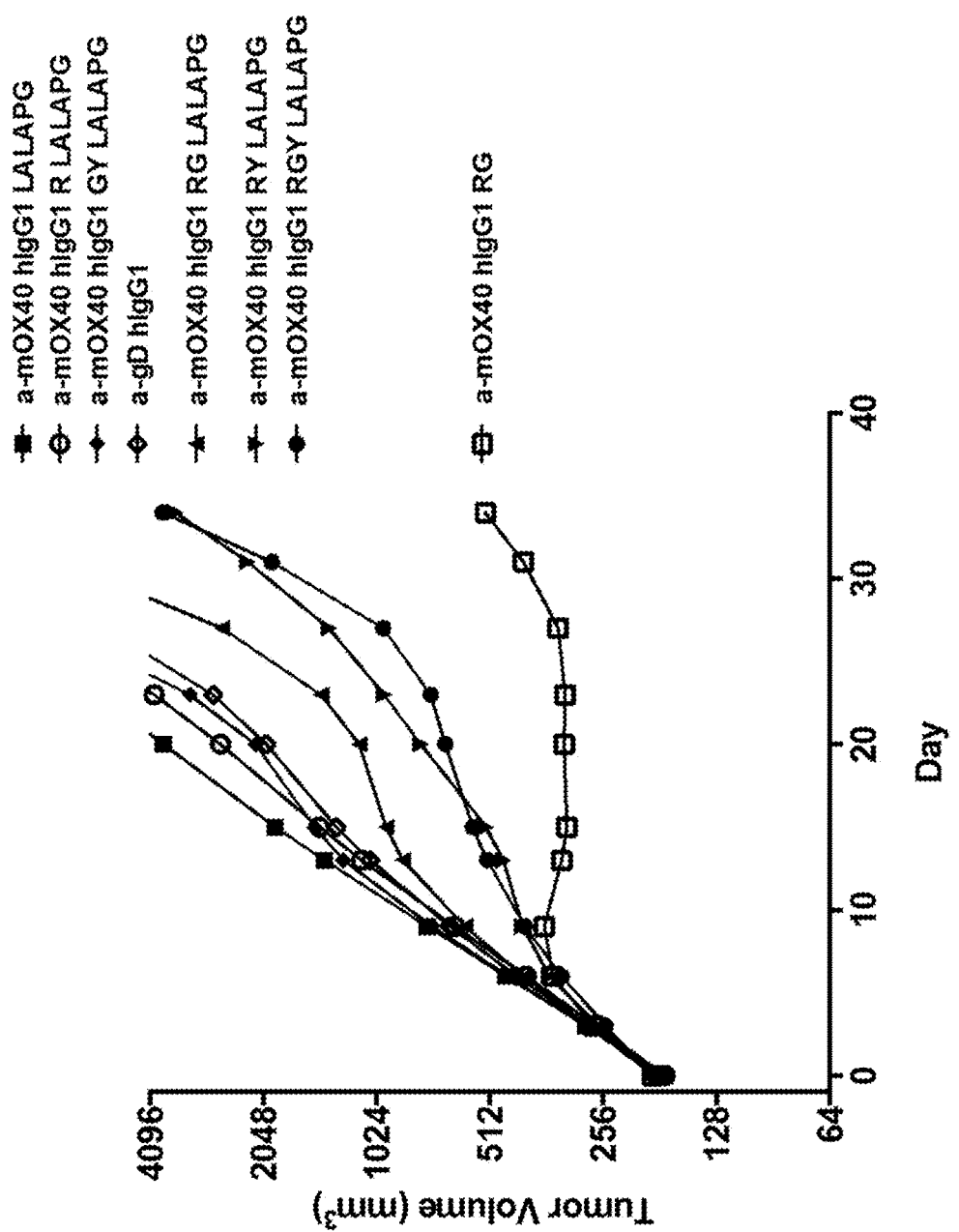
FIG. 14 shows tumor volume data from the syngeneic EMT6 mouse cancer model demonstrating that RG and RY variant antibodies enhance anti-tumor activity relative to their parental antibodies and promote agonist activity of the OX40 receptor in the absence of Fc receptor-mediated crosslinking.

Tumor volume data are shown in FIG. 14. The RY LALAPG and RG LALAPG variants showed some anti-tumor activity whereas the other double and single variants (GY LALAPG and R LALAPG) did not. Notably, the hIgG1 version of the RG that does not comprise the LALAPG variant and thus can still engage Fc receptors showed strong activity. These data suggest that the hIgG1 RY variant should have even greater anti-tumor potency. Overall, together the in vitro and in vivo data indicate that formation of solution hexamer is not necessary for enhanced T cell activation in the absence of FcR-mediated crosslinking. Without wishing to be bound by theory, one hypothesis is that the single and double variants that behave as monomeric IgG species in solution form hexameric complexes upon engaging target receptor.

Figure 15:
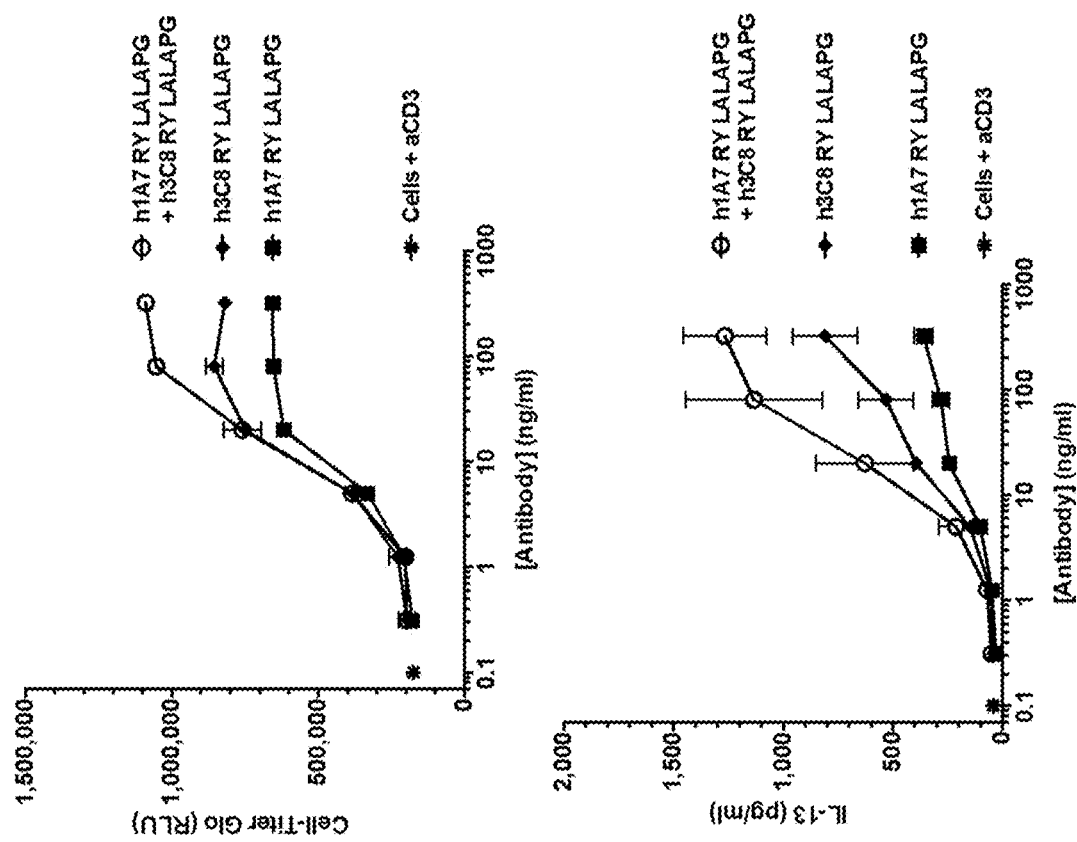
FIG. 15 shows the T cell proliferation (top graph) and cytokine release (bottom graph) data of RY LALAPG variants of h1A7 and h3C8 tested alone and as a 1:1 mixture. The antibody concentration on the x axis represents total antibody, and thus for the mixture (h1A7 RY LALAPG+ h3C8 RY LALAPG) each of the component antibodies is at 50% of its concentration relative to points at which it was tested alone. Cells+aCD3 indicates cells only plus anti-CD3, i.e. no h1A7 or h3C8 antibody (negative control).

Example 6. Exchange of Hexameric Antibodies and Conception of Mixed and Biepitopic Hexameric Antibodies The exchange experiment described above (FIG. 9) suggested that mixed hexameric complexes could be generated from two or more different antibodies. To test the effect of this on anti-OX40 agonist activity, RY LALAPG variants of h1A7 and h3C8 were tested for T cell activation activity alone and as a mixture. FIG. 15 shows the T cell proliferation and cytokine release data from this experiment. The results show that the mixed h1A7/h3C8 RY LALAPG variant antibodies enhance activity relative to either antibody alone. These data suggest that mixed hexameric complexes are formed upon OX40 receptor engagement, thus providing multivalent agonism and T cell activation in the absence of FcR-mediated crosslinking. It is comtemplated herein that hexameric variants could be engineered into a bispecific antibody to capitalize on this epitopic synergy. For example a bispecific antibody could be engineered, as is known in the art (e.g. Spiess et al., Nature Biotechnology) wherein one arm is h1A7 and the other arm is h3C8 that comprises an RY, RG, RGY, or other hexamer-promoting variant.

Example 7. Agonist Activity of Hexamer Variant Anti-DR5 Antibodies

Death Receptor 5 (DR5), also known as TNF-related apoptosis inducing ligand receptor 2 (TRAIL-R2), is a cell surface receptor that transduces apoptosis signal when bound and activated by its ligand TNF-related apoptosis inducing ligand (TNFSF10/TRAIL/APO-2L). DR5 has been a promising target for cancer therapy because it initiates apoptosis through the cell-extrinsic pathway independently of p53 and is selective for tumor cells relative to normal cells. The reliance of antibody agonists of DR5 on FcR-mediated crosslinking has been well established (Wilson et al., 2011, Cancer Cell 19:101-13).

Figure 16:
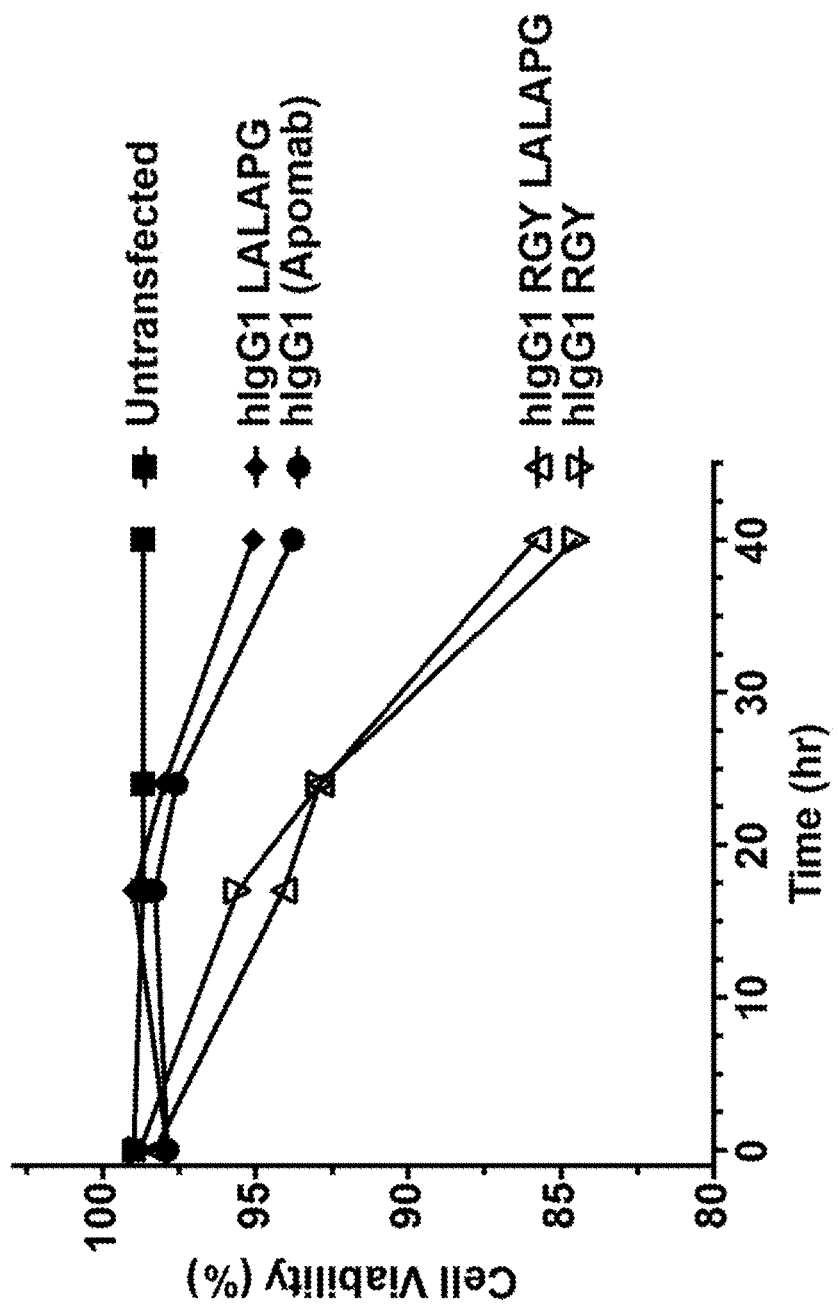
FIG. 16 shows cell viability data comparing RGY and RGY/LALAPG variant anti-DR5 antibodies against non-hexameric hIgG1 controls.

RGY and RGY/LALAPG variants were constructed in the context of an hIgG1 comprising the variable region of Apomab, an anti-DR5 antibody that has advanced into clinical development (Camidge 2008, Expert Opin. Biol. Ther. 8(8)). pRK vector DNA encoding heavy and light chains were co-transfected into HEK293 cells for expression. Cells expressing RGY variant Apomab antibodies did not grow well and produced little protein. HEK293 cells express DR5, and thus it was possible that hexameric RGY antibodies promoted apoptosis by agonizing DR5. Cell viability was measured post-transfection using a cell counter. Data are shown in FIG. 16. The results confirmed that RGY and RGY/LALAPG variant antibodies reduced cell viability relative to hIgG1 controls.

Figure 17:
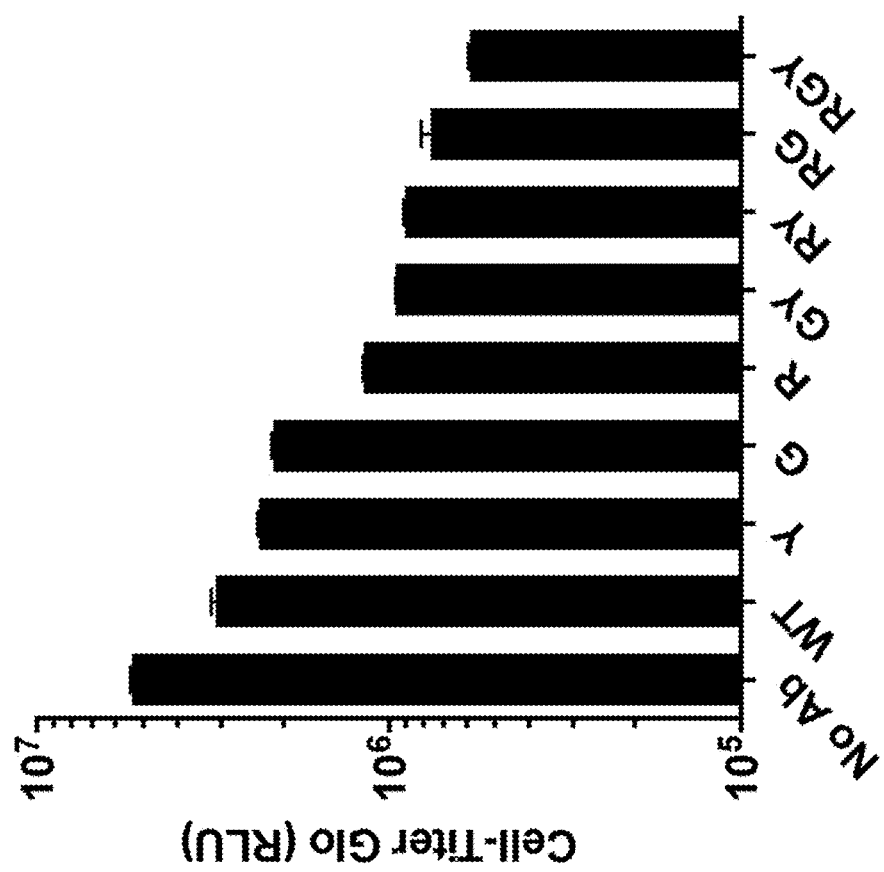
FIG. 17 shows the ability of variant anti-DR5 antibodies to promote apoptosis against HEK293 cells. Activity data represent luminescence in a cell titer glo assay 24 hours post-transfection of antibody heavy and light chain DNA.

Single and double RGY variants were additionally constructed into anti-DR5 Apomab hIgG1 antibodies. DNA encoding heavy and light chains were co-transfected into HEK293 cells, and cell proliferation was monitored using cell titer glo (Promega). The ability of the variant antibodies to reduce viability of HEK293 cells was tested by monitoring cell proliferation using cell titer glo. Luminescence at 24 hours post-transfection are shown in FIG. 17. The results demonstrate that all variants reduce cell proliferation, with the RGY triple variant eliciting the greatest apoptosis, the three double variants GY, RY, and RG mediating slightly less activity, and the three single variants R, G, and Y showing more modest levels of activity with the R being the strongest anti-DR5 agonist of the three.

Figure 18:
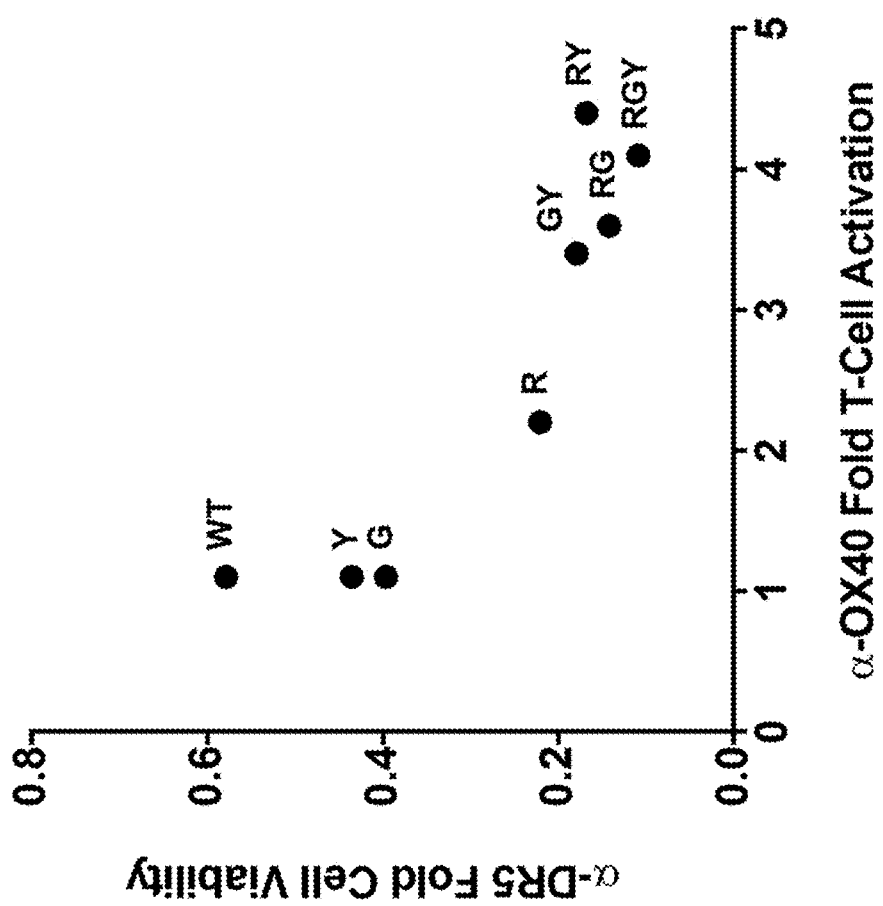
FIG. 18 shows the correlation between fold cell viability of variant anti-DR5 antibodies relative to untransfected cells (calculated from FIG. 17) and fold T-cell activation of h1A7 anti-OX40 antibodies for the same single, double, and triple RGY variants.

Both DR5 and OX40 are members of the TNFR superfamily. Fold cell viability relative to untransfected cells was calculated from the data in FIG. 17 and plotted as a function of fold T-cell activation of h1A7 anti-OX40 antibodies for the same single, double, and triple RGY variants. Results are shown in FIG. 18. The correlation of the anti-DR5 and anti-OX40 data suggests a generalizeable mechanism of antibody-mediated agonism for the hexamer-promoting variants. Application of these variants are contemplated to enhance the agonist activity of antibodies that target other members of the TNFR superfamily, including in particular GITR, CD27, and CD137.

Example 8. Engineering of Other Hexamer Promoting Variants

The E345R, E430G, and S440Y substitutions reside at the elbow region between the antibody heavy constant CH2 and CH3 domains. A series of additional substitutions was engineered at this interface to explore whether other substitutions would promote hexamer formation and enable enhanced and/or FcR-independent agonist activity. These substitutions are listed in Table 4 supra. Variants were constructed in the heavy chain of the anti-DR5 Apomab hIgG1 antibody.

Figure 22A:
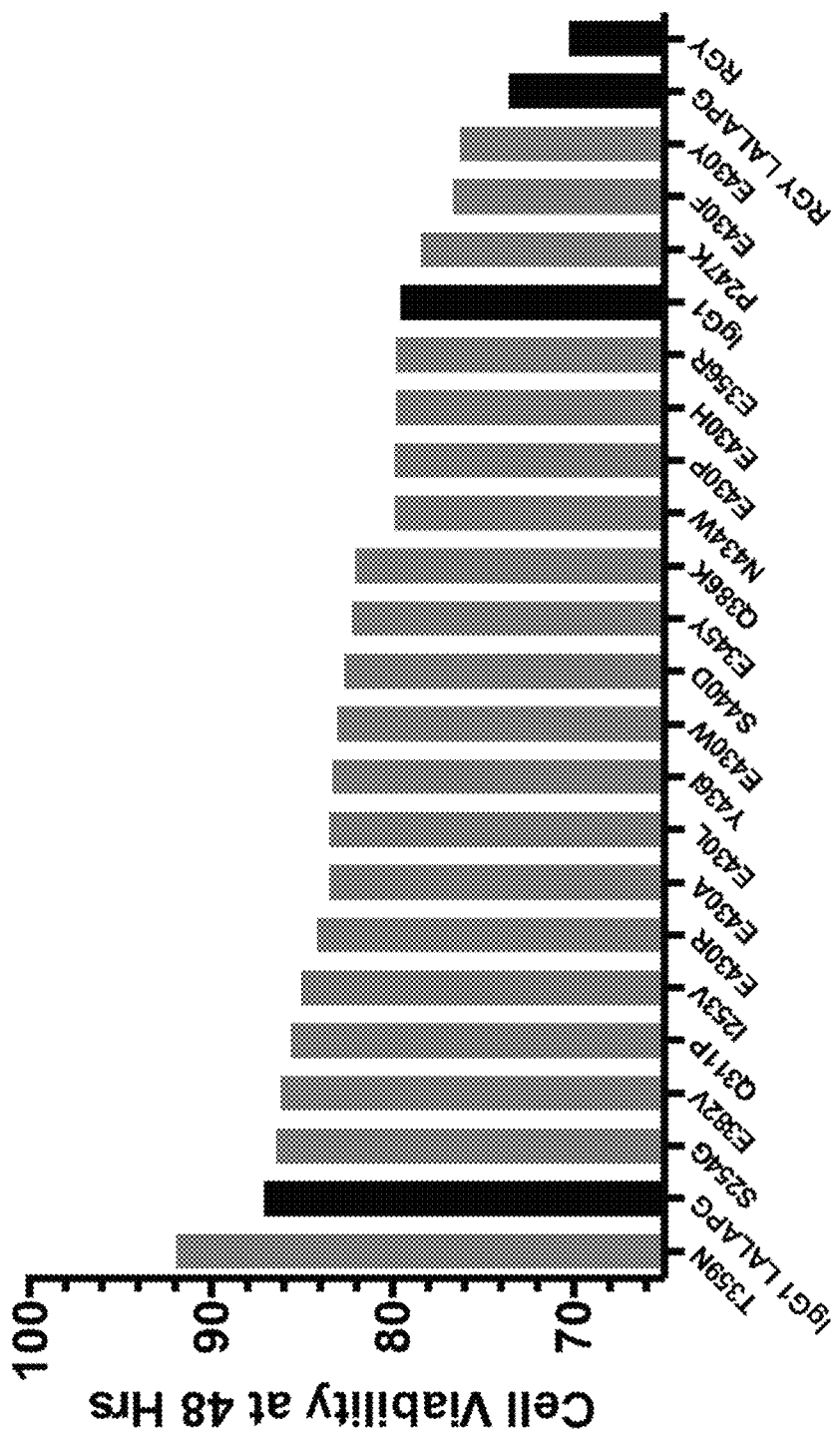
FIGS. 22A & 22B show anti-proliferative activity of Fc engineered anti-DR5 antibodies against 293 cells. Data represent cell viability at 48 hrs (FIG. 22A) or 22 hrs (FIG. 22B) post-transfection. Black bars highlight data for untransfected, native IgG1, IgG1 LALAPG, RGY, and RGY LALAPG variants. The bar for untransfected cells in 22B represents cell viability at 0 hrs.
Figure 22B:
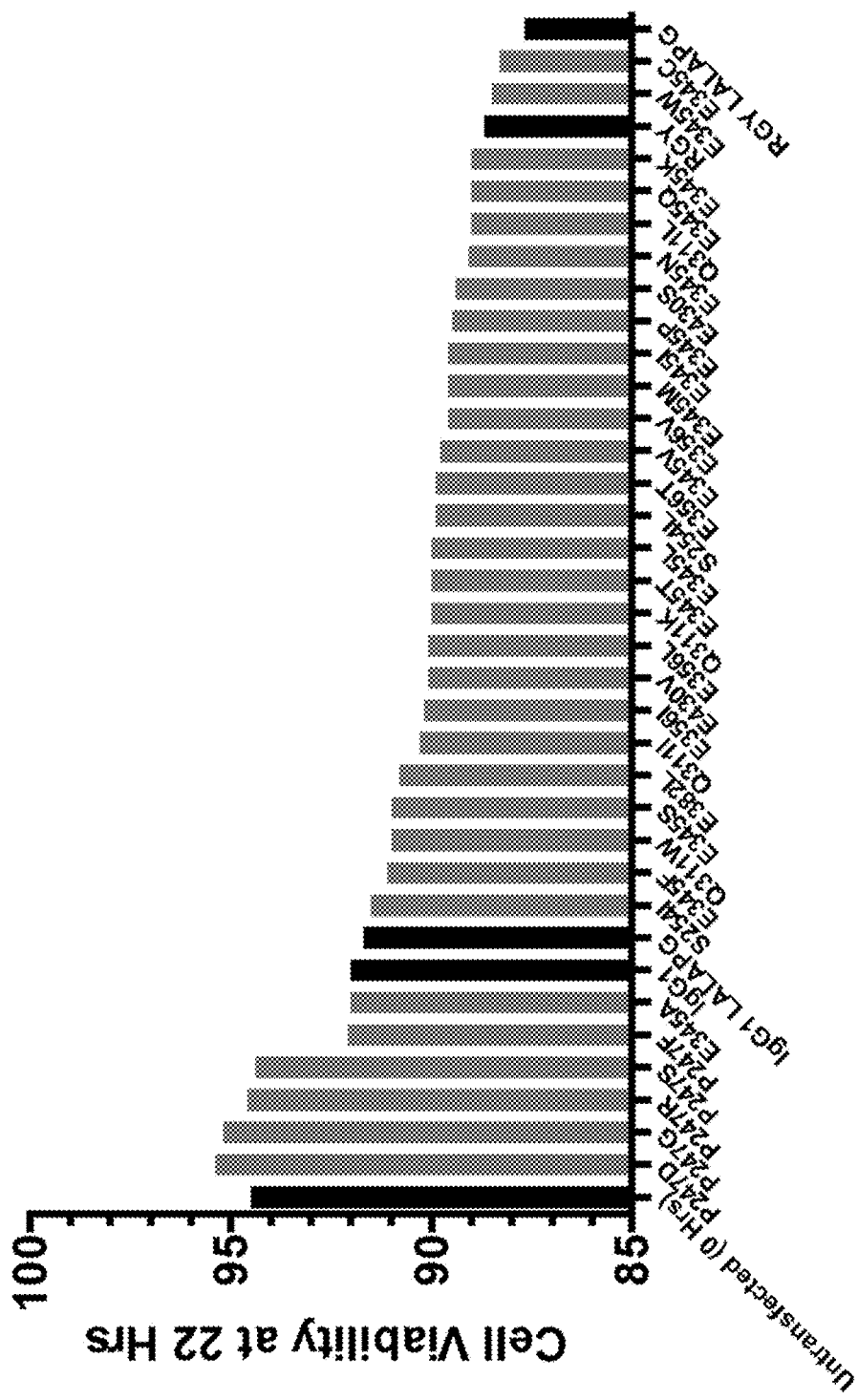

Variants were screened in the context of anti-DR5 Apomab hIgG1 for anti-proliferative activity. Expi293F cells were grown until cell density was ~1.7×10$^6$ cells/ml. 100 μl of Opti-MEM I Reduced Serum Medium was aliquotted into each single well in a 24 well-block, followed by 1 μg of DNA/chain into a single well for each variant. A master mix solution using 2.7 μl of DNA-ExpiFectamine 293 Reagent & 50 μl of Opti-MEM I Reduced Serum Medium was prepared for each transfection, then mixed gently and incubated at room temperature for 5 min After 5 min, diluted ExpiFectamine 293 Reagent was added to the diluted DNA. The mixture was allowed to incubate at room temperature for 20-30 minutes. 2 mL of the 293 cells was added to each well with the DNA mixtures. The block was covered with a sterile breathable sealer, and samples were transferred to a 37° C. incubator. At 22 hrs post-transfection, 300 μl of the transfected cells was taken and mixed with 300

µl of Expi293 Expression Medium. Cell viability was measured with a Vi-CELL XR Cell counter (Beckman Coulter). FIGS. 22A & 22B show cell viability at 48 hrs and 22 hrs (respectively) post-transfection for native and variant Apomab antibodies.

Example 9. Agonist Activity of Hexameric Anti-Tie2 Antibodies

Tie2 is a cell surface receptor that plays a key role in the formation of blood vessels (angiogenesis). Tie2 is bound by protein growth factors known as angiopoietins (Ang1, Ang2, Ang3, Ang4). Ang1 and Ang4 function as agonistic or activating ligands for Tie2, whereas Ang2 and Ang3 behave as competitive antagonists. Ang1 is a multimeric ligand, and it is known that cross-linking of Tie2 is required for effective signaling and activation (Barton et al., 2006, Nat Struct & Mol Biol).

Figure 19:
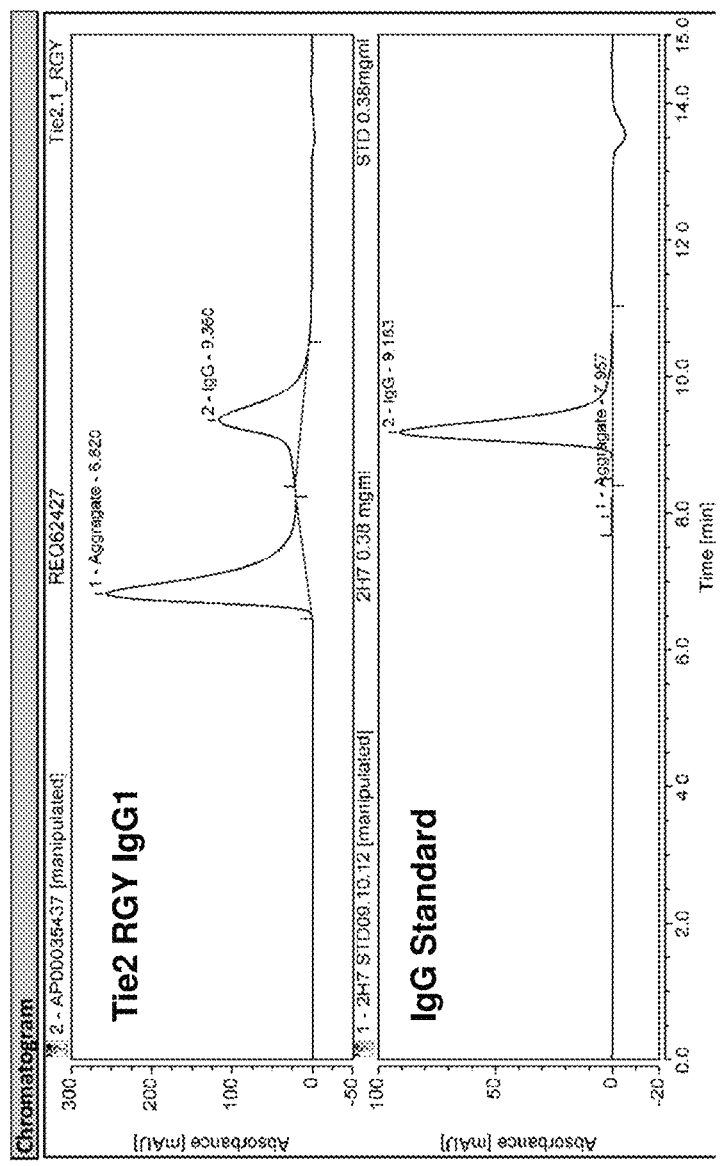
FIG. 19 shows analytical SEC chromatograms for anti-Tie2 antibodies.

A series of anti-Tie2 monoclonal antibodies were generated by phage display. One of the human anti-Tie2 antibodies was subcloned into constant regions encoding human native IgG1 and RGY IgG1. pRK vector DNA encoding heavy and light chains for each antibody were co-transfected into HEK293 cells for expression, and resulting protein was purified from the supernatant using protein A affinity chromatography. Purified antibodies were run on an analytical size exclusion column (SEC) to characterize their apparent molecular weight. The data are shown in FIG. 19. Consistent with results from antibodies containing other human variable regions, the Tie2 RGY IgG1 antibody formed hexamers.

Figure 20:
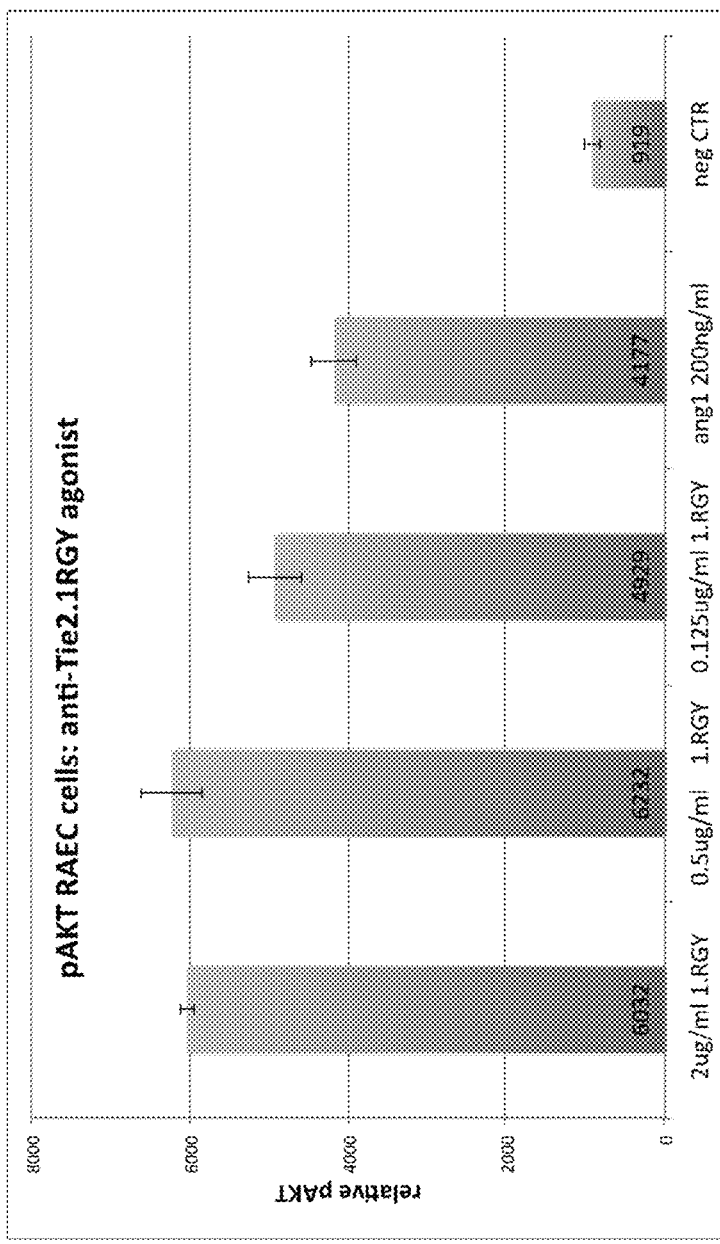
FIG. 20 shows that agonist activity of RGY anti-Tie2 exceeds natural ligand Ang1.
Figure 21:
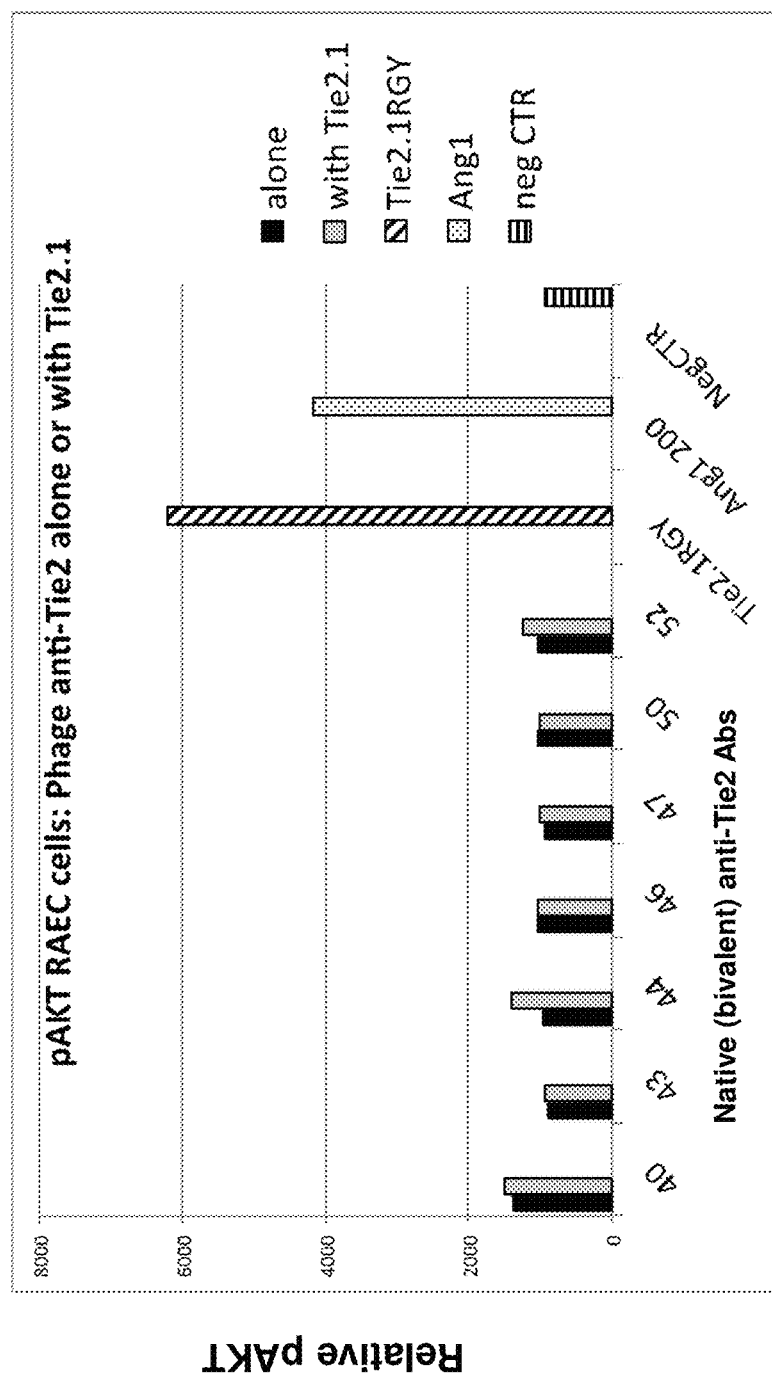
FIG. 21 demonstrates that RGY anti-Tie2 shows strong agonist activity relative to bivalent anti-Tie2 Abs. Activity measured phosphorylation of AKT (pAKT) in rat aortic endothelial cells (RAECs) using a commercial homogenous time-resolved fluorescence (HTRF) assay (Cisbio).

Tie2 RGY IgG1 antibody was tested for agonist activity by measuring phosphorylation of AKT (pAKT) in rat aortic endothelial cells (RAECs) using a commercial homogenous time-resolved fluorescence (HTRF) assay (Cisbio). Agonist activity of RGY anti-Tie2 exceeds natural ligand Ang1 (FIG. 20), and RGY anti-Tie2 shows strong activity relative to bivalent anti-Tie2 Abs (FIG. 21).

Example 10. Contribution of Complement and Fc Receptor Binding to Hexameric Agonist Antibody Activity To further investigate the mechanism of enhanced agonist activity of Fc variant antibodies, substitution K322A was combined with the RGY LALAPG variant in the context of the hu1A7 anti-OX40 antibodies. K322A is a substitution that ablates binding to complement protein C1q and complement-dependent cellular cytotoxicity (CDC).

Figure 23:
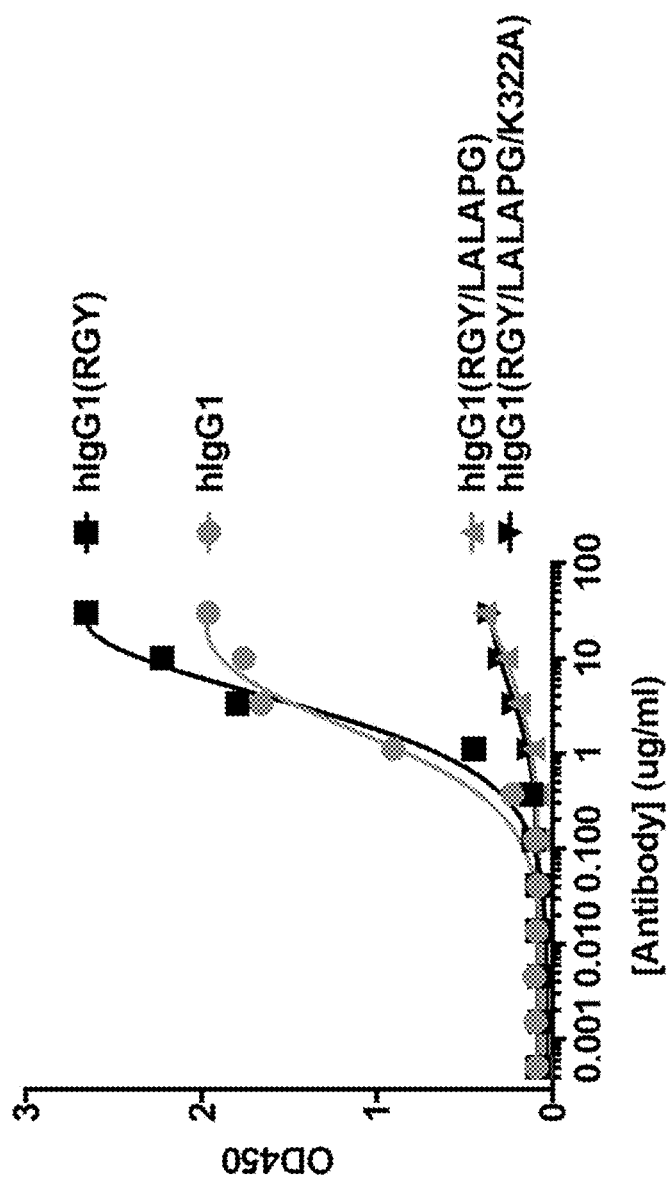
FIG. 23 shows ELISA data demonstrating that LALAPG and LALAPG/K322A variants ablate binding of RGY hexameric antibodies to human C1q.

The binding of the variants to human C1q protein was assessed by an ELISA binding assay (described in Idusogie et al., 2000, J Immunol 164:4178-4184). High binding Costar 96-well plates (Corning, N.Y.) were coated overnight at 4° C. with varying concentrations of anti-OX40 antibodies in coating buffer (0.05 M sodium carbonate buffer, pH 9). The plates were washed after each incubation step with PBS/0.05% Tween 20, pH 7.4, and incubations after coating were performed at room temperature. After coating, the plates were blocked with 200 µl of ELISA diluent (0.1 M NaPO4/0.1 M NaCl/0.1% gelatin/0.05% Tween 20/0.05% ProClin300) for 1 h, and incubated for 2 h with 100 µl of 2 µg/ml human C1q (Abcam, ab96363) in ELISA diluent. Then, 100 µl of a 1:1000 dilution of sheep anti-human C1q peroxidase-conjugated antibody (Abcam ab46191) in ELISA diluent was added and incubated for 1 h. The plates were developed with 100 µl TMB peroxidase substrate (KPL 50-65). The reactions were stopped by the addition of 100 µl of 4.5 N $H_2SO_4$, and the OD was measured at 450 nm using a microplate reader (Thermo Labsystems Multiskan Ascent). The binding efficiency of each variant to the plate was examined using an anti-human IgG Fc peroxidase-conjugated antibody as the probe (Jackson ImmunoResearch). ELISA data (FIG. 23) showed that the RGY variant provides enhanced binding to human C1q relative to human IgG1, and demonstrated that both LALAPG and LALAPG/K322A ablate binding of RGY hexameric antibodies to C1q.

Figure 24A:
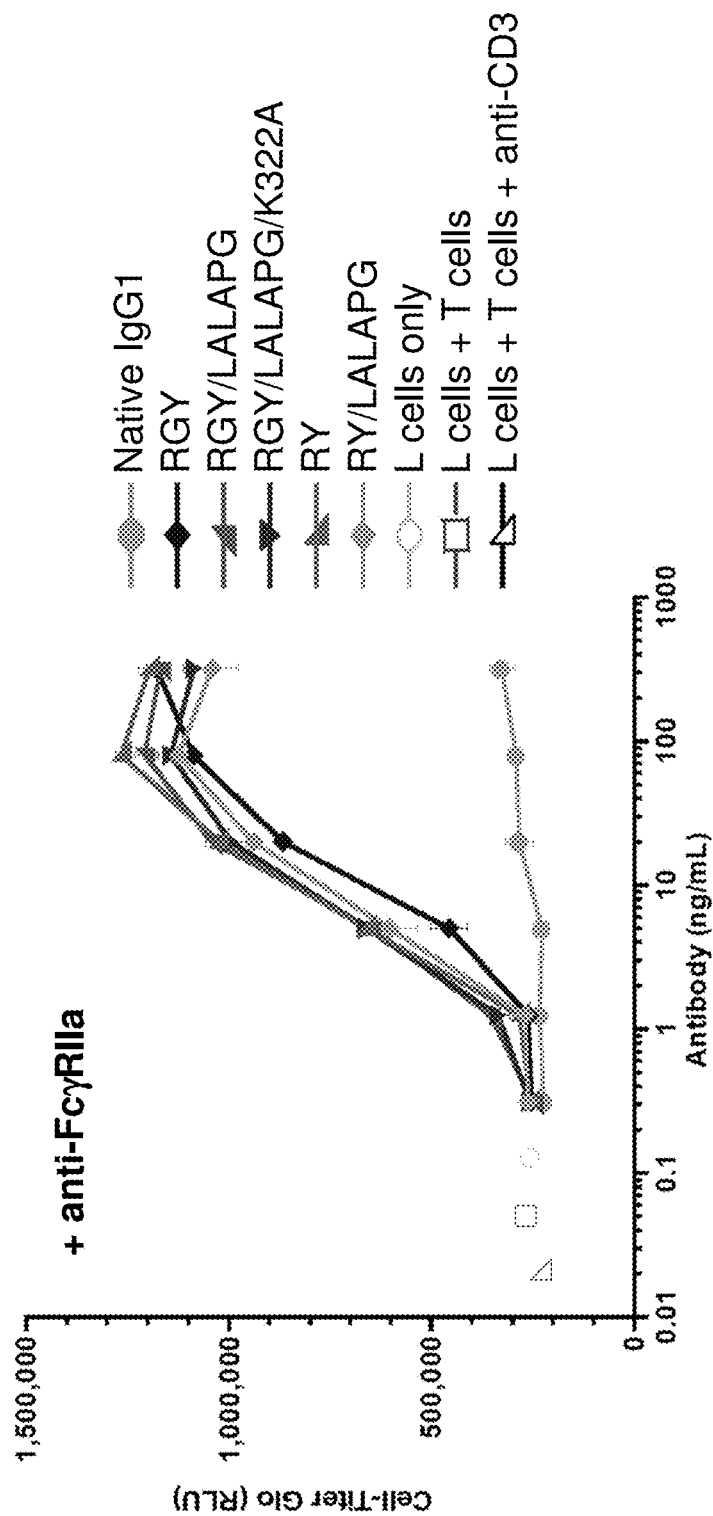
FIGS. 24A & 24B show T cell activation by Fc variant anti-OX40 antibodies in the presence (FIG. 24A) or absence (FIG. 24B) of Fc receptor blocking antibodies.
Figure 24B:
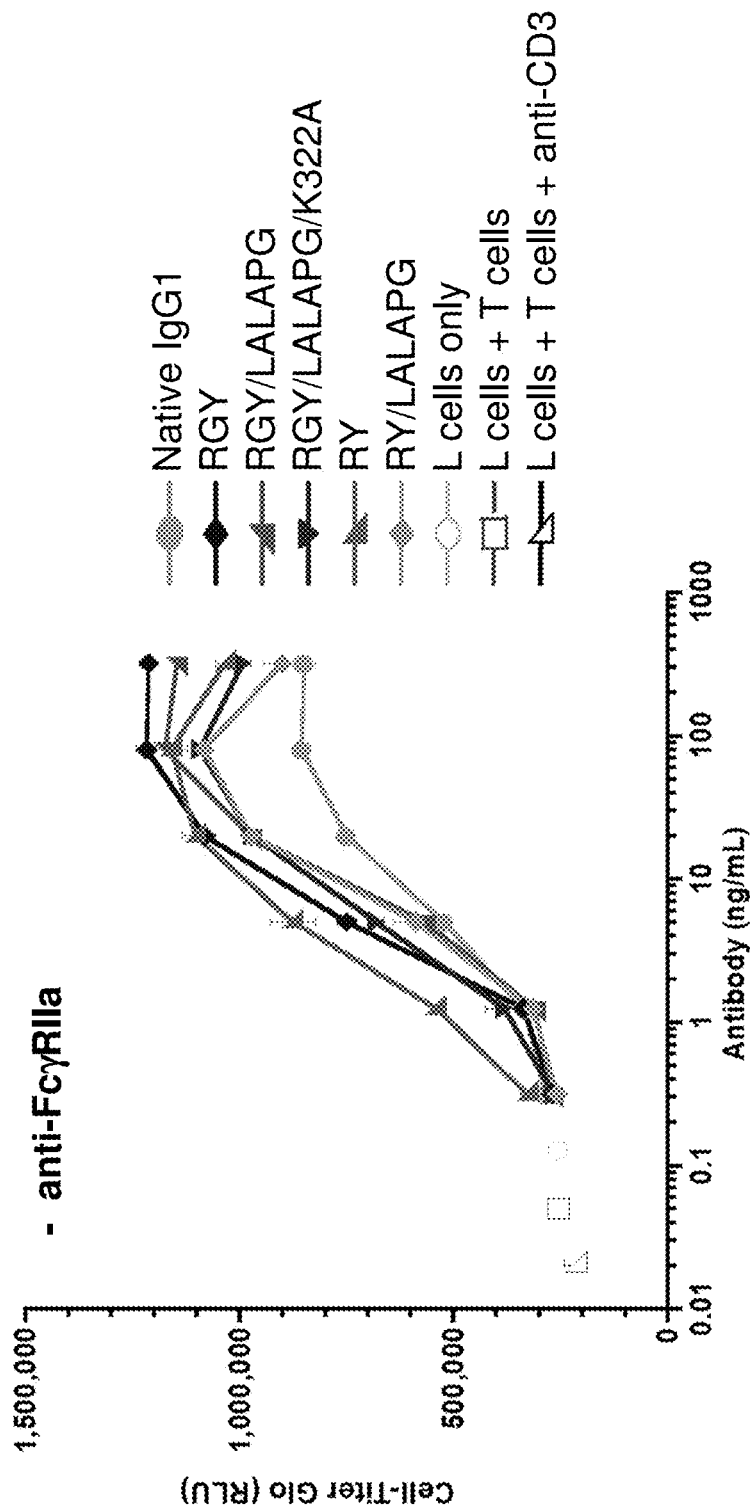

Fc variant anti-OX40 antibodies were tested for their ability to activate T cells in the presence or absence of Fc receptor blocking antibodies using the human primary T cell assay described above. T cell assays were carried out as described above, with or without the addition of anti-FcγRIIa antibody (R&D Systems, catalog # AF1875) at a final concentration of 1 µg/mL. T cell proliferation data are shown in FIGS. 24A & 24B. The data show that while the native human IgG1 version of the hu1A7 anti-OX40 antibodies has no activity in the absence of Fc engagement with FcγRIIa (CD32a) on the L cells, the RGY and RY variant versions (RGY, RGY/LALAPG, RGY/LALAPG/K322A, RY, and RY/LALAPG) all show strong activity independent of whether Fc receptor is blocked. Together with the C1q binding data in FIG. 23, the results demonstrate that the agonist activity of the RGY and RY variants does not rely on Fc engagement with either Fc receptors on accessory L cells or C1q present in the media.

Figure 25A:
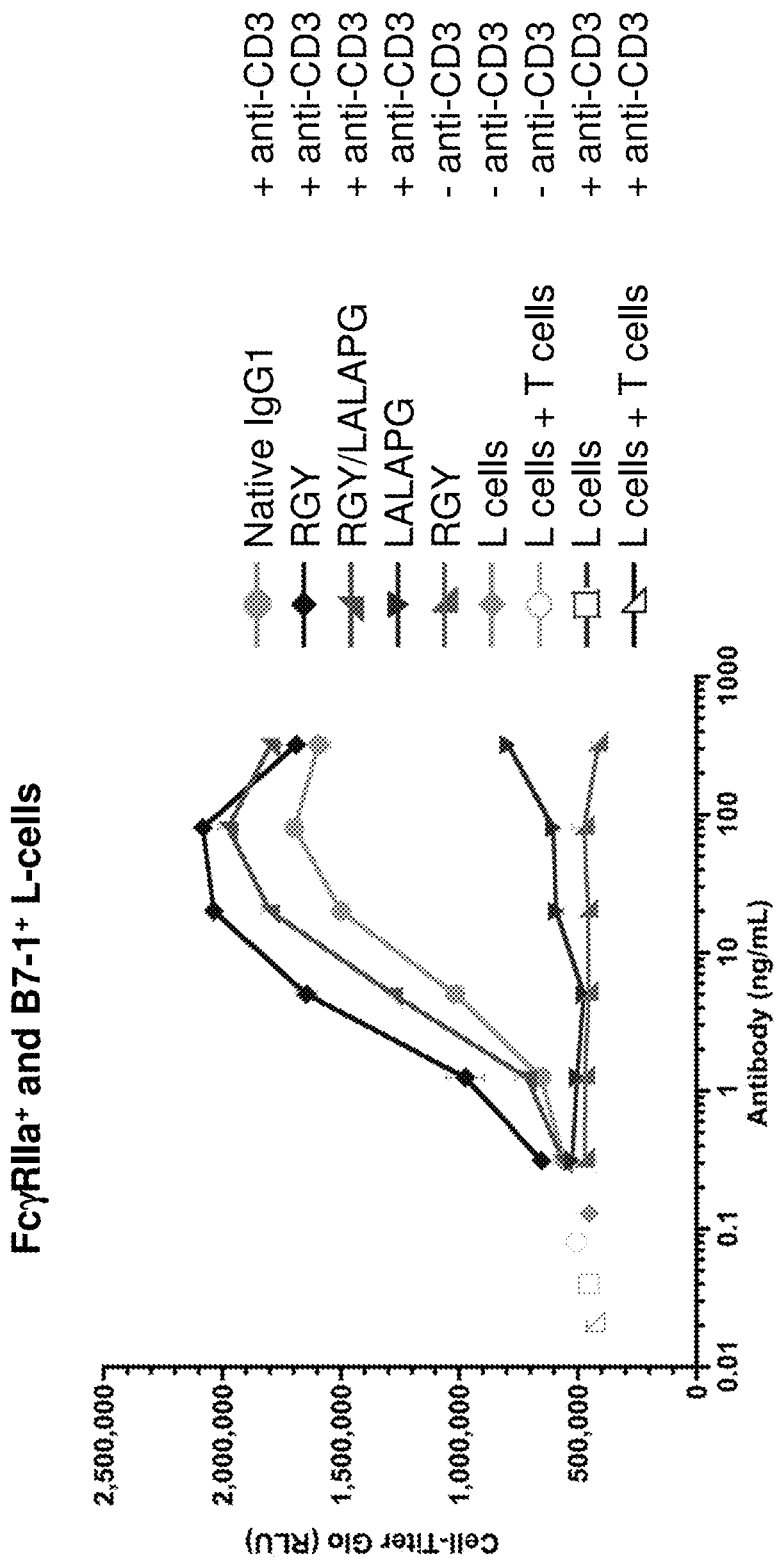
FIGS. 25A & 25B show T cell co-activation by variant hu1A7 anti-OX40 antibodies in the presence of L cells expressing either both FcγRIIa and B7-1 (FIG. 25A), or only FcγRIIa (FIG. 25B).
Figure 25B:
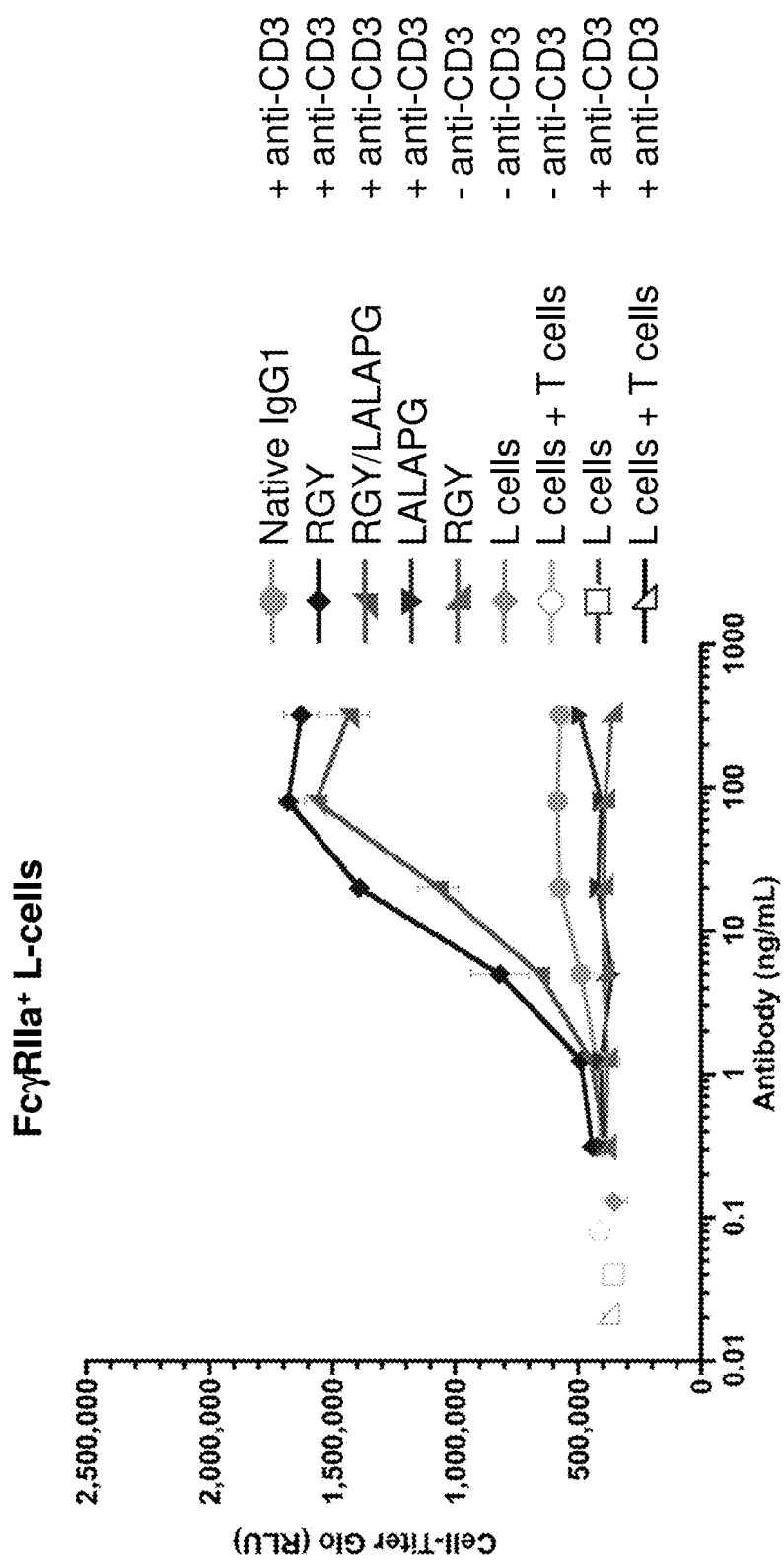
Figure 26A:
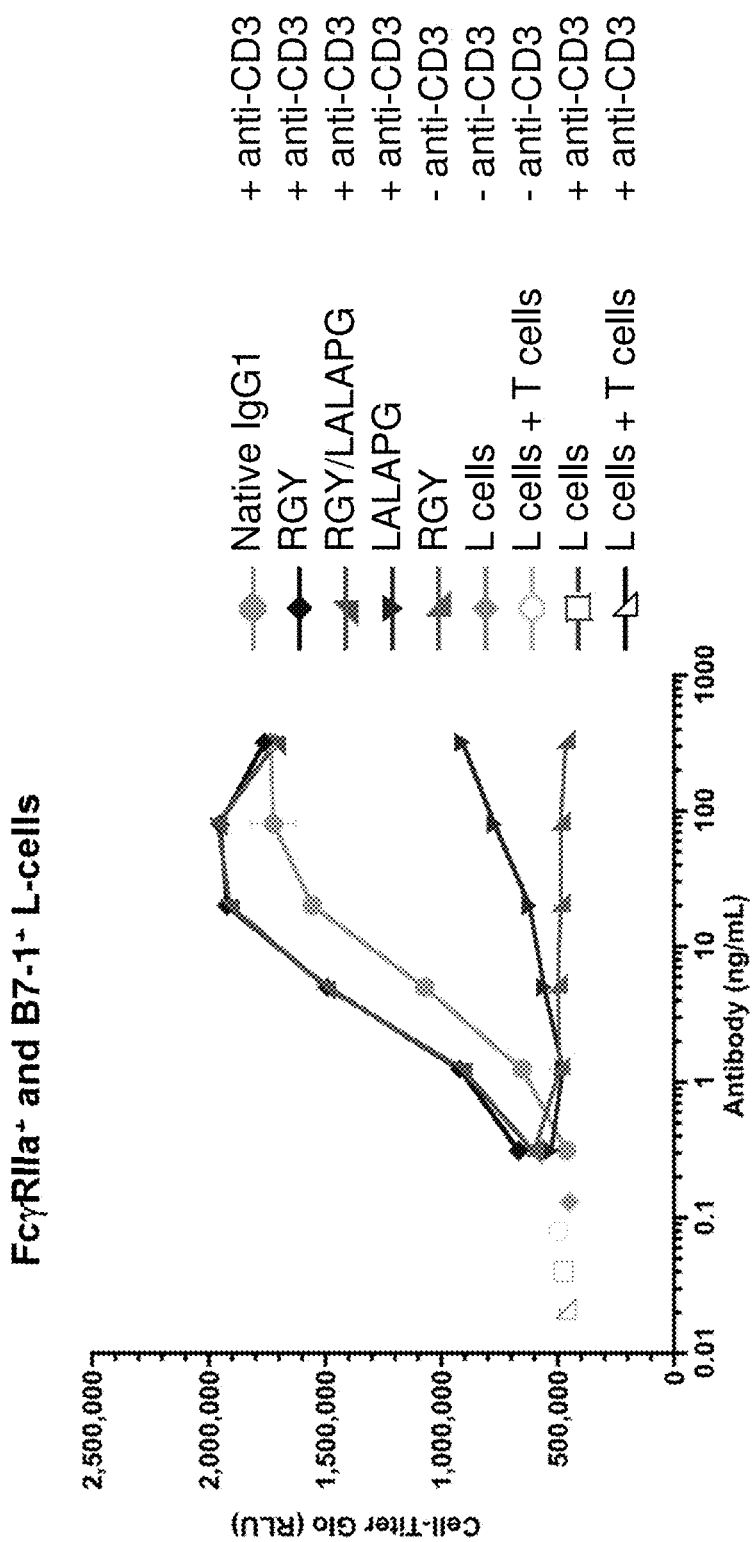
FIGS. 26A & 26B show T cell co-activation by variant hu3C8 anti-OX40 antibodies in the presence of L cells either expressing both FcγRIIa and B7-1 (FIG. 26A), or only FcγRIIa (FIG. 26B).
Figure 26B:
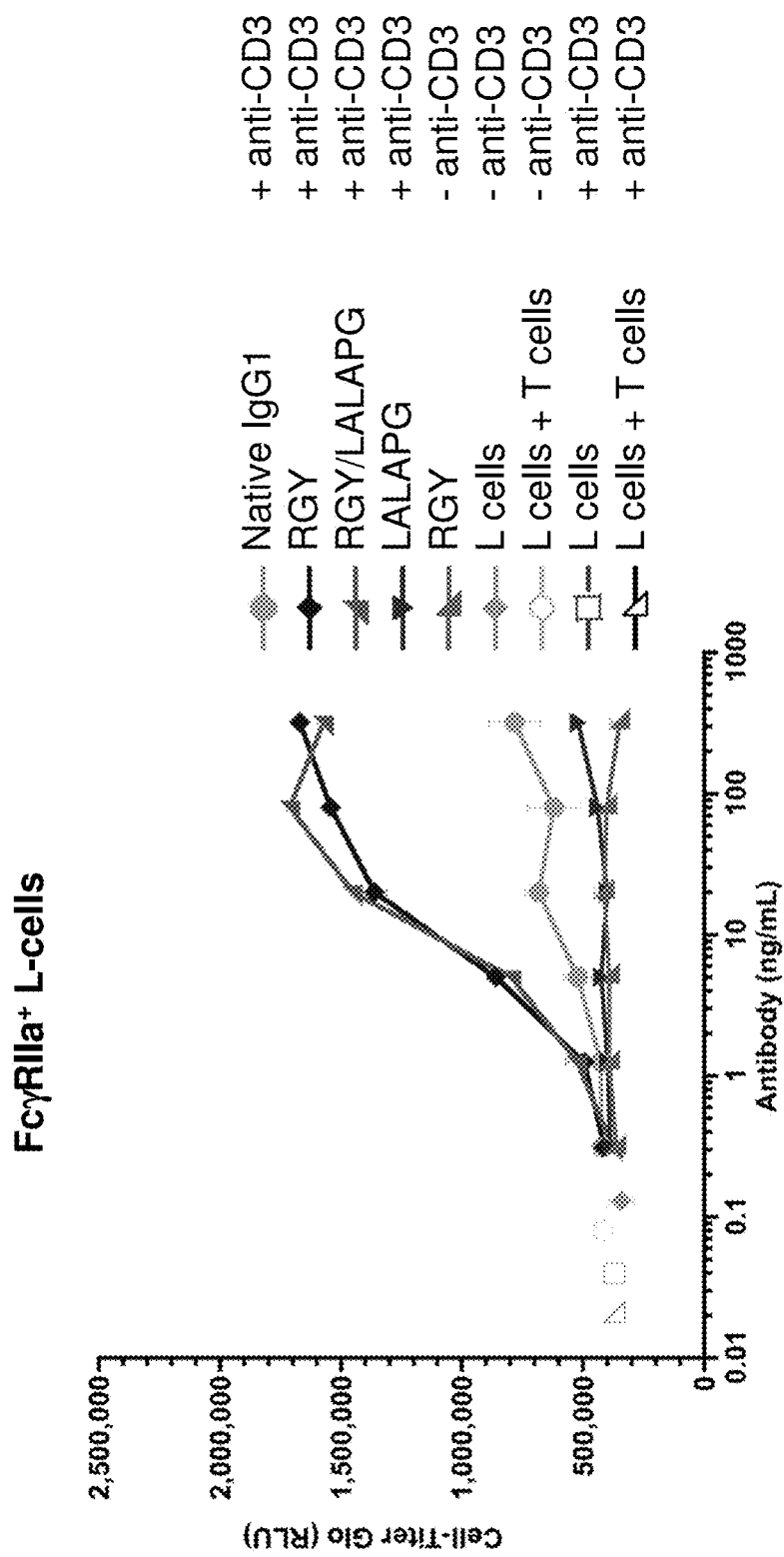

Example 11. Further Characterization of Engineered Anti-OX40 Agonist Antibodies The T cell assay used thus far has utilized an accessory L cell that expresses both FcγRIIa (CD32a) and B7-1 (CD80). The dependence of anti-OX40 agonist activity on B7-1 in the human primary T cell assay was tested. T cell proliferation data are shown for variant hu1A7 (FIGS. 25A & 25B) and variant hu3C8 (FIGS. 26A & 26B) in the presence of L cells either expressing both FcγRIIa and B7-1, or only FcγRIIa. The data demonstrate that while native human IgG1 anti-OX40 antibodies show marginal T cell activation in the absence of B7-1 co-stimulation, Fc variant antibodies (RGY and RGY/LALAPG) show strong T cell activation without relying on CD28 co-activation on the T cells by B7 ligand. In addition, the data also demonstrate that RGY variant antibody does not activate T cells in the absence of CD3 stimulation. In this assay CD3 was activated using anti-CD3 antibody, but more broadly these results indicate that engagement of T-cell receptor with peptide-loaded MHC would be a requisite for T cell co-activation by variant anti-OX40 antibodies.

Figure 27:
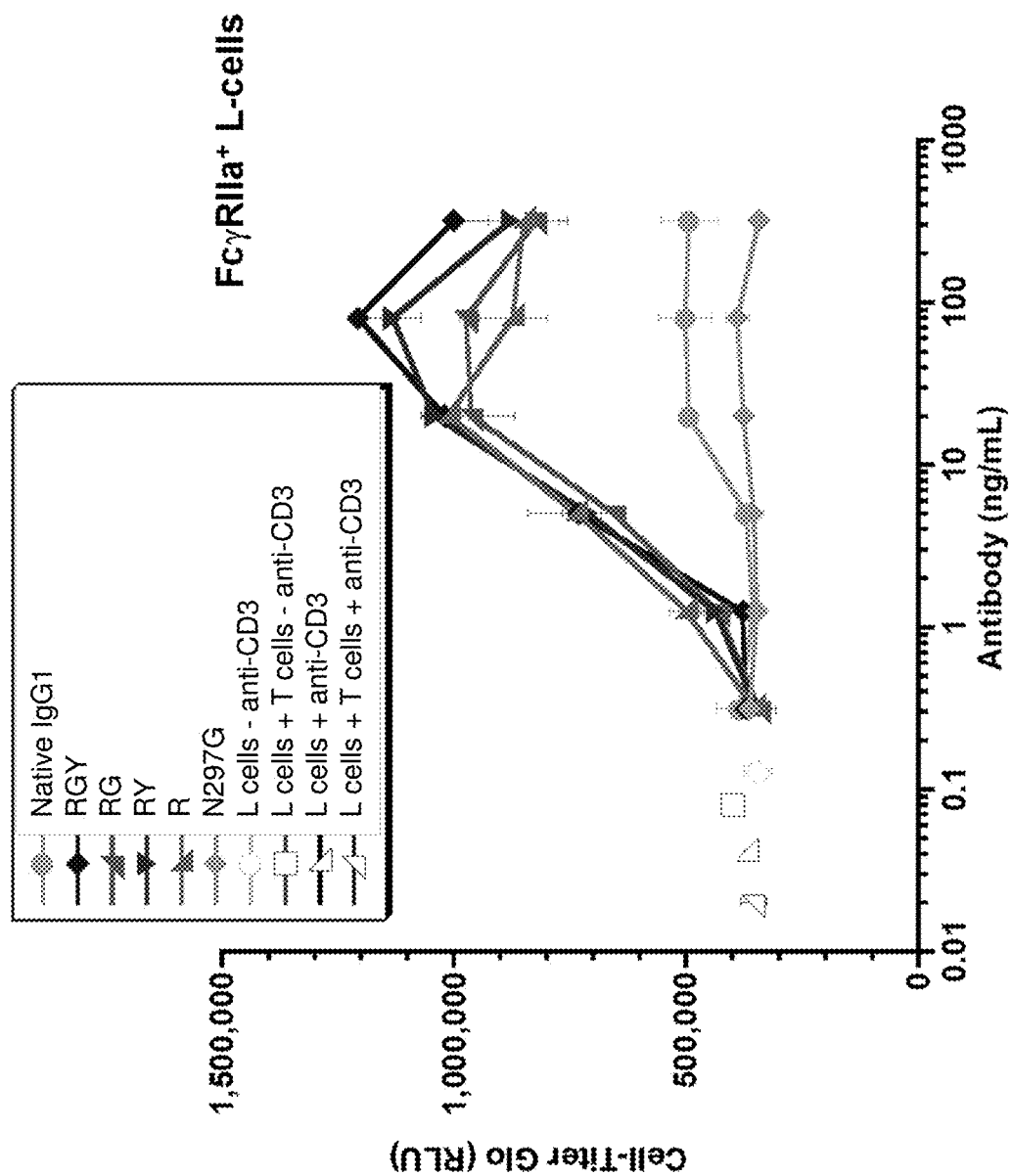
FIG. 27 shows T cell co-activation by variant hu1A7 anti-OX40 antibodies in the presence of L cells either expressing only FcγRIIa. All groups run with antibodies included CD3 stimulation using anti-CD3 antibody.

A set of triple (RGY), double (RG and RY), and single (R) Fc variant anti-OX40 antibodies were tested in the FcγRIIa+ L cells (lacking B7-1 expression). The data, shown in FIG. 27, demonstrate that all Fc variant antibodies co-stimulate T cells in the absence of B7-1 engagement of CD28 on T cells, irrespective of whether Fc variants form hexamers in solution.

The disclosures of all patent and scientific literature cited herein are expressly incorporated in their entirety by reference.

What is claimed is:

1. A hexameric antigen binding complex having agonist activity comprising six subunits, wherein each subunit comprises at least one antigen binding polypeptide comprising at least one antigen binding region from an antibody that binds to OX40 and a modified human IgG1 Fc region that comprises amino acid substitutions E345R, E430G and S440Y, positions according to EU numbering based on native human IgG1, wherein the complex has agonist activity for OX40 bound by the complex.

2. The complex according to claim 1, wherein each antigen binding polypeptide binds to the same epitope on OX40.

3. The complex according to claim 1, wherein the antigen binding region is selected from the group consisting of Fv, Fab, Fab', F(ab')$_2$ and scFv.

4. The complex according to claim 1, wherein the Fc region further comprises a modification for diminished C1q binding and/or Complement Dependent Cytotoxicity (CDC).

5. The complex according to claim 4, wherein the modification for diminished C1q binding and/or CDC comprises a K322A amino acid substitution in the Fc region of a human IgG1 (EU numbering).

6. The complex according to claim 1, wherein the antigen binding region comprises an antigen binding region from a monospecific antibody, bispecific antibody or multispecific antibody.

7. The complex according to claim 1, wherein the complex comprises at least one subunit that comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and/or (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7.

8. The complex according to claim 7, wherein each of the six subunits comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and/or (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7.

9. The complex according to claim 1, wherein the complex comprises at least one subunit that comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and/or (b) a VL domain comprising (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

10. The complex according to claim 9, wherein each of the six subunits comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and/or (b) a VL domain comprising (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

11. The complex according to claim 1, wherein the complex comprises (a) at least a first subunit that binds a first epitope of OX40; and (b) at least a second subunit that binds a second epitope of OX40, wherein the first epitope of OX40 is different from the second epitope of OX40.

12. The complex according to claim 11, wherein the first subunit comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and/or (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; and wherein the second subunit comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and/or (b) a VL domain comprising (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

13. The complex according to claim 1, wherein the antibody is a bispecific antibody that comprises (a) at least a first arm that binds a first epitope of OX40 and (b) at least a second arm that binds a second epitope of OX40, wherein the first epitope of OX40 is different from the second epitope of OX40.

14. The complex according to claim 13, wherein the first arm comprises (a) a VH domain comprising (i) HVR-H1 comprising the amino acid sequence of SEQ ID NO:2, (ii) HVR-H2 comprising the amino acid sequence of SEQ ID NO:3, (iii) HVR-H3 comprising the amino acid sequence of SEQ ID NO:4; and/or (b) a VL domain comprising (i) HVR-L1 comprising the amino acid sequence of SEQ ID NO:5, (ii) HVR-L2 comprising the amino acid sequence of SEQ ID NO:6, and (iii) HVR-L3 comprising an amino acid sequence selected from SEQ ID NO:7; and wherein the second arm comprises (a) a VH domain comprising (i) HVR-H1 comprising the amino acid sequence of SEQ ID NO:29, (ii) HVR-H2 comprising the amino acid sequence of SEQ ID NO:30, and (iii) HVR-H3 comprising the amino acid sequence of SEQ ID NO:33; and/or (b) a VL domain comprising (i) HVR-L1 comprising the amino acid sequence of SEQ ID NO:37, (ii) HVR-L2 comprising the amino acid sequence of SEQ ID NO:39, and (iii) HVR-L3 comprising an amino acid sequence selected from SEQ ID NO:42.

15. The complex according to claim 1, wherein the Fc region further comprises a modification for attenuating effector function.

16. The complex according to claim 15, wherein the modification for attenuating effector function does not result in a modification of the glycosylation pattern of the Fc region.

17. A pharmaceutical composition comprising the complex according to any claim 1 and a pharmaceutically acceptable carrier.

* * * * *